United States Patent
Becker et al.

(10) Patent No.: US 11,155,668 B2
(45) Date of Patent: Oct. 26, 2021

(54) CONTACT-KILLING, QAC FUNCTIONALIZED THERMOPLASTIC POLYURETHANE FOR CATHETER APPLICATIONS

(71) Applicants: THE UNIVERSITY OF AKRON, Akron, OH (US); COOK MEDICAL TECHNOLOGIES, LLC, Bloomington, IN (US)

(72) Inventors: Matthew L. Becker, Stow, OH (US); Zachary K. Zander, Stow, OH (US); Sean Chambers, Bloomington, IN (US); Alec Cerchiari, Bloomington, IN (US); Willie C. McRoy, Jr., West Lafayette, IN (US)

(73) Assignees: The University of Akron, Akron, OH (US); Cook Medical Technologies, LLC, Bloomington, IN (US)

( * ) Notice: Subject to any disclaimer, the term of this patent is extended or adjusted under 35 U.S.C. 154(b) by 0 days.

(21) Appl. No.: 16/154,074

(22) Filed: Oct. 8, 2018

(65) Prior Publication Data
US 2019/0106525 A1 Apr. 11, 2019

Related U.S. Application Data

(60) Provisional application No. 62/569,248, filed on Oct. 6, 2017.

(51) Int. Cl.
*C08G 18/08* (2006.01)
*A61L 15/26* (2006.01)
(Continued)

(52) U.S. Cl.
CPC .......... *C08G 18/0814* (2013.01); *A61L 15/26* (2013.01); *A61L 15/46* (2013.01); *A61L 17/005* (2013.01); *A61L 17/04* (2013.01); *A61L 27/18* (2013.01); *A61L 27/34* (2013.01); *A61L 29/041* (2013.01); *A61L 29/06* (2013.01); *A61L 29/16* (2013.01); *A61L 31/06* (2013.01); *A61L 31/16* (2013.01); *C07C 319/20* (2013.01); *C08G 18/244* (2013.01); *C08G 18/3206* (2013.01); *C08G 18/4837* (2013.01); *C08G 18/6674* (2013.01); *C08G 18/675* (2013.01); *C08G 18/758* (2013.01); *C08G 18/833* (2013.01); *C08G 18/834* (2013.01); *C08G 18/835* (2013.01); *C08L 75/04* (2013.01); *C09D 175/04* (2013.01); *A61L 2300/208* (2013.01); *A61L 2300/404* (2013.01); *C07C 323/25* (2013.01); *C07C 323/52* (2013.01); *C08L 2203/02* (2013.01)

(58) Field of Classification Search
CPC ............ C08G 18/0814; C08G 18/6674; C08G 18/835; C08G 18/3206; C08G 18/675; C08G 18/4837; C08G 18/758; C08G 18/833; C08G 18/244; C08G 18/834; A61L 15/26; A61L 29/06; A61L 15/46; A61L 31/16; A61L 17/04; A61L 29/16; A61L 17/005; A61L 31/06; A61L 27/18; A61L 27/34; A61L 29/041; A61L 2300/404; A61L 2300/208; C09D 175/04; C07C 319/20; C07C 323/25; C07C 23/52; C08L 75/04; C08L 2203/02
See application file for complete search history.

(56) References Cited

U.S. PATENT DOCUMENTS

| | | | |
|---|---|---|---|
| 4,282,366 | A | 8/1981 | Eudy |
| 2011/0195104 | A1 | 8/2011 | Jiang et al. |
| 2016/0347900 | A1* | 12/2016 | Becker .............. C08G 18/0814 |

FOREIGN PATENT DOCUMENTS

| | | | | |
|---|---|---|---|---|
| JP | 62073419 | A | * | 4/1987 |
| JP | 04070660 | A | * | 3/1992 |

OTHER PUBLICATIONS

Asri, L. A. T. W.; Crismaru, M.; Roest, S.; Chen, Y.; Ivashenko, O.; Rudolf, P.; Tiller, J. C.; van der Mei, H. C.; Loontjens, T. J. A.; Busscher, H. J ., A Shape-Adaptive, Antibacterial-Coating of Immobilized Quaternary-Ammonium Compounds Tethered on Hyperbranched Polyurea and its Mechanism of Action. Advanced Functional Materials 2014, 24 (3), 346-355.
(Continued)

*Primary Examiner* — Rabon A Sergent
(74) *Attorney, Agent, or Firm* — Renner, Kenner, Greive, Bobak, Taylor & Weber

(57) ABSTRACT

In various embodiments, the present invention provides a functionalized thermoplastic polyurethane (TPU) containing bulk incorporated or surface-grafted quaternary ammonium compounds (QAC)s for contact-killing of a variety of microbes, where the QACs are on the surface of TPU to provide a sterile surface material that prevents bacteria commonly involved in device-associated infections (DAIs) from proliferating. The functionalized TPUs of the present invention can be formed into a wide variety of 3-dimensional shapes, such as catheters, medical tubing, laryngeal or tracheal stents, sutures, prosthetics, wound dressings, and/or a coating for medical devices and contains the residue of either a QAC containing diol monomer or an alkene functional diol monomer, which then allows the TPU to be functionalized with a QAC containing disulfide or free thiol compound, to form a quaternary ammonium functionalized thermoplastic polyurethane compound having antimicrobial properties for use in medical devices.

20 Claims, 37 Drawing Sheets

(51) Int. Cl.

| | |
|---|---|
| A61L 29/06 | (2006.01) |
| A61L 15/46 | (2006.01) |
| C08G 18/66 | (2006.01) |
| C08G 18/83 | (2006.01) |
| C08G 18/32 | (2006.01) |
| C08G 18/67 | (2006.01) |
| C08G 18/48 | (2006.01) |
| A61L 31/16 | (2006.01) |
| A61L 17/04 | (2006.01) |
| C08G 18/75 | (2006.01) |
| A61L 29/16 | (2006.01) |
| A61L 17/00 | (2006.01) |
| C08G 18/24 | (2006.01) |
| A61L 31/06 | (2006.01) |
| C09D 175/04 | (2006.01) |
| A61L 27/18 | (2006.01) |
| A61L 27/34 | (2006.01) |
| A61L 29/04 | (2006.01) |
| C07C 319/20 | (2006.01) |
| C08L 75/04 | (2006.01) |
| C07C 323/25 | (2006.01) |
| C07C 323/52 | (2006.01) |

(56) References Cited

OTHER PUBLICATIONS

Cheng, G.; Xue, H.; Zhang, Z.; Chen, S.; Jiang, S ., A Switchable Biocompatible Polymer Surface with Self-Sterilizing and Nonfouling Capabilities. Angewandte Chemie International Edition 2008. 47 (46), 8831-8834.

Deng, J.; Ma, L.; Liu, X.; Cheng, C.; Nie, C.; Zhao, C ., Dynamic Covalent Bond-Assisted Anchor of PEG Brushes on Cationic Surfaces with Antibacterial and Antithrombotic Dual Capabilities. Advanced Materials Interfaces 2016,3 (4), 1500473-n/a.

Gottenbos, B.; van der Mei, H. C.; Klatter, F.; Nieuwenhuis, P.; Busscher, H. J ., In vitro and in vivo antimicrobial activity of covalently coupled quaternary ammonium silane coatings on silicone rubber. Biomaterials 2002. 23 (6).1417-1423.

Hamey, M. B.; Pant, R. R.; Fulmer, P. A.; Wynne, J. H ., Surface Self-Concentrating Amphiphilic Quaternary Ammonium Biocides as Coating Additives. ACS Applied Materials & Interfaces 2009. 1 (1 ). 39-41.

Huang, J.; Koepsel, R. R.; Murata, H.; Wu, W.; Lee. S. B.; Kowalewski, T.; Russell, A. J.; Matyjaszewski. K .. Nonleaching Antibacterial Glass Surfaces via "Grafting Onto"; The Effect of the Number of Quaternary Ammonium Groups on Biocidal Activity. Langmuir 2008. 24 (13). 6785-6795.

Lee, S. B.; Koepsel, R. R.; Morley, S. W.; Matyjaszewski, K.; Sun, V.; Russell. A. J ., Permanent. Nonleaching Antibacterial Surfaces. 1. Synthesis by Atom Transfer Radical Polymerization. Biomacromolecules 2004. 5 (3). 877-882.

Thebault, P.; Taffin de Givenchy, E.; Lew, R.; Vandenberghe, V.; Guittard, F.; Garibaldi, S ., Preparation and antimicrobial behaviour of quaternary ammonium thiol derivatives able to be grafted on metal surfaces. European Journal of Medicinal Chemistry 2009. 44 (2). 717-724.

Vaterrodt, A.; Thallinger, B.; Daumann, K.; Koch, D.; Guebitz, G. M.; Ulbricht. M ., Antifouling and Antibacterial Multifunctional Polyzwitterion/Enzyme Coating on Silicone Catheter Material Prepared by Electrostatic Layer-by-Layer Assembly. Langmuir 2016. 32 (5).1347-1359.

Xu, W. Z.; Gao, G.; Kadla, J. F ., Synthesis of antibacterial cellulose materials using a "clickable" quaternary ammonium compound. Cellulose 2013. 20 (3). 1187-1199.

Yan, S.; Luan, S.; Shi. H.; Xu, X.; Zhang, J.; Yuan, S.; Yang, V.; Yin, J ., Hierarchical Polymer Brushes with Dominant Antibacterial Mechanisms Switching from Bactericidal to Bacteria Repellent. Biomacromolecules 2016.17 (5).1696-1704.

Yao, C.; Li, X.; Neoh, K. G.; Shi, Z.; Kang, E. T ., Surface modification and antibacterial activity of electrospun polyurethane fibrous membranes with quaternary ammonium moieties. Journal of Membrane Science 2008. 320 (1). 259-267.

Yu, Q.; Wu, Z.; Chen, H ., Dual-function antibacterial surfaces for biomedical applications. Acta Biomaterialia 2015.16.1-13

* cited by examiner

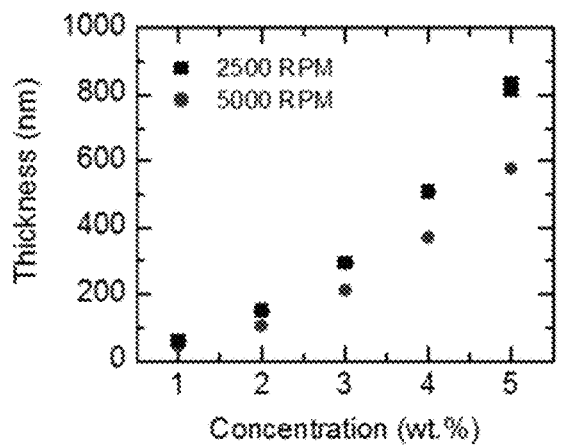 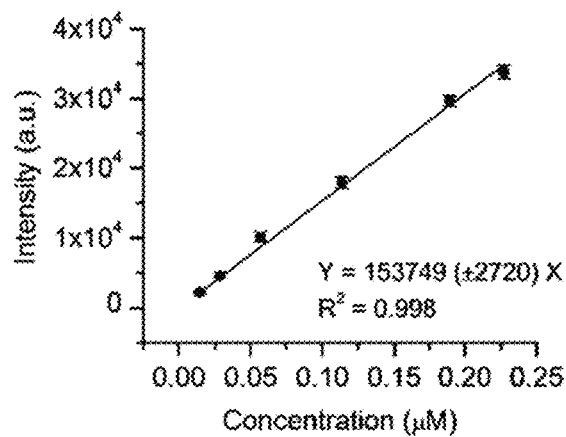
FIG. 22  FIG. 23
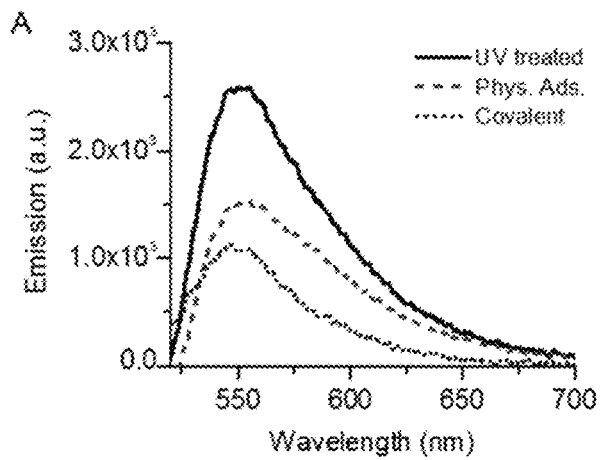 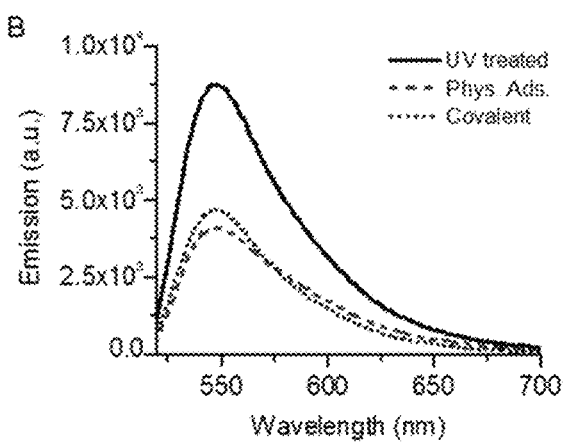
FIG. 24A  FIG. 24B
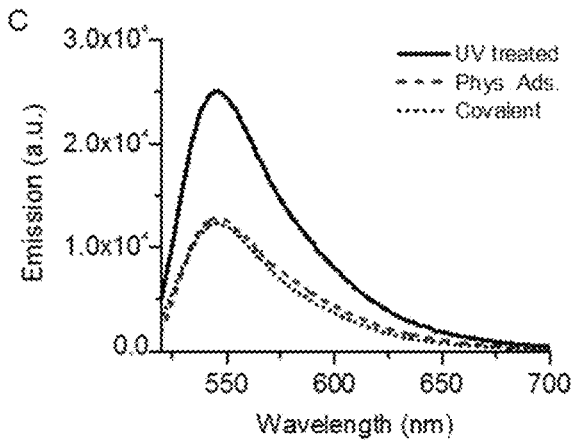 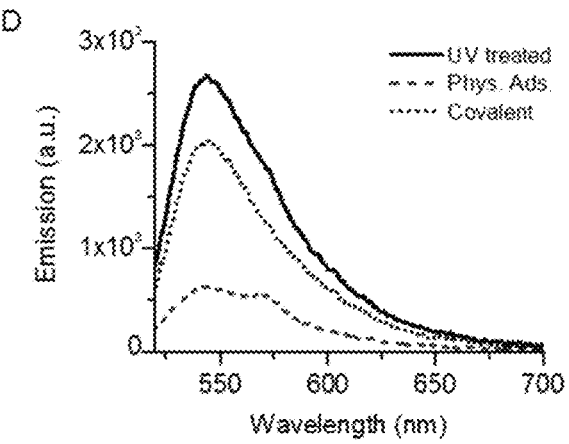
FIG. 24C  FIG. 24D

CONTACT-KILLING, QAC FUNCTIONALIZED THERMOPLASTIC POLYURETHANE FOR CATHETER APPLICATIONS

CROSS REFERENCE TO RELATED APPLICATIONS

This application claims the benefit of U.S. provisional patent application Ser. No. 62/569,248 entitled "Contact-Killing, QAC Functionalized Thermoplastic Polyurethane for Catheter Applications," filed Oct. 6, 2017, and incorporated herein by reference in its entirety.

NAMES OF THE PARTIES TO A JOINT RESEARCH AGREEMENT

The present application stems from work done pursuant to a Joint Research Agreement between The University of Akron of Akron Ohio and Cook Medical Technologies, LLC of Bloomington, Ind.

FIELD OF THE INVENTION

One or more embodiments of the present invention relates to functionalized thermoplastic polyurethanes. In certain embodiments, the present invention relates to antimicrobial thermoplastic polyurethanes for catheter and other medical applications.

BACKGROUND OF THE INVENTION

Catheterization is commonplace in emergency and routine medical care; concomitantly, urinary catheters and intravascular catheters are the two most common causes of hospital-acquired septicemia. Estimates indicate that 5 million central venous catheters (CVCs) and >30 million urinary catheters are inserted annually in the U.S. with an incidence of infection between 3-8% and 10-30%, respectively. Patients with a diminished health status are particularly susceptible to catheter-associated infections (CAIs), with reports from intensive care units (ICUs) showing that as many as 87% of bloodstream infections (BSIs) are associated CVCs and 95% of urinary tract infections (UTIs) are catheter-associated. This equates to nearly 80,000 CVC-associated BSIs in ICUs each year, which suffer a 12-25% mortality rate. While the attributable mortality rate from CA-UTIs is <5%, the usage of urinary catheters are 6× higher than CVCs. Overall, the magnitude of catheter-associated infections from a financial perspective is estimated to be $296 million to $2.3 billion, annually.

Microorganisms can attach to catheters as a growth surface and form biofilms. These biofilms are often resistant to antibiotic treatment due to reduced antimicrobial uptake through the chemical and architectural structure of the exopolysaccharide film, and changes in the metabolic state of the bacteria present. Such catheter colonization is particularly problematic for patients with CVCs, as biofilm detachment will deliver a bolus of microorganisms intravenously to the patient, decreasing the ability of the immune system to clear the infection. Furthermore, bacteria infecting peri-implant tissues pose a high-risk for developing antibiotic resistance via point-mutation when antibiotic monotherapy is used. To reduce the risk of catheter infections, some physicians resort to antibiotic prophylaxis; however, concerns over cost, side effects, and the emergence of antibiotic-resistant pathogens exist. An unintended consequence of the excessive use of antibiotics has been the emergence of various antibiotic-resistant pathogens which are becoming a globally-known epidemic. As such, catheter-related infections become a multi-fold problem not only because of the infections they cause, but also the method by which they are treated. It has been well established that antibiotics suppress the immune system, making humans less adept at naturally overcoming bacterial infections. In addition, the looming fear associated with bacterial-resistance and a lack of new antibiotics to fight them has highlighted our need to prevent and care for infections using alternative methods. One such method includes the development of sterile surface materials. Together, these issues emphasize the need for alternative methods to prevent bacterial colonization and biofilm formation on catheters.

Understanding the route by which catheter-related infections occur and the variety of bacteria involved is crucial for designing antimicrobial devices. Since catheters are hollow tubes consisting of an internal lumen and exterior surface, contamination may occur through extraluminal or intraluminal routes. Extraluminal infections are more common, and arise either when the catheter is inserted (by contact with the patient's own skin flora or the medical professional's hands), or later as a consequence of conditioning film formation. Intraluminal infections are primarily a result of bacterial migration from a source of contamination within the drainage bag system (i.e. exudate/urine), or the injection port in the case of CVCs. Thus, the catheter should possess antimicrobial or antifouling properties on both the internal lumen and the outer surface, which potentially poses engineering challenges. In addition, catheter infections may be caused by Gram-negative and Gram-positive bacteria, as well as fungi (such as yeast and *Candida albicans*). Although the majority of CA-UTIs are extraluminal infections caused by Gram-positive bacteria, it should be noted that intraluminal infections are primarily caused by Gram-negative bacteria; in particular, uropathogenic *E. coli*, which is a subset strain known to cause the majority of UTIs. In general, Gram-negative bacteria are notoriously more difficult to kill because they possess a double layered cytoplasmic membrane, and have demonstrated the ability to become multidrug resistant. For CVCs, it is generally believed that Gram-positive bacteria, specifically *S. epidermidis* and *S. aureus*, gain access via the skin insertion site and lead to biofilm formation. However, these bacteria may also bind post-insertion provided the conditioning film is present, especially when there is significant thrombosis. While *S. aureus* and other Gram-positive bacteria cause the majority of CRBSIs, Gram-negative bacteria and *Candida* infections also occur. For long term catheterization, mature biofilms may contain a variety of these microbes and produce complicated infections from a treatment standpoint.

Knowing the types of bacteria and the routes by which they cause catheter-related infections (CRI) evokes the question of how the bacteria actually interact with the material. Whether the catheter is intended for urinary or intravascular use, biofilm accumulation is central to the pathogenesis of catheter-associated infections. A biofilm may be composed of one or potentially many different strains of bacteria that have adhered to a surface, and secreted their own matrix to form the architectural structure of the film. The associated bacteria can divide and form colonies, or migrate to form new microenvironments for proliferation. In a mature biofilm, the bacteria can detach and become planktonic in the patients urine or bloodstream, potentially leading to systemic infection.

If the catheter or medical device is inhospitable for microbial attachment, then it may prevent biofilm formation. However, in many cases, a "conditioning film" forms on the surface of the medical device/catheter, which can mask the catheter properties and eventually lead to microbial attachment and biofilm formation. The conditioning film in vascular catheters is typically an accumulation of albumin, fibrin and fibronectin, whereas urinary catheters usually become layered with proteins and electrolytes from the patient's urine. The accumulation of this conditioning film promotes bacterial adhesion and proliferation, leading to colonization of the device. This is especially true in the case of catheter-induced thrombosis, which causes a thrombin sheath rich in fibrin and fibronectin to form around the catheter. Naturally, the three most common microbes responsible for catheter infections (*S. aureus, S. epidermidis,* and *Candida albicans*) can adhere to fibrin and produce coagulase enzymes that further promote thrombogenesis.

While a conditioning film may promote bacterial adhesion, it is clearly not the only mechanism by which bacteria can associate with surfaces. The commonality between existing theories includes a multistep process which usually begins with Brownian motion or mass transport to bring the bacteria within long-range Lifshitz-van der Waals interaction distances (hundreds of nanometers). As the bacteria approach the surface, the forces at work become a complex mixture of Lifshitz-van der Waals, electrostatic, and hydrophobic interactions which are difficult to decouple. Furthermore, the highly dynamic structures located on cell surfaces, such as fimbriae and flagella, are crucial to cell attachment and have the ability to undergo conformational changes depending on their environment. The final step for bacterial attachment is believed to be either covalent or hydrogen bonding, probably the result of site-specific adhesion receptors. Thus, bacteria employ a complex set of interactions in order to attach to surfaces, which ultimately leads to biofilm formation and almost inevitably a CRI. Approaches using sterile surface materials to reduce catheter infections have focused on preventing this bacterial adhesion process, or utilizing biocides that eliminate bacteria altogether.

The majority of current anti-infective materials, however, focus on releasing biocides and have demonstrated marginal success; their effectiveness is limited by the inevitable loss of activity once the anti-infective compound has been released. In addition, sub-lethal doses of antibiotics have been shown to accelerate the development of resistance in bacteria, making biofilm-associated infections even more difficult to eradicate. To address this, some researchers have turned attention to "contact-active" materials, which generally employ active monomers, functional side chains, or surface grafted moieties that are lethal to various bacteria upon contact. The majority of contact-active materials employ some form of quaternary ammonium compounds (QACs) as the biocidal component, which have demonstrated ability to kill bacteria while remaining non-cytotoxic to human cells. In contrast to biocide release methods, contact-actives are ideally non-leaching and should retain their activity for extended durations, limiting pathways for developing bacterial-resistance.

Thus, what is needed in the art is a commercially relevant functionalized TPU containing surface-grafted QACs for contact-killing activity towards a variety of microbes where the QACs are on the surface of TPU to provide a sterile surface material that prevents bacteria commonly involved in CRIs from proliferating. In addition to contact-killing activity, the functionalized TPU should possess backbone characteristics that also prohibit fouling of the device with proteins and microbes which would otherwise cause biofilm formation and infection.

SUMMARY OF THE INVENTION

In one or more embodiments, the present invention provides a functionalized TPU containing bulk incorporated or surface-grafted QACs for contact-killing of a variety of microbes, where the QACs are on the surface of TPU to provide a sterile surface material that prevents bacteria commonly involved in device-associated infections (DAIs) from proliferating. The functionalized TPUs of the present invention can be formed into a wide variety of 3-dimensional shapes, such as catheters, medical tubing, laryngeal or tracheal stents, sutures, prosthetics, wound dressings, and/or a coating for medical devices. The functionalized TPUs contain the residue of either a QAC containing diol monomer or an alkene functional diol monomer, which allows the TPU to be functionalized with a QAC containing disulfide or free thiol compound, to form a quaternary ammonium functionalized thermoplastic polyurethane compound having antimicrobial properties for use in medical devices. In one or more embodiments, the functionalized TPUs of the present invention comprise a polyurethane polymer backbone having one or more side chains extending from said polyurethane polymer backbone wherein said side chains comprise a quaternary ammonium ion or an alkene functional group that allows for post-processing functionalization with a quaternary ammonium ion. In one of more embodiments, the functionalized TPUs of the present invention comprise the residue of one or more diisocyanates, one or more short chain diol chain extenders (chain extenders), one or more QAC or alkene functionalized diols (functionalized diols) and longer chain diols (soft segment diols). In some embodiments, the functionalized TPUs of the present invention are formed as the reaction product of one or more diisocyanates, one or more short chain diol chain extenders, one or more QAC functionalized diols and one or more longer chain (soft segment) diols, in which case the functionalized TPUs will have QAC containing side chains throughout the bulk of the polymer.

In some other embodiments, the functionalized TPUs of the present invention are formed as the reaction product of one or more diisocyanates, one or more short chain diol chain extenders, one or more alkene functionalized diols and one or more longer chain (soft segment) diols, in which case the functionalized TPUs will have alkene functionalized side chains throughout the bulk of the polymer. These embodiments, the polymer may then be processed into a desired shape or configuration and then reacted with a QAC functionalized disulfide or free thiol compound to add the QAC to the allyl functionalized side chains on the surfaces of the processed polymer having alkene (allyl) groups available for bonding.

In a first aspect, the present invention is directed to a quaternary ammonium functionalized thermoplastic polyurethane compound having antimicrobial properties for use in medical devices comprising: a polyurethane polymer backbone; and a plurality of side chains, the side chains extending from the polyurethane polymer backbone and comprising a quaternary ammonium group. In one or more embodiment, the polyurethane polymer backbone comprises the residues of one or more diisocyanates, one or more soft segment diols, one or more functionalized diols, and one or more diol chain extenders, and the plurality of side chains comprise a quaternary ammonium group connected to the polyurethane polymer backbone through the one or more functionalized diols.

In one or more embodiments, the quaternary ammonium functionalized thermoplastic polyurethane compound of the present invention includes any one or more of the above referenced embodiments of the first aspect of the present invention wherein the one or more diisocyanates are selected from the group consisting of 4,4'-methylenebis(phenyl isocyanate) (MDI), 4,4'-methylenebis(cyclohexyl isocyanate) (HMDI), isophorone diisocyanate, toluene diisocyanate (TDI), 1,3-bis(isocyanatomethyl)cyclohexane, 1,4-diisocyanatobutane, hexamethylene diisocyanate, 1,8-diisocyanatooctone, 1,12-diisocyanatododecane, and combinations thereof.

In one or more embodiments, the quaternary ammonium functionalized thermoplastic polyurethane compound of the present invention includes any one or more of the above referenced embodiments of the first aspect of the present invention wherein the one or more long chain soft segment diols comprise two hydroxyl groups separated by from about 50 to about 500 carbon, oxygen, or nitrogen atoms. In one or more embodiments, the quaternary ammonium functionalized thermoplastic polyurethane compound of the present invention includes any one or more of the above referenced embodiments of the first aspect of the present invention wherein the one or more long chain diol soft segments are selected from the group consisting of polyester diols, polycarbonate diols, polyether diols polysiloxanes, polyethylene, polypropylene, polytetrafluoroethylene, poly(propylene oxide-co-ethylene oxide) and combinations thereof.

In one or more embodiments, the quaternary ammonium functionalized thermoplastic polyurethane compound of the present invention includes any one or more of the above referenced embodiments of the first aspect of the present invention wherein the residues of one or more functionalized diols comprises from 0.5 to 50 mole percent of the polyurethane polymer backbone. In one or more embodiments, the quaternary ammonium functionalized thermoplastic polyurethane compound of the present invention includes any one or more of the above referenced embodiments of the first aspect of the present invention wherein the one or more functionalized diols are allyl functionalized diols selected from the group consisting of 3-allyloxy-1,2-propanediol, 2-allyloxy-2-ethyl-1,3-propanediol, 1-(allyloxy)-1,2-propanediol, pentaerythritol allyl ether, trimethylolpropane diallyl ether, trimethylolpropane allyl ether, 1,5-hexadiene-3,4-diol, 2-methylene-1,3-propanediol, 7-Octene-1,2-diol, 5-norbornene-2-endo,3-endo-dimethanol, 5-norbornene-2-exo,3-exo-dimethanol, 5-Norbornene-2,2-dimethanol, and combinations thereof. In one or more embodiments, the quaternary ammonium functionalized thermoplastic polyurethane compound of the present invention includes any one or more of the above referenced embodiments of the first aspect of the present invention wherein the one or more functionalized diol comprises 3-allyloxy-1,2-propanediol.

In one or more embodiments, the quaternary ammonium functionalized thermoplastic polyurethane compound of the present invention includes any one or more of the above referenced embodiments of the first aspect of the present invention wherein the one or more diol chain extenders comprise two hydroxyl groups separated by from about 2 to about 10 carbon, oxygen, or nitrogen atoms.

In one or more embodiments, the quaternary ammonium functionalized thermoplastic polyurethane compound of the present invention includes any one or more of the above referenced embodiments of the first aspect of the present invention wherein the side chains further comprise a spacer connecting the quaternary ammonium group to the polyurethane polymer backbone. In one or more embodiments, the quaternary ammonium functionalized thermoplastic polyurethane compound of the present invention includes any one or more of the above referenced embodiments of the first aspect of the present invention wherein spacer comprises from about 2 to about 18 carbon, oxygen, nitrogen or sulfur atoms. In one or more embodiments, the quaternary ammonium functionalized thermoplastic polyurethane compound of the present invention includes any one or more of the above referenced embodiments of the first aspect of the present invention wherein the quaternary ammonium group comprises at least one alkyl chain having from about 1 to about 18 carbon atoms.

In one or more embodiments, the quaternary ammonium functionalized thermoplastic polyurethane compound of the present invention includes any one or more of the above referenced embodiments of the first aspect of the present invention comprising the reaction product of: an allyl functionalized polyurethane polymer; and a disulfide or thiol compound containing at least one quaternary ammonium group.

In one or more embodiments, the quaternary ammonium functionalized thermoplastic polyurethane compound of the present invention includes any one or more of the above referenced embodiments of the first aspect of the present invention wherein the allyl functionalized polyurethane polymer has a formula selected from:

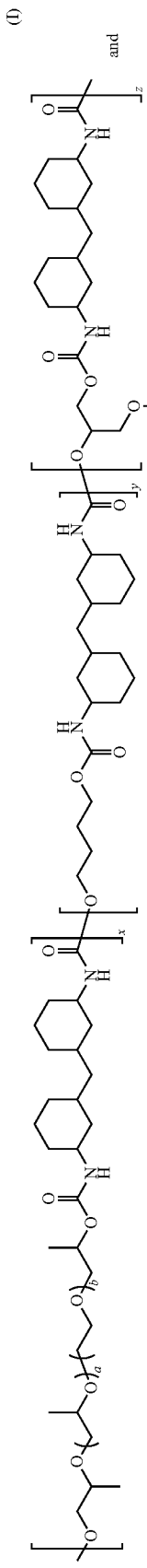
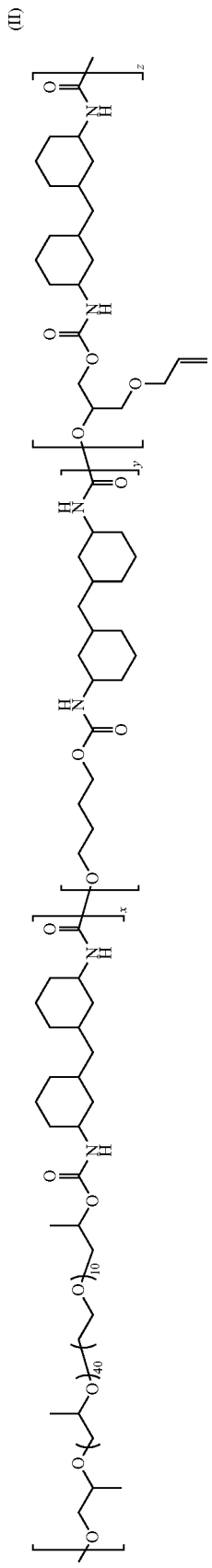

where a is an integer from 2 to 50; b is an integer from 2 to 50; x is a mole fraction from 0.01 to 0.8; y is a mole fraction from 0.01 to 0.8; and z is a mole fraction ranging from 0.01 to 0.8; and the sum of x, y, and z is equal to 1.

In one or more embodiments, the quaternary ammonium functionalized thermoplastic polyurethane compound of the present invention includes any one or more of the above referenced embodiments of the first aspect of the present invention wherein the disulfide or thiol compound is a disulfide compound selected from the group consisting of 3,3'-dithiodipropionic acid, 4,4'-dithiodibutyric acid, dithiodiglycolic acid, 2-hydroxyethyl disulfide, cystamine dihydrochloride, and combinations thereof. In one or more embodiments, the quaternary ammonium functionalized thermoplastic polyurethane compound of the present invention includes any one or more of the above referenced embodiments of the first aspect of the present invention wherein the disulfide or thiol compound is a disulfide or thiol compound having a formula selected from:

(III)

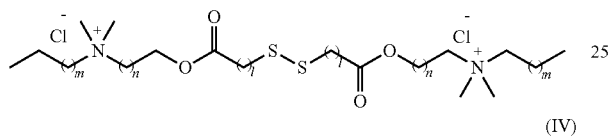

(IV)

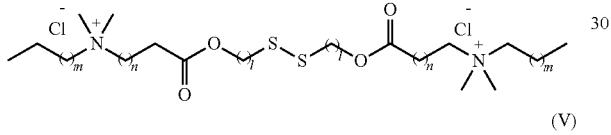

(V)

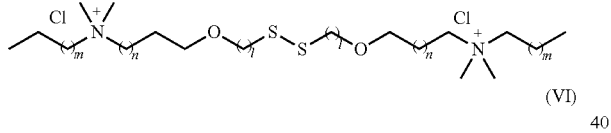

(VI)

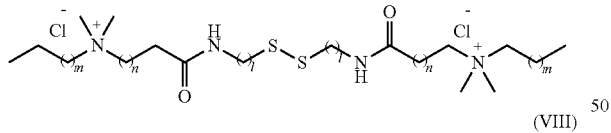

(VII)

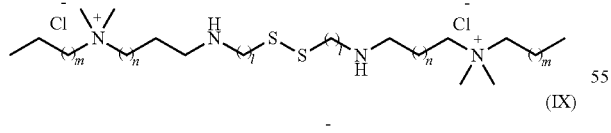

(VIII)

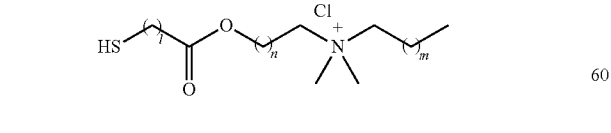

(IX)

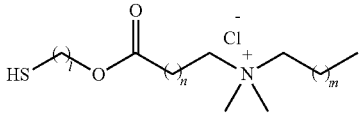

(X)

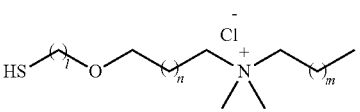

(XI)

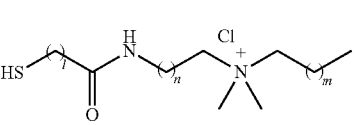

(XII)

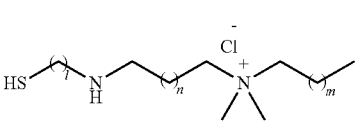

(XIII)

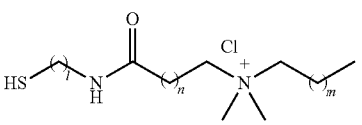

(XIV)

wherein m is an integer from 1 to 18, n is an integer from 1 to 19, and A is an integer from 1 to 3.

In one or more embodiments, the quaternary ammonium functionalized thermoplastic polyurethane compound of the present invention includes any one or more of the above referenced embodiments of the first aspect of the present invention having a number average molecular weight ($M_n$) of from about 5,000 g/mol to about 5,000,000 g/mol as measured by Size Exclusion Chromatography (SEC). In one or more embodiments, the quaternary ammonium functionalized thermoplastic polyurethane compound of the present invention includes any one or more of the above referenced embodiments of the first aspect of the present invention having a mass distribution ($Đ_m$) of from about 1.5 to about 5 as measured by Size Exclusion Chromatography (SEC). In one or more embodiments, the quaternary ammonium functionalized thermoplastic polyurethane compound of the present invention includes any one or more of the above referenced embodiments of the first aspect of the present invention having a glass transition temperature ($T_g$) of from about −40° C. to about −100° C. as measured by Differential Scanning calorimetry (DSC). In one or more embodiments, the quaternary ammonium functionalized thermoplastic polyurethane compound of the present invention includes any one or more of the above referenced embodiments of the first aspect of the present invention having a shore durometer hardness of from about 50 to about 100 as measured by a shore A durometer.

In one or more embodiments, the quaternary ammonium functionalized thermoplastic polyurethane compound of the present invention includes any one or more of the above referenced embodiments of the first aspect of the present invention having a formula selected from:

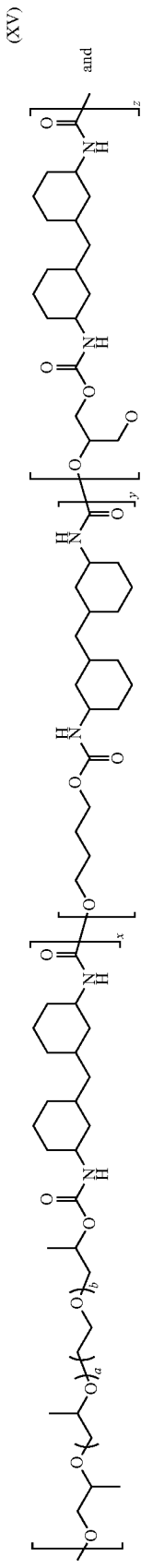
(XV)
and
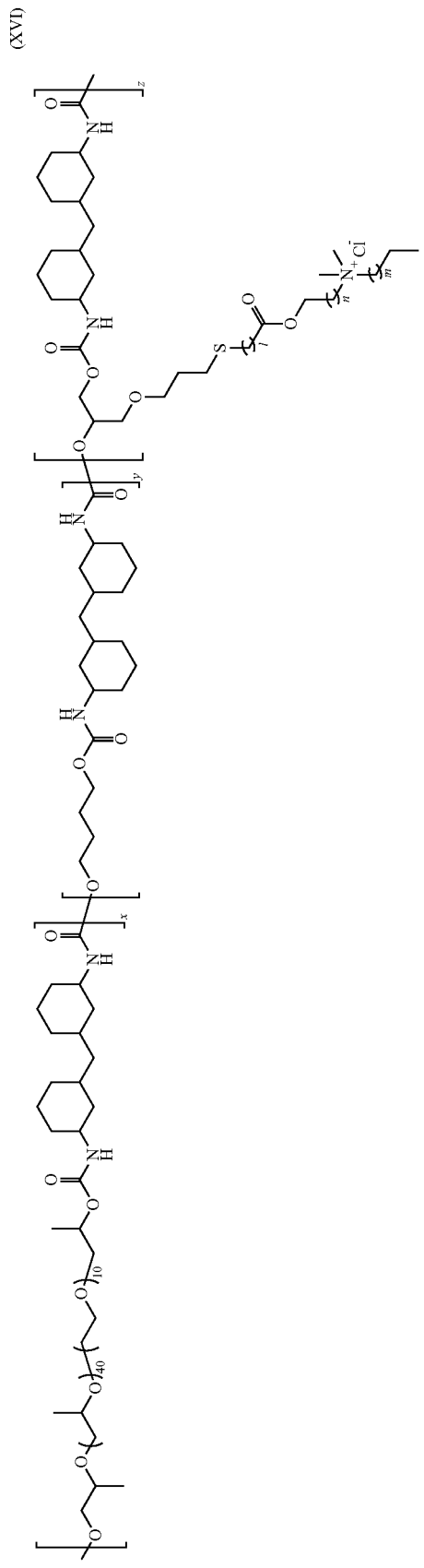
(XVI)

where a is an integer from 2 to 50; b is an integer from 2 to 50; x is a mole fraction from 0.01 to 0.8; y is a mole fraction from 0.01 to 0.8; and z is a mole fraction ranging from 0.01 to 0.8; the sum of x, y, and z is equal to 1; m is an integer from 1 to 18, n is an integer from 1 to 19, and l is an integer from 1 to 4.

In a second aspect, the present invention is directed to a method for making the quaternary ammonium functionalized thermoplastic polyurethane compound described above comprising: preparing an allyl functionalized polyurethane polymer; preparing a bi-quaternary ammonium functionalized disulfide compound or a quaternary ammonium functionalized thiol compound; combining the allyl functionalized polyurethane polymer, the bi-quaternary ammonium functionalized disulfide compound or quaternary ammonium functionalized thiol compound, and an initiating catalyst under an inert atmosphere; activating the initiating catalyst to produce the quaternary ammonium functionalized thermoplastic polyurethane. In one or more embodiments, the method of making quaternary ammonium functionalized thermoplastic polyurethane compound of the present invention includes any one or more of the above referenced embodiments of the second aspect of the present invention wherein the initiating catalyst is a photoinitiator and the step of activating comprises irradiating the combination with ultraviolet light. In one or more embodiments, the method of making quaternary ammonium functionalized thermoplastic polyurethane compound of the present invention includes any one or more of the above referenced embodiments of the second aspect of the present invention wherein the initiating catalyst is a thermal initiator and the step of activating comprises heating the combination.

In one or more embodiments, the method of making quaternary ammonium functionalized thermoplastic polyurethane compound of the present invention includes any one or more of the above referenced embodiments of the second aspect of the present invention wherein the allyl functionalized polyurethane polymer has a formula selected from:

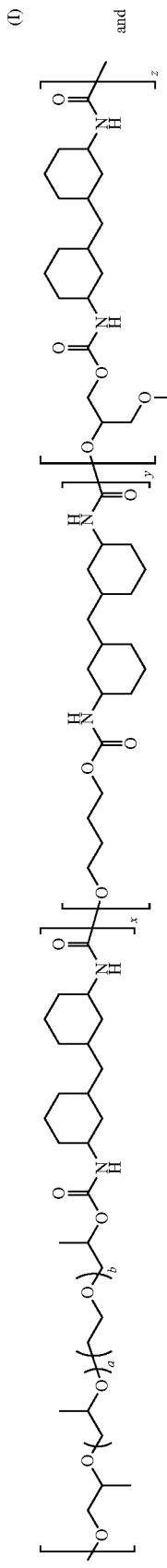
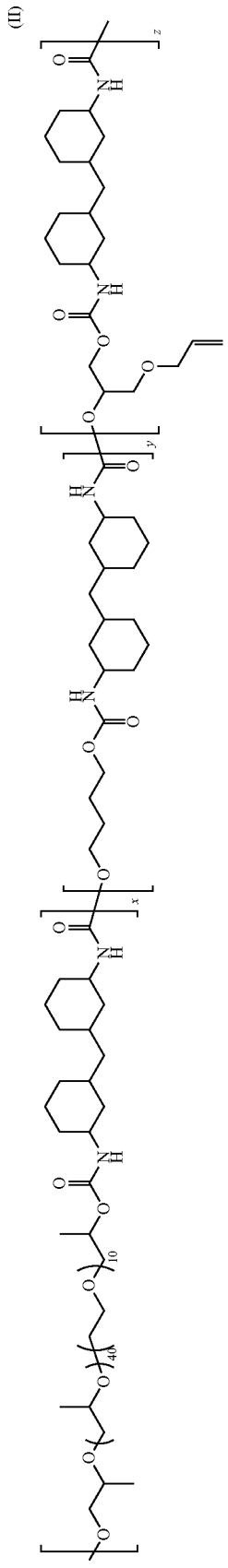

where a is an integer from 2 to 50; b is an integer from 2 to 50; x is a mole fraction from 0.01 to 0.8; y is a mole fraction from 0.01 to 0.8; and z is a mole fraction ranging from 0.01 to 0.8; and the sum of x, y, and z is equal to 1.

In one or more embodiments, the method of making quaternary ammonium functionalized thermoplastic polyurethane compound of the present invention includes any one or more of the above referenced embodiments of the second aspect of the present invention wherein the bi-quaternary ammonium functionalized disulfide compound comprises two quaternary ammonium functional groups each attached to a disulfide group by a spacer or the quaternary ammonium functionalized thiol compound comprises a quaternary ammonium functional group attached to a thiol group by a spacer. In one or more embodiments, the method of making quaternary ammonium functionalized thermoplastic polyurethane compound of the present invention includes any one or more of the above referenced embodiments of the second aspect of the present invention wherein the spacer comprises from about 2 to about 20 carbon or oxygen atoms.

In one or more embodiments, the method of making quaternary ammonium functionalized thermoplastic polyurethane compound of the present invention includes any one or more of the above referenced embodiments of the second aspect of the present invention wherein the bi-quaternary ammonium functionalized disulfide compound is synthesized from a compound selected from the group consisting of 3,3'-dithiodipropionic acid, 4,4'-dithiodibutyric acid, dithiodiglycolic acid, 2-hydroxyethyl disulfide, cystamine dihydrochloride, and combinations thereof. In one or more embodiments, the method of making quaternary ammonium functionalized thermoplastic polyurethane compound of the present invention includes any one or more of the above referenced embodiments of the second aspect of the present invention wherein the bi-quaternary ammonium functionalized disulfide compound or the quaternary ammonium functionalized thiol compound is a disulfide or thiol compound having a formula selected from:

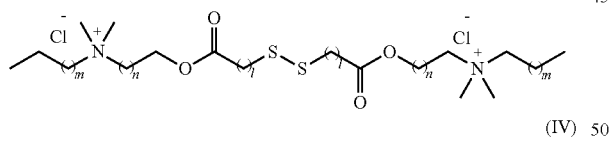

(III)

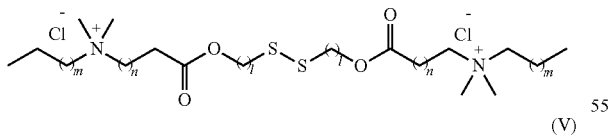

(IV)

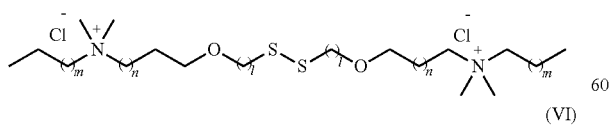

(V)

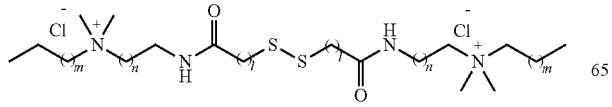

(VI)

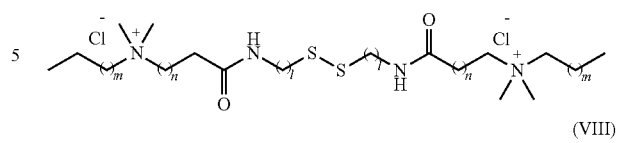

(VII)

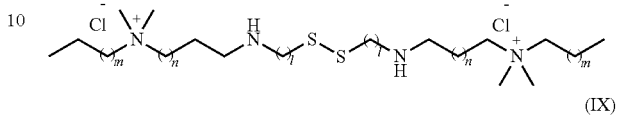

(VIII)

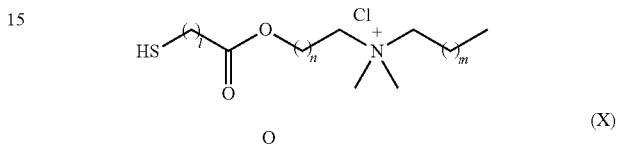

(IX)

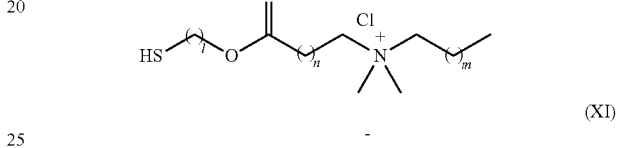

(X)

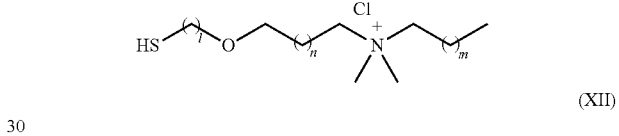

(XI)

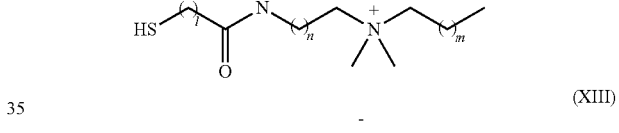

(XII)

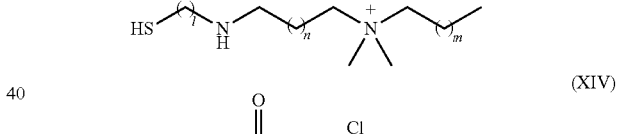

(XIII)

(XIV)

wherein l is an integer from 1 to 3, m is an integer from 1 to 18, and n is an integer from 1 to 19.

In one or more embodiments, the method of making quaternary ammonium functionalized thermoplastic polyurethane compound of the present invention includes any one or more of the above referenced embodiments of the second aspect of the present invention wherein the initiating catalyst is selected from the group consisting of 2-hydroxy-4'-(2-hydroxyethoxy)-2-methylpropiophenone (Irgacure-2959), lithium phenyl-2,4,6-trimethylbenzoylphosphinate, 2,2-dimethoxy-2-phenylacetophenone, sodium 4-[2-(4-morpholino)benzoyl-2-dimethylamino]butylbenzenesulfonate, 2-(carboxymethoxy) thioxanthone, or other acetophenone, benzophenone, benzoin, thioxanthone derived photoinitiators, UV light, and combinations thereof. In one or more embodiments, the method of making quaternary ammonium functionalized thermoplastic polyurethane compound of the present invention includes any one or more of the above referenced embodiments of the second aspect of the present invention wherein the initiating catalyst is selected from the group consisting of 4,4-azobis(4-cyanovalericacid), 2,2'- azobisisobutyronitrile, benzoyl peroxide, potassium persulfate, azo and peroxide derived thermal initiators, heat, and combinations thereof.

In one or more embodiments, the method of making quaternary ammonium functionalized thermoplastic polyurethane compound of the present invention includes any one or more of the above referenced embodiments of the second aspect of the present invention wherein the step of preparing an allyl functionalized polyurethane polymer further comprises forming the allyl functionalized polyurethane polymer into a three dimensional shape, film, or coating prior to the step of combining. In one or more embodiments, the method of making quaternary ammonium functionalized thermoplastic polyurethane compound of the present invention includes any one or more of the above referenced embodiments of the second aspect of the present invention wherein the three dimensional shape comprises a catheter, medical tubing, or a coating for medical devices.

In one or more embodiments, the method of making quaternary ammonium functionalized thermoplastic polyurethane compound of the present invention includes any one or more of the above referenced embodiments of the second aspect of the present invention wherein the bi-quaternary ammonium functionalized disulfide compound is prepared by the method comprising: reacting a chlorinated alcohol with a tri-substituted amine to form a chlorinated quaternary ammonium alcohol intermediate; combining 3,3'-dithiodipropionic acid, 4,4'-dithiodibutyric acid, or dithiodiglycolic acid with an excess of thionyl chloride or oxalyl chloride in a suitable container under an inert atmosphere and heating the combination to reflux for from about 4 to about 24 h to produce the corresponding acid chloride; dissolving the chlorinated quaternary ammonium alcohol intermediate in a suitable solvent; cooling the solution to a temperature of from about 25° C. to about 0° C. and adding the acid chloride disulfide under an inert atmosphere; heating the combination to reflux for from about 12 to about 24 h to produce the bi-quaternary ammonium functionalized disulfide compound. In one or more embodiments, the method of making quaternary ammonium functionalized thermoplastic polyurethane compound of the present invention includes any one or more of the above referenced embodiments of the second aspect of the present invention wherein the quaternary ammonium functionalized thiol compound is prepared by the method comprising reacting the bi-quaternary ammonium disulfide compound with a solution of tris(2-carboxyethyl) phosphine hydrochloride at a pH from about 4 to about 7.

In a third aspect, the present invention is directed to a medical device for use in the body of a patient comprising the quaternary ammonium functionalized thermoplastic polyurethane compound described above.

BRIEF DESCRIPTION OF THE DRAWINGS

For a more complete understanding of the features and advantages of the present invention, reference is now made to the detailed description of the invention along with the accompanying figures in which:

(FIG. 5A) first heating scan; (FIG. 5B) cooling following the first heating scan. Exothermic behavior is up in these scans, and the curves have been vertically displaced for clarity. The first heating scans reveal a main melting transition near 120° C. for these TPUs, which is somewhat suppressed in the 10% QAC-TPU, and much more notable in the 8% alloc-TPU. Additionally, the 5% QAC-TPU has a significantly broadened melt transition, which starts from 15° C. and continues up to the main melt transition. The cooling scans show that the TPUs have a $T_g$ between −60 and −65° C., but did not exhibit any significant crystallization on this time scale. Re-heating and re-cooling scans were uneventful with the exception of the glass transition.

In FIG. 7A, the control, 5% QAC-TPU, and 10% QAC-TPU were tested for antimicrobial activity against gram-negative (*E. coli*) and gram-positive (*S. aureus* and *S. epidermidis*) bacteria. A 2 log reduction in CFU of *E. coli* was observed for both QAC-TPUs, as well as a complete reduction of *S. epidermidis*. However, the 5% QAC-TPU exhibited ca. 2 log reduction in *S. aureus* while the 10% QAC-TPU showed a complete reduction. In FIG. 7B, a series of controls, QAC-TPUs, and covalently attached QACs were tested for activity against *E. coli*. Notably, the 8-Q14-S-S surface functionalized sample demonstrated a 6 log (complete) reduction.

Also, the introduction of hydrocarbons from 8-chloro-1-octanol produces additional upfield peaks, b'-c'.

Figure 12:
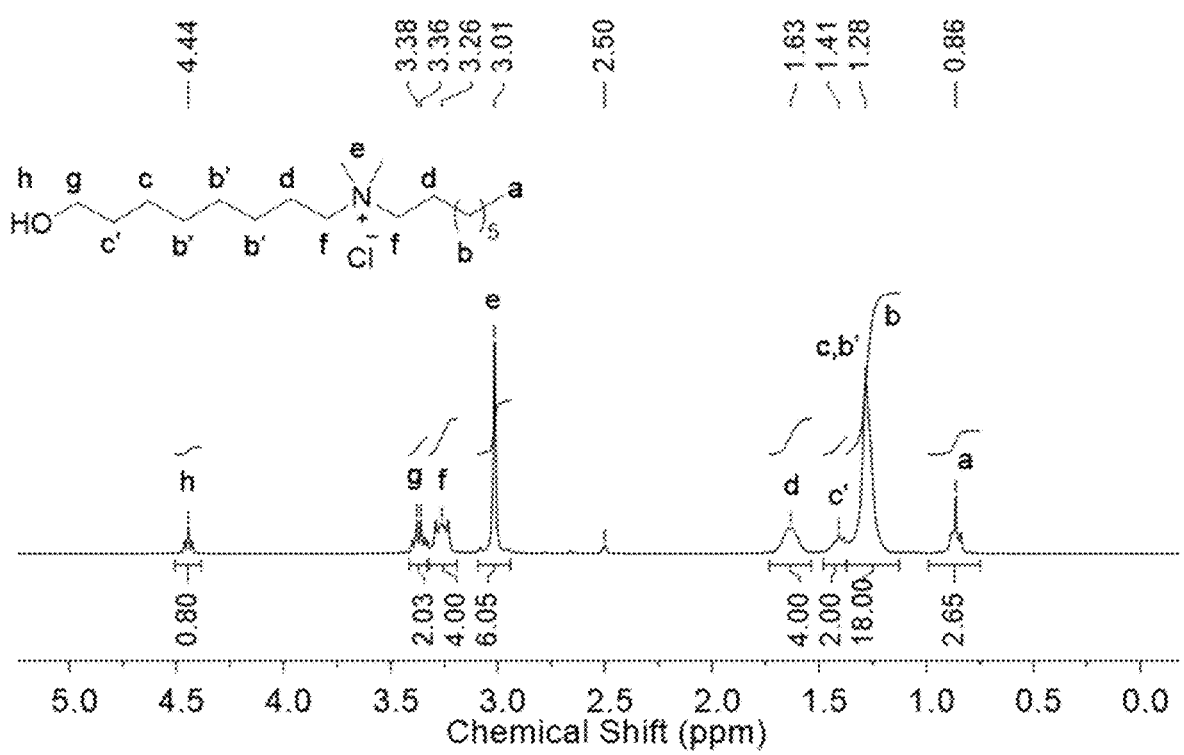

FIG. 12 is a ¹H-NMR spectra of 8-Q8-OH demonstrating a 1:1 molar ratio of peaks e and g, which indicates the formation of the desired quaternary ammonium compound. Also, the introduction of hydrocarbons from 8-chloro-1-octanol produces additional upfield peaks, b'-c'.

Figure 13:
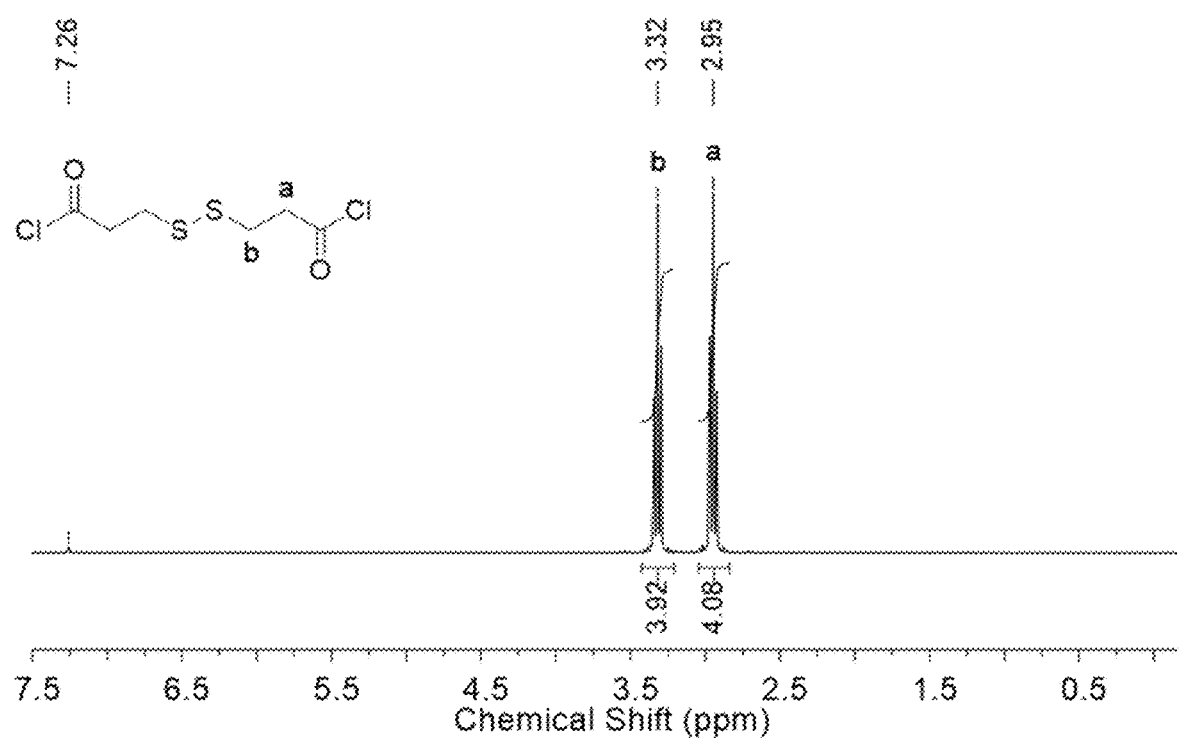

FIG. 13 is a ¹H-NMR spectra of 3,3'-dithiodipropanoyl chloride confirming the purity of the compound, and demonstrating quantitative conversion to the acid chloride.

Figure 14:
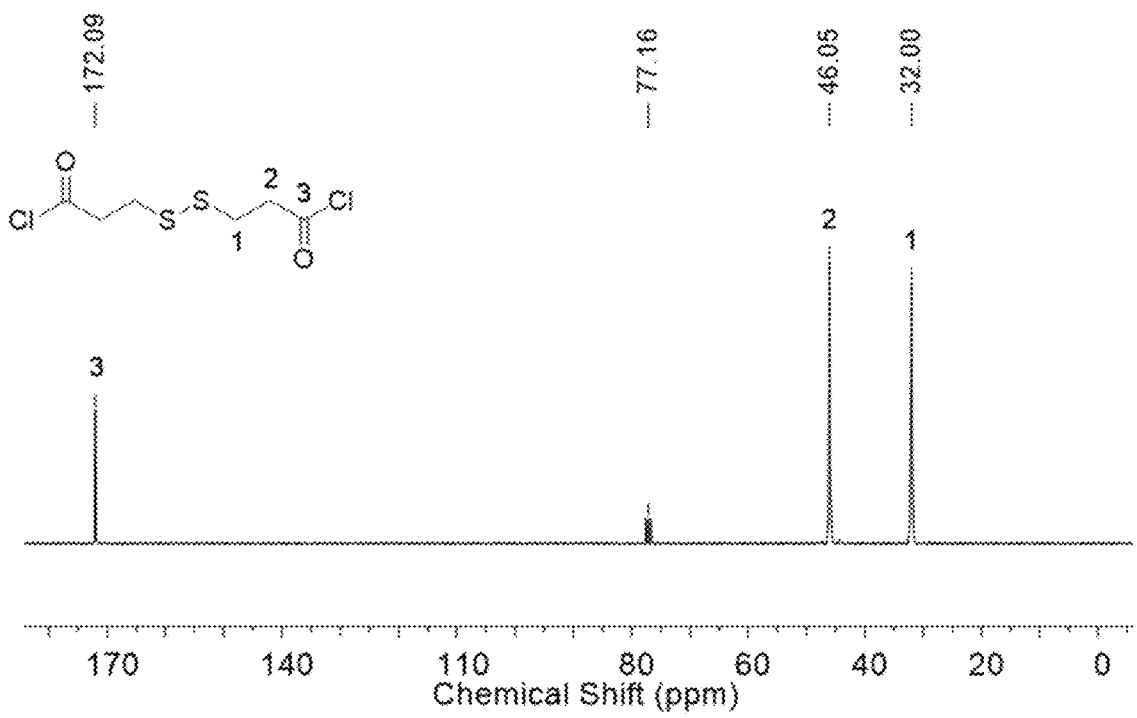

FIG. 14 is a ¹³C-NMR spectra of 3,3'-dithiodipropanoyl chloride confirming the purity of the compound, and demonstrating quantitative conversion to the acid chloride.

Figure 15:
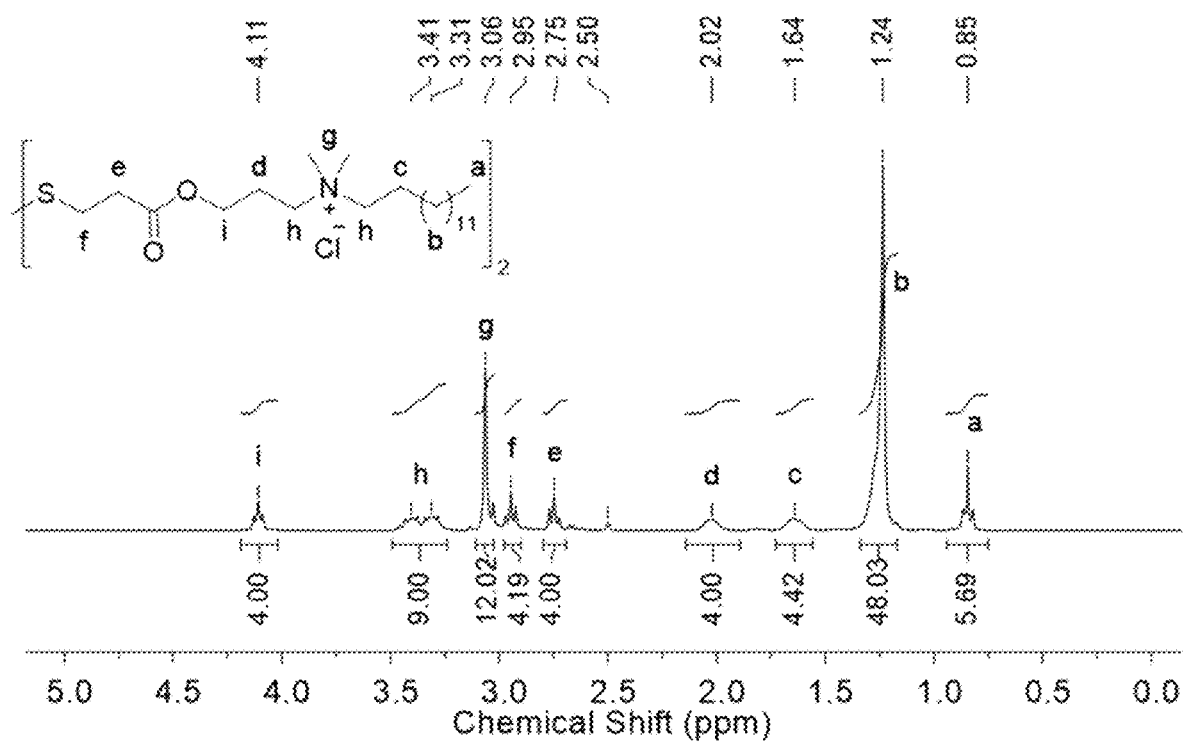

FIG. 15 is a ¹H-NMR spectra of 3-Q14-S-S showing the appearance of peaks e and f, which are approximately equimolar to peaks c, d, and g from the corresponding 3-Q14-OH. Peak c is inflated by excess starting material and peak h overlaps with HDO ($\delta$=3.30 ppm).

Figure 16:
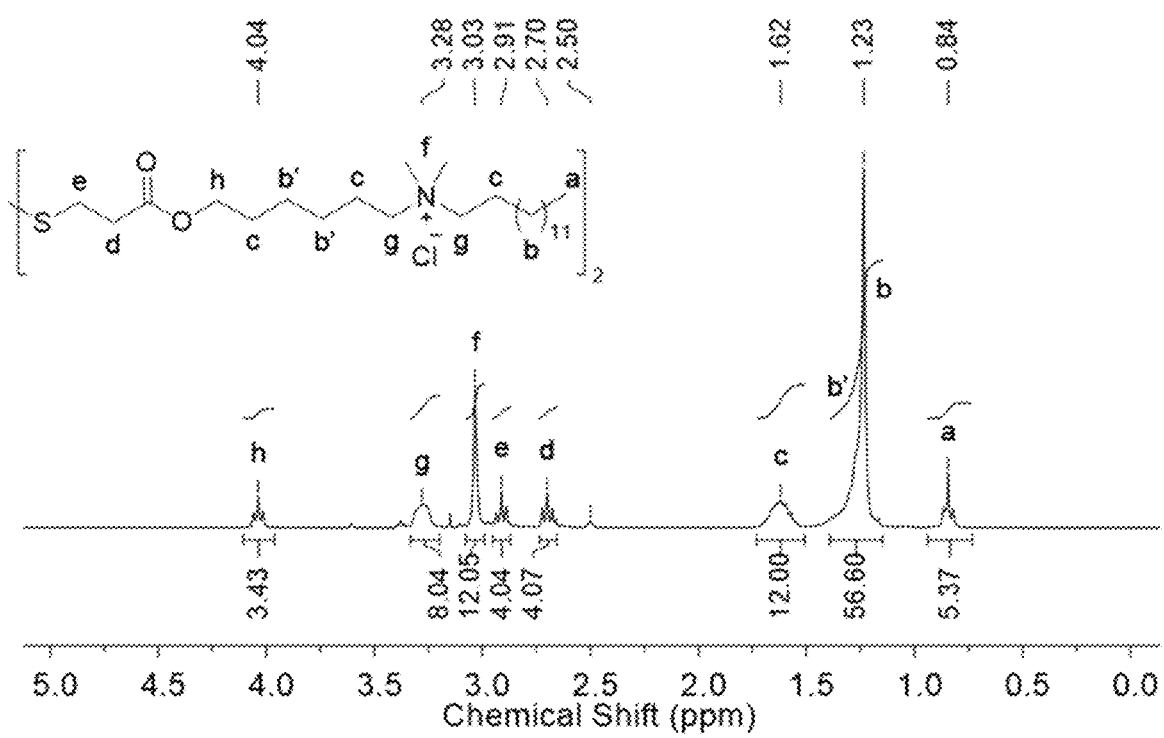

FIG. 16 is a ¹H-NMR spectra of 6-Q14-S-S showing the appearance of peaks d and e, which are approximately equimolar to peaks c, f, and g from the corresponding 6-Q14-OH, indicating complete conversion to the desired disulfide.

Figure 17:
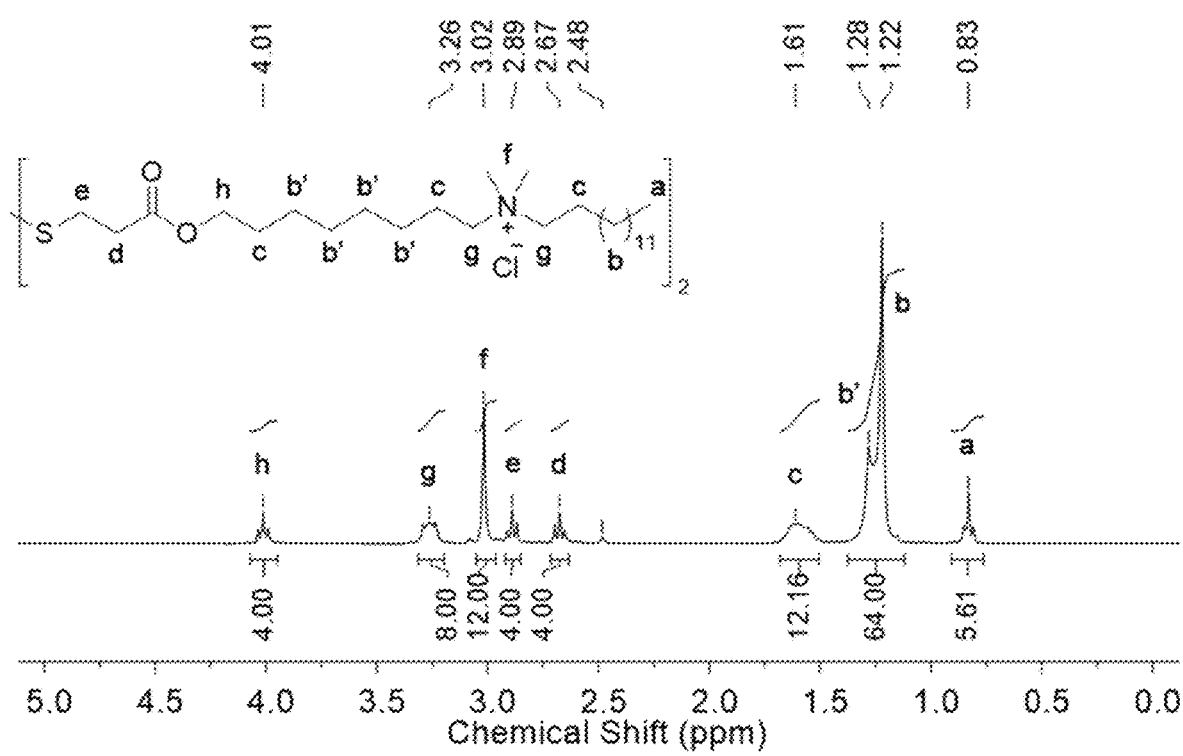

FIG. 17 is a ¹H-NMR spectra of 8-Q14-S-S showing the appearance of peaks d and e, which are approximately equimolar to peaks c, f, and g from the corresponding 8-Q14-OH, indicating complete conversion to the desired disulfide.

Figure 18:
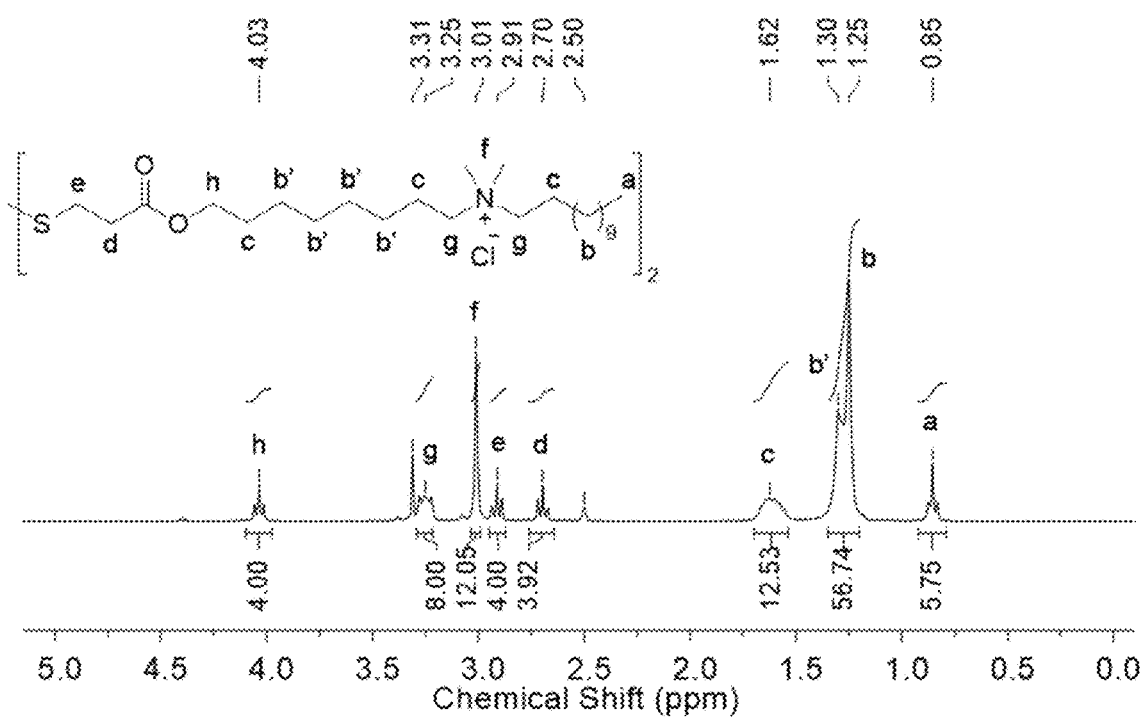

FIG. 18 is a ¹H-NMR spectra of 8-Q12-S-S showing the appearance of peaks d and e, which are approximately equimolar to peaks c, f, and g from the corresponding 8-Q12-OH, indicating complete conversion to the desired disulfide.

Figure 19:
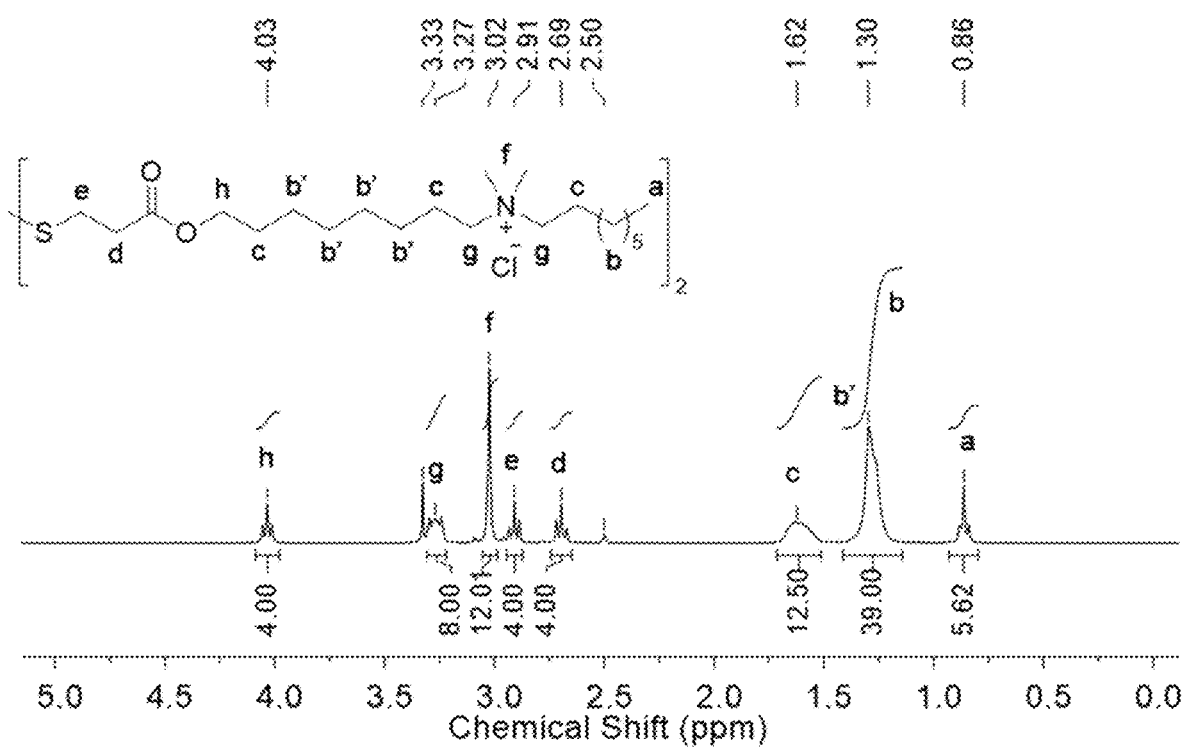

FIG. 19 is a ¹H-NMR spectra of 8-Q8-S-S showing the appearance of peaks d and e, which are approximately equimolar to peaks c, f, and g from the corresponding 8-Q8-OH, indicating complete conversion to the desired disulfide.

Figure 20:
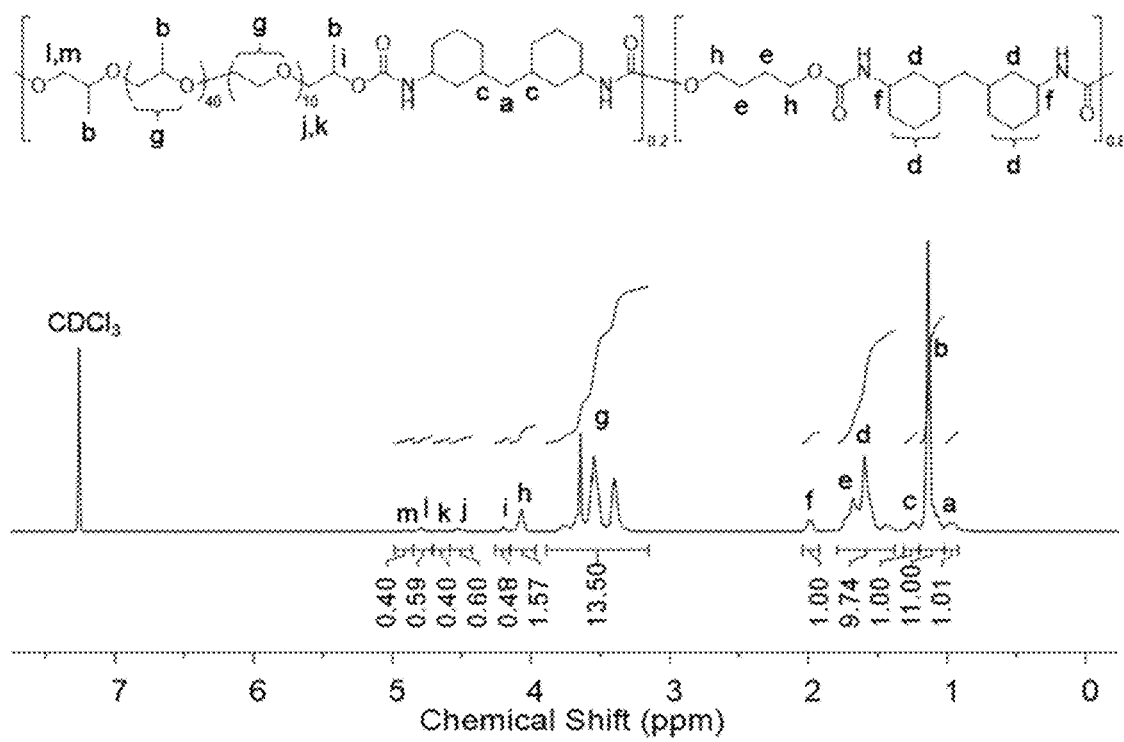

FIG. 20 is a ¹H-NMR spectrum of a 30 wt. % (50 mol %) HMDI control TPU. The proton integrations confirm the molar composition of HMDI:Acrol-E351:BDO is approximately 0.5:0.1:0.4.

Figure 21:
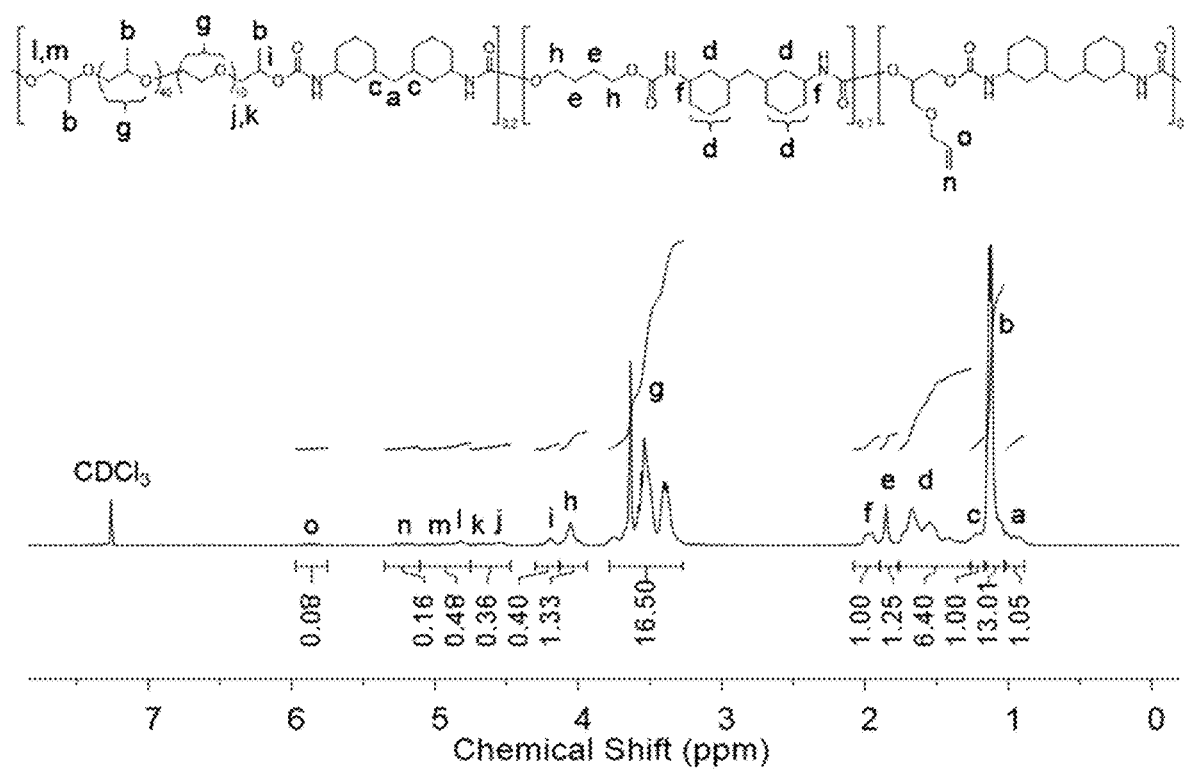

FIG. 21 is a ¹H-NMR spectrum of 8% alloc-TPU showing the appearance of peaks "n" and "o" relative to the control TPU, which correspond to the protons from the allyl functional group. The integrations indicate an incorporation of ca. 8 mol %, wherein the overall molar composition of HMDI:Acrol-E351:BDO: allyl is approximately 0.5:0.1:0.32:0.08.

FIG. 22 is a graph showing film thickness as a function of the concentration (weight percent) of 8% alloc-TPU. Ellipsometry was used to determine film thickness for spin coated films at various concentrations (1-5 wt. %) and at spin rates of 2500 (■) and 5000 (•) RPM.

FIG. 23 is a graph showing the fluorescence intensities of various FITC-PEG-SH solutions in DMSO were plotted as a function of concentration to generate the fluorophore standard curve. The y-intercept was fixed to zero and linear fitting generated the equation: y=153749 (±2720) x, with an $R^2$ value of 0.998.

FIGS. 24A-D are graphs showing the average (n=3) fluorescence data for 50 nm (FIG. 24A), 250 nm (FIG. 24B), 600 nm (FIG. 24C), and 50 μm (FIG. 24D) thin films functionalized with FITC-PEG-SH. Full spectrum scans were taken from $\lambda$=520-700 nm at an excitation wavelength of $\lambda_{ex}$=490 nm, and provided the $\lambda_{max}$ (545 nm) for each sample; the UV treated samples and their respective physical adsorption controls, as well as the calculated covalent attachment spectra are shown. Using the fluorophore standard curve and $\lambda_{max}$, the covalent attachment and physical adsorption of FITC-PEG-SH to the 8% alloc-TPU samples of varying thickness was quantified.

Figure 25:
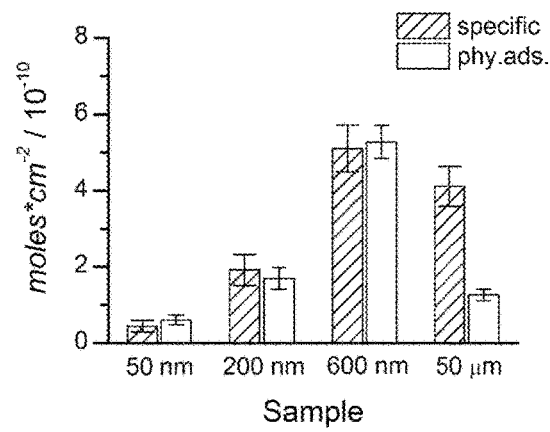

FIG. 25 is a graph providing a statistical summary of FITC-PEG-SH surface quantification experiments; the moles/cm² of fluorophore for each sample is plotted against the sample thickness for specifically attached and physically adsorbed dye. The bar graphs represent the average of three samples and the error bars account for standard deviations propagated with the slope error obtained from the FITC-PEG-SH calibration curve.

Figure 26A:
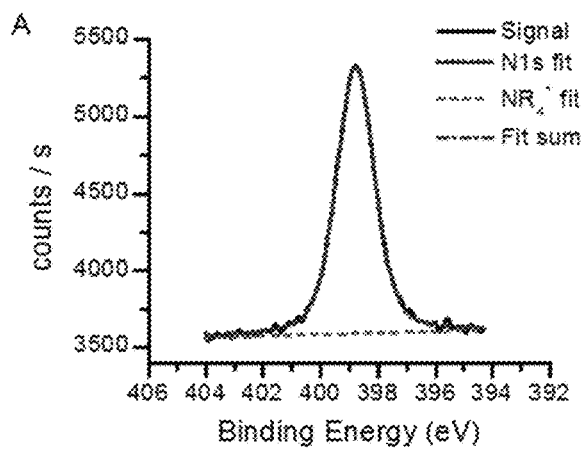
Figure 26B:
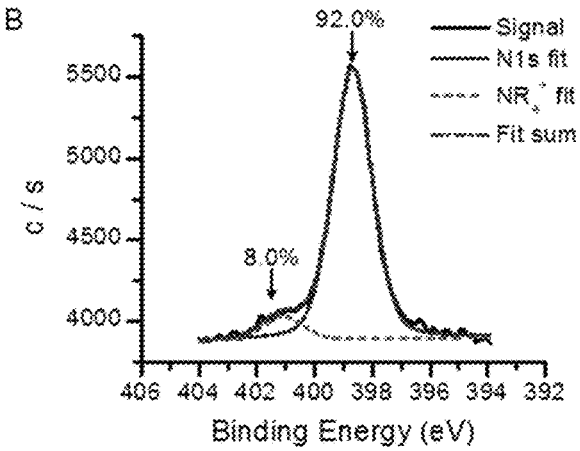
Figure 26C:
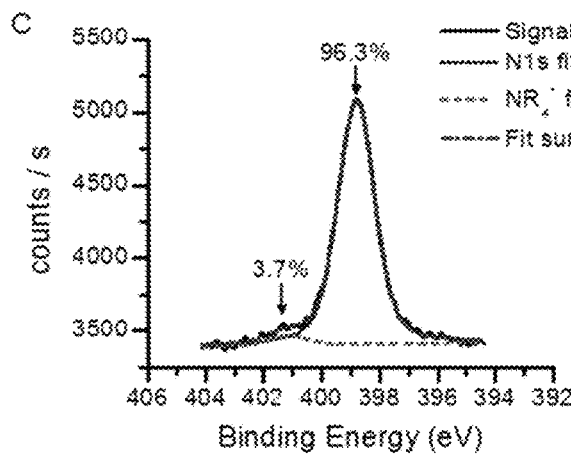
Figure 26D:
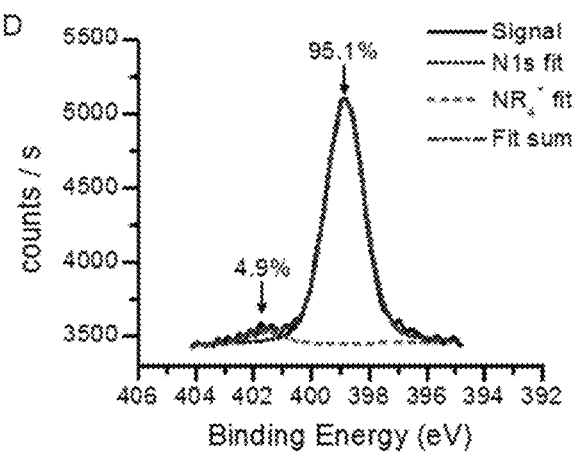

FIGS. 26A-D are XPS high resolution N1s spectra for an untreated 50 nm 8% alloc-TPU film (FIG. 26A), and 8-Q14-S-S functionalized films with a thickness of 50 nm (FIG. 26B), 250 nm (FIG. 26C) and 600 nm (FIG. 26D). The small peak between 401-402 eV shouldering the main nitrogen peak (398.5 eV) is indicative of a quaternary ammonium compound on the surface of the film. The spectra were decomposed into two components by using the curve fitting routine in MultiPak; raw data is interpolated with a cubic b-spline curve, and the curve fits for the nitrogen peak, quaternary ammonium peak, and the summation of curve fits are displayed.

Figure 27A:
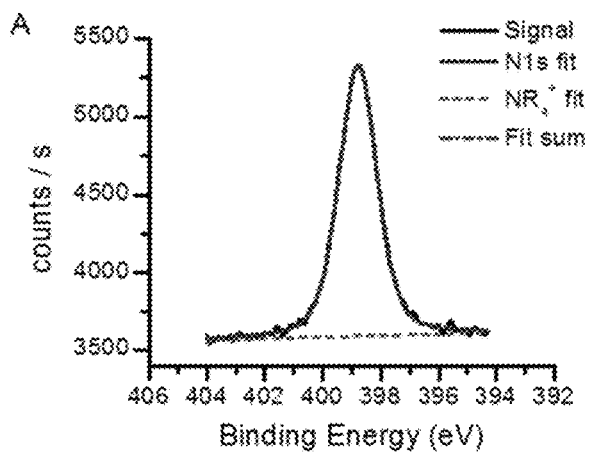
Figure 27B:
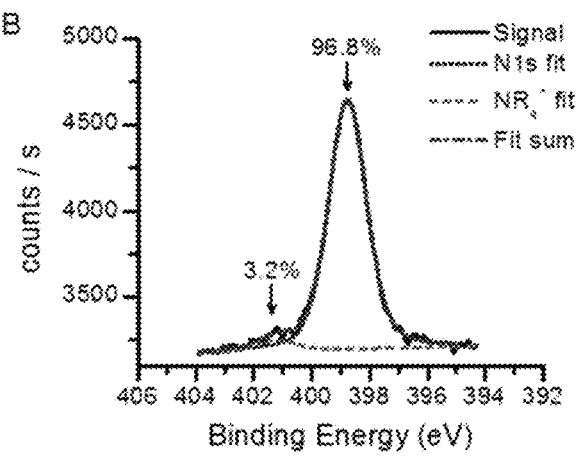
Figure 27C:
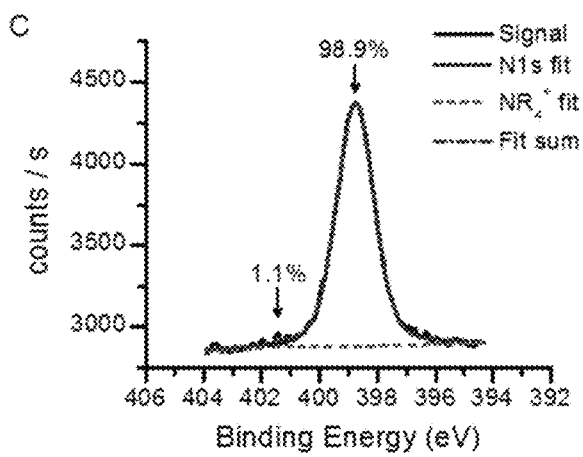
Figure 27D:
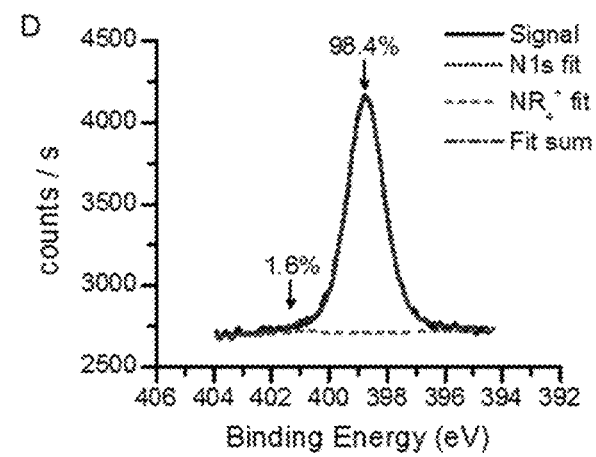

FIGS. 27A-D is an XPS high resolution N1s spectra for an untreated 50 nm 8% alloc-TPU film (FIG. 27A), and physical adsorption control films with a thickness of 50 nm (FIG. 27B), 250 nm (FIG. 27C), and 600 nm (FIG. 27D). The presence of a small peak between 401-402 eV shouldering the main nitrogen peak is indicative of physically adsorbed quaternary ammonium compound on the surface of the film. The spectra were decomposed into two components by using the curve fitting routine in MultiPak; raw data is interpolated with a cubic b-spline curve, and the curve fits for the nitrogen peak, quaternary ammonium peak, and the summation of curve fits are displayed.

Figure 28A:
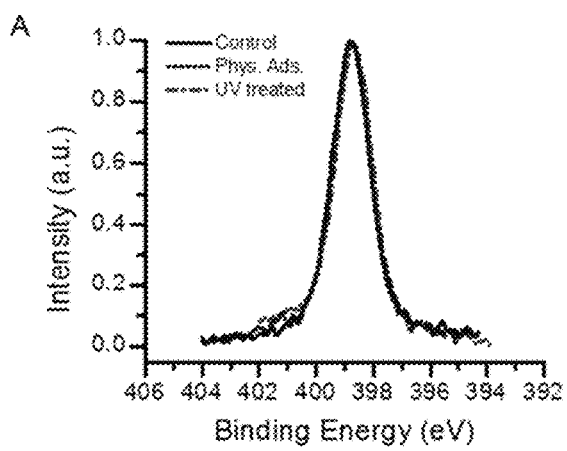
Figure 28B:
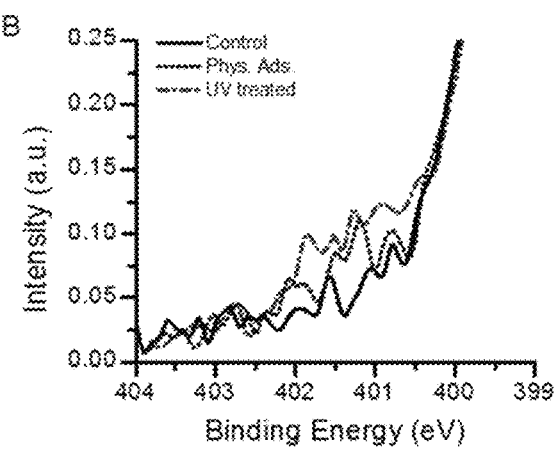

FIGS. 28A-B are a XPS high resolution N1s spectral overlay of the control, physically adsorbed and functionalized samples of 50 nm film thickness (FIG. 28A) and an expanded spectra from 399-404 eV (FIG. 28B) resolving the shouldering of the quaternary ammonium peak (400-402 eV). The solid lines represent raw data interpolated with a cubic b-spline curve, while the dashed lines represent the sum of the individual curve fits.

Figure 28C:
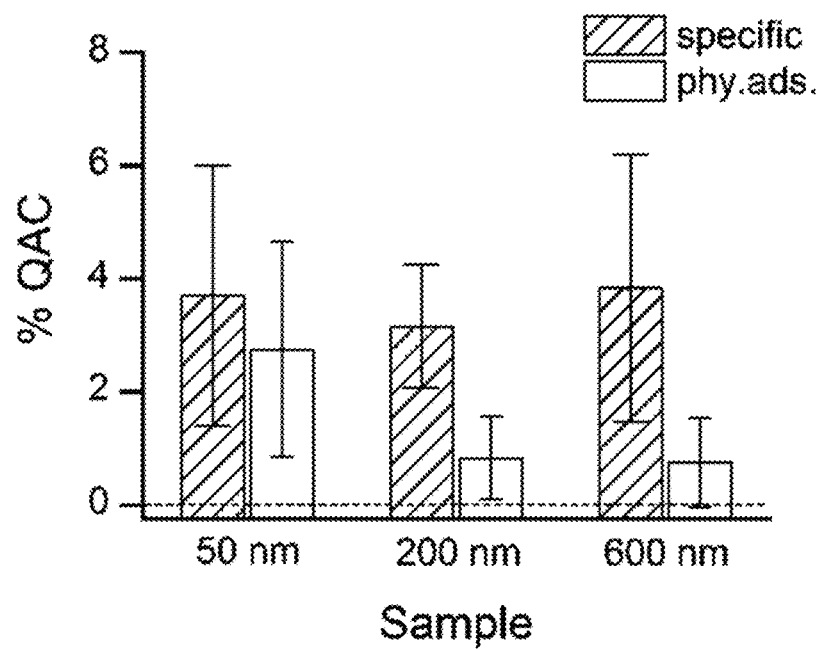

FIG. 28C is an XPS high resolution N1s data summary for surface detection of QAC compounds; the % QAC relative to tertiary nitrogen is plotted as a function of sample thickness for physical adsorption and covalent attachment. XPS measurements were taken on three independent locations per sample, and the average with standard deviations are displayed.

Figure 29:
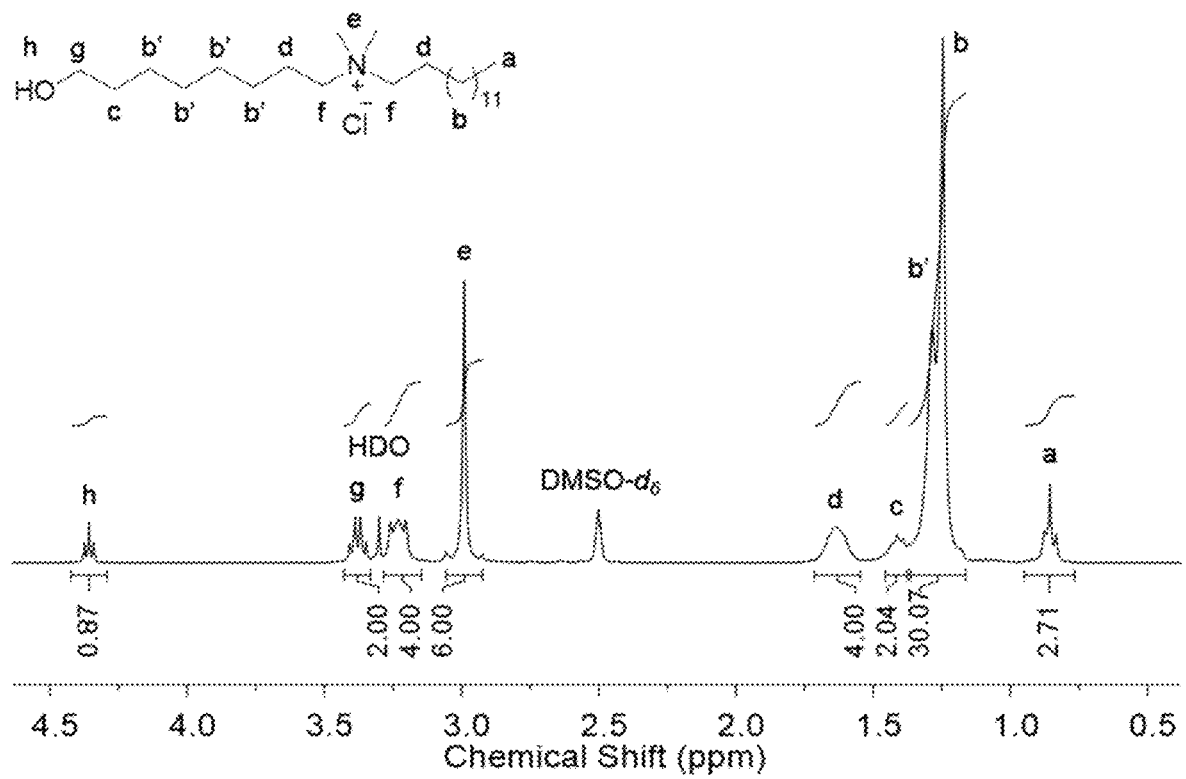

FIG. 29 is a ¹H-NMR spectrum of Q14-OH demonstrating a 1:1 molar ratio of peaks e and g, which indicates the formation of the desired quaternary ammonium compound.

Figure 30:
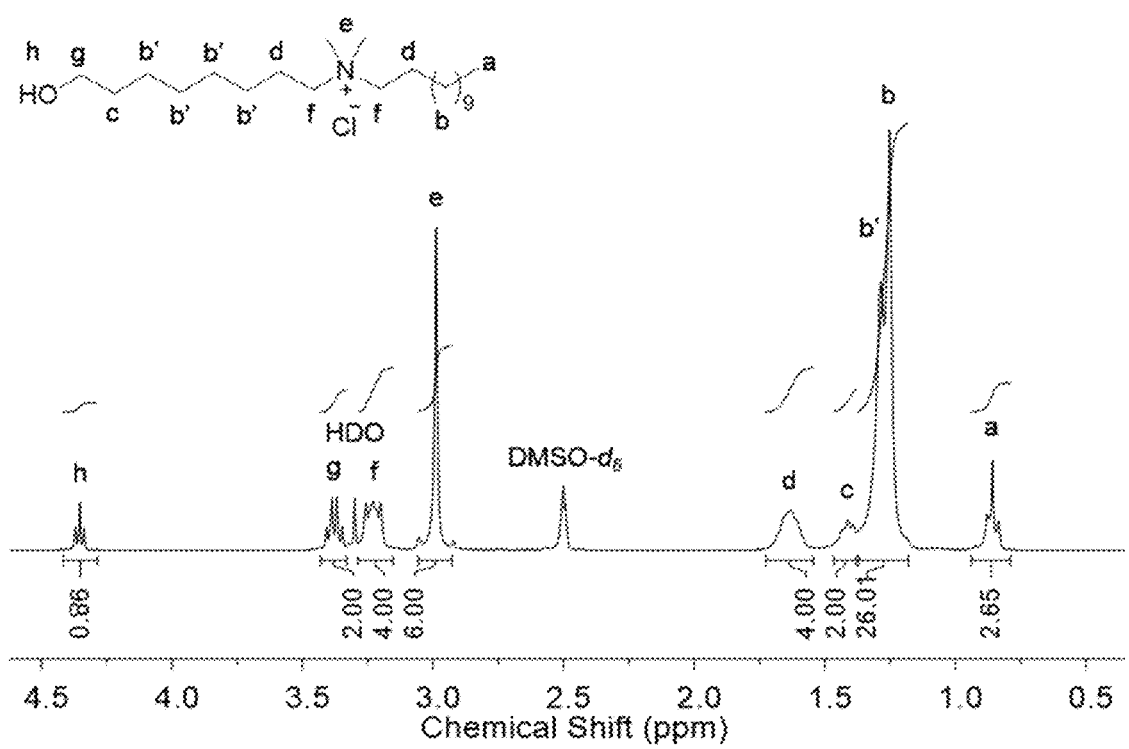

FIG. 30 is a ¹H-NMR spectrum of Q12-OH demonstrating a 1:1 molar ratio of peaks e and g, which indicates the formation of the desired quaternary ammonium compound.

Figure 31:
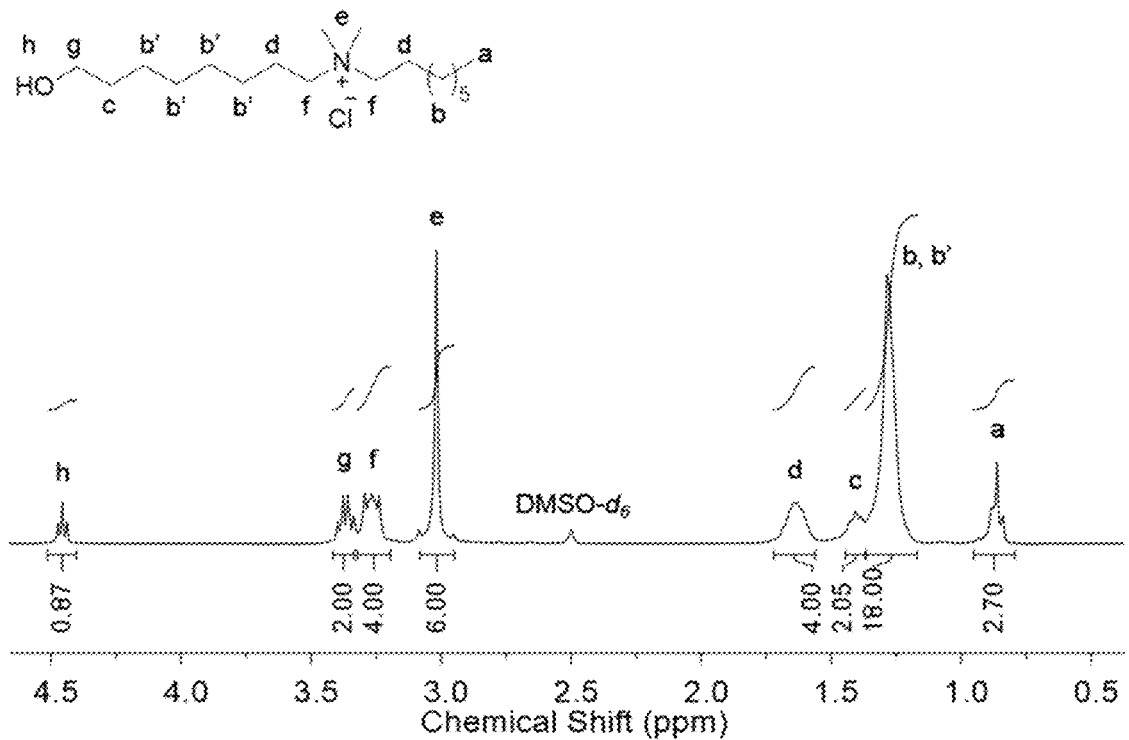

FIG. 31 is a ¹H-NMR spectrum of Q8-OH demonstrating a 1:1 molar ratio of peaks e and g, which indicates the formation of the desired quaternary ammonium compound.

Figure 32:
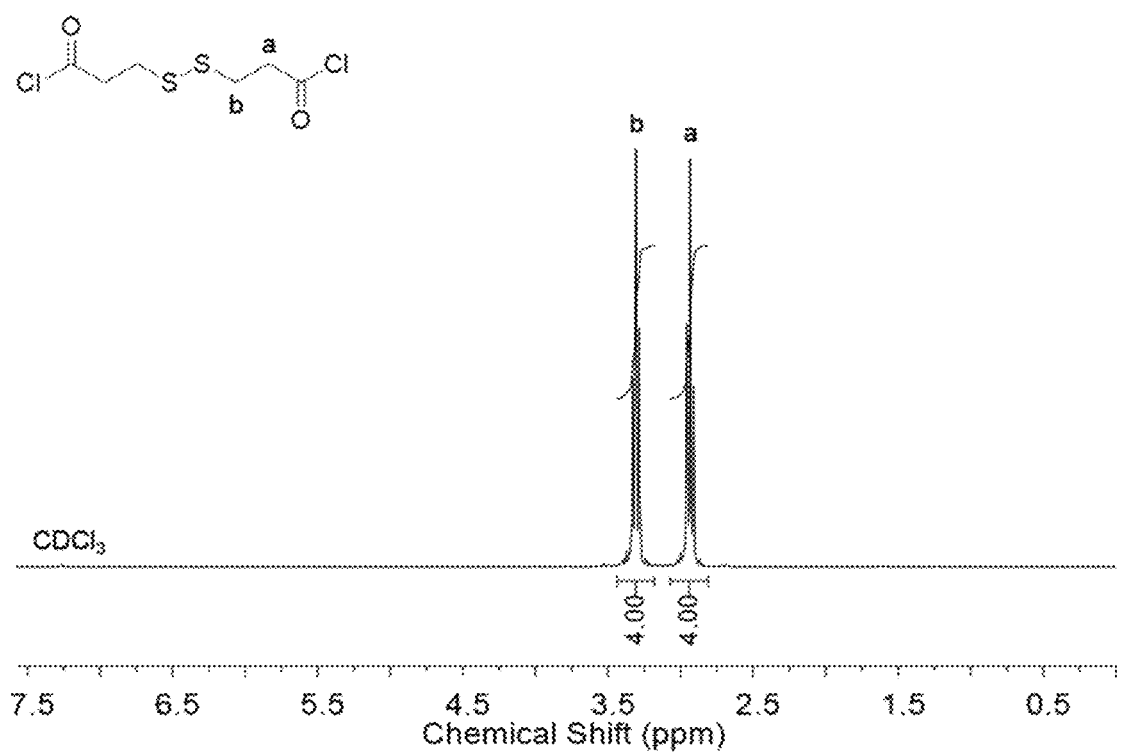

FIG. 32 is a ¹H-NMR spectrum of 3,3'-dithiodipropanoyl chloride displaying two triplets which confirms the purity of the compound, and demonstrating quantitative conversion to the acid chloride.

Figure 33:
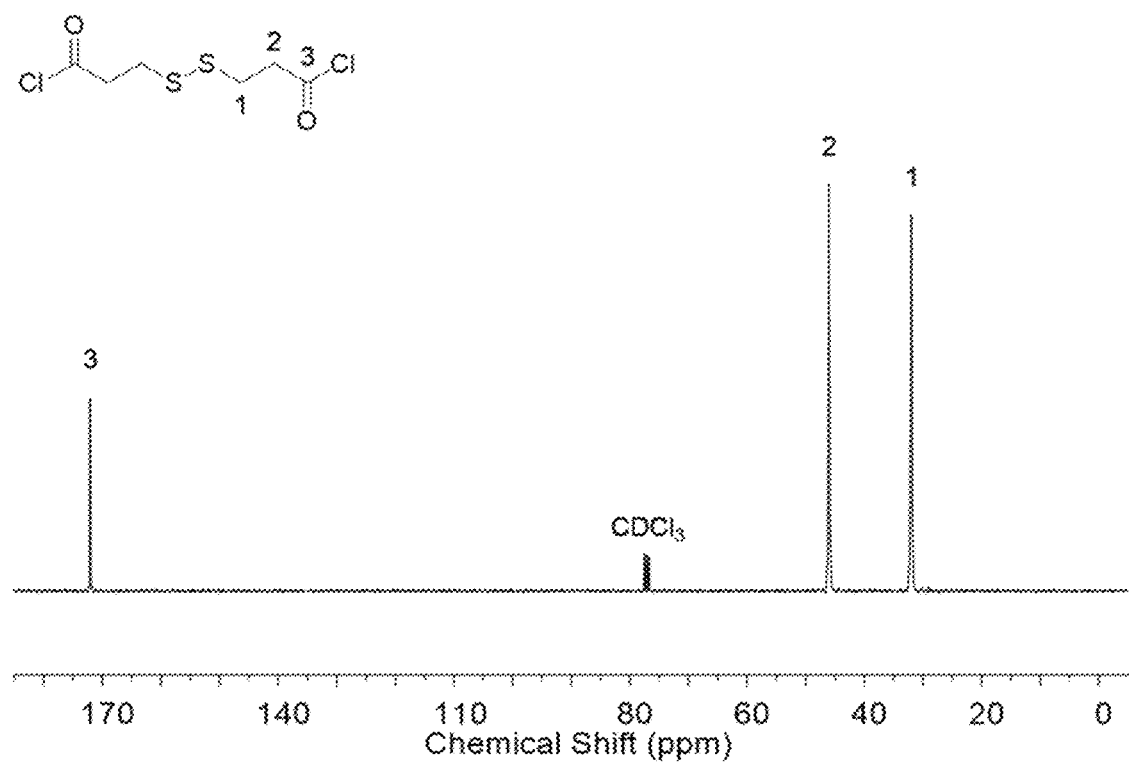

FIG. 33 is a $^{13}$C-NMR spectrum of 3,3'-dithiodipropanoyl chloride confirming the purity of the compound, and demonstrating quantitative conversion to the acid chloride.

Figure 34:
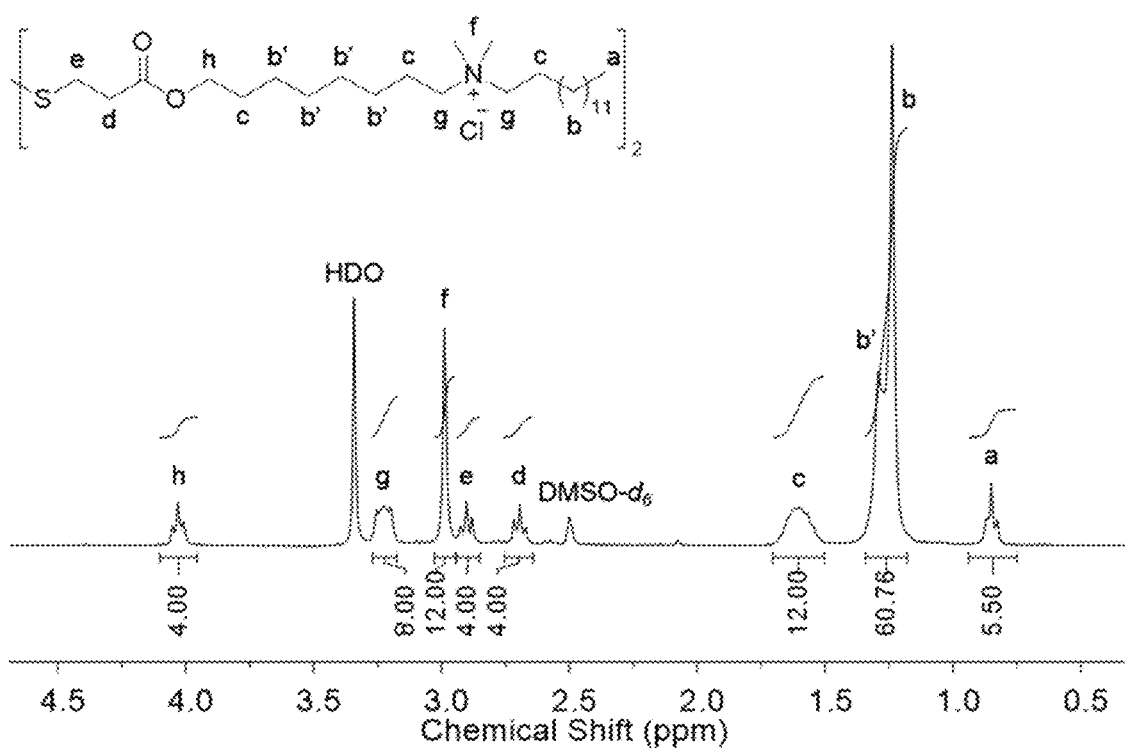

FIG. 34 $^{1}$H-NMR spectrum of Q14-S-S showing the appearance of peaks d and e, which are equimolar to peaks c, f, and g from the corresponding Q14-OH, indicating complete conversion to the desired disulfide.

Figure 35:
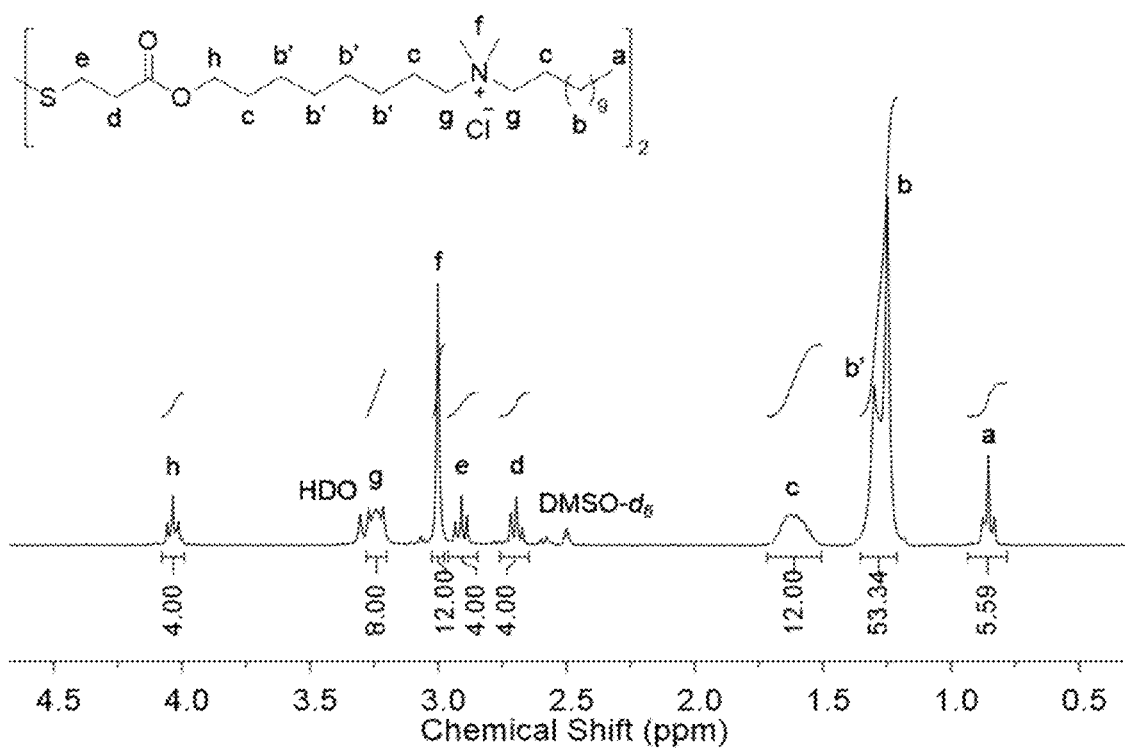

FIG. 35 is a $^{1}$H-NMR spectrum of Q12-S-S shows the appearance of peaks d and e, which are equimolar to peaks c, f, and g from the corresponding Q12-OH, indicating complete conversion to the desired disulfide.

Figure 36:
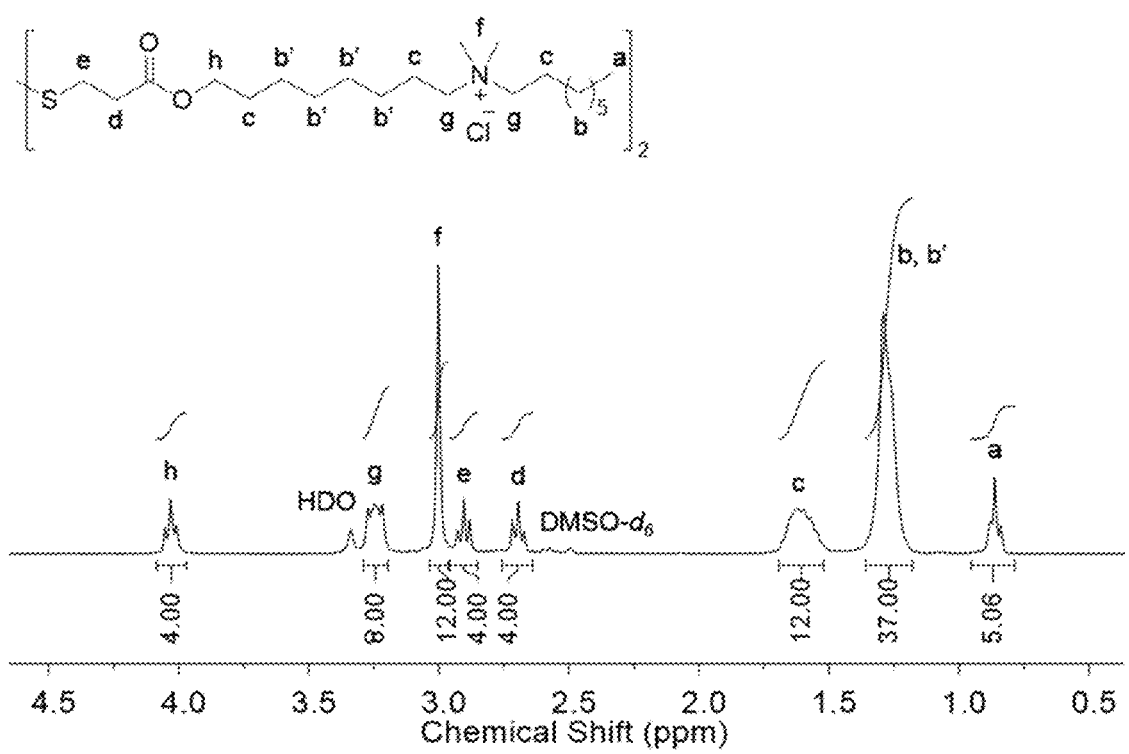

FIG. 36 is a $^{1}$H-NMR spectrum of Q8-S-S showing the appearance of peaks d and e, which are equimolar to peaks c, f, and g from the corresponding Q8-OH, indicating complete conversion to the desired disulfide.

Figure 37:
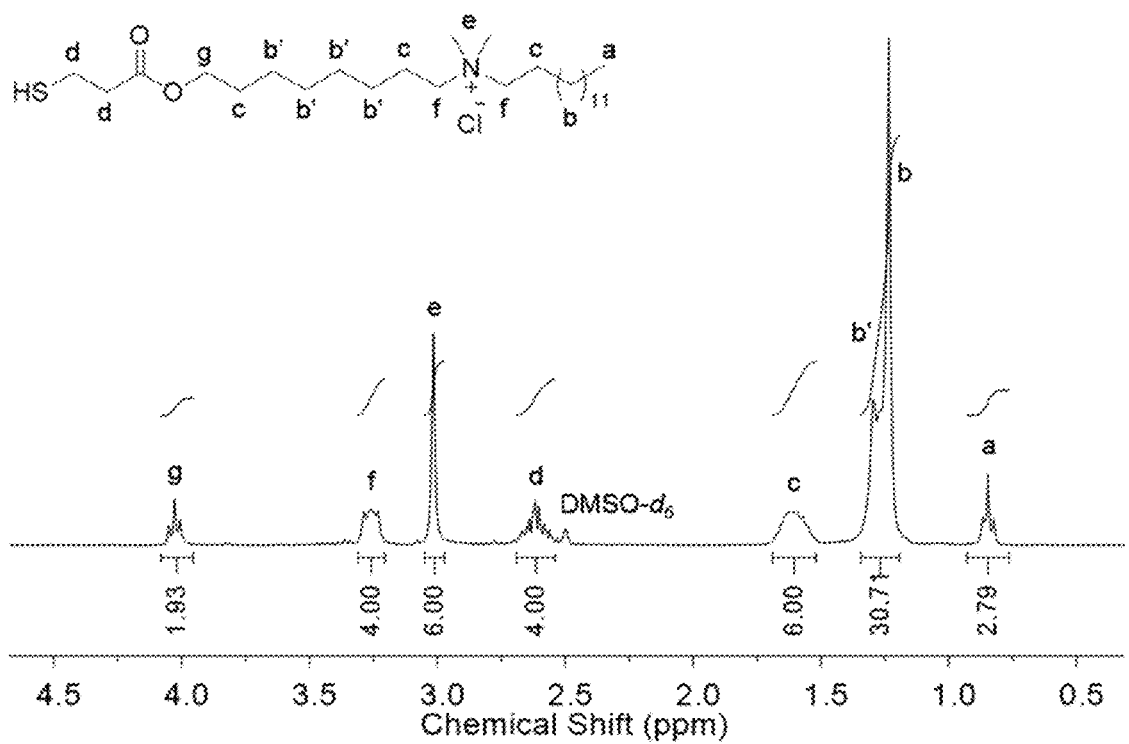

FIG. 37 is a $^{1}$H-NMR spectrum of Q14-SH showing the proton resonances α and ß to the carbonyl (peak d) converge, and are equimolar to peaks c, e, and f from the corresponding Q14-S-S, indicating complete conversion to the desired thiol.

Figure 38:
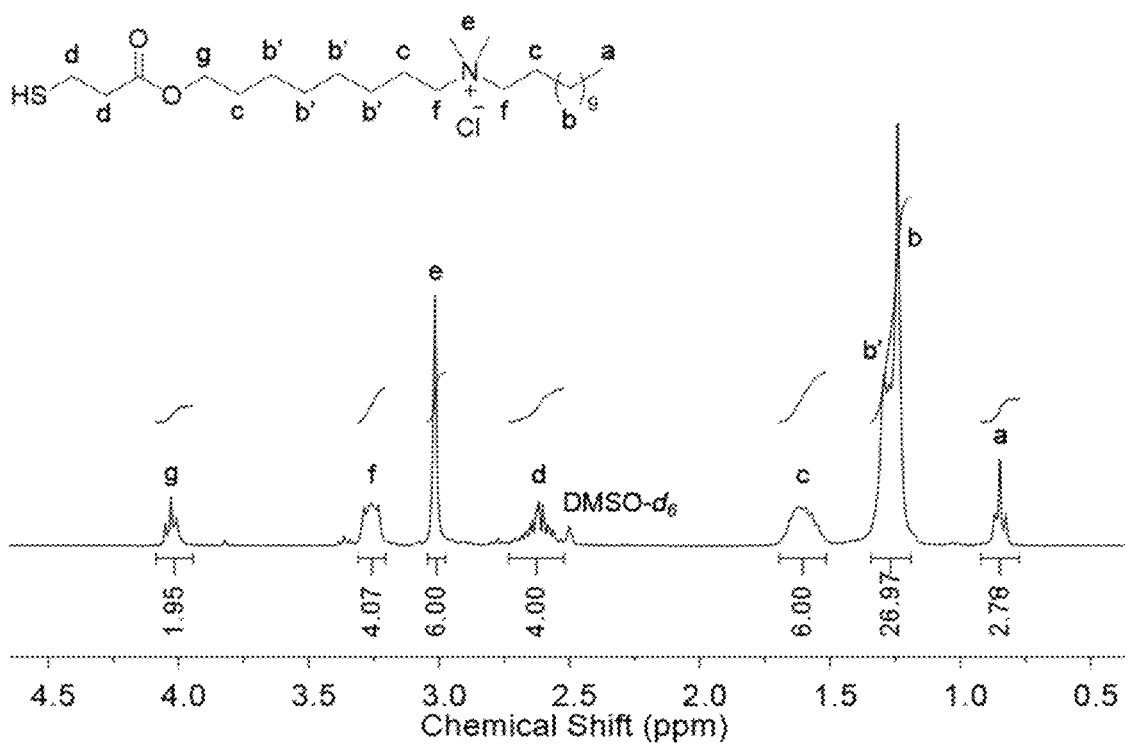

FIG. 38 is a $^{1}$H-NMR spectrum of Q12-SH showing the proton resonances α and ß to the carbonyl (peak d) converge, and are equimolar to peaks c, e, and f from the corresponding Q12-S-S, indicating complete conversion to the desired thiol.

Figure 39:
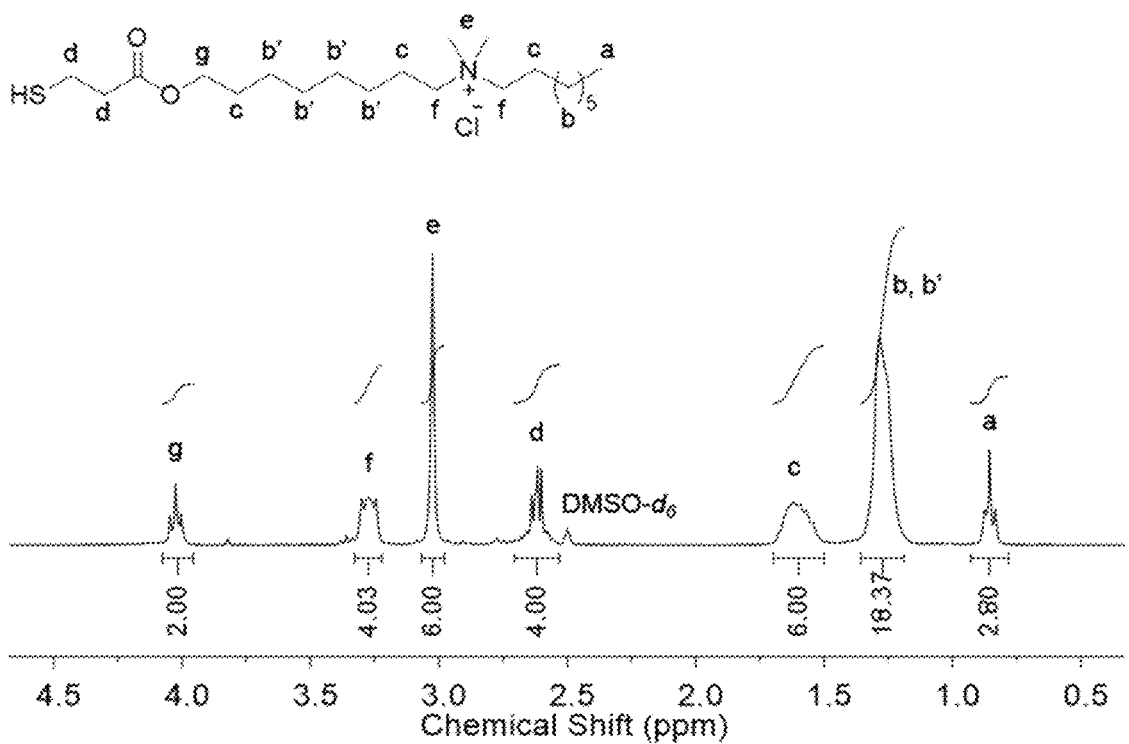

FIG. 39 is a $^{1}$H-NMR spectrum of Q8-SH showing the proton resonances α and ß to the carbonyl (peak d) converge, and are equimolar to peaks c, e, and f from the corresponding Q8-S-S, indicating complete conversion to the desired thiol.

Figure 40:
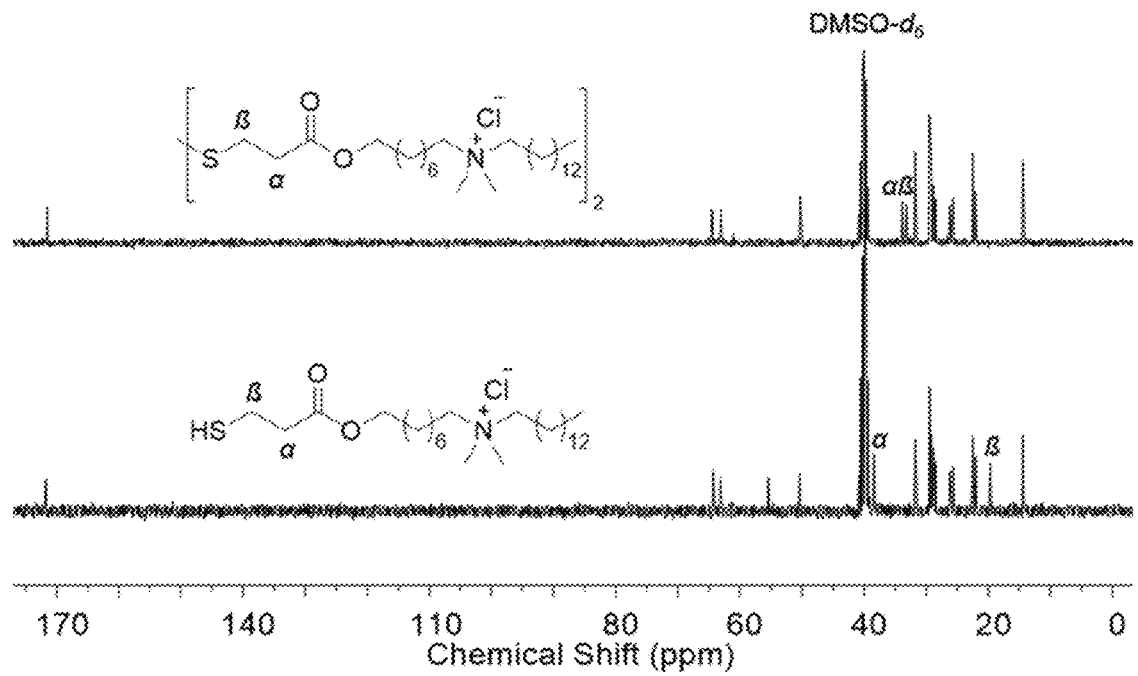

FIG. 40 is a $^{13}$C-NMR spectra overlay of Q14-S-S and Q14-SH showing the shifting of the carbon α to the carbonyl downfield and the ß carbon upfield, indicating conversion to the desired thiol.

Figure 41:
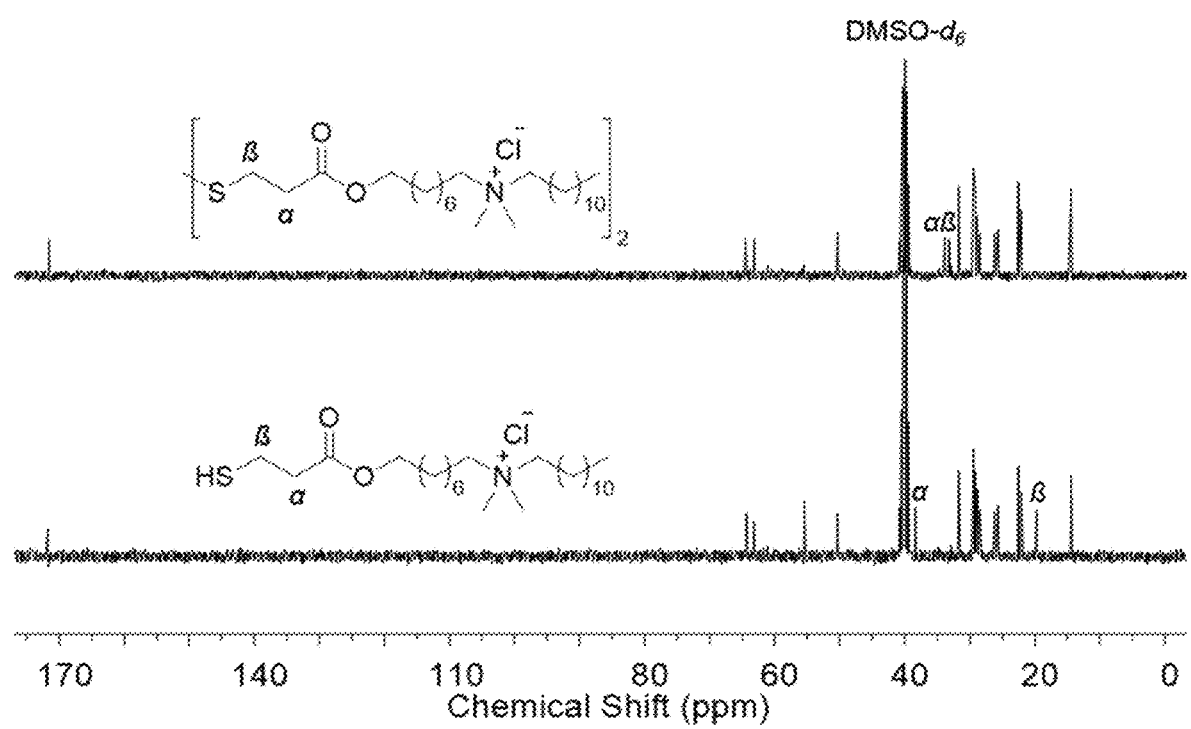

FIG. 41 is a $^{13}$C-NMR spectra overlay of Q12-S-S and Q12-SH showing the shifting of the carbon α to the carbonyl downfield and the ß carbon upfield, indicating conversion to the desired thiol.

Figure 42:
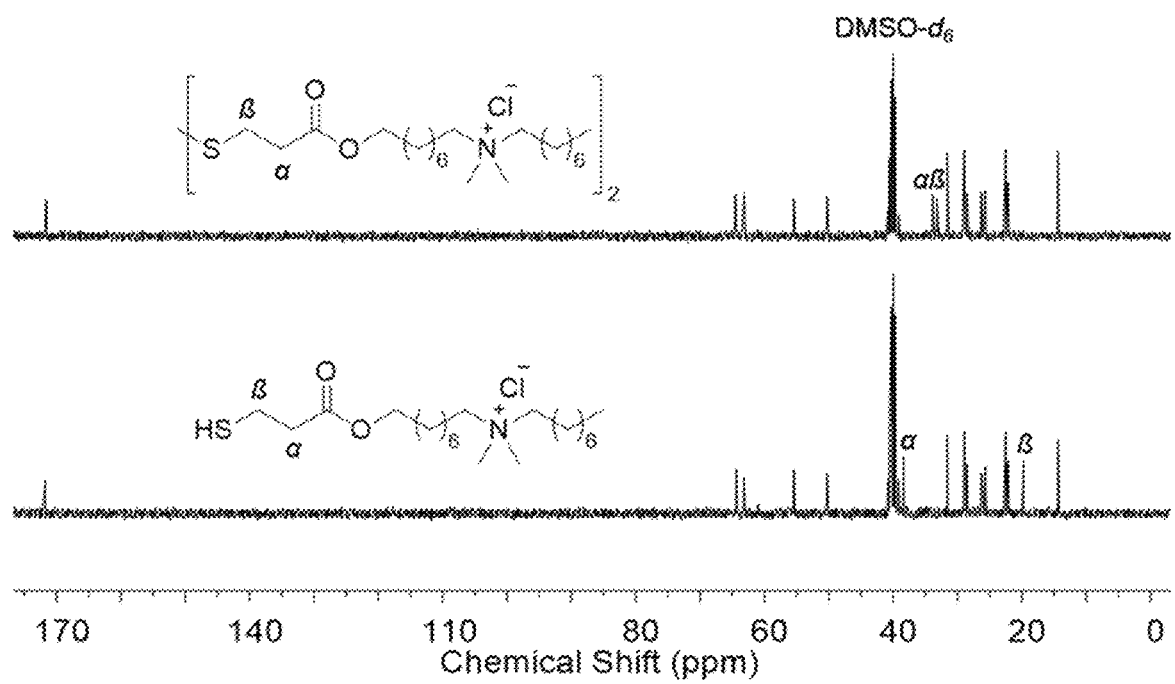

FIG. 42 is a $^{13}$C-NMR spectra overlay of Q8-S-S and Q8-SH showing the shifting of the carbon α to the carbonyl downfield and the ß carbon upfield, indicating conversion to the desired thiol.

Figure 43:
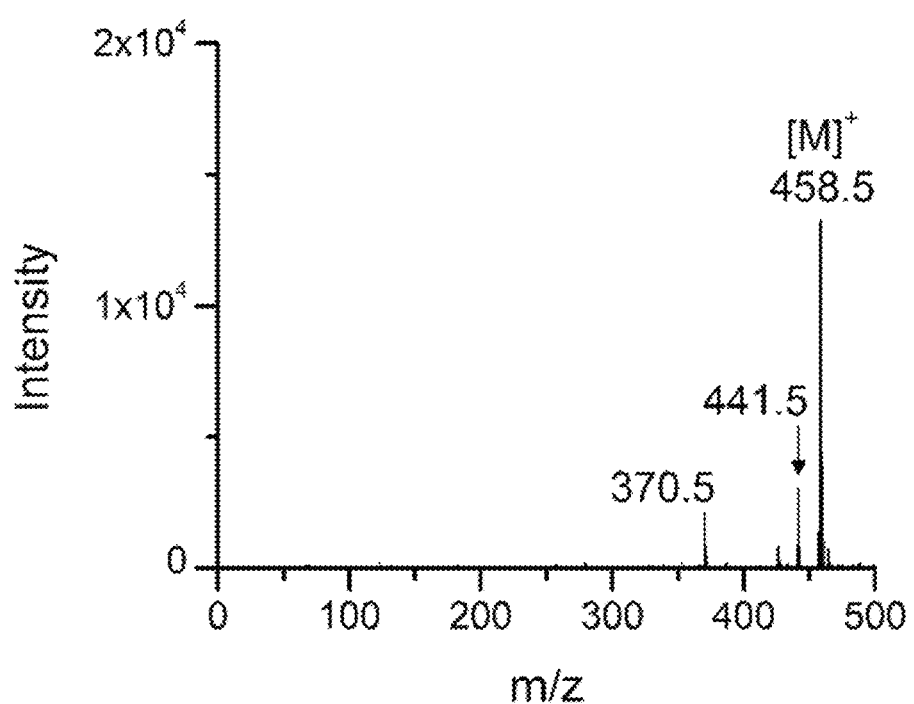

FIG. 43 is an ESI-MS of Q14-SH showing the molecular ion $[M]^{+}$=458.5 Da (calculated=458.40 Da). The peak at 370.5 m/z is Q14-OH, while 441.5 m/z is a doubly charged dimer of the molecular ion −34 Da, which is a characteristic loss of $H_2S$.

Figure 44:
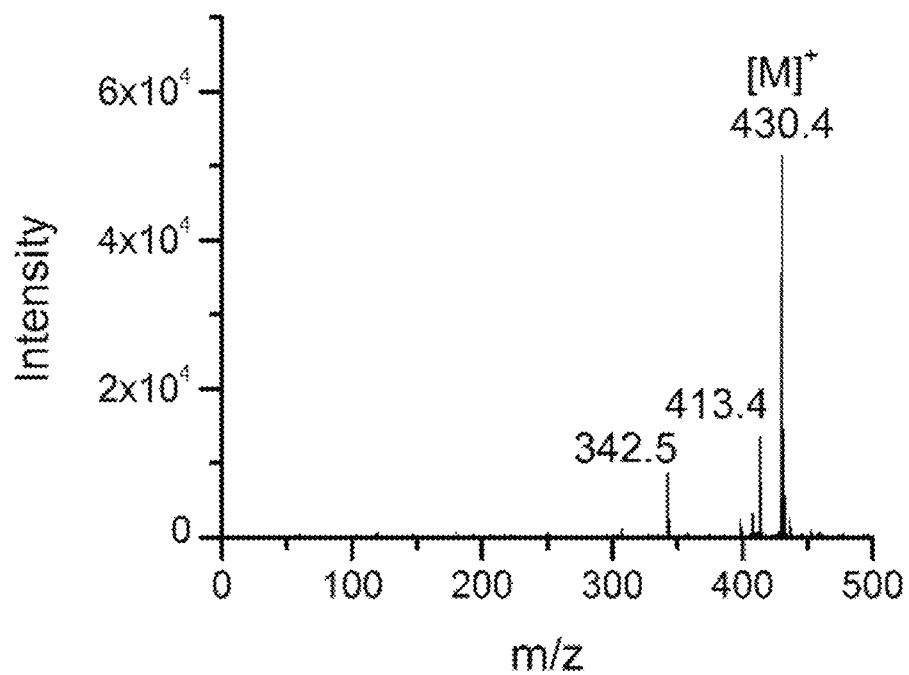

FIG. 44 is an ESI-MS of Q12-SH showing the molecular ion $[M]^{+}$=430.4 Da (calculated=430.37 Da). The peak at 342.5 m/z is Q12-OH, while 413.4 m/z is a doubly charged dimer of the molecular ion −34 Da, which is a characteristic loss of $H_2S$.

Figure 47:
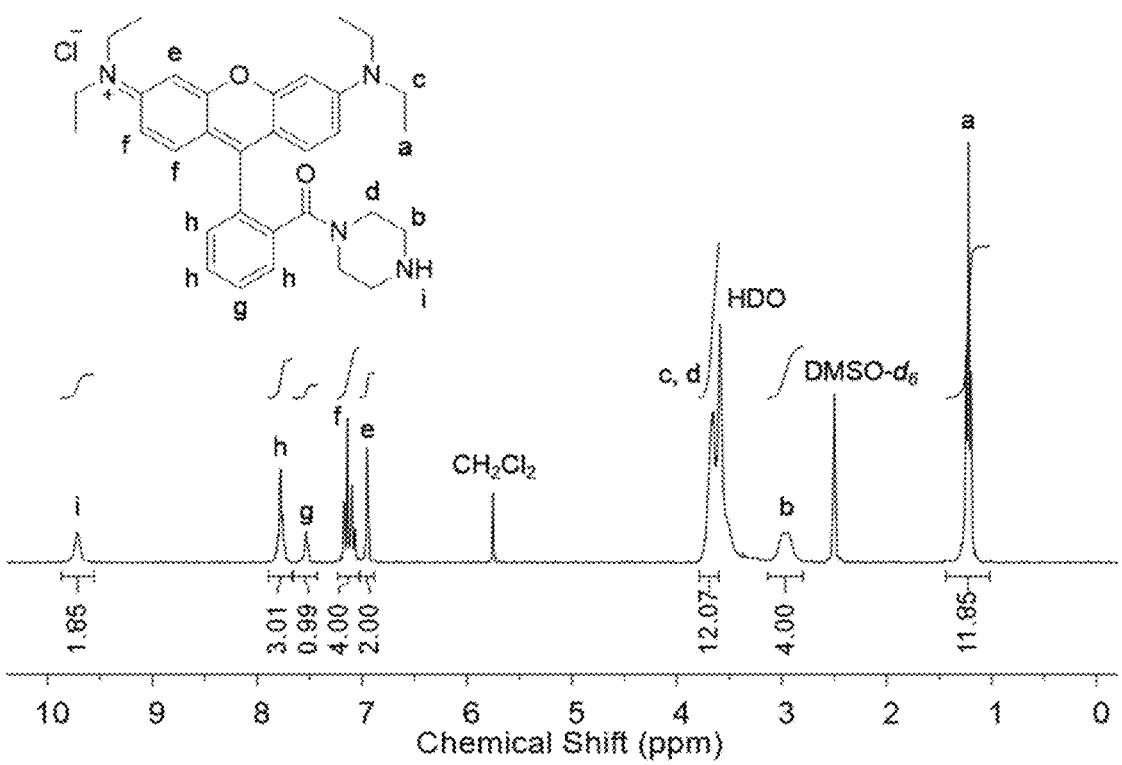

FIG. 47 is an ESI-MS of Q8-SH showing the molecular ion $[M]^{+}$=374.4 Da (calculated=374.31 Da). The peak at 286.4 m/z is Q8-OH, while 357.4 m/z is a doubly charged dimer of the molecular ion −34 Da, which is a characteristic loss of $H_2S$.

Figure 46:
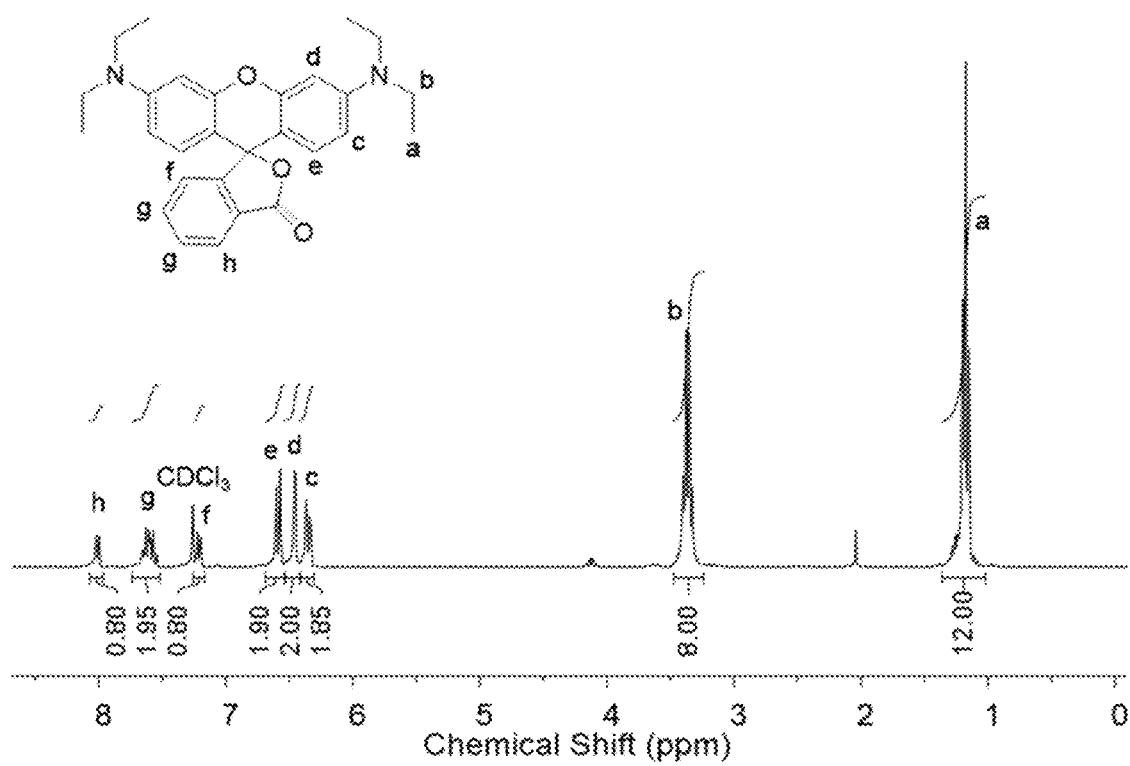

FIG. 46 is a $^{1}$H-NMR spectrum of rhodamine B base.

FIG. 47 is a $^{1}$H-NMR spectrum of rhodamine B piperazine amide showing the introduction of peaks b, d, and i from piperazine, and the integration of peaks a and b indicate the amidation reaction was successful. HDO overlaps with peaks c and d.

Figure 48:
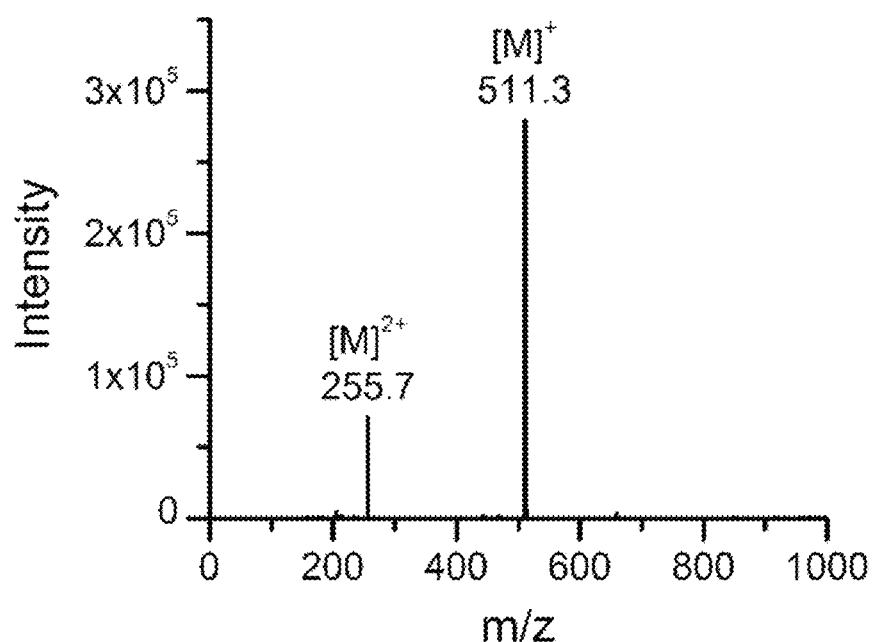

FIG. 48 is an ESI-MS of rhodamine B piperazine amide showing the molecular ion $[M]^{+}$=511.3 Da (calculated=511.31 Da), as well as the doubly charged ion, $[M]^{2+}$ at m/z=255.7.

Figure 49:
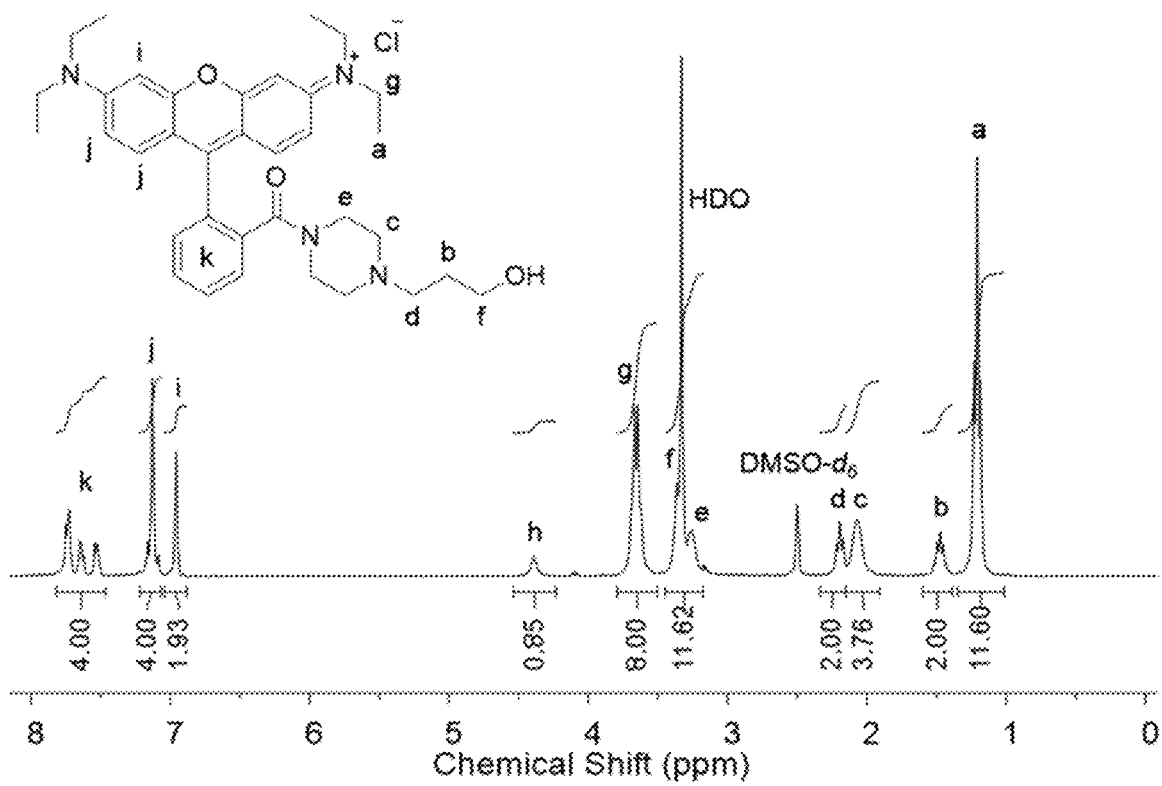

FIG. 49 is a $^{1}$H-NMR spectrum of rhodamine B 4-(3-hydroxylpropyl) piperazine amide demonstrating the appearance of peaks b and d, as well as the upfield shifting of the piperazine proton resonances (peaks e and c). The proton integrations indicate successful substitution.

Figure 50:
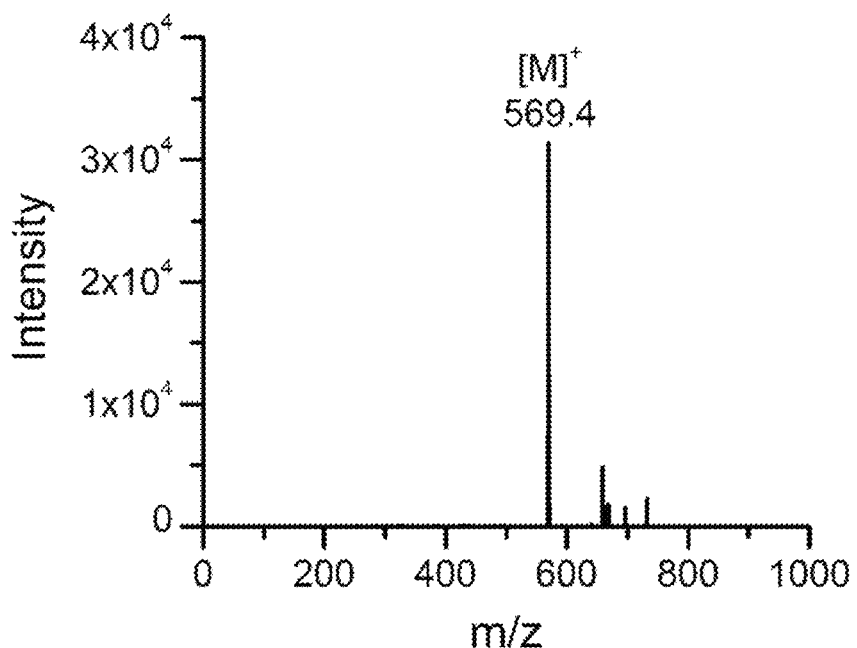

FIG. 50 is an ESI-MS of rhodamine B 4-(3-hydroxylpropyl) piperazine amide showing the molecular ion $[M]^{+}$=569.4 Da (calculated=569.35 Da) with minimal impurities.

Figure 51:
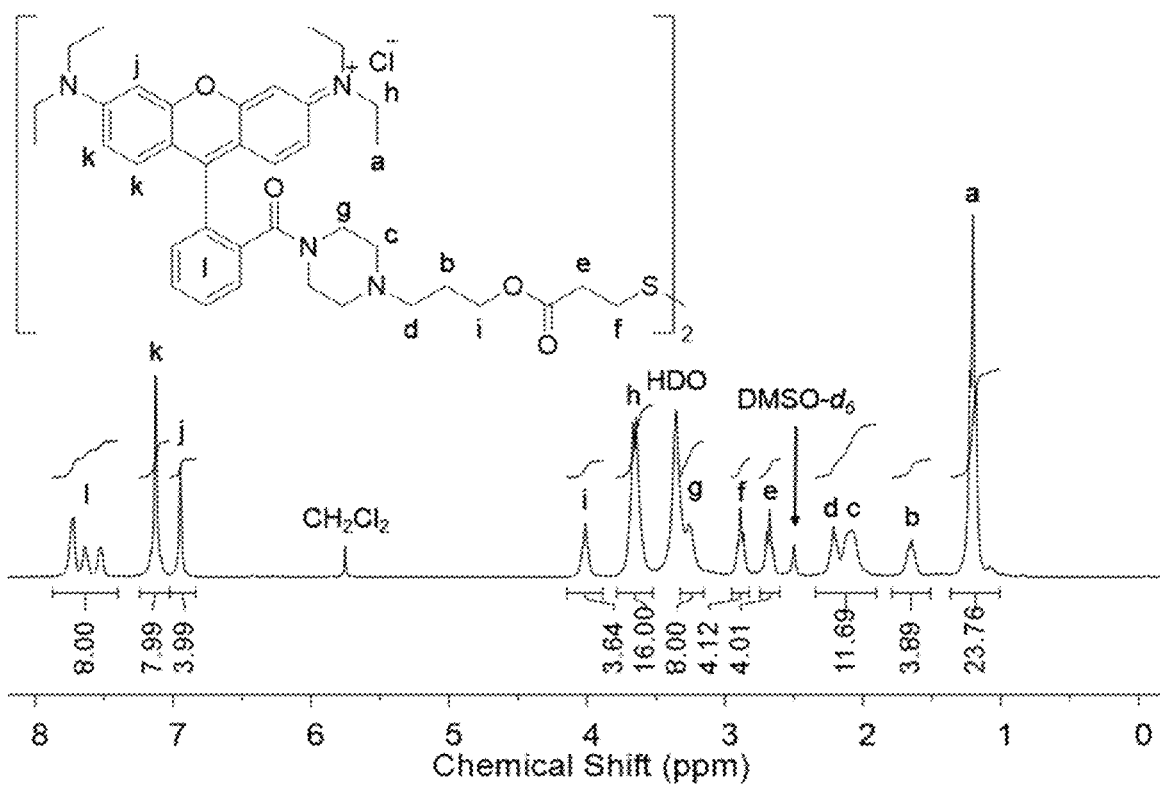

FIG. 51 is a $^{1}$H-NMR spectrum of rhodamine B disulfide. The shifting of peak i downfield, as well as the emergence and integration of peaks e and f indicate the esterification was successful.

Figure 52:
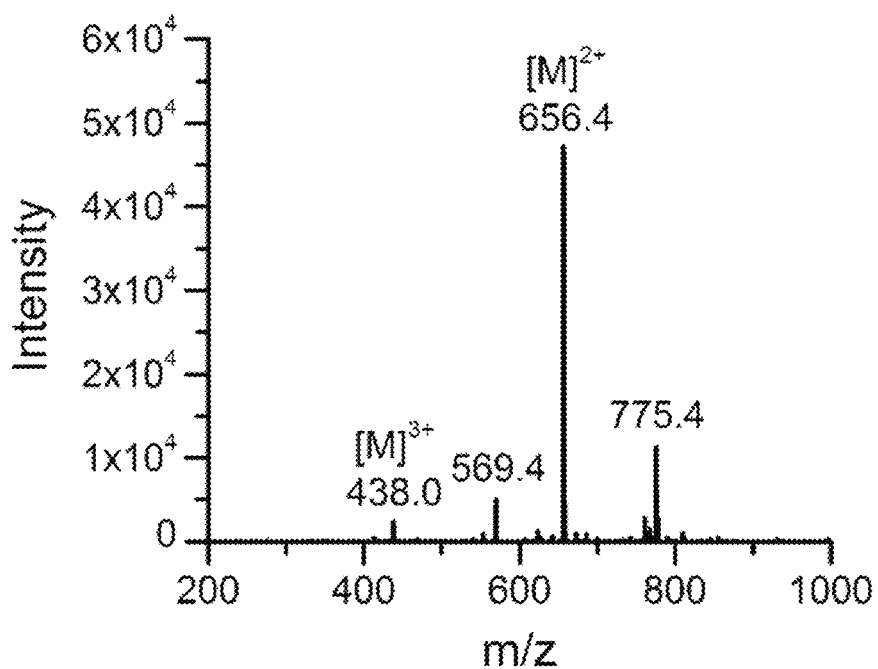

FIG. 52 is an ESI-MS of rhodamine B disulfide showing the doubly charged ion $[M]^{2+}$=656.4 m/z which is 1312.8 Da (calculated=1312.68 Da), as well as the triply charged ion, $[M]^{3+}$ at m/z=438.0. The peaks 569.4 and 775.4 are singly charged ions produced in the mass spectrometer by methanolysis, resulting in rhodamine B 4-(3-hydroxylpropyl) piperazine amide (569.4 Da) and the corresponding methyl ester (775.4 Da) cleavage products.

Figure 53:
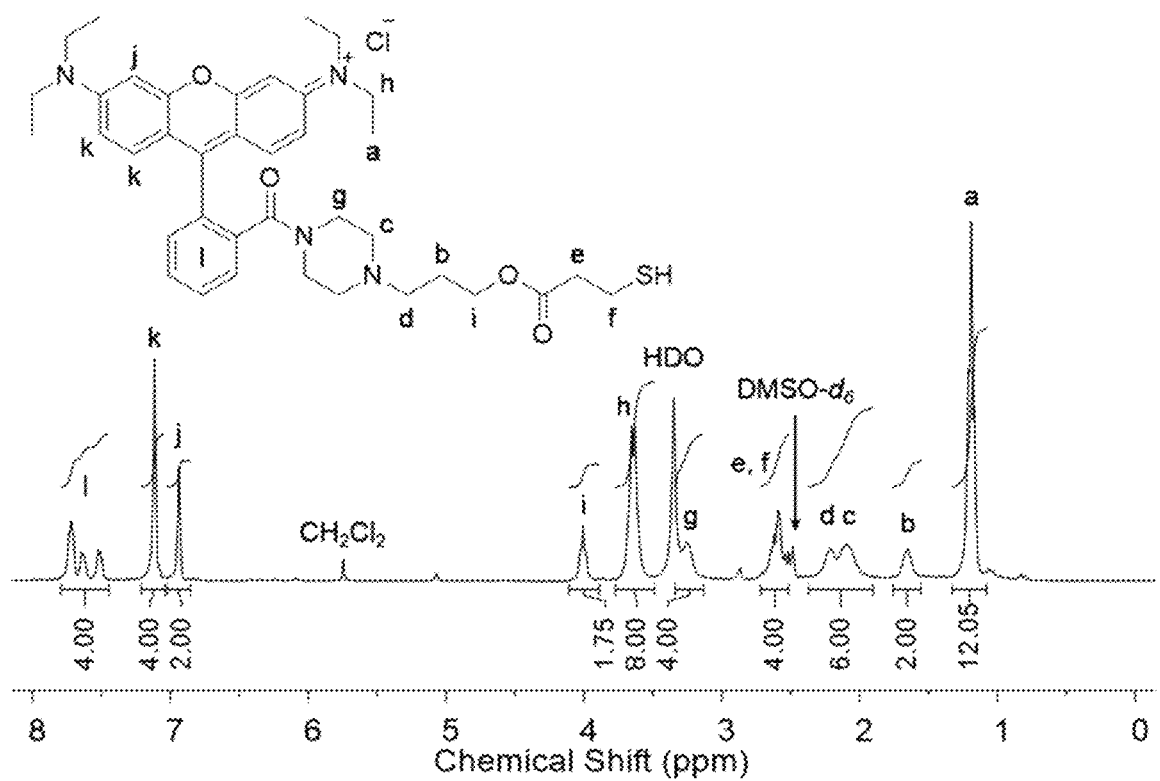

FIG. 53 is a $^{1}$H-NMR spectrum of rhodamine-SH showing the proton resonances α and ß to the carbonyl (peaks e and f, respectively) converge, and are equimolar to all other peaks from the corresponding rhodamine B disulfide, indicating complete conversion to the desired thiol.

Figure 54:
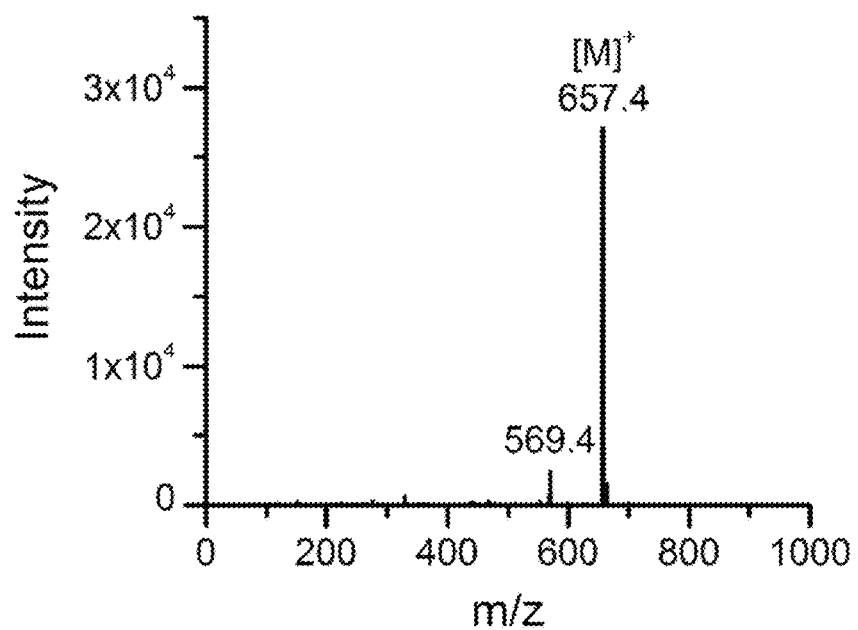

FIG. 54 is a ESI-MS of rhodamine-SH showing the molecular ion $[M]^{+}$=657.4 Da (calculated=657.35 Da) with minimal impurities. The peak at 569.4 is the rhodamine B 4-(3-hydroxylpropyl) piperazine amide fragment resulting from ester cleavage.

Figure 55:
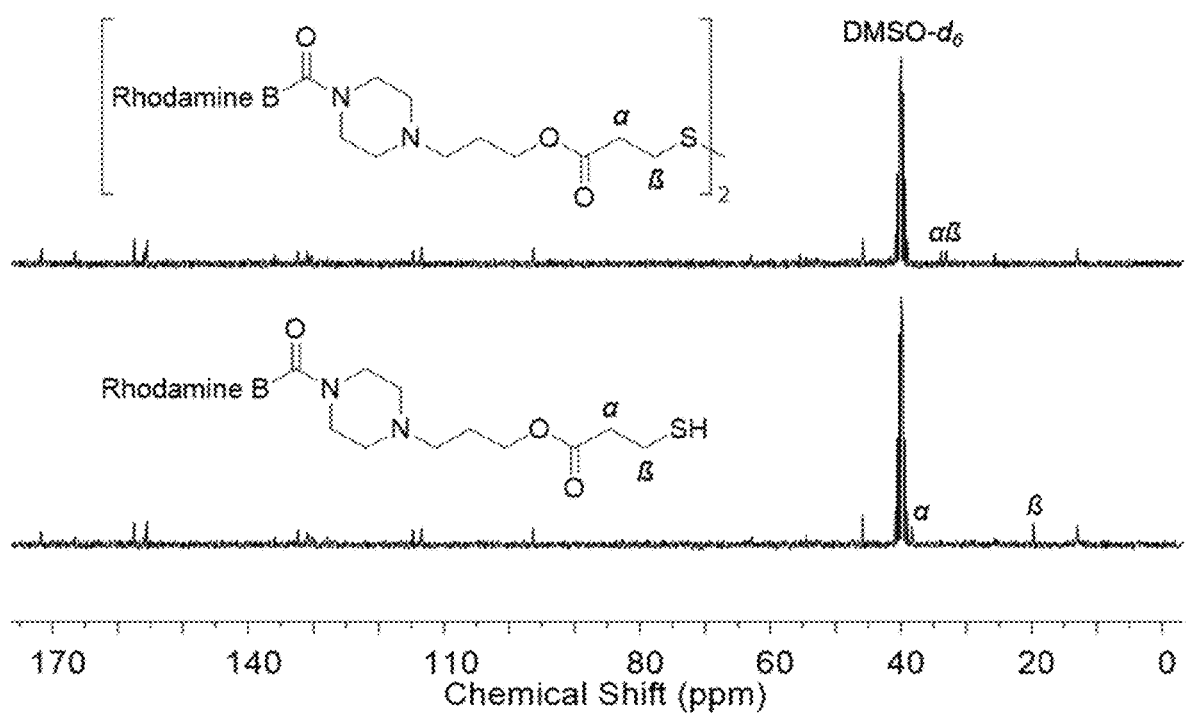

FIG. 55 is a $^{13}$C-NMR spectra overlay of rhodamine B disulfide and rhodamine-SH showing the shifting of the carbon α to the carbonyl downfield and the ß carbon upfield, indicating conversion to the desired thiol.

Figure 56:
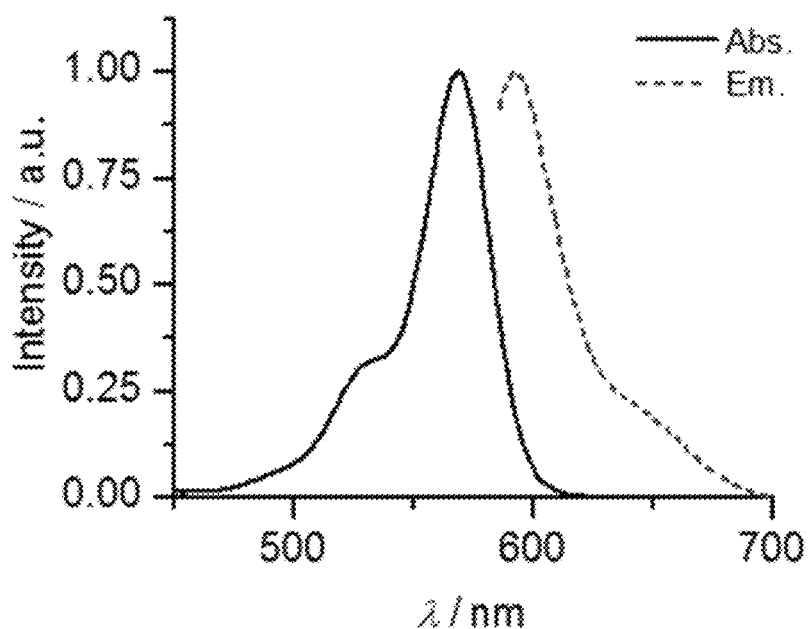

FIG. 56 is a normalized absorbance and emission spectra for rhodamine-SH. The $\lambda_{abs}$=568 nm and the $\lambda_{em}$=592 nm.

Figure 57:
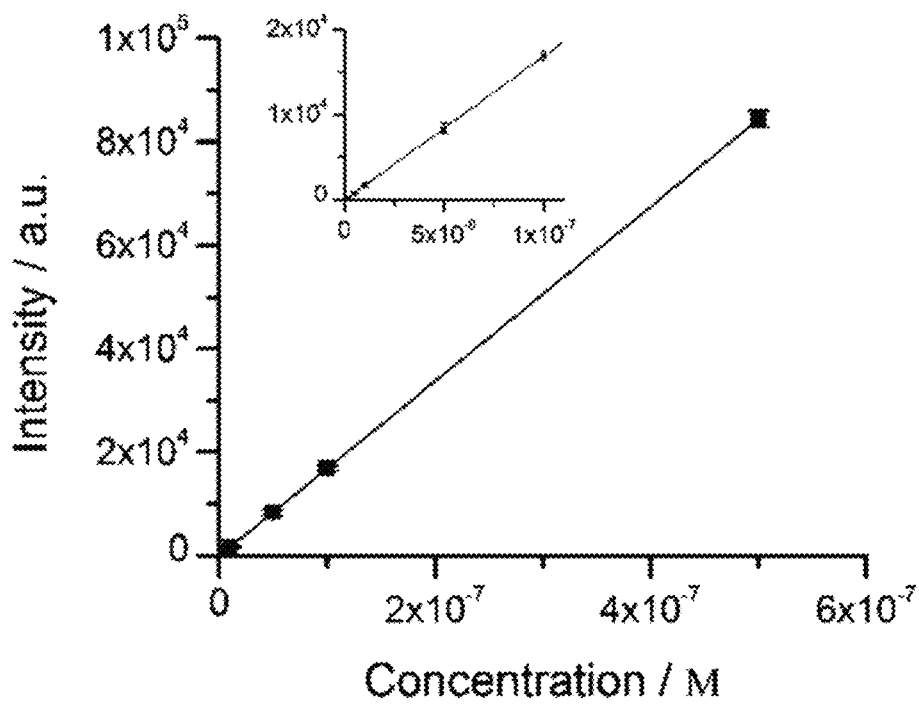

FIG. 57 is a fluorescence standard curve for various concentrations of rhodamine-SH in DMSO. The linear fit yielded an $R^2$ value=0.99 with a slope of $(168.7\pm0.1)\times 10^9 M^{-1}$.

Figure 58:
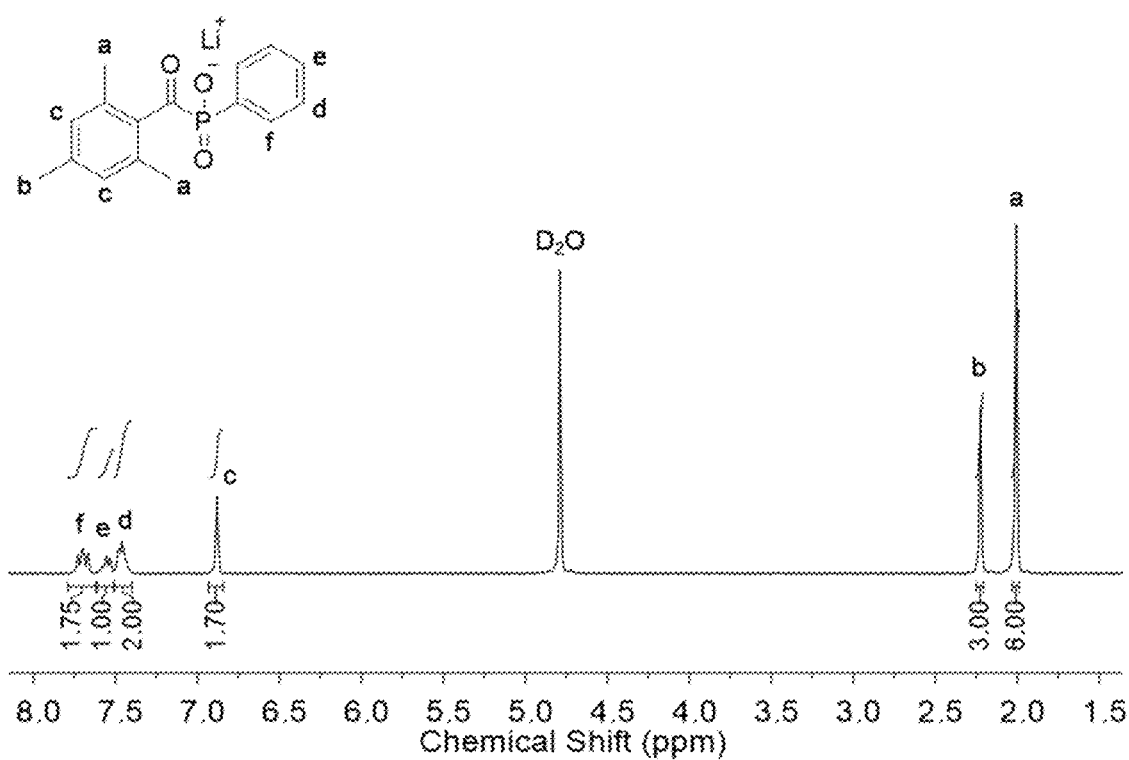

FIG. 58 is a $^{1}$H-NMR spectrum of LAP. The integrations of peaks a-c compared to peaks d-f confirm a 1:1 substitution occurred.

Figure 59A:
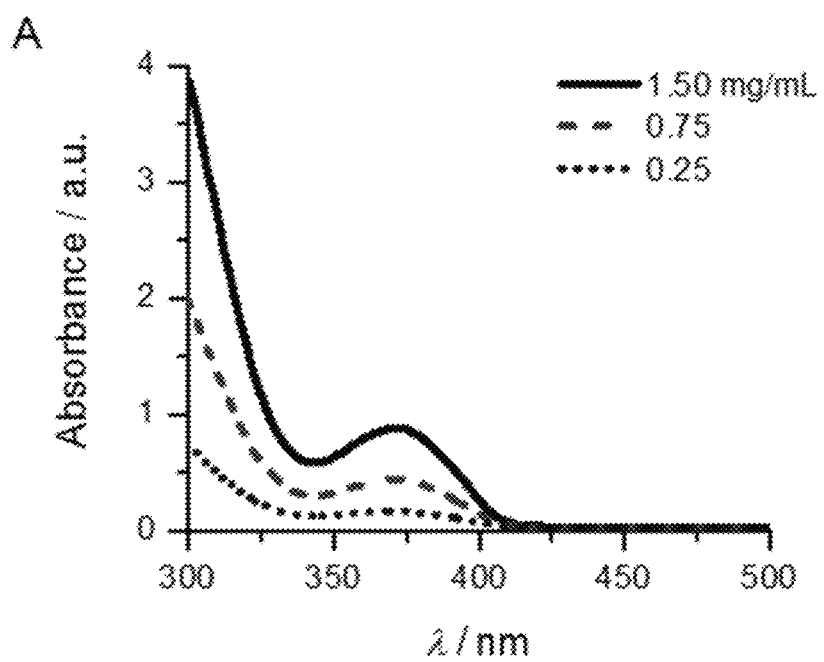
Figure 59B:
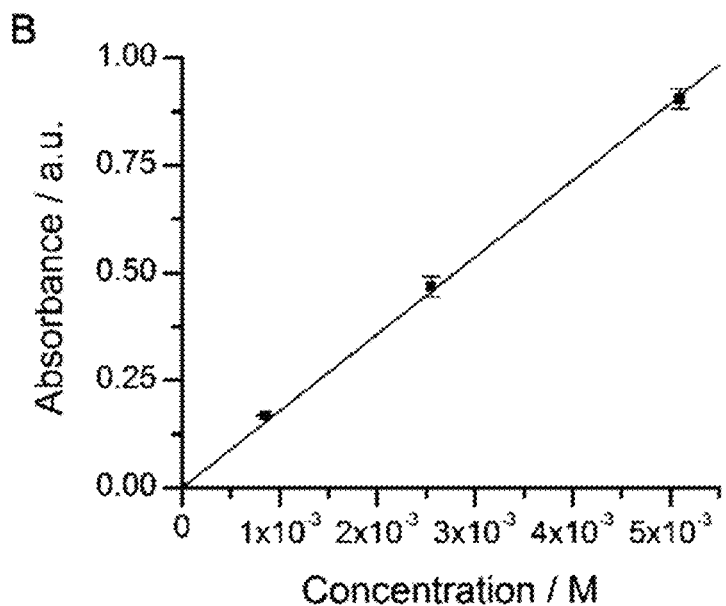

FIG. 59 are a UV-vis absorption spectra for LAP photoinitiator at several concentrations (FIG. 59A) and a graph showing the absorbance at λ=365 nm vs. concentration for determination of the molar absorptivity (ε) of LAP (FIG. 59B). The linear fit yielded an $R^2$ value=0.99 with a slope (E)=179±3 $M^{-1} \cdot cm^{-1}$.

Figure 60:
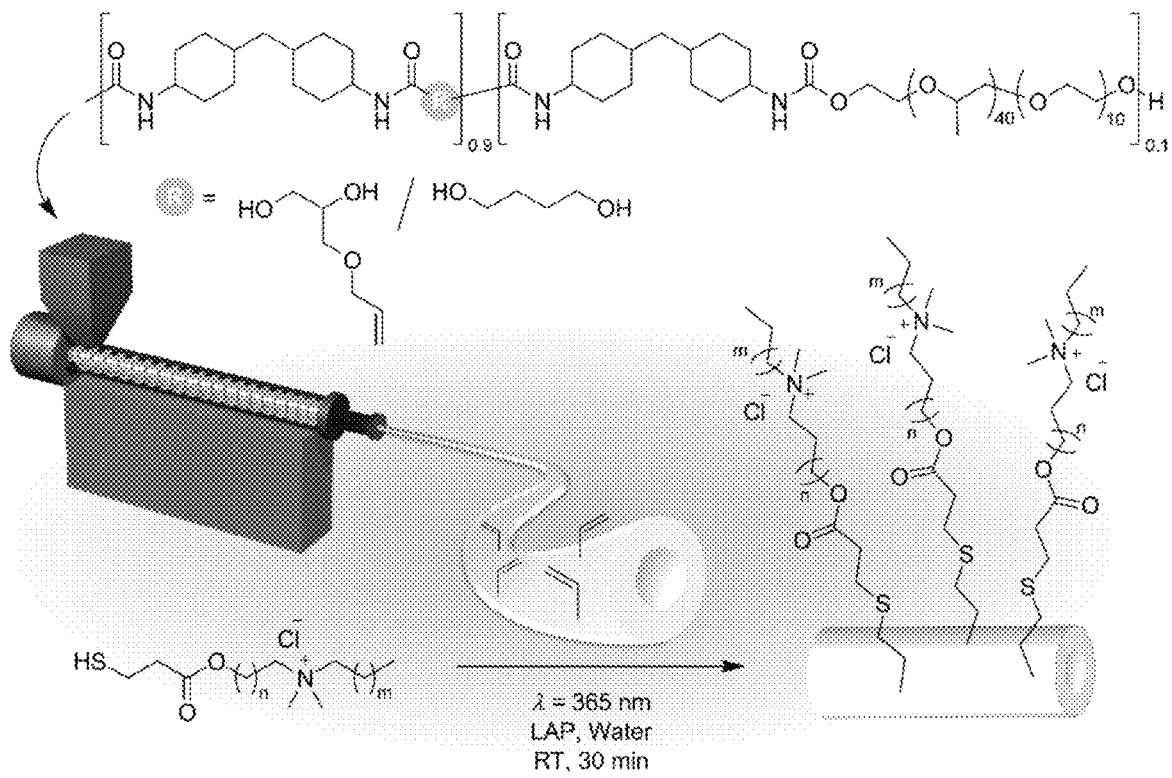

FIG. 60 is a schematic drawing showing post-fabrication, surface functionalization of an allyl-TPU with Qx-SH reagents carried out in DI water at room temperature using LAP photoinitiator and UV light (365 nm, I=1.2 $mW \cdot cm^{-2}$). m is an integer from 1 to 18, and n is an integer from 1 to 19.

Figure 61:
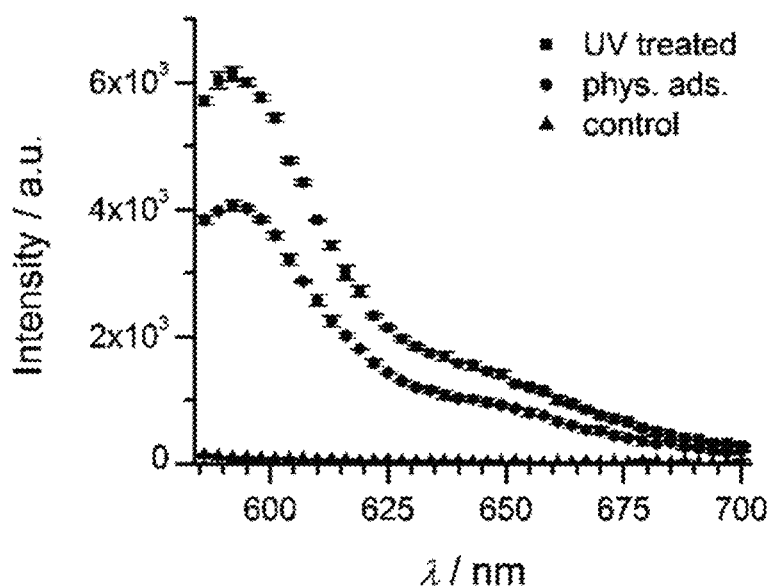

FIG. 61 is a graph showing fluorescence data for the untreated control, phys. ads., and UV-treated allyl-TPU samples modified using "click" reaction conditions with rhodamine-SH. Emission scans were taken from λ=586-700 nm at an excitation wavelength of $\lambda_{ex}$=568 nm, which provided the intensity at $\lambda_{max}$ (592 nm) for each sample. Experiments were performed in triplicate and the average fluorescence intensities with standard deviations are plotted (n=3).

Figure 62A:
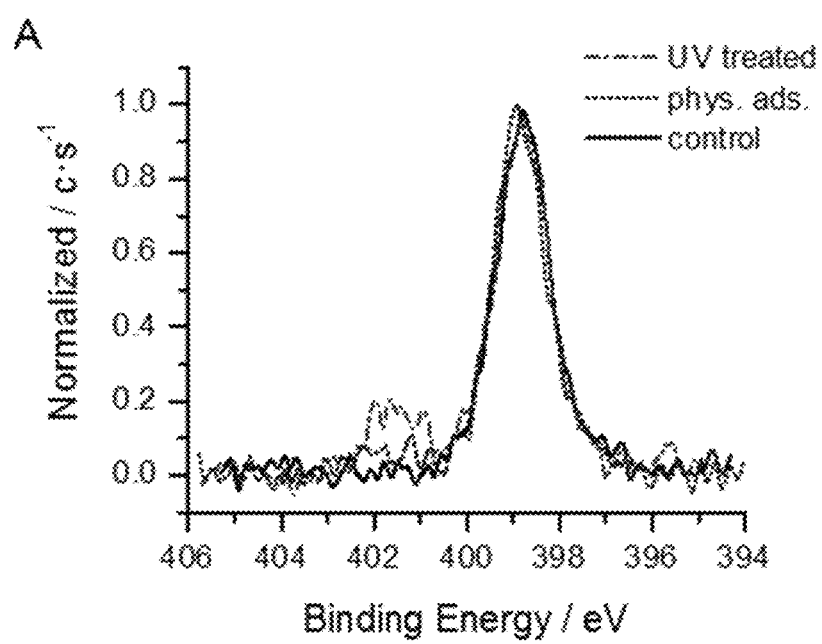
Figure 62B:
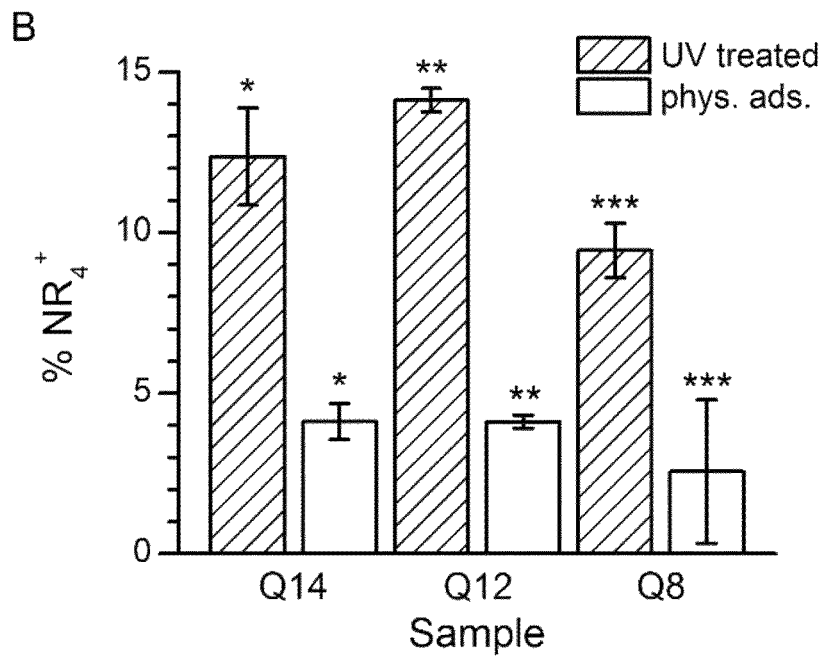

FIGS. 62A-B are (FIG. 62A) XPS high-resolution N1s spectra overlay of an untreated control, phys. ads., and UV-treated sample demonstrating the appearance of a quaternary ammonium peak (400-402 eV). The solid lines represent raw data interpolated with a cubic b-spline curve, while the dashed lines represent the total curve fits for each sample. FIG. 62B is a graph showing the % $NR_4^+$ relative to urethane N is shown for UV-treated and phys. ads. samples modified with the Qx-SH series. XPS measurements were taken on three separate batches of allyl-TPU blade-coated samples and the averages with standard deviations are displayed. Statistical significance is indicated by *, , and * with p values <0.05 between UV-treated and phys. ads. samples for each Qx-SH compound.

Figure 63A:
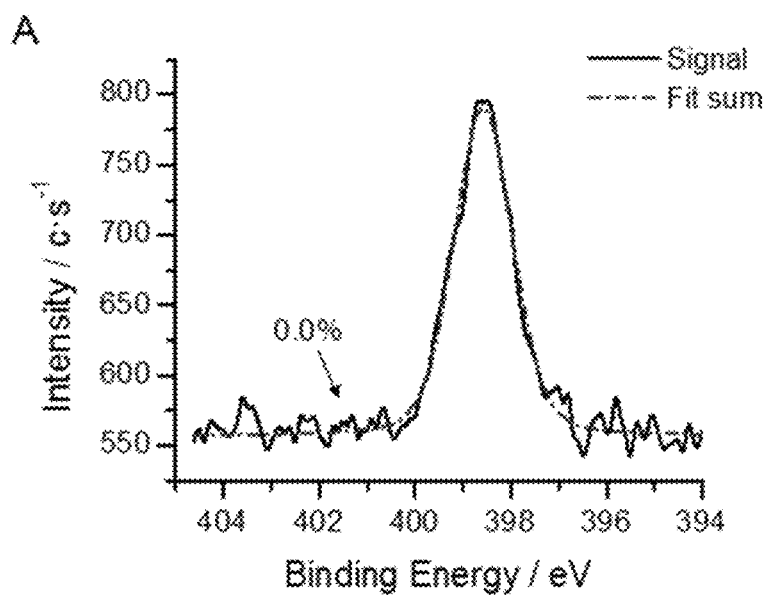
Figure 63B:
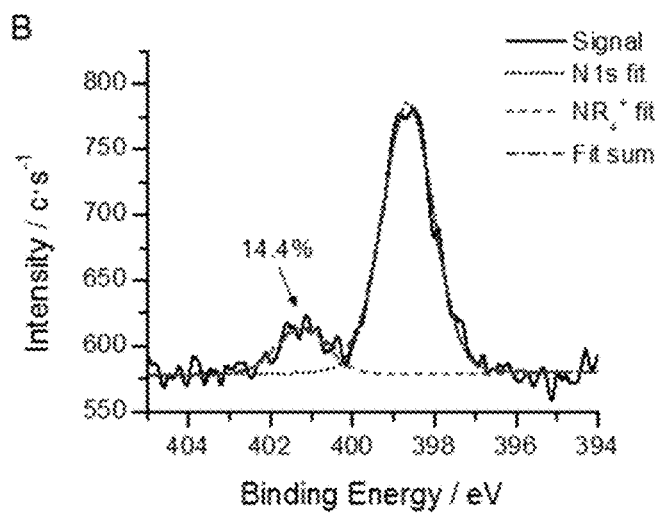

FIG. 63 is a high resolution N1s XPS spectra of inner lumen of (FIG. 63A) phys. ads. and UV treated catheter prototype (longitudinal sections) (FIG. 63B). The raw data is interpolated with a cubic b-spline (solid lines) and the individual fits of the N, $NR_4^+$, and total fit are represented by dashed lines. The phys. ads. control did not exhibit QACs on the surface, while the UV treated sample contained 14.4% $NR_4^+$ relative to urethane N following modification with Q8-SH.

Figure 64:
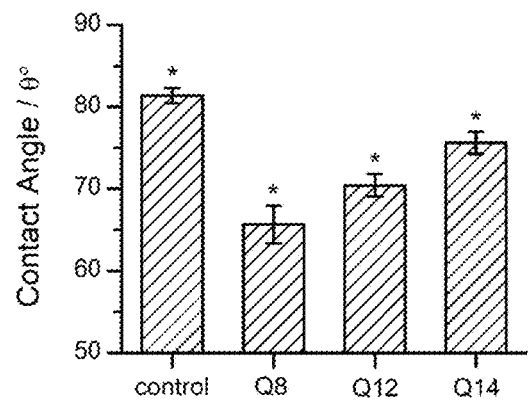

FIG. 64 is a graph showing contact angle data for UV-treated blade-coated samples modified with Qx-SH series. Statistical significance is indicated by * with p values <0.05 (tukey post-hoc).

Figure 65:
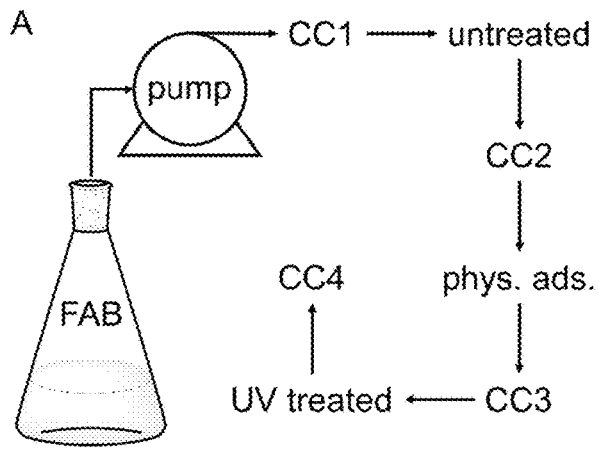

FIG. 65 is a schematic diagram of the biofilm formation test, displaying the upstream to downstream ordering of catheter segments (CC=COOK™ BEACON™ TIP TORCON NB™ Advantage Catheter segments). The catheters were inoculated for 2 h with $P.$ $aeruginosa$ ($OD_{600}$=0.1) in TSB followed by 48 h of FAB media flowing at 1.5 mL·min$^{-1}$.

Figure 66A:
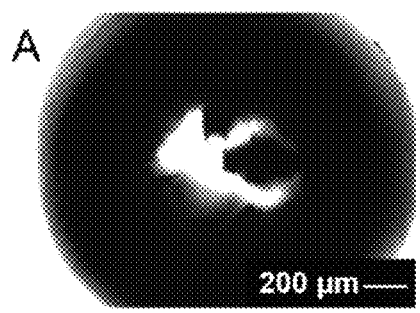
Figure 66B:
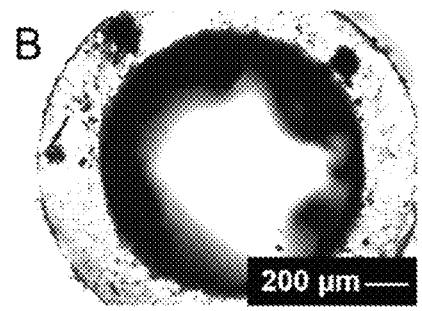
Figure 66C:
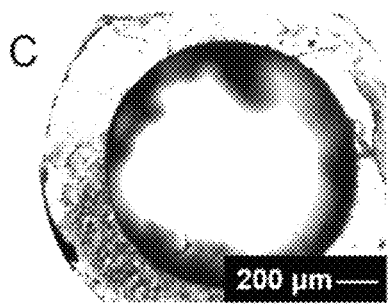
Figure 66D:
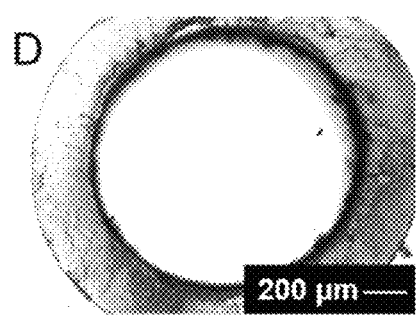
Figure 66E:
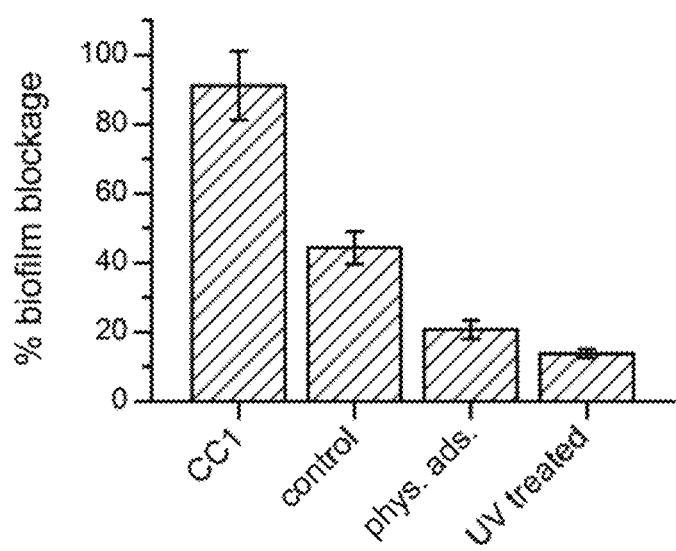
Figure 66F:
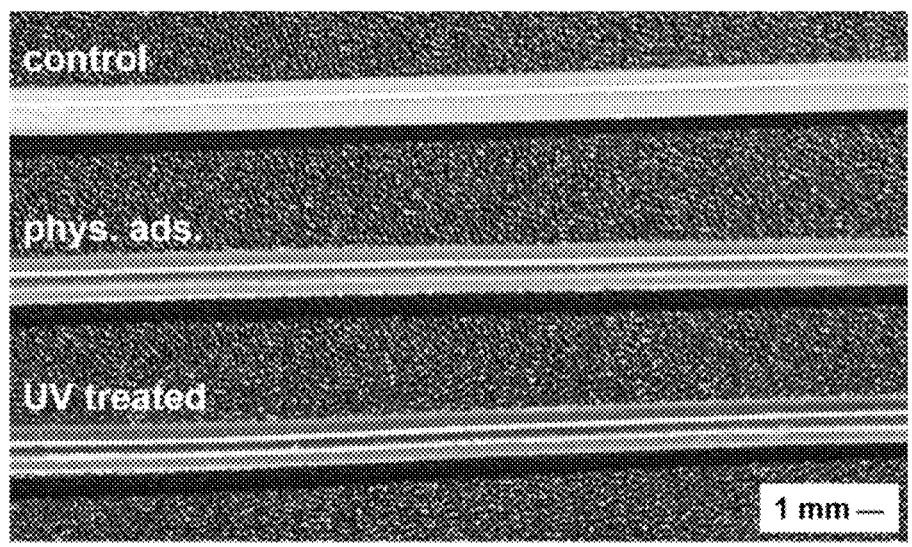
Figure 67A:
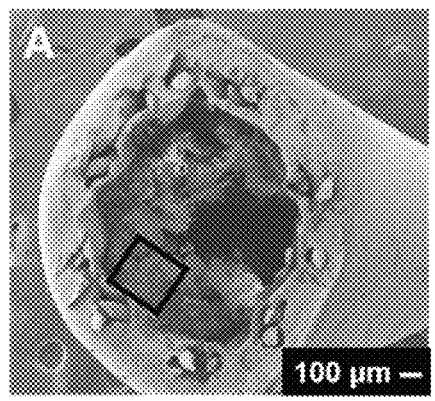
Figure 67B:
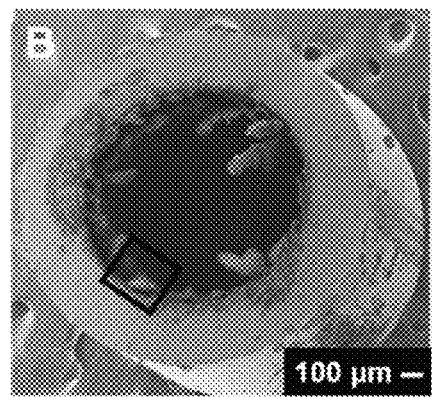
Figure 67C:
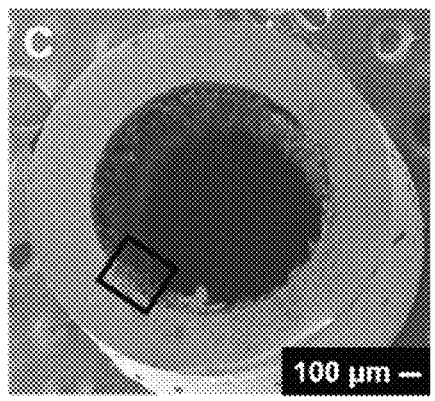
Figure 67D:
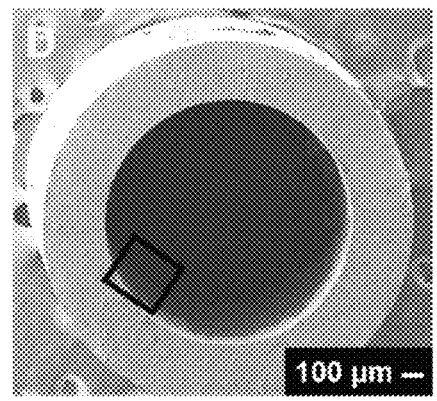
Figure 67E:
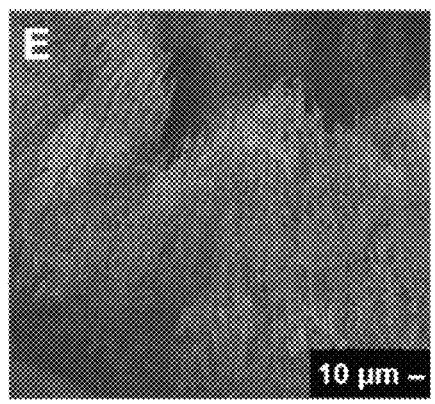
Figure 67F:
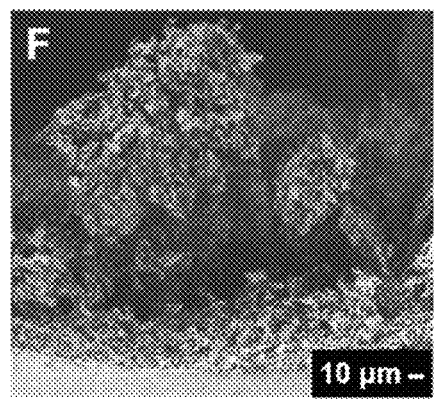
Figure 67G:
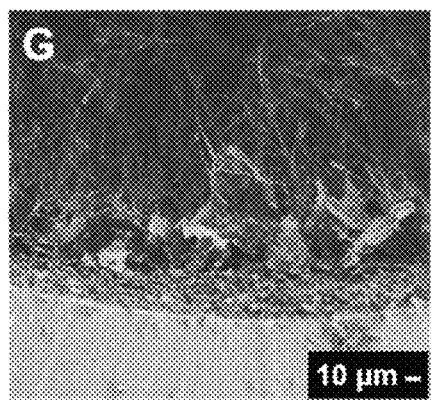
Figure 67H:
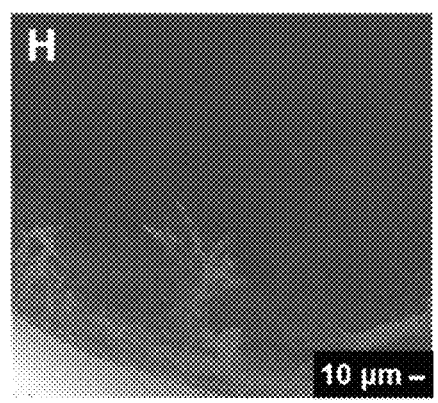

FIGS. 66A-F are brightfield microscopy images of catheter cross-sections (3.0 mm segments) from the 48 h biofilm assay were taken for (FIG. 66A) CC1, (FIG. 66B) untreated control, (FIG. 66C) phys. ads., and (FIG. 66D) UV-treated samples modified with Q8-SH; FIG. 66E) is a graphs showing the % biofilm blockage as determined using Olympus VS-Desktop software and displaying the averages and standard deviations (n=3); and (FIG. 66F) is a photograph of the untreated control, phys. ads., and UV-treated catheters following completion of the 48 h biofilm assay.

FIGS. 67A-H are SEM images demonstrating the appearance of bacterial EPS on catheter cross-sections from the 48 h biofilm assay were taken for (FIG. 67A) CC1, (FIG. 67B) untreated control, (FIG. 67C) phys. ads., and (FIG. 67D) UV-treated samples modified with Q8-SH at 45× and (FIGS. 67E-H) at 300× magnification, respectively.

Figure 68:
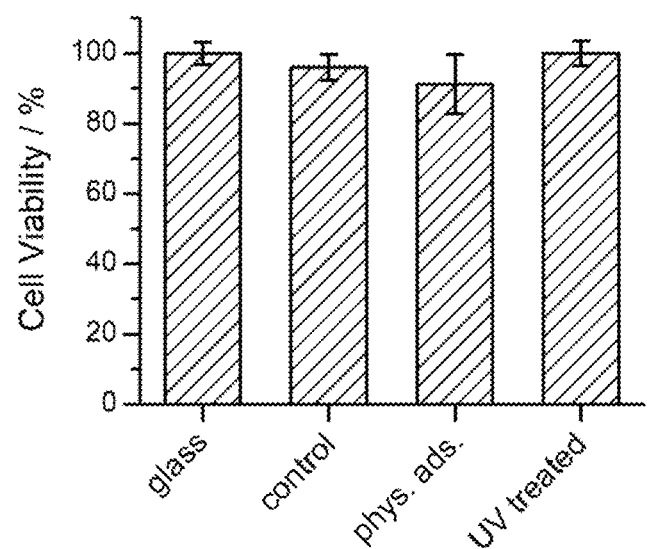

FIG. 68 is a graphs showing the results of cell viability assays using NIH/3T3 fibroblast cells performed on control, phys. ads. and UV-treated samples modified with Q8-SH, and compared to a glass slide control. The results indicate that the allyl-TPU and Q8-SH treated samples are non-cytotoxic towards mammalian cells.

DETAILED DESCRIPTION OF THE ILLUSTRATIVE EMBODIMENTS

In one or more embodiments, the present invention provide a commercially relevant functionalized TPU containing QACs throughout the backbone or surface-grafted post-processing for contact-killing activity towards a variety of microbes where the QACs are available at the surface of TPU to provide a sterile surface material that prevents bacteria commonly involved in DAIs from proliferating. The functionalized TPUs of the present invention can be formed into a wide variety of 3-dimensional shapes, such as catheters, medical tubing, laryngeal or tracheal stents, sutures, prosthetics, wound dressings, and/or a coating for medical devices. These TPUs contain either a QAC monomer, or are functionalized with an alkene (allyl) or other functional group that allows the TPU to be functionalized with a QAC containing disulfide or free thiol compound to form the quaternary ammonium functionalized TPU compound of the present invention.

In various embodiments, the quaternary ammonium functionalized TPU compound of the present invention are constructed in much the same fashion as a conventional TPU in that it will be the reaction product of one or more diisocyanates, one or more short chain diol chain extenders (chain extenders), and one or more longer chain diols (soft segment diols) and, as a result, will comprise the residues of those diisocyanates, chain extenders, and soft segment diols. In the present invention, however, one or more functionalized diols that contain either an antimicrobial QAC or an alkene (allyl) or other functional group (functionalized diols) are added to the TPU in place of some portion of the short chain diol chain extenders and, as a result, the quaternary ammonium functionalized TPU compounds of the present invention will contain residues of these functionalized diols. As will be apparent, these functionalized diols are incorporated in the backbone of the TPU during polymerization and the antimicrobial QAC or an alkene (allyl) or other functional groups on these functional diol residues will form side chains extending out from the TPU backbone.

As used herein, the term "residue(s)" is used to refer generally to the part of a monomer or other chemical unit that has been incorporated into a polymer or large molecule. By extension, the terms "residue of the short chain diol chain extender," "short chain diol chain extender residues," "chain extender residues" all refer to the portion of the short chain diol chain extenders that have been incorporated into the TPU polymer during polymerization; the terms "diisocyanate residue" and "the residues of one or more diisocyanates" both refer to the portion of the one or more diisocyanate monomers that have been incorporated into the TPU polymer during polymerization; the terms "the residue(s) of one or more long chain soft segment diols," "the residue(s) of one or more soft segment diols," "soft segment diol residues" and "long chain diol residue" all refer to the portion of the one or more long chain soft segment diols monomers that have been incorporated into the TPU polymer during polymerization; and the terms "residue(s) of the one or more functionalized diols," "functionalized diol residue(s)" refer to the portion of the one or more functionalized diol monomers that have been incorporated into the TPU polymer during polymerization.

Accordingly, in some embodiments, the functionalized TPUs of the present invention are the reaction product of one or more diisocyanates, one or more short chain diol chain extenders, one or more QAC functionalized diols and one or more longer chain (soft segment) diols, in which case the functionalized TPUs will have QAC containing side chains throughout the bulk of the polymer without further functionalization. In some other embodiments, however, the functionalized TPUs of the present invention are instead formed as the reaction product of one or more diisocyanates, one or more short chain diol chain extenders, and one or more longer chain (soft segment) diols and one or more alkene (allyl) functionalized diols, in which case the functionalized TPUs will have alkene (allyl) functionalized side chains throughout the bulk (and on the surface) of the polymer. These embodiments, the polymer may then be processed into a desired shape or configuration, such as a catheter, and then reacted with a QAC functionalized disulfide or thiol compound to add the QAC to the allyl functionalized side chains on the surface of the processed polymer having alkene (allyl) groups available for bonding.

The terms "quaternary ammonium (QA)," "quaternary ammonium ion," "antimicrobial quaternary ammonium ion," "quaternary ammonium moiety," and "antimicrobial quaternary ammonium moiety" are all used interchangeably to refer to a positively charged nitrogen atom having four alkyl or aryl groups bonded to it. Accordingly, the term quaternary ammonium compound (QAC) is used herein to refer to a chemical compound containing a quaternary ammonium functional group, as defined above.

Further, as used herein, the terms "functional group" and "functional moiety" are used interchangeably to refer a chemically active species or a group containing a chemically active species. The term "quaternary ammonium functional group," "antimicrobial quaternary ammonium functional group," "QA functional group," and "QAC functional group" are all used herein interchangeably to refer to a group containing a quaternary ammonium moiety, as defined above. The terms "allyl functional group" and "alkene functional group" are used interchangeably herein to refer to a group containing a chemically active terminal carbon to carbon double bond. The alkene functional group is preferably an allyl group, but is not limited thereto and may be any alkene, including, without limitation, allylic alkenes, vinyl alkenes, internal alkenes, cyclic alkenes (e.g. norbornene), provided that they can be incorporated into a diol which is readily polymerizable with diisocyanates. As follows, the term "functionalized" refers to a monomer, polymer, chemical compound, or other substance that includes, or has been modified to include, a functional group and the broader term "functionalization" refers to a process, method and/or reaction whereby a functional group is added to a monomer, polymer, chemical compound, or other substance.

Accordingly, the terms "quaternary ammonium functionalized TPU," "quaternary ammonium functionalized TPU compound," "QAC functionalized TPU compound," "quaternary ammonium functionalized thermoplastic polyurethane compound(s)" are all used to refer to a thermoplastic polyurethane (TPU) that includes, or has been modified to include, a quaternary ammonium functional group, as defined above. Similarly, the terms "allyl-functionalized TPU," and "allyl functionalized polyurethane polymer" are used herein to refer to a thermoplastic polyurethane (TPU) that includes, or has been modified to include, an allyl functional group, as defined above. As used herein, the term "alloc-TPU" refers to a allyl-functionalized TPU, as defined above, comprising the residue of a 3-allyloxy-1,2-propanediol ("alloc") monomer, which provides the allyl functional group.

The term "functionalized diol" broadly refers to a diol monomer that includes, or has been modified to include, a functional group, as defined above, and in particular to a diol monomer that contains, or has been functionalized to contain, a QAC functional group or an ally functional group as defined above. Accordingly, the terms "alkene (allyl) functionalized diol," "alloc functionalized diol" and "allyl functionalized diol" are used herein interchangeably to refer to a diol monomer that contains, or has been functionalized to contain, an ally functional group, as defined above, and the terms "QAC functionalized diols," "QA functionalized diols," are "quaternary ammonium functionalized diols" are used herein interchangeably to refer to a diol monomer that contains, or has been functionalized to contain, a QAC functional group, as defined above. Similarly, the terms "QAC functionalized disulfide," "QA functionalized disulfide," "bi-quaternary ammonium functionalized disulfide compound" are all used herein interchangeably to refer to a disulfide compound that contains, or has been functionalized to contain, two QAC functional groups and terms "QAC functionalized thiol," "QA functionalized thiol," "quaternary ammonium functionalized thiol compound," "quaternary ammonium functionalized thiol" are all used herein interchangeably to refer to a thiol compound that contains, or has been functionalized to contain, a QAC functional group.

As used herein, the terms "TPU polymer backbone," "urethane polymer backbone," and "polyurethane polymer backbone" all refer the longest series of covalently bonded atoms in the TPU polymer that together create the continuous chain of the molecule. As follows, the term "functionalized polyurethane polymer backbone" refers to a polyurethane polymer backbone that includes, or has been modified to include, a functional group, as defined above and the term "allyl functionalized polyurethane polymer backbone" refers to a polyurethane polymer backbone that includes, or has been modified to include, an allyl functional group, as defined above.

As used herein, the term "side chain" refers to a chain of atoms attached to and extending outwardly from the TPU polymer backbone. As follows, the terms "QAC containing side chains" and "antimicrobial quaternary ammonium ion side chains" are used herein interchangeably to refer to chains of atoms attached to and extending outwardly from the TPU polymer backbone that contain a QAC functional group and the terms "allyl functionalized side chains," "alkene functionalized side chains," and "alkene (allyl) functionalized side chains," are used herein interchangeably to refer to chains of atoms attached to and extending outwardly from the TPU polymer backbone that contain an alkene functional group as defined above. As follows, the term "alloc-functionalized side chains," as used herein, refers to allyl functionalized side chains, as defined above, refers to side chains extending outwardly from the TPU polymer backbone that contain an allyl functional group as defined above afforded by the residue of a 3-allyloxy-1,2-propanediol (alloc)monomer.

In a first aspect the present invention is directed to a quaternary ammonium functionalized thermoplastic polyurethane compound having antimicrobial properties for use in medical devices comprising: a polyurethane polymer backbone having one or more side chains that contain either a quaternary ammonium ion or an alkene (allyl) or other functional group that allows for functionalization with a quaternary ammonium ion post-processing. As used herein, the term "antimicrobial" refers to molecules and/or compositions that kill (i.e., microbicidal), inhibit the growth of (i.e., microbistatic), and/or prevent fouling by, microorganisms including, but not limited to, bacteria, yeast, fungi, *mycoplasma*, viruses or virus infected cells, and/or protozoa. As follows, the term "antimicrobial properties" is used herein to refer to the ability of a molecule and/or composition to kill (i.e., microbicidal), inhibit the growth of (i.e., microbistatic), and/or prevent fouling by, microorganisms including, but not limited to, bacteria, yeast, fungi, *mycoplasma*, viruses or virus infected cells, and/or protozoa.

In various embodiments, the polyurethane polymer backbone will, as set forth above, comprise the residues of one or more diisocyanates, one or more soft segment diols, one or more functionalized diols, and one or more chain extenders.

The polyurethane polymer backbone will, as set forth above, comprise the residues of one or more diisocyanates.

The diisocyanates used to form the polyurethane polymer backbone are not particularly limited, and any conventional diisocyanate used in the art for forming TPUs may be used provided that it does not impart water-solubility to the resulting polyurethane or disrupt the crystallinity of the resulting polyurethane to an extent which limits its ability to be thermally processed (using standard industrial practices and within a reasonable time frame). In one or more embodiment, the diisocyanate residue may be the residue of any diisocyanate conventionally used in the synthesis of polyurethanes including, without limitation, diisocyanates are selected from the group consisting of 4,4'-methylenebis (phenyl isocyanate) (MDI), 4,4'-methylenebis(cyclohexyl isocyanate) (HMDI), isophorone diisocyanate, toluene diisocyanate (TDI), 1,3-bis(isocyanatomethyl)cyclohexane, 1,4-diisocyanatobutane, hexamethylene diisocyanate, 1,8-diisocyanatooctone, 1,12-diisocyanatododecane, and/or combinations thereof. In one or more of these embodiments, the diisocyanate residue may be the residue of HDMI.

In one or more embodiments, these diisocyanate residues may comprise from about 1 to about 80 weight percent (wt %) of the polyurethane polymer backbone. In some embodiments, these diisocyanate residues will comprise 10 wt % or more, in other embodiments 20 wt % or more, in other embodiments 30 wt % or more, in other embodiments 40 wt % or more, in other embodiments 50 wt % or more, and in other embodiments 60 wt % or more of the polyurethane polymer backbone. In some embodiments, these diisocyanate residues will comprise 70 wt % or less, in other embodiments 60 wt % or less, in other embodiments 50 wt % or less, in other embodiments 40 wt % or less, in other embodiments 30 wt % or less, and in other embodiments 20 wt % or less of the polyurethane polymer backbone. Here, as well as elsewhere in the specification and claims, individual range values can be combined to form additional non-disclosed ranges.

The polyurethane polymer backbone will, as set forth above, comprise the residues of one or more short chain diol chain extenders. As used herein, the term "short chain diol chain extender" or "chain extenders" refers to a relatively short diol comprising two hydroxyl groups separated by from about 2 to about 50 carbon, oxygen or nitrogen atoms and having a number average molecular weight ($M_n$) of from about 60 g/mol to 750 g/mol.

In one or more embodiments, the short chain diol chain extenders may comprise two hydroxyl groups separated by from about 2 to about 20 carbon, oxygen or nitrogen atoms. In some embodiments, the short chain diol chain extenders may comprise two hydroxyl groups separated by from about 2 to about 18, in other embodiments, from about 2 to about 14, in other embodiments, from about 2 to about 10, in other embodiments, from about 2 to about 6, in other embodiments, from about 4 to about 20, in other embodiments, from about 8 to about 20, in other embodiments, from about 12 to about 20, and in other embodiments, from about 15 to about 20 carbon, oxygen, or nitrogen atoms. In some embodiments, the short chain diol chain extenders may have a number average molecular weight ($M_n$) of from about 100 g/mol to 750 g/mol, in other embodiments, from about 200 g/mol to about 750 g/mol, in other embodiments, from about 300 g/mol to about 750 g/mol, in other embodiments, from about 300 g/mol to about 750 g/mol, in other embodiments, from about 400 g/mol to about 750 g/mol, in other embodiments, from about 60 g/mol to about 650 g/mol, in other embodiments, from about 60 g/mol to about 450 g/mol, in other embodiments, from about 60 g/mol to about 350 g/mol and in other embodiments, from about 60 g/mol to about 250 g/mol. Here, as well as elsewhere in the specification and claims, individual range values can be combined to form additional non-disclosed ranges.

The short chain diol chain extenders used to form the polyurethane polymer backbone are not particularly limited, and any conventional short chain diol chain extenders used in the art for forming TPUs may be used provided that it does not disrupt the crystallinity of the resulting polyurethane to an extent which limits its ability to be thermally processed (using standard industrial practices and within a reasonable time frame). Suitable short chain diol chain extenders may include, without limitation, 1,3-propanediol, 1,4-butanediol (BDO), 1,5-pentanediol, 1,6-hexanediol, 1,7-heptanediol, 1,8-octanediol, 1,9-nonanediol, 1,10-decanediol, 1,12-dodecanediol, 1,14-tetradecanediol, ethylene glycol, polyethylene glycol (up to 750 g/mol), 2,2,3,3,4,4,5,5-Octafluoro-1,6-hexanediol, polypropylene glycol (up to 750 g/mol). In one or more embodiment, the short chain diol chain extender is 1,4-butanediol (BDO).

In some embodiments, the short chain diol chain extenders comprise from about 0.1 to about 80 mole percent of the functionalized polyurethane polymer backbone. In some embodiments, these short chain diol chain extenders will comprise 10 wt % or more, in other embodiments 20 wt % or more, in other embodiments 30 wt % or more, in other embodiments 40 wt % or more, in other embodiments 50 wt % or more, and in other embodiments 60 wt % or more of the polyurethane polymer backbone. In some embodiments, these short chain diol chain extenders will comprise 70 wt % or less, in other embodiments 60 wt % or less, in other embodiments 50 wt % or less, in other embodiments 40 wt % or less, in other embodiments 30 wt % or less, and in other embodiments 20 wt % or less of the polyurethane polymer backbone. Here, as well as elsewhere in the specification and claims, individual range values can be combined to form additional non-disclosed ranges.

The polyurethane polymer backbone will, as set forth above, also comprise the residues of one or more long chain soft segment diols. As used herein, the terms "long chain soft segment diols" or "soft segment diols" are used interchangeably to refer to a longer chain diols comprising two hydroxyl groups separated more than 50 carbon, oxygen or nitrogen atoms and/or having a number average molecular weight of 750 g/mol or more. In one or more embodiments, long chain soft segment diols may comprise from about 51 to about 4,170 carbon, oxygen or nitrogen atoms and have a number average molecular weight of from about 750 g/mol to 50,000 g/mol. Here, as well as elsewhere in the specification and claims, individual range values can be combined to form additional non-disclosed ranges.

In some embodiments, the long chain soft segment diols comprise two hydroxyl groups separated by from about 51 to about 3,100, in other embodiments, from about 51 to about 2,000, in other embodiments, from about 51 to about 1,500, in other embodiments, from about 51 to about 1,000, in other embodiments, from about 51 to about 500, in other embodiments, from about 51 to about 250, in other embodiments, from about 100 to about 4,000, in other embodiments, from about 250 to about 4,000, in other embodiments, from about 500 to about 4,000, in other embodiments, from about 1,000 to about 4,000, in other embodiments, from about 2,000 to about 4,000, and in other embodiments, from about 3,000 to about 4,000 carbon, oxygen, or nitrogen atoms. In some embodiments, the long chain diols comprise two hydroxyl groups separated by from about 50 to about 1000 carbon, oxygen, or nitrogen atoms. In some embodiments, the long chain diols comprise two hydroxyl groups separated by from about 50 to about 500 carbon, oxygen, or nitrogen atoms. Here, as well as elsewhere in the specification and claims, individual range values can be combined to form additional non-disclosed ranges.

In some embodiments, the long chain soft segment diols may have a number average molecular weight ($M_n$) of from about 750 g/mol to 40,000 g/mol, in other embodiments, from about 750 g/mol to about 30,000 g/mol, in other embodiments, from about 750 g/mol to about 20,000 g/mol, in other embodiments, from about 750 g/mol to about 10,000 g/mol, in other embodiments, from about 750 g/mol to about 5,000 g/mol, in other embodiments, from about 60 g/mol to about 50,000 g/mol, in other embodiments, from about 10,000 g/mol to about 50,000 g/mol, in other embodiments, from about 20,000 g/mol to about 50,000 g/mol and in other embodiments, from about 30,000 g/mol to about 50,000 g/mol. In one or more embodiments, the long chain diol chain extender comprises poly(propylene oxide-co-ethylene oxide). In some embodiments, the long chain diol soft segments comprise a linear polyether having a molecular weight of from about 750 g/mol to about 50,000 g/mol. In some other embodiments, the long chain diol soft segments comprise a linear polyether having a molecular weight of from about 750 g/mol to about 5,000 g/mol. Here, as well as elsewhere in the specification and claims, individual range values can be combined to form additional non-disclosed ranges.

The long chain soft segment diols used to form the polyurethane polymer backbone are not particularly limited, and any be conventional long chain diol known in the art for forming TPUs may be used provided that it does not degrade rapidly when implanted in patient, and it does not impart water-solubility to the resulting polyurethane. In various embodiments, the long chain diol soft segments may comprise polyester diols, polycarbonate diols, polyether diols, polysiloxanes, polyethylene, polypropylene, polytetrafluoroethylene, poly(propylene-co-ethylene glycol) or combinations thereof. Suitable long chain diol soft segments may include, without limitation, ARCOL™ polyether polyols, DESMOPHEN™ polyols, ACCLAIM™ polyether polyol, HYPERLITE™ polyols, SOFTCEL™ polyether polyols, ULTRACEL™ polyether polyols, VORANOL™ polyether polyols, CARADOL™ polyols, polydimethylsiloxane (hydroxy terminated), polyethylene glycol (hydroxy terminated), polypropylene glycol (hydroxy terminated), poly (propylene-co-ethylene glycol). In some embodiments, the long chain diol will comprise Arcol E-351™ polyol (Covestro, AG).

In one or more embodiments, the residues of the long chain diol soft segment comprise from about 1 to about 50 mole percent of the functionalized polyurethane polymer backbone. In some embodiments, the residues of the long chain diol soft segment comprise from about 2 to about 50, in other embodiments, from 5 to 50, in other embodiments, from 10 to 50, in other embodiments, from 20 to 50, in other embodiments, from 30 to 50, in other embodiments, from 5 to 40, in other embodiments, from 5 to 30, in other embodiments, from 5 to 20, and in other embodiments, from 5 to 10 mole percent of the functionalized polyurethane polymer backbone. Here, as well as elsewhere in the specification and claims, individual range values can be combined to form additional non-disclosed ranges.

As set forth above, the QAC functionalized TPU polymers of the present invention will include the residue of one or more functionalized diol monomers containing either a antimicrobial QAC or an alkene (allyl) or other functional group. As will be apparent to those of skill in the art, in some embodiments, the functionalized diol residues in the polyurethane polymer backbone will be formed when functionalized diol monomers containing one or more functionalized side chains are incorporated into the polyurethane polymer backbone during formation of the polyurethane. In various embodiments, these functionalized diol residues are residues of functionalized diol compounds having two hydroxyl groups separated by a chain of from 2 to 200 carbon, nitrogen or oxygen atoms, and will have at least one functional group. In some of these embodiments, the two hydroxyl groups will be separated by a chain of from about 10 to about 200, in other embodiments, from about 25 to about 200, in other embodiments, from about 50 to about 200, in other embodiments, from about 75 to about 200, in other embodiments, from about 100 to about 200, in other embodiments, from about 125 to about 175, in other embodiments, from about 150 to about 200, in other embodiments, from about 2 to about 150, in other embodiments, from about 2 to about 100, and in other embodiments, from about 2 to about 50, carbon, nitrogen or oxygen atoms. Here, as well as elsewhere in the specification and claims, individual range values can be combined to form additional non-disclosed ranges.

As set forth above, in various embodiments these functionalized diol residues will comprise functionalized side chains having a quaternary ammonium moiety or an allyl functional group. As will be apparent, TPU polymers made with QAC functionalized diols will have QAC containing side chains and TPU polymers made with allyl functionalized diols will have allyl functionalized side chains. As will also be apparent, because the QAC and allyl functional groups are added through the QAC functionalized diols prior to polymerization, the QAC containing side chains and allyl functionalized side chains will be distributed throughout the TPU polymer. While this does not create an issue with the TPUs having allyl functionalized side chains, since the QAC functional groups are added later, a significant amount of the QAC functional groups may be sequestered within the polymer and unavailable for antimicrobial purposes.

In one or more of these embodiments, suitable QAC functionalized diols may include, without limitation, synthetic adducts via reaction of a tertiary amine-containing diols with aliphatic residues containing primary bromine or chlorine atoms such as the quaternary ammonium adduct of N-methyldiethanolamine and 1-chlorotetradecane. In one or more embodiments, suitable functionalized diols may include, without limitation, synthetic adducts via reaction of a bromine or chlorine-containing diols with aliphatic tertiary amines such as the quaternary ammonium adduct of 3-chloro-1,2-propanediol with N,N-dimethyltetradecylamine. The bromine or chlorine-containing diols may be selected from the following without limitation including 2-chloromethyl-2-methyl-1,3-propanediol, 3-bromo-1,2-propanediol, 3-chloro-1,2-propanediol, 2,2-bis-chloromethyl-propane-1,3-diol, 2,2-bis(bromomethyl)-1,3-propanediol, and the aliphatic tertiary amines may include without limitation trimethylamine, N,N-dimethylethylamine, N,N-dimethylpropylamine, N,N-dimethylbutylamine, N,N-dimethylhexylamine, N,N-dimethyloctylamine, N,N-dimethyldecylamine, N,N-dimethyldodecylamine, N,N-dimethyltetradecylamine, N,N-dimethylhexadecylamine, N,N-dimethyloctadecylamine, N-methyldibutylamine, N-methyldihexylamine, N-methyldioctylamine, N-methyldidodecylamine, N-methyl, ditetradecylamine, dibutyltetradecylamine and combinations thereof.

In one or more embodiments, the functionalized diol residues may be residues of one or more diols having the formula:

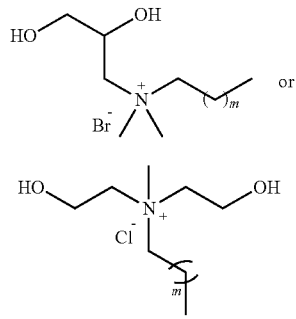

where m is an integer from about 1 to about 20.

In one or more of these embodiments, the quaternary ammonium functionalized thermoplastic polyurethane compound of the present invention may have the formula:

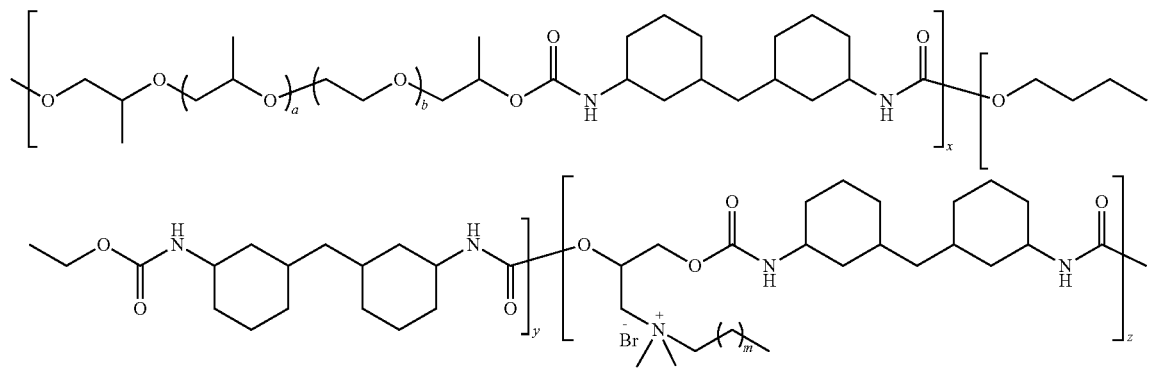

where a is an integer from 2 to 50; b is an integer from 2 to 50; x is a mole fraction from 0.01 to 0.8; y is a mole fraction from 0.01 to 0.8; and z is a mole fraction ranging from 0.01 to 0.8; and the sum of x, y, and z is equal to 1.

In some of these embodiments, a is an integer from about 2 to about 45, in other embodiments from about 2 to about 40, in other embodiments from about 2 to about 35, in other embodiments from about 2 to about 30, in other embodiments from about 2 to about 20, in other embodiments from about 10 to about 50, in other embodiments from about 20 to about 50, in other embodiments from about 30 to about 50, and in other embodiments from about 40 to about 50. In some of these embodiments, b is an integer from about 2 to about 45, in other embodiments from about 2 to about 40, in other embodiments from about 2 to about 35, in other embodiments from about 2 to about 30, in other embodiments from about 2 to about 20, in other embodiments from about 10 to about 50, in other embodiments from about 20 to about 50, in other embodiments from about 30 to about 50, and in other embodiments from about 40 to about 50. Here, as well as elsewhere in the specification and claims, individual range values can be combined to form additional non-disclosed ranges.

In some of these embodiments, x is a mole fraction of from about 0.01 to about 0.7, in other embodiments, from about 0.01 to about 0.6, in other embodiments, from about 0.01 to about 0.4, in other embodiments, from about 0.01 to about 0.2, in other embodiments, from about 0.01 to about 0.1, in other embodiments, from about 0.1 to about 0.8, in other embodiments, from about 0.2 to about 0.8, in other embodiments, from about 0.3 to about 0.8, and in other embodiments, from about 0.5 to about 0.8. In some of these embodiments, y is a mole fraction of from about 0.01 to about 0.7, in other embodiments, from about 0.01 to about 0.6, in other embodiments, from about 0.01 to about 0.4, in other embodiments, from about 0.01 to about 0.2, in other embodiments, from about 0.01 to about 0.1, in other embodiments, from about 0.1 to about 0.8, in other embodiments, from about 0.2 to about 0.8, in other embodiments, from about 0.3 to about 0.8, and in other embodiments, from about 0.5 to about 0.8. In some of these embodiments, z is a mole fraction of from about 0.01 to about 0.7, in other embodiments, from about 0.01 to about 0.6, in other embodiments, from about 0.01 to about 0.4, in other embodiments, from about 0.01 to about 0.2, in other embodiments, from about 0.01 to about 0.1, in other embodiments, from about 0.1 to about 0.8, in other embodiments, from about 0.2 to about 0.8, in other embodiments, from about 0.3 to about 0.8, and in other embodiments, from about 0.5 to about 0.8. Here, as well as elsewhere in the specification and claims, individual range values can be combined to form additional non-disclosed ranges.

As set forth above, in some other embodiments, the antimicrobial quaternary ammonium moiety of the functionalized thermoplastic polyurethane of the present invention is added after formation of the polyurethane. This allows the TPU to be formed into a desired shape, such as a catheter, without concern of damaging the QAC functional groups and avoids sequestration of QAC functional groups within the polymer as happens using QAC functionalized diols, as described above.

In these embodiments, a functionalized diol will contain at least one side chain that will: (1) survive polymerization into the polyurethane polymer backbone; and (2) will contain at least one functional group to which the antimicrobial quaternary ammonium moiety can later be added. These functional groups are not particularly limited, but are preferably functional groups capable of bonding using a "click" reaction. As used herein, the terms "click reaction," "click chemistry," "click chemistry methods," and "click chemistry reactions," are used interchangeably to refer to a group of orthogonal conjugation reactions, generally referred to in the art as "click" reactions, that fulfill the following prerequisites: (i) high yield, nearly quantitative conversion; (ii) biologically benign conditions (aqueous solution, ambient temperature, and near physiologic pH); (iii) limited or no residual byproduct and include at least the following known types of reactions: copper (I) catalyzed azide-alkyne cycloaddition (CuAAC) reactions (a.k.a. Huisgen cycloaddition reactions), thiol-ene radical addition reactions, oxime ligation reactions, Michael-addition reactions, thiol-Michael-addition reactions, Mannich-type addition reactions, "ene-type" addition reactions, thiol-ene radical addition, strain promoted azide-alkyne cycloaddition (SPAAC) reactions, non-traceless Staudinger ligation, traceless Staudinger ligation, Diels-Alder reactions, hetero Diels-Alder reactions, inverse electron demand Diels-Alder reactions, tandem [3+2] cycloaddition-retro-Diels-Alder (tandem crD-A) reactions, thiol-alkyne reactions, thiol-pyridyl disulfide reactions, and thiol-halogen ligation. Similarly, the term "clickable" refers to a molecule or functional group capable of bonding via a click reaction. In one or more embodiments, "clickable" moieties may include, without limitation, alkyne groups, alkene groups, azide groups, ketones or strained cyclooctyne groups.

Suitable functional groups for use in adding the antimicrobial quaternary ammonium moiety may include without limitation, allyl groups, alkene groups, alkyne groups, azide groups, ketones or strained cyclooctyne groups, preferably alkene, allyl, or alkyne groups, and most preferably alkene or allyl groups. As set forth above, while allyl groups are the preferred alkene groups, the invention is not limited thereto and any alkene group, including, without limitation, allylic alkenes, vinyl alkenes, internal alkenes, cyclic alkenes (e.g. norbornene), may be used provided that they can be incorporated into a molecule having at least to hydroxyl groups, which is readily polymerizable with diisocyanates. Suitable functionalized diols for use in these embodiments may include, without limitation, trimethylolpropane diallyl ether, 2-methylene-1,3-propanediol, 7-octene-1,2-diol, 5-norbornene-2-endo,3-endo-dimethanol, 5-norbornene-2-exo,3-exo-dimethanol, 5-norbornene-2,2-dimethanol. In some embodiments, the functionalized diol residue may be the residue of an allyl functionalized diol including, without limitation, 3-allyloxy-1,2-propanediol, 2-allyloxy-2-ethyl-1,3-propanediol, 1-(allyloxy)-1,2-propanediol, pentaerythritol allyl ether, trimethylolpropane diallyl ether, trimethylolpropane allyl ether, 1,5-hexadiene-3,4-diol, 2-methylene-1,3-propanediol, 7-octene-1,2-diol, 5-norbornene-2-endo,3-endo-dimethanol, 5-norbornene-2-exo,3-exo-dimethanol, 5-norbornene-2,2-dimethanol, and combinations thereof.

In one or more embodiments, these functionalized diol residues may comprise from about 0.1 to about 90 weight percent (wt %) of the polyurethane polymer backbone. In some embodiments, these functionalized diol residues will comprise 10 wt % or more, in other embodiments 20 wt % or more, in other embodiments 30 wt % or more, in other embodiments 40 wt % or more, in other embodiments 50 wt % or more, and in other embodiments 60 wt % or more of the polyurethane polymer backbone. In some embodiments, these functionalized diol residues will comprise 70 wt % or less, in other embodiments 60 wt % or less, in other embodiments 50 wt % or less, in other embodiments 40 wt % or less, in other embodiments 30 wt % or less, and in other embodiments 20 wt % or less of the polyurethane polymer backbone. Here, as well as elsewhere in the specification and claims, individual range values can be combined to form additional non-disclosed ranges.

In one or more embodiments, the quaternary ammonium functionalized thermoplastic polyurethane compound of the present invention will comprise the residue of an allyl functionalized polyurethane polymer backbone having the formula:

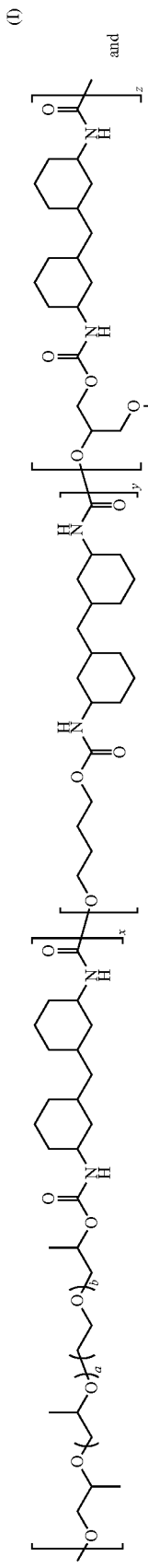
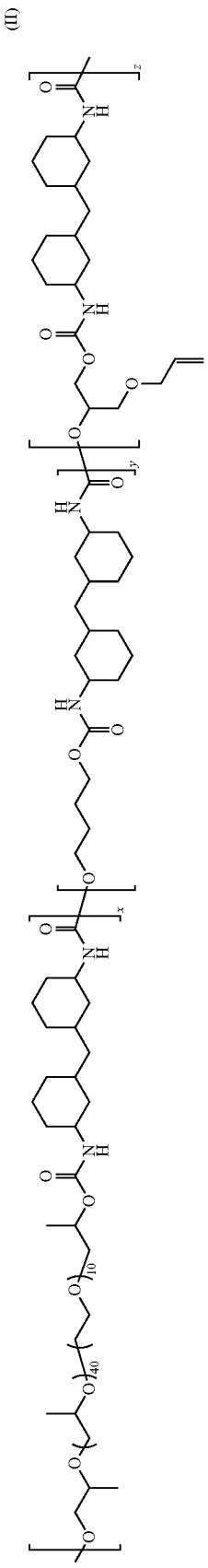

where a is an integer from 2 to 50; b is an integer from 2 to 50; x is a mole fraction from 0.01 to 0.8; y is a mole fraction from 0.01 to 0.8; and z is a mole fraction ranging from 0.01 to 0.8; and the sum of x, y, and z is equal to 1. In various embodiments, a, b, x, y, and z may be as set forth above. Here, as well as elsewhere in the specification and claims, individual range values can be combined to form additional non-disclosed ranges.

As set forth above, the quaternary ammonium functionalized thermoplastic polyurethane compounds of the present invention further includes a plurality of side chains that have a QAC functional group. As set forth above, the QAC functional group will comprise a nitrogen bonded to 4 carbon constituent groups, such as alkyl or aryl groups. In some embodiments, at least one constituent on the nitrogen atom of the QAC functional group will be an alkyl chains having from about 1 to about 18 carbon atoms. As will be apparent, the quaternary ammonium functional groups are connected to the allyl functionalized diol residues in the polyurethane polymer backbone by one of these constituent groups. In some of these embodiments, the other constituents on the nitrogen atom of the QAC functional group will be two methyl groups and an alkyl chains having from about 1 to about 18 carbon atoms (sometimes referred to herein as a "tail").

In various embodiments, there is a spacer in the side chain between the QAC functional group and the polyurethane polymer backbone. In one or more embodiments, the spacer comprises from about 1 to about 20 carbon, oxygen, nitrogen or sulfur atoms. In some embodiments, the spacer will comprises from about 5 to 20, in other embodiments, from 10 to 25, in other embodiments, from 15 to 20, in other embodiments, from 1 to 15, in other embodiments, from 1 to 10, and in other embodiments, from 1 to 5 carbon, oxygen, nitrogen or sulfur atoms.

As will be appreciated by those of skill in the art, the quaternary ammonium functionalized thermoplastic polyurethane compound of the present invention will have a plurality of hard segments comprising the diisocyanate residues described above, residues of the short chain diol chain extenders and residues of the functionalized diols and a plurality of soft segments comprising the residues of one or more long chain soft segment diols, as described above. In one or more embodiments, the hard segments comprise from about 10 to about 70 mole percent of said quaternary ammonium functionalized thermoplastic polyurethane compound. In some embodiments, the hard segments comprise from about 10 mole percent (mol %) to about 70 mol %, in other embodiments, from about 10 mol % to about 50 mol %%, in other embodiments, from about 10 mol % to about 30 mol %, in other embodiments, from about 10 mol % to about 20 mol %%, in other embodiments, from about 20 mol % to about 70 mol %, in other embodiments, from about 40 mol % to about 70 mol %%, and in other embodiments, from about 60 mol % to about 70 mol % of said quaternary ammonium functionalized thermoplastic polyurethane compound.

In some embodiments, the soft segments comprise from about 10 to about 70 mole percent of said quaternary ammonium functionalized thermoplastic polyurethane compound. In some embodiments, the soft segments comprise from about 10 mole percent (mol %) to about 70 mol %, in other embodiments, from about 10 mol % to about 50 mol %%, in other embodiments, from about 10 mol % to about 30 mol %, in other embodiments, from about 10 mol % to about 20 mol %%, in other embodiments, from about 20 mol % to about 70 mol %, in other embodiments, from about 40 mol % to about 70 mol %%, and in other embodiments, from about 60 mol % to about 70 mol % of said quaternary ammonium functionalized thermoplastic polyurethane compound.

In one or more embodiments, the quaternary ammonium functionalized thermoplastic polyurethane compound of the present invention will be the reaction product of an allyl functionalized polyurethane polymer backbone as described above and a disulfide compound containing at least one quaternary ammonium group. In these embodiments, an allyl functionalized polyurethane polymer backbone as described above is synthesized and may then be formed into a desired shape via thermal (extrusion, injection/compression molding) or solvent (electrospinning, blade/spin coating) processing methods.

In some embodiments, the residues of one or more allyl functionalized diols comprises from 0.5 to 50 mole percent of said allyl functionalized polyurethane polymer backbone. In some of these embodiments, the residues of said one or more diisocyanates comprise from about 2 to about 70 mole percent of said allyl functionalized polyurethane polymer backbone. In one or more of these embodiments, the residues of said one or more long chain diols comprise from about 2 to about 70 mole percent of said allyl functionalized polyurethane polymer backbone. In some embodiments, the residues of said one or more long chain diols comprise from about 2 mole percent (mol %) to about 60 mol %, in other embodiments, from about 2 mol % to about 50 mol %%, in other embodiments, from about 2 mol % to about 30 mol %, in other embodiments, from about 2 mol % to about 20 mol %%, in other embodiments, from about 10 mol % to about 70 mol %, in other embodiments, from about 30 mol % to about 70 mol %%, and in other embodiments, from about 50 mol % to about 70 mol % of said allyl functionalized polyurethane polymer backbone.

In some of these embodiments, the allyl functional groups on the polyurethane polymer backbone are reacted with a disulfide compound containing two quaternary ammonium functional groups each connected to the disulfide group by a spacer. As set forth above, the spacer may comprise from about 2 to about 20 carbon, oxygen, nitrogen or sulfur atoms. Suitable disulfide compounds may include, without limitation, 3,3'-dithiodipropionic acid, 4,4'-dithiodibutyric acid, dithiodiglycolic acid, 2-hydroxyethyl disulfide, cystamine dihydrochloride, and/or combinations thereof. In some embodiments, the disulfide compound has a formula selected from:

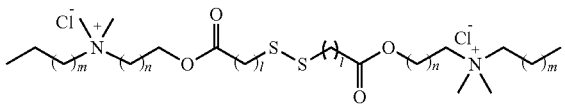

(III)

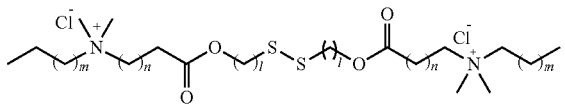

(IV)

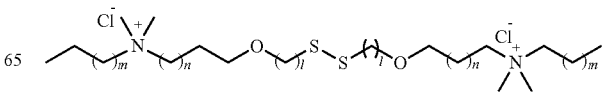

(V)

-continued

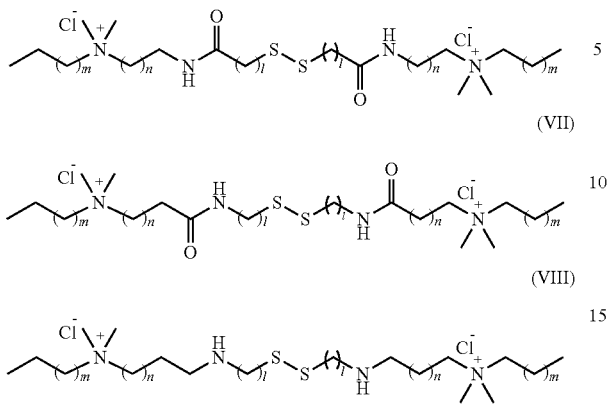

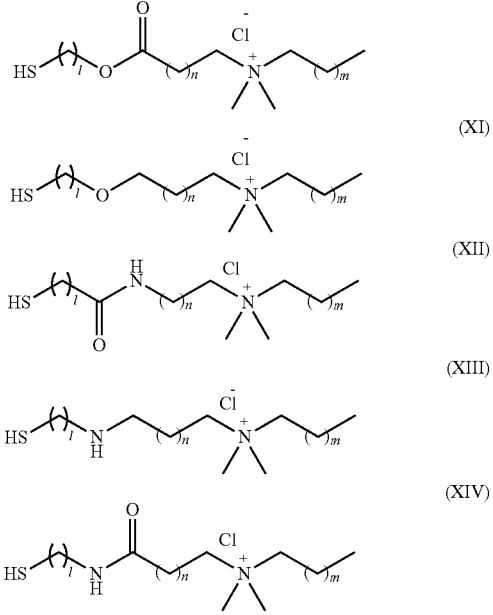

wherein l is an integer from 1 to 4, m is an integer from 1 to 18, and n is an integer from 1 to 19. In various embodiments, l, m, and n are as set forth above. Here, as well as elsewhere in the specification and claims, individual range values can be combined to form additional non-disclosed ranges.

In some embodiments, l is an integer from about 1 to about 3, in other embodiments, from about 1 to about 2, in other embodiments, from about 2 to about 4, and in other embodiments, from about 3 to about 4. In some embodiments, m is an integer from about 1 to about 16, in other embodiments, from about 1 to about 12, in other embodiments, from about 1 to about 10, in other embodiments, from about 1 to about 8, in other embodiments, from about 1 to about 6, in other embodiments, from about 1 to about 4, in other embodiments, from about 2 to about 18, in other embodiments, from about 4 to about 18, in other embodiments, from about 6 to about 14, in other embodiments, from about 10 to about 18, in other embodiments, from about 10 to about 18, and in other embodiments, from about 14 to about 18. In some embodiments, n is an integer from about 2 to about 16, in other embodiments, from about 1 to about 12, in other embodiments, from about 1 to about 8, in other embodiments, from about 1 to about 4, in other embodiments, from about 3 to about 19, in other embodiments, from about 7 to about 13, in other embodiments, from about 11 to about 19, and in other embodiments, from about 15 to about 19. Here, as well as elsewhere in the specification and claims, individual range values can be combined to form additional non-disclosed ranges.

In some other embodiments, the allyl functional groups on the polyurethane polymer backbone are reacted with a free thiol compound containing a quaternary ammonium functional group connected to the thiol group by a spacer. Suitable free thiol compounds may include, without limitation, quaternary ammonium functionalized amino acids, peptides, and proteins, having one or more available thiol groups. In one or more embodiments, the allyl functional groups on the polyurethane polymer backbone are reacted with a free thiol compound having the formula:

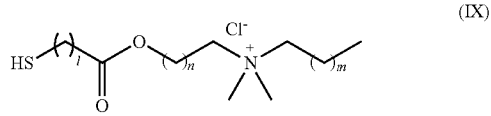

where l is an integer from 1 to 4, m is an integer from 1 to 18, n is an integer from 1 to 19. In various embodiments, l, m, and n are as set forth above. Here, as well as elsewhere in the specification and claims, individual range values can be combined to form additional non-disclosed ranges.

In some of these embodiments, the allyl functionalized polyurethane polymer backbone is formed into a coating or 3-dimensional shape before reacting it with the disulfide or thiol compound containing the quaternary ammonium groups. Accordingly, in these embodiments, the QA functional group is attached to the quaternary ammonium functionalized thermoplastic polyurethane compounds of the present invention through a carbon-sulfur bond formed between the allyl functional group on the allyl functionalized polyurethane polymer backbone and the disulfide or thiol group on the compound containing the QA functional group. As should be apparent, in these embodiments only the allyl functional groups located near the surface of the allyl functionalized polyurethane polymer backbone accessible by the disulfide or thiol compounds containing the quaternary ammonium groups are available to react with and bond to those compounds and thereby form the QAC containing side chains of the quaternary ammonium functionalized thermoplastic polyurethane compounds of the present invention. In these embodiments, quaternary ammonium functionalized thermoplastic polyurethane compounds of the present invention may be in the form of a polyurethane coating or 3-dimensional shape, such as a catheter or fiber mat, having an antimicrobial quaternary ammonium surface coating, for use as, or in conjunction with, a medical device for implantation or other use within the body.

In one or more embodiment, the quaternary ammonium functionalized thermoplastic polyurethane compound of the present invention has the formula:

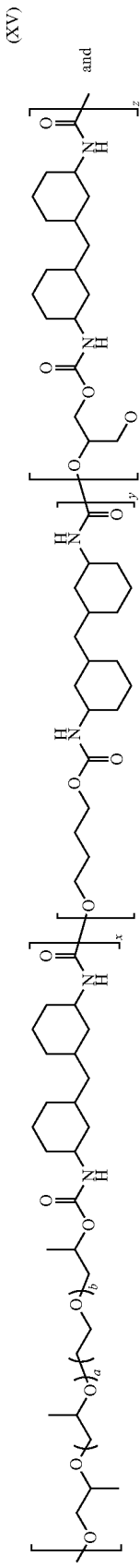
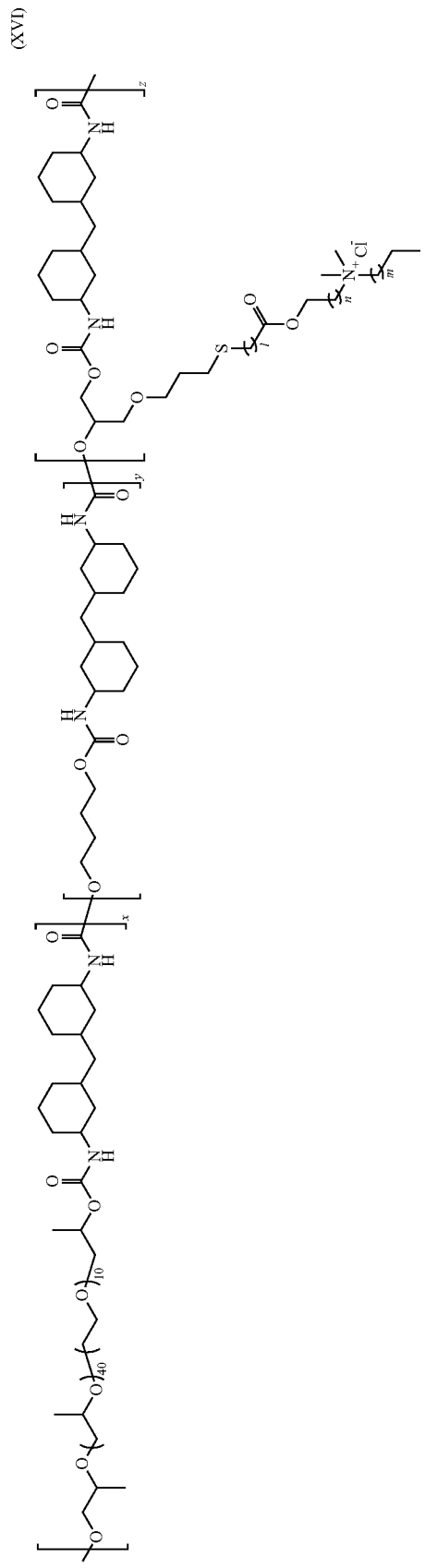

where a is an integer from 2 to 50; b is an integer from 2 to 50; x is a mole fraction from 0.01 to 0.8; y is a mole fraction from 0.01 to 0.8; and z is a mole fraction ranging from 0.01 to 0.8; and the sum of x, y, and z is equal to 1; n is an integer from 1 to 18, m is an integer from 1 to 19, and l is an integer from 1 to 4. In various embodiments, a, b, x, y, z, m and n may be as set forth above. Here, as well as elsewhere in the specification and claims, individual range values can be combined to form additional non-disclosed ranges.

In various embodiments, the quaternary ammonium functionalized thermoplastic polyurethane compounds of the present invention has a number average molecular weight ($M_n$) of from about 5000 g/mol to about 5,000,000 g/mol as measured by Size Exclusion Chromatography (SEC). In one or more embodiments, the quaternary ammonium functionalized thermoplastic polyurethane compound of the present invention has a number average molecular weight ($M_n$) of about 5000 g/mol or more, in other embodiments 50,000 g/mol or more, in other embodiments 100,000 g/mol or more, in other embodiments 500,000 g/mol or more, in other embodiments 1,000,000 g/mol or more, in other embodiments 2,000,000 g/mol or more, and in other embodiments 3,000,000 g/mol or more. In one or more embodiments, the quaternary ammonium functionalized thermoplastic polyurethane compound of the present invention has a number average molecular weight ($M_n$) of about 2,000,000 g/mol or less, in other embodiments 1,000,000 g/mol or less, in other embodiments 750,000 g/mol or less, in other embodiments 500,000 g/mol or less, in other embodiments 400,000 g/mol or less, in other embodiments 300,000 g/mol or less, and in other embodiments 200,000 g/mol or less. Here, as well as elsewhere in the specification and claims, individual range values can be combined to form additional non-disclosed ranges.

In one or more embodiment, the quaternary ammonium functionalized thermoplastic polyurethane compound of the present invention has a mass distribution ($Đ_m$) of from about 1.5 to about 5 as measured by Size Exclusion Chromatography (SEC). In one or more embodiments, the quaternary ammonium functionalized thermoplastic polyurethane compound of the present invention has a mass distribution ($Đ_m$) of about 1.8 or more, in other embodiments 2.0 or more, in other embodiments 2.3 or more, in other embodiments 2.6 or more, in other embodiments 3.0 or more, in other embodiments 3.3 or more, and in other embodiments 3.5 or more. In one or more embodiments, the quaternary ammonium functionalized thermoplastic polyurethane compound of the present invention has a mass distribution ($Đ_m$) of about 4.5 or less, in other embodiments 4.0 or less, in other embodiments 3.5 or less, in other embodiments 3.0 or less, in other embodiments 2.5 or less, in other embodiments 2.0 or less, and in other embodiments 1.5 or less. Here, as well as elsewhere in the specification and claims, individual range values can be combined to form additional non-disclosed ranges.

In one or more embodiment, the quaternary ammonium functionalized thermoplastic polyurethane compound of the present invention has a glass transition temperature ($T_g$) of from about −20° C. to about −100° C. as measured by Differential Scanning calorimetry (DSC). In one or more embodiments, the quaternary ammonium functionalized thermoplastic polyurethane compound of the present invention has a glass transition temperature ($T_g$) of about −100° C. or more, in other embodiments −80° C. or more, in other embodiments −60° C. or more, in other embodiments −40° C. or more, in other embodiments −20° C. or less, in other embodiments −50° C. or less, and in other embodiments −70° C. or less. Here, as well as elsewhere in the specification and claims, individual range values can be combined to form additional non-disclosed ranges.

In one or more embodiment, the quaternary ammonium functionalized thermoplastic polyurethane compound of the present invention has a degradation temperature ($T_d$) of from about 150° C. to about 300° C. as measured by Thermogravimetric Analysis (TGA). In one or more embodiments, the quaternary ammonium functionalized thermoplastic polyurethane compound of the present invention has a degradation temperature ($T_d$) of about 175° C. or more, in other embodiments 190° C. or more, in other embodiments 200 or more, in other embodiments 210° C. or more, in other embodiments 220° C. or more, in other embodiments 230° C. or more, and in other embodiments 250° C. or more. In one or more embodiments, the quaternary ammonium functionalized thermoplastic polyurethane compound of the present invention has a degradation temperature ($T_d$) of about 290° C. or less, in other embodiments 270° C. or less, in other embodiments 250° C. or less, in other embodiments 230° C. or less, in other embodiments 210 or less, in other embodiments 200° C. or less, and in other embodiments 190° C. or less. Here, as well as elsewhere in the specification and claims, individual range values can be combined to form additional non-disclosed ranges.

In one or more embodiment, the quaternary ammonium functionalized thermoplastic polyurethane compound of the present invention has a melting temperature ($T_m$) of from about 50° C. to about 150° C. as measured by Differential Scanning calorimetry (DSC). In one or more embodiments, the quaternary ammonium functionalized thermoplastic polyurethane compound of the present invention has a melting temperature ($T_m$) of about 60° C. or more, in other embodiments 70 or more, in other embodiments 80 or more, in other embodiments 90° C. or more, in other embodiments 100° C. or more, in other embodiments 110 or more, and in other embodiments 120° C. or more. In one or more embodiments, the quaternary ammonium functionalized thermoplastic polyurethane compound of the present invention has a melting temperature ($T_m$) of about 140° C. or less, in other embodiments 130° C. or less, in other embodiments 120 or less, in other embodiments 110° C. or less, in other embodiments 100° C. or less, in other embodiments 90° C. or less, and in other embodiments 80° C. or less. Here, as well as elsewhere in the specification and claims, individual range values can be combined to form additional non-disclosed ranges.

In one or more embodiment, the quaternary ammonium functionalized thermoplastic polyurethane compound of the present invention has a shore durometer hardness of from about 50 to about 100, as measured by a shore A durometer. In one or more embodiments, the quaternary ammonium functionalized thermoplastic polyurethane compound of the present invention has a shore durometer hardness of about 55 or more, in other embodiments 60 or more, in other embodiments 65 or more, in other embodiments 70 or more, in other embodiments 75 or more, in other embodiments 80 or more, and in other embodiments 85 or more. In one or more embodiments, the quaternary ammonium functionalized thermoplastic polyurethane compound of the present invention has a shore durometer hardness of about 95 or less, in other embodiments 90 or less, in other embodiments 85 or less, in other embodiments 80 or less, in other embodiments 75 or less, in other embodiments 70 or less, and in other embodiments 65 or less. Here, as well as elsewhere in the specification and claims, individual range values can be combined to form additional non-disclosed ranges.

In another aspect, the present invention is directed to methods for making the quaternary ammonium functionalized thermoplastic polyurethane compound described above. As set forth above, in some embodiments, the QA functional group is added to the polyurethane by incorporating a QAC functionalized diol into the polyurethane chain during polymerization and in other embodiments, a diol containing a functional group, preferably an allyl functional group, is incorporated into the polyurethane chain during polymerization and the QA functional group is added to the functionalized polyurethane later.

In embodiments where the QA functional groups are added after polymerization via a thiol-ene click reaction, the method will comprise the following general steps: preparing an allyl functionalized polyurethane polymer; preparing a bi-quaternary ammonium functionalized disulfide or quaternary ammonium functionalized thiol compound; combining said allyl functionalized polyurethane polymer, said bi-quaternary ammonium functionalized disulfide compound or quaternary ammonium functionalized thiol compound, and an initiating catalyst under an inert atmosphere; activating the initiating catalyst to produce the quaternary ammonium functionalized thermoplastic polyurethane compound described above.

In these embodiments, the allyl functionalized polyurethane polymer used in the method of the present invention may be any of the allyl functionalized polyurethane polymers described above. In one or more embodiments, the allyl functionalized diols comprising from about 0.5 to about 50 mole percent of said allyl functionalized polyurethane polymer. In some embodiments, the allyl functionalized polyurethane polymer has a number average molecular weight ($M_n$) of from about 5,000 g/mol to about 5,000,000 g/mol as measured by Size Exclusion Chromatography (SEC). In some embodiments, the allyl functionalized polyurethane polymer has a mass distribution ($Đ_m$) of from about 1.5 to about 5 as measured by Size Exclusion Chromatography (SEC). In some embodiments, the allyl functionalized polyurethane polymer has a glass transition temperature ($T_g$) of from about −40° C. to about −100° C. as measured by Differential Scanning calorimetry (DSC). In some embodiments, the allyl functionalized polyurethane polymer has a melting temperature ($T_m$) of from about 50° C. to about 150° C. as measured by Differential Scanning calorimetry (DSC). In some embodiments, the allyl functionalized polyurethane polymer has the formula:

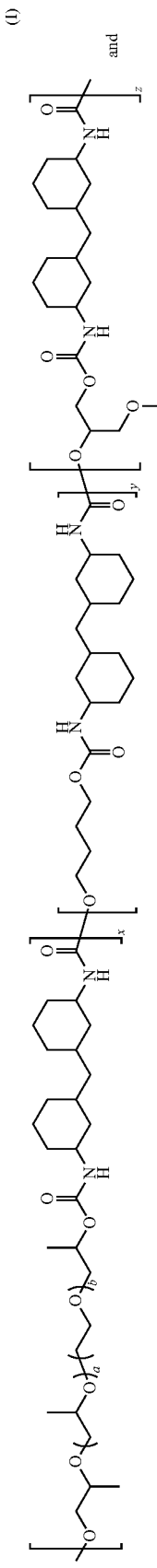
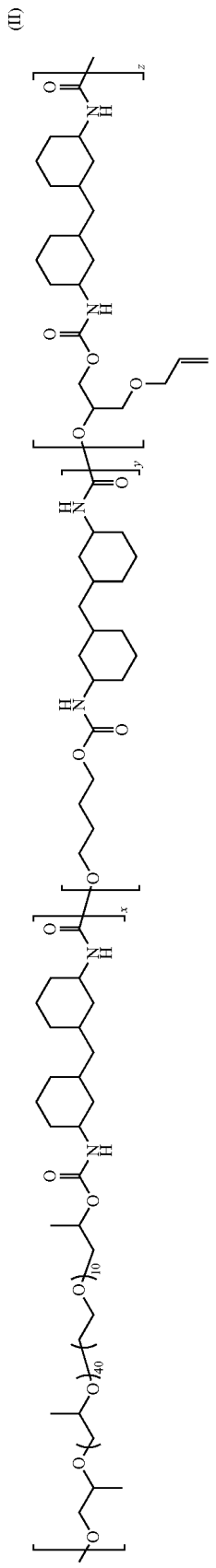

where a is an integer from 2 to 50; b is an integer from 2 to 50; x is a mole fraction from 0.01 to 0.8; y is a mole fraction from 0.01 to 0.8; and z is a mole fraction ranging from 0.01 to 0.8; and the sum of x, y, and z is equal to 1. In these embodiments, a, b, x, y, and z may be as set forth above. In various embodiments, a, b, x, y, and z may be as set forth above. Here, as well as elsewhere in the specification and claims, individual range values can be combined to form additional non-disclosed ranges.

In one or more embodiments, the allyl functionalized polyurethane polymer may be prepared as follows. First, a suitable allyl functionalized diol as described above may be prepared or purchased. In various embodiments, the allyl functionalized diol may be any of the allyl functionalized diols described above. Suitable functionalized diols are commercially available and may include, without limitation, 3-allyloxy-1,2-propanediol, 2-allyloxy-2-ethyl-1,3-propanediol, 1-(allyloxy)-1,2-propanediol, pentaerythritol allyl ether, trimethylolpropane diallyl ether, trimethylolpropane allyl ether, 1,5-hexadiene-3,4-diol, 2-methylene-1,3-propanediol, 7-Octene-1,2-diol, 5-norbornene-2-endo,3-endo-dimethanol, 5-norbornene-2-exo,3-exo-dimethanol, 5-Norbornene-2,2-dimethanol, and combinations thereof.

Next, the allyl functionalized diol, one or more short chain diol chain extenders, and one or more long chain diol soft segments are combined in a suitable container and pre-heated to a temperature of from about 80° C. to about 150° C. In various embodiments, the short chain diol chain extenders and long chain diol soft segments may be any of those described above. One of ordinary skill in the art will be able to choose suitable short chain diol chain extenders and long chain diol soft segments without undue experimentation. Suitable short chain diol chain extenders may include, without limitation, 1,3-propanediol, 1,4-butanediol (BDO), 1,5-pentanediol, 1,6-hexanediol, 1,7-heptanediol, 1,8-octanediol, 1,9-nonanediol, 1,10-decanediol, 1,12-dodecanediol, 1,14-tetradecanediol, ethylene glycol, polyethylene glycol (up to 750 g/mol), 2,2,3,3,4,4,5,5-Octafluoro-1,6-hexanediol, polypropylene glycol (up to 750 g/mol). In various embodiments, the long chain diol soft segments may comprise polyester diols, polycarbonate diols, polyether diols, polysiloxanes, polyethylene, polypropylene, polytetrafluoroethylene, poly(propylene-co-ethylene glycol or combinations thereof. Suitable long chain diol soft segments may include, without limitation, ARCOL™ polyether polyols, DESMOPHEN™ polyols, ACCLAIM™ polyether polyol, HYPERLITE™ polyols, SOFTCEL™ polyether polyols, ULTRACEL™ polyether polyols, VORANOL™ polyether polyols, CARADOL™ polyols, polydimethylsiloxane (hydroxy terminated), polyethylene glycol (hydroxy terminated), polypropylene glycol (hydroxy terminated), poly(propylene-co-ethylene glycol or combinations thereof. In one or more embodiments, the long chain diol soft segment will comprise poly(propylene oxide-co-ethylene oxide). In some embodiments, the long chain diol soft segments will comprise a linear polyether having a molecular weight of from about 750 g/mol to about 50,000 g/mol. In some embodiments, the long chain diol chain extender will comprise Arcol E-351™ polyol (Covestro, AG).

The diisocyanate and an inorganic catalyst, such as stannous octoate, are then added and the mixture stirred for from about 1 to about 5 minutes or until the mixture becomes too viscous to stir to produce the allyl functionalized polyurethane polymer. In various embodiments, feed ratios of the various components may be as shown in Table 1, below.

As set forth above, the diisocyanate is not particularly limited and any suitable diisocyanate conventionally used for the formation of polyurethanes may be used. Suitable diisocyanates may include without limitation, 4,4'-methylenebis(phenyl isocyanate) (MDI), 4,4'-methylenebis(cyclohexyl isocyanate) (HMDI), isophorone diisocyanate, toluene diisocyanate (TDI), 1,3-bis(isocyanatomethyl)cyclohexane, 1,4-diisocyanatobutane, hexamethylene diisocyanate, 1,8-diisocyanatooctane, 1,12-diisocyanatododecane, aliphatic diisocyanates, and/or combinations thereof. In one or more embodiments, any of the metal salts of organic acids or tertiary amine based catalysts which are commonly used to catalyze polyurethane polymerizations may be used as the catalyst. In various embodiments, suitable catalysts may include, without limitation, stannous octoate, 1,4-diazabicyclo[2.2.2]octane (DABCO), bis[2-(N,N-dimethylamino)ethyl] ether, dibutyltin dilaurate, bismuth octoate, BICAT™ catalysts, UV light, or combinations thereof.

In some embodiments, the allyl functionalized polyurethane polymer may then be cured at a temperature of from about 75° C. to about 150° C. for from about 12 to about 48 hours to produce a cured allyl functionalized polyurethane polymer.

In the QAC diol embodiments, the same polymerization conditions used to produce the allyl functionalized polyurethane polymer described above may be used, except that a quantity of QAC diol "Qx-(OH)$_2$" is used in place of the allyl-functionalized diol and/or some portion of the short chain diol chain extender. As set for above, in these embodiments, the QAC functional group is directly added into the polyurethane during polymerization with no further functionalization step required.

As set forth above, the allyl functionalized polyurethane polymer may be formed into any desirable three-dimensional shape, film, or coating prior to is reacted with a bi-quaternary ammonium functionalized disulfide compound to form the quaternary ammonium functionalized thermoplastic polyurethane compound described below. In some embodiments, the allyl functionalized polyurethane polymer may be formed into a catheter, medical tubing, or a coating for medical devices.

As set forth above, the QAC functional group is then added to the allyl functionalized polyurethane polymer to form the quaternary ammonium functionalized thermoplastic polyurethane compound described above. In various embodiments, the quaternary ammonium compound may be added to the functionalized polyurethane polymer by any means known in the art for the combination, but is preferably added by means of a "click" reaction. These reactions are preferred because they are typically simple to perform, high yielding, stereospecific, wide in scope, create only byproducts that can be removed without chromatography, and can be conducted in easily removable or benign solvents. In one or more embodiments, the QAC functional group is then added to the allyl functionalized polyurethane polymer by reacted it with a quaternary ammonium functionalized disulfide or thiol compound using a thiol-ene click reaction to form the quaternary ammonium functionalized thermoplastic polyurethane compound described above.

In some embodiments, a bi-quaternary ammonium functionalized disulfide compounds may be used to form the quaternary ammonium functionalized thermoplastic polyurethane compound of the present invention. These bi-quaternary ammonium functionalized disulfide compounds will comprises two quaternary ammonium functional groups as described above, each attached to a disulfide group by from about 2 to about 20 carbon oxygen, or nitrogen atoms. Suitable bi-quaternary ammonium functionalized disulfide compounds may include, without limitation, 3,3'-dithiodipropionic acid, 4,4'-dithiodibutyric acid, dithiodiglycolic acid, 2-hydroxyethyl disulfide, cystamine dihydrochloride, and/or combinations thereof.

In some embodiments, the bi-quaternary ammonium functionalized disulfide compound may have a formula selected from:

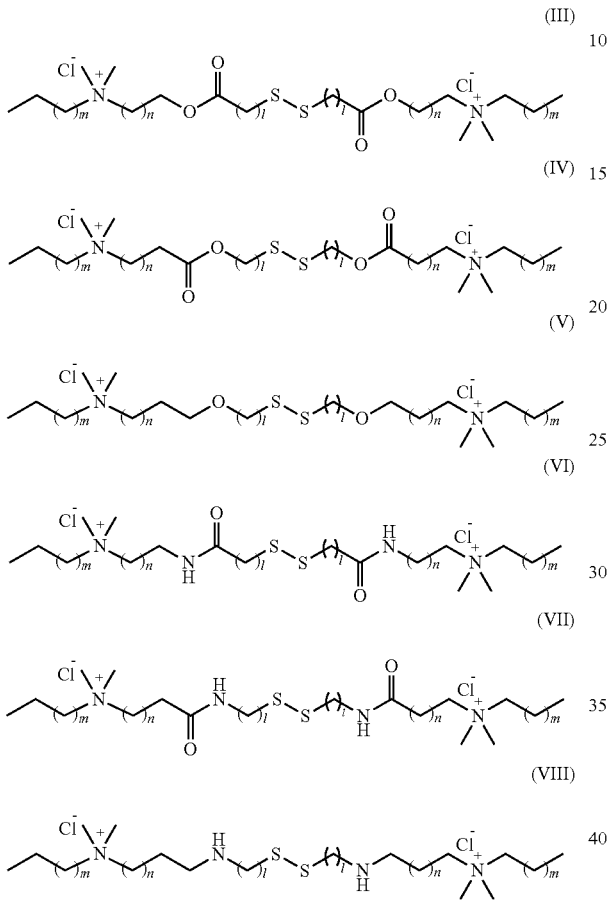

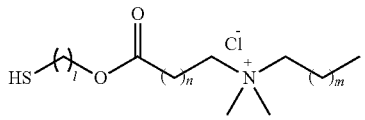

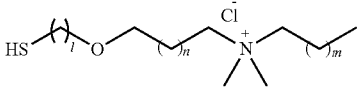

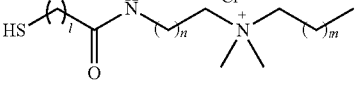

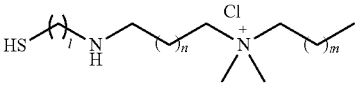

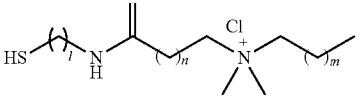

wherein l is an integer from 1 to 3, m is an integer from 1 to 18, and n is an integer from 1 to 19. In various embodiments, l, m, and n are as set forth above.

In some other embodiments, the QAC functional groups may be added to the polyurethane polymer backbone by reacting the allyl functional groups on the polyurethane polymer backbone with a free thiol compound containing the QAC functional group using a thiol-ene click reaction. Suitable free thiol compounds may include, without limitation, quaternary ammonium functionalized amino acids, peptides, and proteins, having one or more available thiol groups. In some embodiments, the QAC functional group may be connected to the thiol group by a spacer, as described above. In some other embodiments, the allyl functional groups on the polyurethane polymer backbone are reacted with a free thiol compound having the formula:

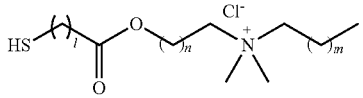

where l is an integer from 1 to 4, m is an integer from 1 to 18, and n is an integer from 1 to 19. In various embodiments, l, m, and n are as set forth above.

While, as set forth above, both free thiols and disulfides may be used in these embodiments to add the QAC functional group, the free thiols are preferred. In reactions using the QAC functionalized disulfide compounds, it is believed that the radical initiator acts to break the disulfide into two thiyl radicals, which are then added to the allyl functional group in a similar way as the thiol group in a thiol-ene reaction (which proceeds via thiyl radical addition to the alkene). This reaction has been found to be less efficient than the typical thiol-ene reaction however, and while not wishing to be bound by theory, it is believed that the thiyl radicals recombine rapidly to reform the disulfide, and there is a lack of protons available for radical hydrogen abstraction to complete the thiol-ene reaction, reducing the efficiency of the reaction.

In various embodiments, the QAC functional groups may be added to the allyl functional groups on the polyurethane polymer backbone using conventional thiol-ene click chemistry techniques. In these embodiments, the allyl-functionalized polyurethane polymer and QAC functionalized disulfide or thiol compound are combined with an initiating catalyst, which is then activated to produce the quaternary ammonium functionalized thermoplastic polyurethane compound of the present invention. The initiating catalyst is not particularly limited and may include any initiator capable of producing a radical when activated and may include, without limitation, photoinitiators or thermal initiators. In some embodiments, the initiating catalyst may be a photoinitiator, and will be activated by exposure to ultraviolet light of a designated wavelength. In some other embodiments, the initiating catalyst may be a thermal initiator, and will be activated by exposure to heat.

While in the embodiments exemplified herein, the quaternary ammonium functional group is attached to the functionalized polyurethane using a thiol-ene reaction, the invention is not so limited. In one or more embodiments, the quaternary ammonium may be attached to a functionalized polyurethane containing a reactive group that is complementary and suitable for other known "click" reactions, e.g. the quaternary ammonium may contain an azide, and the polyurethane an alkyne (or vice-versa) and employ azide-alkyne cycloadditions for attachment. Likewise, the quaternary ammonium ion may contain a hydroxylamine group and the functionalized polyurethane may contain a ketone or aldehyde group and employ the oxime "click" reaction for attachment. In other embodiments, the functionalized polyurethane may contain an alkyne functional group and employ the thiol-yne "click" reaction for attachment.

In various embodiments, the bi-quaternary ammonium functionalized disulfide compound may be prepared according to any method known in the art. In one or more embodiments, the bi-quaternary ammonium functionalized disulfide compound may be prepared as follows. First, a chlorinated alcohol is reacted with a tri-substituted amine for from 8 to 36 hours at a temperature of from about 70° C. to about 120° C. to form a chlorinated quaternary ammonium alcohol intermediate. (See, Scheme 1, below).

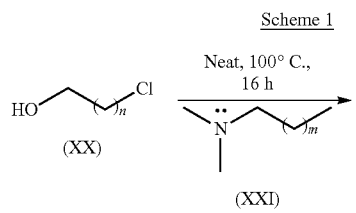

where n is an integer from about 1 to about 13 and m is an integer from about 0 to about 14. In various embodiments, n and m may be as set forth above.

In various embodiments, suitable chlorinated alcohols, may include, without limitation, 3-chloro-1-propanol, 4-chloro-1-butanol, 6-chloro-1-hexanol, 8-chloro-1-octanol, 10-chloro-1-decanol, 12-chloro-1-dodecanol, 14-chloro-1-tetradecanol. One of ordinary skill in the art will be able to select a suitable chlorinated alcohol without undue experimentation. Suitable tri-substituted amines may include, without limitation, trimethylamine, N,N-dimethylethylamine, N,N-dimethylpropylamine, N,N-dimethylbutylamine, N,N-dimethylhexylamine, N,N-dimethyloctylamine, N,N-dimethyldecylamine, N,N-dimethyldodecylamine, N,N-dimethyltetradecylamine, N,N-dimethylhexadecylamine, N,N-dimethyloctadecylamine, N-methyldibutylamine, N-methyldihexylamine, N-methyldioctylamine, N-methyldidodecylamine, N-methyl, ditetradecylamine, dibutyltetradecylamine, 1-butylpyrrolidine, etc. Again, one of ordinary skill in the art will be able to select a suitable tri-substituted amine without undue experimentation.

To provide the disulfide functionality, a dicarboxylic acid disulfide, such as 3,3'-dithiopropionic acid, 4,4'-dithiodibutyric acid, or dithiodiglycolic acid was converted to a diacid chloride as shown in Scheme 2, below.

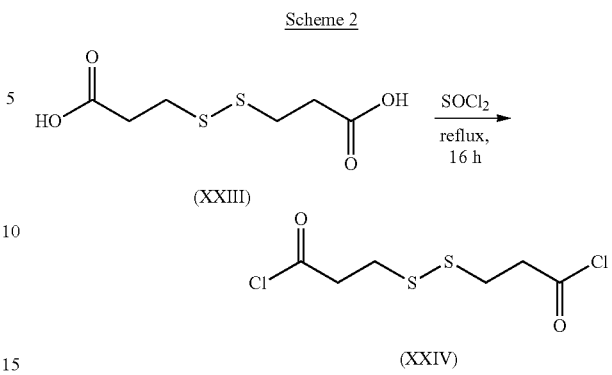

In these embodiments, a dicarboxylic acid disulfide is combined with an excess of an acyl chloride generating reagent, such as thionyl chloride or oxalyl chloride, and then heated to reflux for from about 4 to about 24 h to produce the corresponding acid chloride disulfide. In one or more embodiments, 3,3'-dithiodipropionic acid, are combined with an excess of thionyl chloride or oxalyl chloride to form the corresponding acid chloride disulfide.

In these embodiments, the chlorinated quaternary ammonium alcohol intermediate is then reacted with the acid chloride disulfide as shown in Scheme 3, below to produce the bi-quaternary ammonium functionalized disulfide compound.

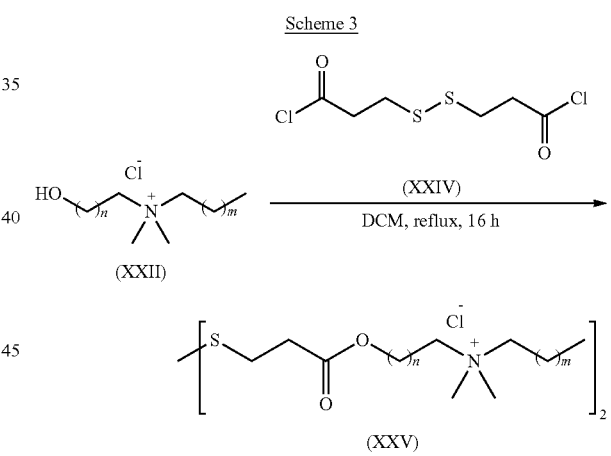

In these embodiments, the chlorinated quaternary ammonium alcohol intermediate is first dissolved in a suitable solvent, such as anhydrous chloroform or dichloromethane, and pyridine is added. The solution is then cooled to a temperature of from about −25° C. to about 0° C. and the acid chloride disulfide compound is added under an inert atmosphere. The mixture is gradually allowed to reach ambient temperature while stirring under an inert atmosphere to produce the crude bi-quaternary ammonium functionalized disulfide compound. The solvent is then removed and the crude product purified to produce the bi-quaternary ammonium functionalized disulfide compound.

The process for purifying the crude bi-quaternary ammonium functionalized disulfide compound is not particularly limited and suitable process known in the art for this purpose may be used. One of ordinary skill in the art will be able to purify the crude bi-quaternary ammonium functionalized disulfide compound without undue experimentation. The In some embodiments, the crude bi-quaternary ammonium functionalized disulfide compound is purified by dialysis in DI water using 100-500 Da dialysis tubing and then lyophilized to obtain the bi-quaternary ammonium functionalized disulfide compound.

In some other embodiments, the method described above may be modified to eliminate the pyridine, and with it the need for its removal. In these embodiments, the chlorinated quaternary ammonium alcohol intermediate is dissolved in a suitable solvent, such as anhydrous chloroform, in a suitable container such as a Schenk flask fixed with a reflux condenser. The acid chloride is then added slowly through the sidearm of the flask at ambient temperature and the flow of inert gas filed to push the HCl gas formed out of the flask through the condenser where it is neutralized with a suitable base. The mixture is then heated to reflux at a temperature of from about 40° C. to about 100° C. for from about 12 to about 24 hours and preferably at least 16 hours, to produce the bi-quaternary ammonium functionalized disulfide compound. In some embodiments, the bi-quaternary ammonium functionalized disulfide compound neutralized by evaporating the solvent, and re-dissolving the bi-quaternary ammonium functionalized disulfide compound in DI water with excess sodium bicarbonate. The water was then removed via rotary evaporation, and the contents re-dissolved in DCM, stirred over magnesium sulfate, filtered, and dried under vacuum.

In some embodiments, the bi-quaternary ammonium functionalized disulfide compound may have the general structure shown in formula (IV) above. In these embodiments, bi-quaternary ammonium functionalized disulfide compound may be made using a core of bis(2-hydroxyethyl) disulfide (or other comparable longer chain hydroxyethyl disulfides, e.g. bis(11-hydroxyundecyl) disulfide), and may be produced by first reacting an amino acid such as 3-dimethylaminopropionic acid, 4-dimethylamino-butyric acid, bis(10-carboxydecyl)disulfide (or other comparable compounds of various alkyl chain lengths) with any excess of hydrocarbons of various alkyl chain lengths containing a primary bromine/chlorine (e.g. 1-chlorobutane, 1-chlorooctane, 1-chlorodecane, 1-bromododecane, etc.) to produce the quaternary ammonium functionality. In these embodiments, the intermediate product is then reacted with bis(2-hydroxyethyl)disulfide by any of the known esterification reactions (e.g. DIC coupling, base/acid catalyzed, or the QAC intermediate is converted to an acid chloride and esterified, similar to the method described herein to produce the bi-quaternary ammonium functionalized disulfide compound.

In some other embodiments, the bi-quaternary ammonium functionalized disulfide compound may have the general structure shown in formula (V) above. In these embodiments, bi-quaternary ammonium functionalized disulfide compound may be made using a core of bis(2-hydroxyethyl) disulfide (or another comparable longer chain hydroxyethyl disulfide, e.g. bis(11-hydroxyundecyl) disulfide, or bis(16-Hydroxyhexadecyl) disulfide, etc.), and reacting it with an excess of a hydrocarbon containing two primary chlorine/bromine (e.g. 1,4-dichlorobutane, 1,6-dichlorohexane, 1,8-dichlorooctane, 1,10-dichlorodecane, or analogous brominated compounds, etc.) to achieve a dichloroalkyl or dibromoalkyl ether disulfide. In these embodiments, the dichloroalkyl ether disulfide intermediate may be subsequently reacted with any excess of tertiary amine compounds (N,N-dimethylethylamine, N,N-dimethylpropylamine, N,N-dimethylbutylamine, N,N-dimethylhexylamine, N,N-dimethyloctylamine, N,N-dimethyldecylamine, N,N-dimethyldodecylamine, N,N-dimethyltetradecylamine, N,N-dimethylhexadecylamine, N,N-dimethyloctadecylamine, N-methyldibutylamine, N-methyldihexylamine, N-methyldioctylamine, N-methyldidodecylamine, N-methyl, ditetradecylamine, dibutyltetradecylamine and combinations thereof) to displace chlorine/bromine via SN2 reaction which yields the desired quaternary ammonium disulfide.

In some other embodiments, the bi-quaternary ammonium functionalized disulfide compound may have the general structure shown in formula (VI) above. In these embodiments, bi-quaternary ammonium functionalized disulfide compound may be made starting from the dicarboxylic acid disulfide core (e.g. 3,3'-dithiodipropionic acid, 4,4'-dithiodibutyric acid, dithiodiglycolic acid, bis(10-carboxydecyl) disulfide), and performing an amidation reaction (using any of the commonly known methods) with an excess of compounds which contain both a primary and tertiary amine group (e.g. 3-(dimethylamino)-1-propylamine, 4-dimethylaminobutylamine, 5-(dimethylamino)amylamine, or similar compounds of longer alkyl chain length). The amidation would proceed through the primary amine and result in a disulfide amide which contains two tertiary amines for subsequent quaternization reactions, having a structure:

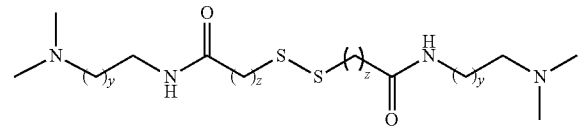

(XXVI)

In various embodiments, this intermediate could be reacted with any of the hydrocarbons containing a primary halide, as mentioned above (e.g. 1-chlorobutane, 1-chlorooctane, 1-chlorodecane, 1-bromododecane, etc.) to produce the desired quaternary ammonium disulfide compound.

In some other embodiments, the bi-quaternary ammonium functionalized disulfide compound may have the general structure shown in formula (VII) above. In these embodiments, bi-quaternary ammonium functionalized disulfide compound may be made using a method similar to that for structure (IV) above, but using a diamino disulfide (e.g. cystamine dihydrochloride, 2-aminophenyl disulfide) as the core disulfide. An amino acid such as 3-dimethylaminopropionic acid or 4-dimethylamino-butyric acid (or other comparable compounds of various alkyl chain lengths) is first reacted with an excess of hydrocarbons having a desired alkyl chain length and containing a primary bromine/chlorine (e.g. 1-chlorobutane, 1-chlorooctane, 1-chlorodecane, 1-bromododecane, etc.) to produce the quaternary ammonium functionality. The intermediate product is then reacted with said diamino disulfide (e.g., cystamine dihydrochloride) via condensation (i.e., amidation) to produce the desired QAC disulfide.

In some other embodiments, the bi-quaternary ammonium functionalized disulfide compound may have the general structure shown in formula (VIII) above. In these embodiments, bi-quaternary ammonium functionalized disulfide compounds may be made using a method similar to that for structure (V) above, but in a slightly different order. First, a tertiary amine of the desired alkyl tail length (e.g., N,N-dimethylethylamine, N,N-dimethylpropylamine, N,N-dimethylbutylamine, N,N-dimethylhexylamine, N,N-dimethyloctylamine, N,N-dimethyldecylamine, N,N-dimethyldodecylamine, N,N-dimethyltetradecylamine, N,N-dimethylhexadecylamine, N,N-dimethyloctadecylamine, N-methyldibutylamine, N-methyldihexylamine, N-methyldioctylamine, N-methyldidodecylamine, N-methyl, ditetradecylamine, dibutyltetradecylamine and combinations thereof) is reacted with an excess of a hydrocarbon containing two primary chlorines/bromines (e.g. 1,4-dichlorobutane, 1,6-dichlorohexane, 1,8-dichlorooctane, 1,10-dichlorodecane, or analogous brominated compounds) to achieve a quaternary ammonium compound containing one remaining primary halide, having the structure:

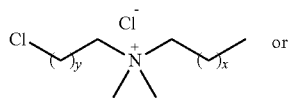

(XXVII)

or

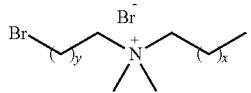

(XXVIII)

The QAC-chloride/bromide intermediate is then reacted with a diamino disulfide (e.g. cystamine dihydrochloride, 2-aminophenyl disulfide) via SN2 reaction, optionally catalyzed using a non-nucleophilic base (e.g. trimethylamine, sodium bicarbonate) to facilitate the reaction/remove hydrogen chloride, yielding the desired quaternary ammonium disulfide.

As set forth above, in one or more embodiments, the QAC functional groups may be added to the polyurethane polymer backbone using a free thiol compound containing the QAC functional group. The methods for synthesizing the QA functionalized thiol are not particularly limited and any suitable method known in the art for this purpose may be used. One of ordinary skill in the art will be able to add a thiol functional group to a QA containing compounds or otherwise generate a QAC functionalized thiol without undue experimentation.

In some embodiments, the QA functionalized thiol compound may be formed by reducing the bi-quaternary ammonium functionalized disulfide compounds described above, as shown in Scheme 4, below.

Scheme 4
Reduction of bi-quaternary ammonium functionalized disulfide compound with TCEP

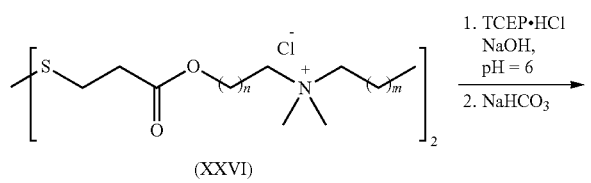

(XXVI)

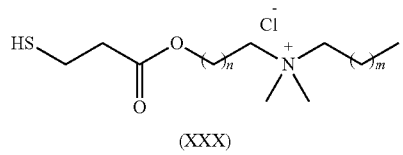

(XXX)

In these embodiments, two quaternary ammonium functionalized thiol compounds were obtained via reduction of the bi-quaternary ammonium functionalized disulfide compound using a reducing agent, such as tris(2-carboxyethyl) phosphine hydrochloride (TCEP), 1,4-dithiothreitol, or 2-mercaptoethanol. In some of these embodiments, the bi-quaternary ammonium functionalized disulfide compound is placed in a suitable reaction vessel under an inert atmosphere and an aqueous solution of a reducing agent, such as TCEP, adjusted to a pH of 6.0 is added at room temperature and the contents stirred for from about 30 to about 240 minutes. The reaction was then saturated with $NaHCO_3$ and stirred for an additional 30 min, then lyophilized for 24 h to remove water. The product was extracted out from the salts by dissolving in $CH_2Cl_2$ and filtering. The filtrate was stirred over $Na_2SO_4$, filtered, and vacuum dried.

In various embodiments, the quaternary ammonium functionalized thermoplastic polyurethane compound of the present invention may be formed from the allyl functionalized polyurethane polymer and bi-quaternary ammonium functionalized disulfide and/or quaternary ammonium functionalized thiol compounds described above by the following method. First, the allyl functionalized polyurethane polymer, the bi-quaternary ammonium functionalized disulfide or quaternary ammonium functionalized thiol compound, and a photoinitiating catalyst are combined in a suitable container under an inert atmosphere. In one or more embodiments, the disulfide or thiol compound and the photoinitiating catalysts are dissolved in a suitable solvent (water) and the allyl functionalized polyurethane polymer is submerged in the solution. Suitable photoinitiating catalysts may include, without limitation, 2-hydroxy-4'-(2-hydroxyethoxy)-2-methylpropiophenone (Irgacure-2959), lithium phenyl-2,4,6-trimethylbenzoylphosphinate, 2,2-dimethoxy-2-phenylacetophenone, sodium 4-[2-(4-morpholino)benzoyl-2-dimethylamino]butylbenzenesulfonate, and 2-(carboxymethoxy) thioxanthone, etc.

Finally, the combination is irradiated with ultraviolet light at an appropriate wavelength for from about 1 min to about 60 min to produce the quaternary ammonium functionalized thermoplastic polyurethane compound described above. As will be apparent, the quaternary ammonium groups are added to the allyl functionalized polyurethane polymer by means of a photocatalyized thiol-ene reaction between the allyl functional groups available on the surface of the allyl functionalized polyurethane polymer and disulfide/thiol groups of the quaternary ammonium functionalized disulfide/thiol compound. In some other embodiments, a thermal initiator is used in place of the photoinitiating catalyst, and heat is used to catalyze the disulfide/thiol-ene reaction between the allyl functional groups available on the surface of the allyl functionalized polyurethane polymer and disulfide groups of the quaternary ammonium functionalized disulfide/thiol compound.

In some other embodiments, a thermal initiator is used to add the QAC functionalized thiol or disulfide to the allyl functionalized polyurethane polymer. In one or more of these embodiments, the allyl functionalized polyurethane polymer, the bi-quaternary ammonium functionalized disulfide or quaternary ammonium functionalized thiol compound, and a thermal initiator are combined in a suitable container under an inert atmosphere. In one or more embodiments, the disulfide or thiol compound and the thermal initiator are dissolved in a suitable solvent (water) and the allyl functionalized polyurethane polymer is submerged in the solution. Suitable thermal initiators may include, without limitation, 4,4-azobis(4-cyanovalericacid), benzoyl peroxide, potassium persulfate, or other water-soluble azo and peroxide derived thermal initiators. The combination is then heated to (or in excess of) the appropriate decomposition temperature for the selected thermal initiator and reacted from about 1 min to about 300 min to produce the quaternary ammonium functionalized thermoplastic polyurethane compound described above.

In yet another aspect, the present invention is directed to a catheter or other medical device for use in the body of a patient comprising the quaternary ammonium functionalized thermoplastic polyurethane compound described above. In some embodiments, the present is directed to a film formed from the QAC functionalized TPUs described above via solvent casting or dip coating from a solution containing the QAC functionalized TPU dissolved in a suitable solvent that may be used to coat a device or a surface which requires antimicrobial properties. In some embodiments, the present is directed to a fiber formed from the QAC functionalized TPUs described above via electrospinning or melt spinning for use in forming an antimicrobial non-woven fiber mat for use in wound care or other suitable antimicrobial uses.

EXPERIMENTAL

In order to more fully illustrate and further reduce the quaternary ammonium functionalized thermoplastic polyurethane compounds of the present invention to practice, the following experiments were conducted. In a first series of experiments, a commercially relevant functionalized TPU containing surface-grafted QACs for contact-killing activity towards a variety of microbes was synthesized and tested. The surface-grafted QACs were compared to an active monomer analogue, and the spacer length and alkyl tail length of the grafted QACs were varied to evaluate the importance of amphiphilicity and separation distance of the head group from the surface of the substrate.

Synthesis and Characterization of QAC Reagents.

First, an active monomer QAC reagent was synthesized in bulk using a quaternization reaction, as shown in Scheme 5, below.

Scheme 5
Synthesis of Q14-(OH)$_2$ neat from 3-bromo-1,2-propandiol and DTDA using a quaternization reaction.

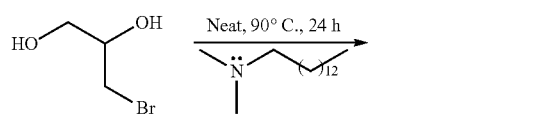

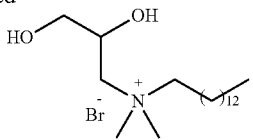

Figure 1:
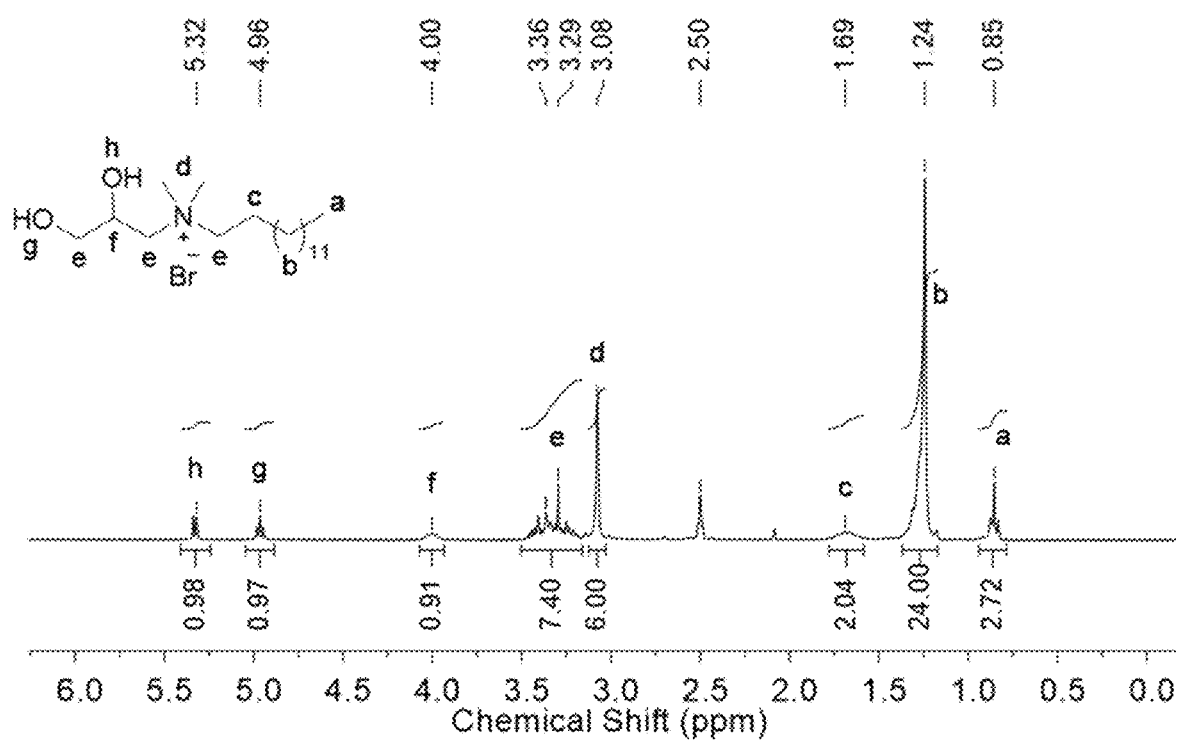
FIG. 1 is a $^1$H-NMR spectra of 3-Q14-(OH)$_2$ confirming the purity of the compound. The proton integrations for peaks a-d compared to f, g, and h reveal a 1:1 substitution occurred. The protons signals labeled e are obscured by HDO (δ=3.30 ppm).

$^1$H-NMR was used to confirm the purity (FIG. 1) and the resulting quaternary ammonium diol, denoted as Q14-(OH)$_2$, was added directly in subsequent polymerizations to produce a series of QAC-TPUs, denoted as 5% QAC-TPU and 10% QAC-TPU. See, FIGS. 2-7.

Second, a series of disulfide based QAC reagents with varying spacer lengths (x) and tail lengths (z) used for surface functionalization of allyl functionalized TPUs according to the present invention were prepared for evaluation and testing. The disulfide "x-Qz-S-S" reagents were produced by first generating the corresponding x-Qz-OH compounds (where x=3, 6, 8 and z=8, 12, 14) via neat quaternization reactions of N,N-dimethyloctylamine (DOA), N,N-dimethyldodecylamine (DDA), N,N-dimethyltetradecylamine (m=6, 10, 12) with various chlorinated alcohols (n=2, 5, and 7), as shown in Scheme 1, above.

$^1$H-NMR confirmed the purity of the compounds (See, FIGS. 8-12). The $^1$H-NMR spectra revealed a sharp singlet peak (δ=3.0) corresponding to the methyl groups of the quaternary amine, which was integrated and compared to various aliphatic peaks of the spacer and tail segments for each x-Qz-OH compound.

To provide the disulfide functionality, 3,3'-dithiopropionic acid was converted to a diacid chloride as shown in Scheme 2, above and subsequently reacted with the x-Qz-OH compounds to yield the corresponding x-Qz-S-S surface functionalization reagents, as shown in Scheme 3, above. The conversion to 3,3'-dithiopropanoyl chloride was quantitative, as confirmed by $^1$H-NMR and $^{13}$C-NMR (FIG. 13 and FIG. 14, respectively), and a simple work-up afforded the x-Qz-S-S reagents, which were also confirmed by $^1$H-NMR (See, FIGS. 15-19). Notably, the $^1$H-NMR spectra for all x-Qz-S-S compounds demonstrated two triplet peaks (δ=2.7, 2.9) corresponding to the methylene protons of disulfide precursor, which was integrated and compared to the methylene protons (δ=4.0) alpha to the newly formed ester, as well as the aliphatic protons of the hydrocarbon spacer and tail.

Characterization of TPUs.

A series of TPUs including a control TPU, 5 mol % and 10 mol % QAC-TPU, as well as an 8 mol % alloc-TPU were synthesized following the conditions shown in Scheme 6.

Scheme 6

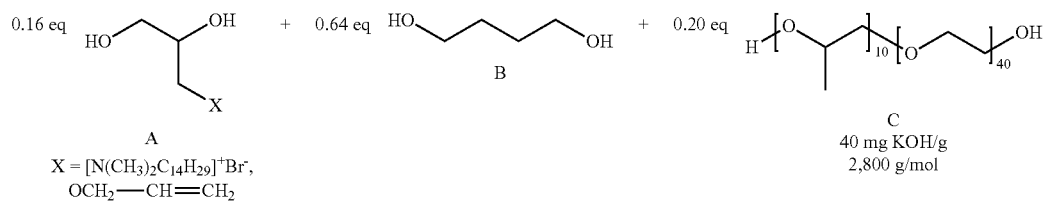

A
X = [N(CH$_3$)$_2$C$_{14}$H$_{29}$]$^+$Br$^-$,
OCH$_2$—CH=CH$_2$

C
40 mg KOH/g
2,800 g/mol

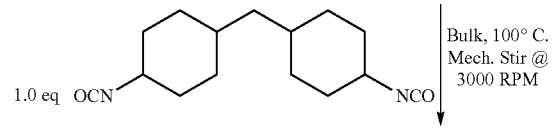

Bulk, 100° C.
Mech. Stir @
3000 RPM

-continued

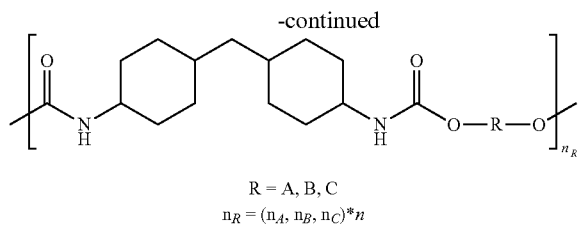

R = A, B, C
$n_R = (n_A, n_B, n_C)*n$

As shown in Scheme 6, the TPUs were synthesized under bulk conditions at 100° C. with mechanical stirring. To incorporate a functional moiety, the feed ratio of BDO was reduced, while maintaining the molar ratio of HMDI:Arcol E-351. For a QAC-TPU, X contains the QAC functionality [N(CH$_3$)$_2$C$_{14}$H$_{29}$]$^+$Br$^-$, and diol A is incorporated into the backbone of the TPU. In order to produce an 8% alloc-TPU, X contains the allyloxy functionality (OCH$_2$—CH=CH$_2$) and diol A is incorporated into the backbone. To produce a 30 wt. % HMDI TPU containing 8 mol % of 3-allyloxy-1, 2-propanediol, the molar ratios are reported in terms of the repeat unit, denoted as $n_R$; where $n_A$=0.16, $n_B$=0.64, $n_C$=0.20, and n is an integer representing the total number of repeat units in the polymer.

The QAC-TPUs contained the active monomer, Q14-(OH)$_2$, while the alloc-TPU contained 3-allyloxy-1,2-propanediol (alloc) to provide an allyl functional group for post-polymerization modification. The feed ratios used for each TPU synthesis can be found in Table 1, below.

Figure 5A:
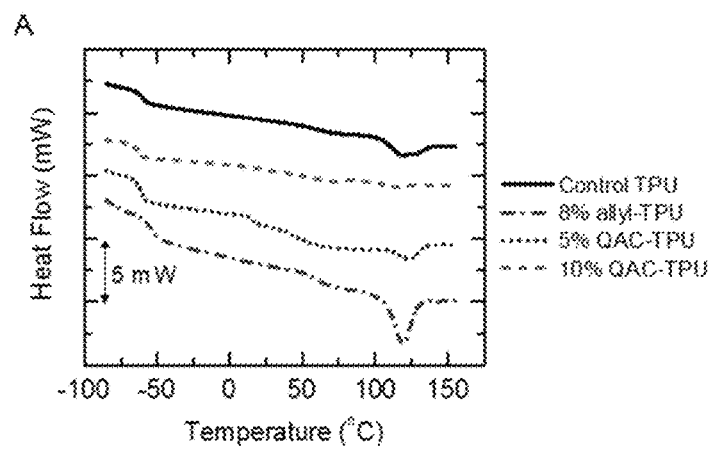
FIGS. 5A-B are example DSC thermograms for the control TPU, 10% QAC-TPU, 5% QAC-TPU, and 8% alloc-TPU showing.
Figure 5B:
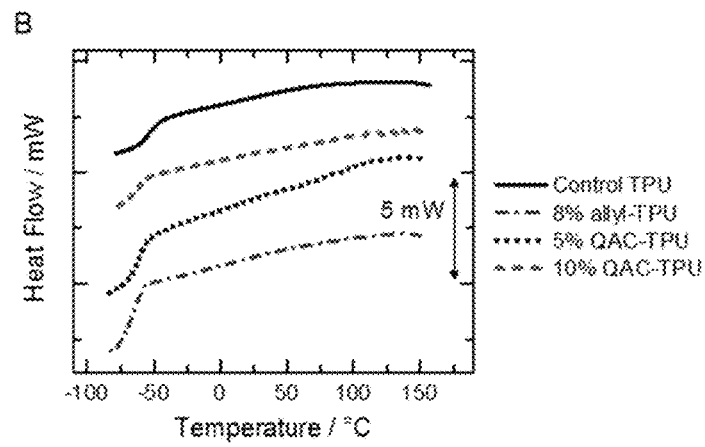

The results indicate that similar molecular weights were obtained for the control TPU and the 8% alloc-TPU, however, the 5% and 10% QAC-TPUs displayed a reduction in molecular weight, which can probably be attributed to the steric bulk of the active monomer impeding the rate of polymerization. In addition, the durometer measurements (See Table 2, above) indicate that increasing the Q14-(OH)$_2$ content in the QAC-TPUs results in significant softening, as the durometer hardness of the control TPU (shore A durometer=90) was decreased 20 points for the 5% QAC-TPU (shore A durometer=70) and 40 points for the 10% QAC-TPU (shore A durometer=50), while the 8% alloc-TPU possessed the same durometer hardness as the control. The softening observed with the QAC-TPUs can be attributed to the disruption of polar-polar interactions of the hard segment by the long aliphatic tail of the QAC, which causes a decrease in the crystallinity as demonstrated by DSC (FIGS. 5A-B). The thermograms provided in FIG. 5A show that the $T_g$ remained unaffected by the introduction of Q14-(OH)$_2$

TABLE 1

Reagent table for compounds used in various TPU polymerizations.

| TPU | HMDI mL (mmol) | Arcol-E351 g (mmol) | BDO mL (mmol) | Q14-(OH)$_2$ g (mmol) | Alloc mL (mmol) |
|---|---|---|---|---|---|
| Control | 28.1 (114.3) | 61.7 (22.0) | 8.2 (92.3) | — | — |
| 8% alloc | 27.9 (113.5) | 61.2 (21.9) | 6.5 (73.5) | — | 2.2 (18.2) |
| 5% QAC | 27.2 (110.5) | 59.6 (21.3) | 6.9 (78.1) | 4.4 (11.0) | — |
| 10% QAC | 26.3 (106.9) | 57.6 (20.6) | 5.8 (64.9) | 8.5 (21.4) | — |

Figure 2:
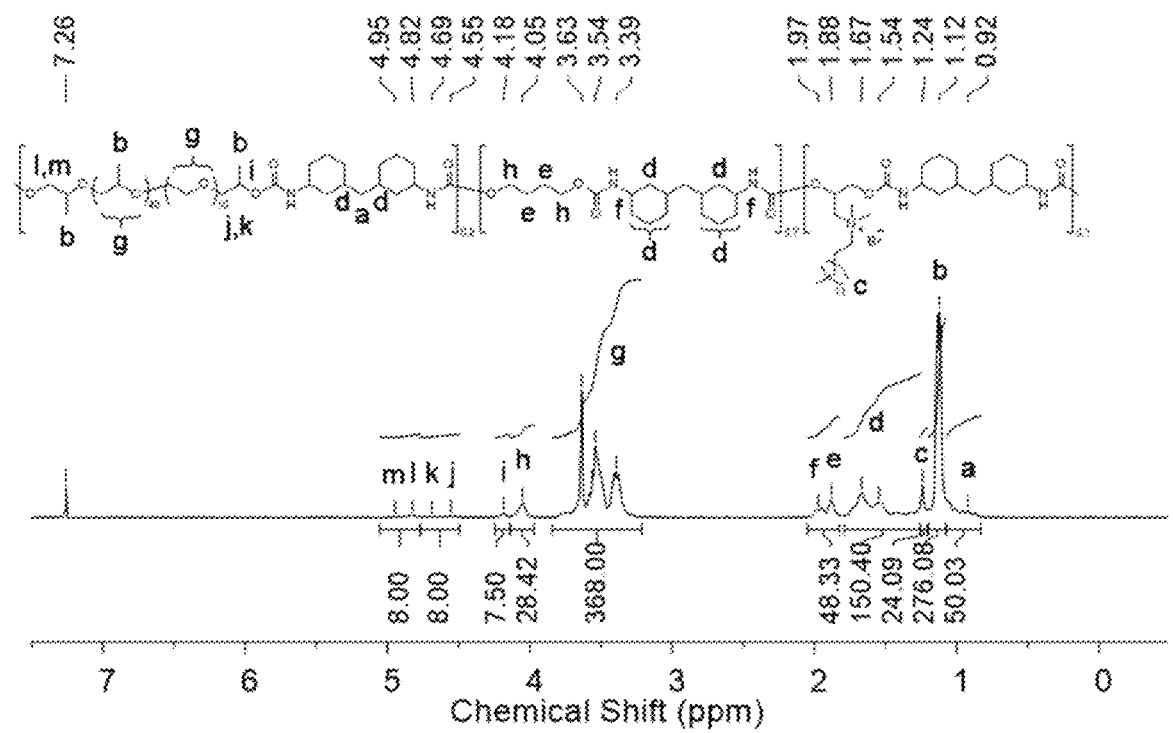
FIG. 2 is a $^1$H-NMR spectra of 5% QAC-TPU showing the appearance of a new peak c relative to the control. This peak corresponds to the aliphatic protons on the hydrocarbon chain of the QAC, and the integrations indicate an incorporation of ca. 5 mol %.
Figure 3:
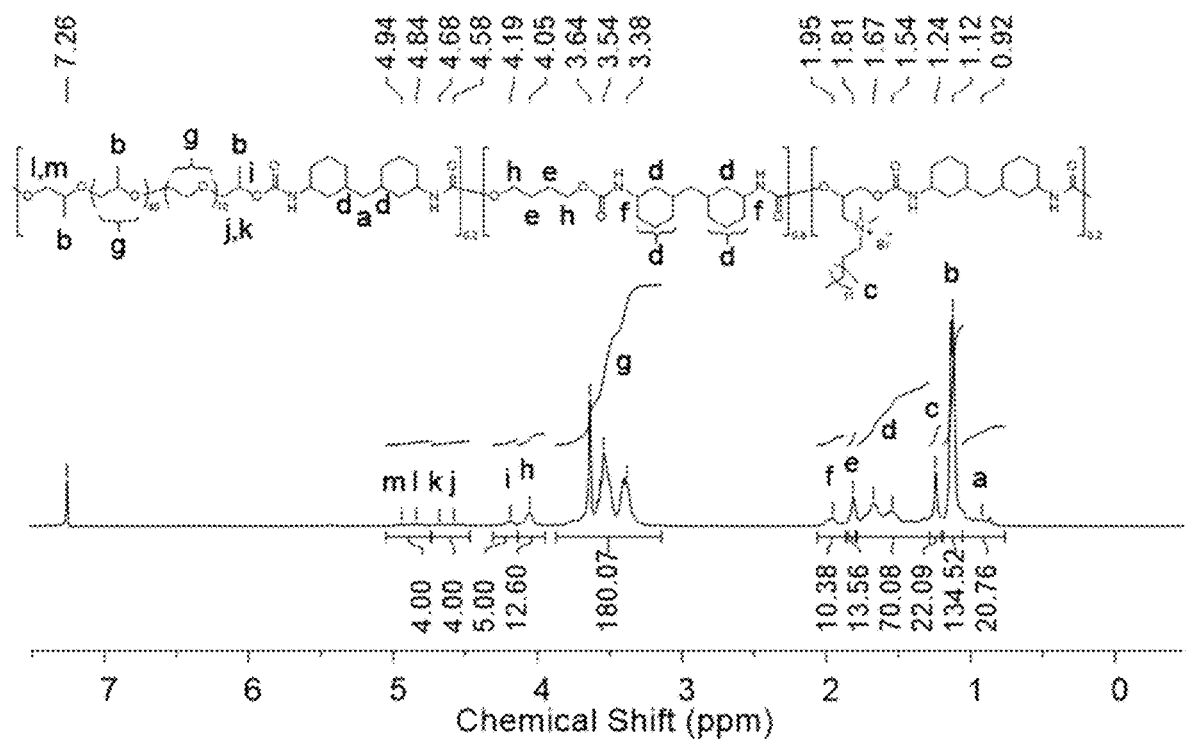
FIG. 3 is a $^1$H-NMR spectra of 10% QAC-TPU showing the appearance of a new peak c relative to the control. This peak corresponds to the aliphatic protons on the hydrocarbon chain of the QAC, and the integrations indicate an incorporation of ca. 10 mol %.
Figure 4:
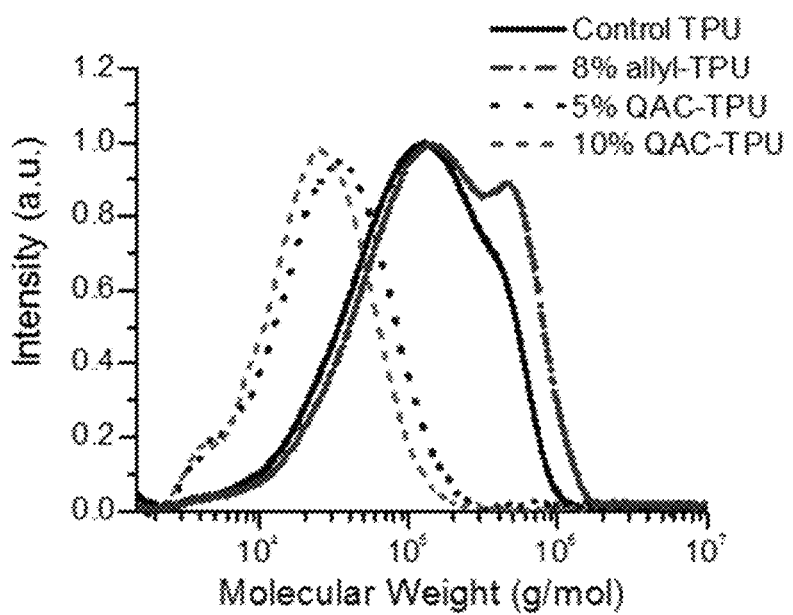
FIG. 4 is a size exclusion chromatography trace in THF affording the molecular weights for the control TPU, 5% QAC-TPU, 10% QAC-TPU, and 8% alloc-TPU. The molecular weights were determined using a polystyrene standard curve.

The TPUs were analyzed by $^1$H-NMR to confirm the presence and quantities of the functional moieties incorporated into each, which is demonstrated in FIGS. 2, 3, 20, and 21. The $^1$H-NMR spectral overlay provided in FIGS. 2 and 3 shows the appearance of a peak (δ=1.24) that corresponds to the alkyl tail of the active monomer in the 5% and 10% QAC-TPUs, while the $^1$H-NMR of 8% alloc-TPU in FIG. 21. FIG. 21 shows the appearance of a doublet of doublet (δ=5.22) and a multiplet (δ=5.85) corresponding to the allylic protons. FIG. 4 displays the SEC traces for each of the TPUs synthesized in this study, and the values are recorded in Table 2, below.

and alloc monomers compared to the control; however, a significant broadening and reduction in the $T_m$ was observed for both the 5% and 10% QAC-TPUs. The suppression and lowering of the melting point compared to the control TPU may be attributed to the formation of small crystallites, and is consistent with the introduction of a non-crystallizable component into the TPU, as previously reported. FIG. 5B shows the cooling scan following the first heating scan and indicates that significant crystallization is not observed for this cooling rate with the TPUs in this study. Notably, a suppression in crystallinity was not observed for the 8% alloc-TPU, as the first heating scan is nearly identical to the

TABLE 2

The molecular weight and physical properties for TPUs synthesized in this study.

Figure 6A:
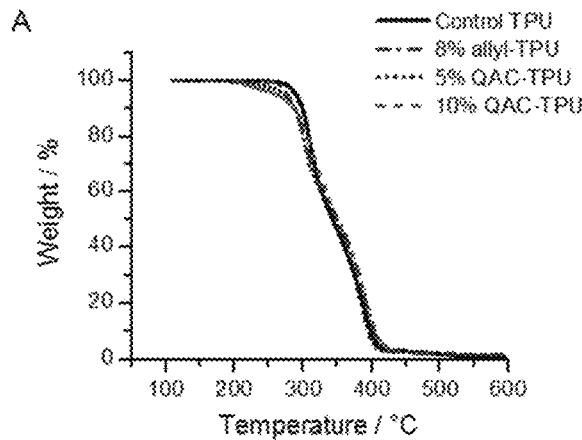
FIGS. 6A-B are graphs showing the results of a thermogravimetric analyses (TGA) performed to determine the onset degradation temperature ($T_d$) of the control TPU, 5% QAC-TPU, 10% QAC-TPU, and 8% alloc-TPU. The full spectra scan (FIG. 6A) reveals the $T_d$ occurs near 200-300° C. for the various TPUs, and decomposition is completed near 450° C. The expanded TGA spectra (FIG. 6B) resolves the $T_d$ for each TPU more clearly.
Figure 6B:
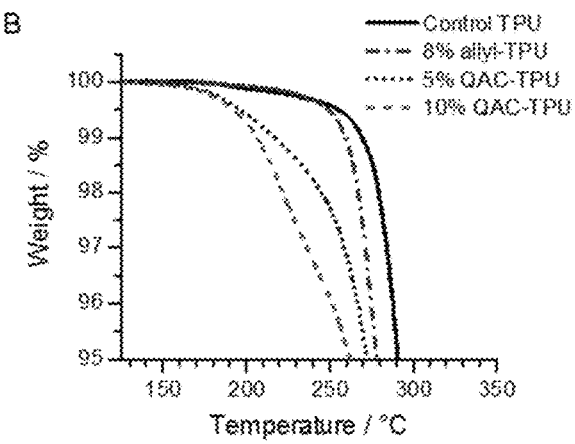
Figure 7A:
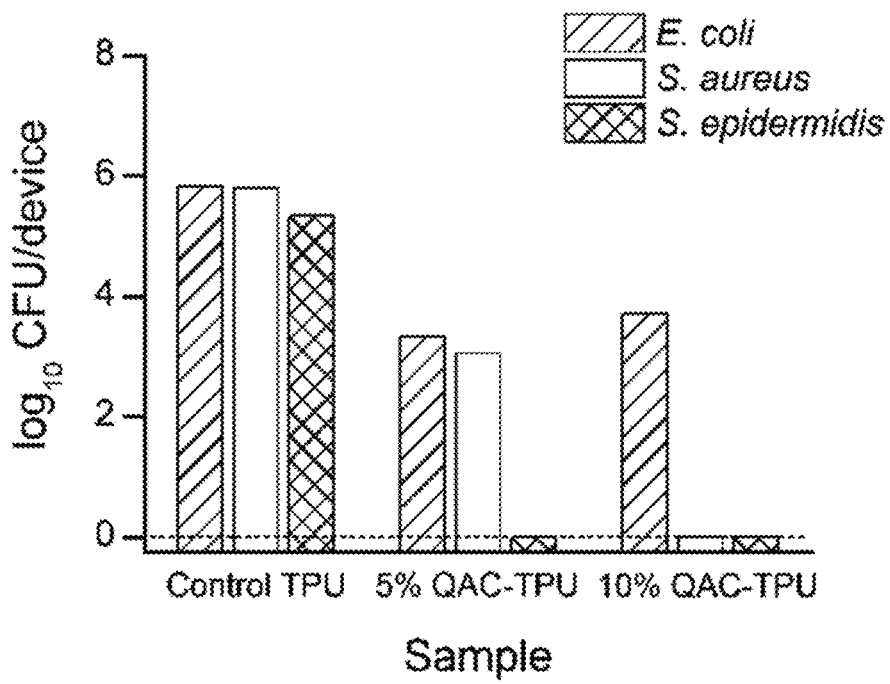
FIGS. 7A-B are graphs showing the results of antimicrobial testing using ISO22196 protocol where the $\log_{10}$ CFU/device is a measure of colony forming units on compression molded samples.
Figure 7B:
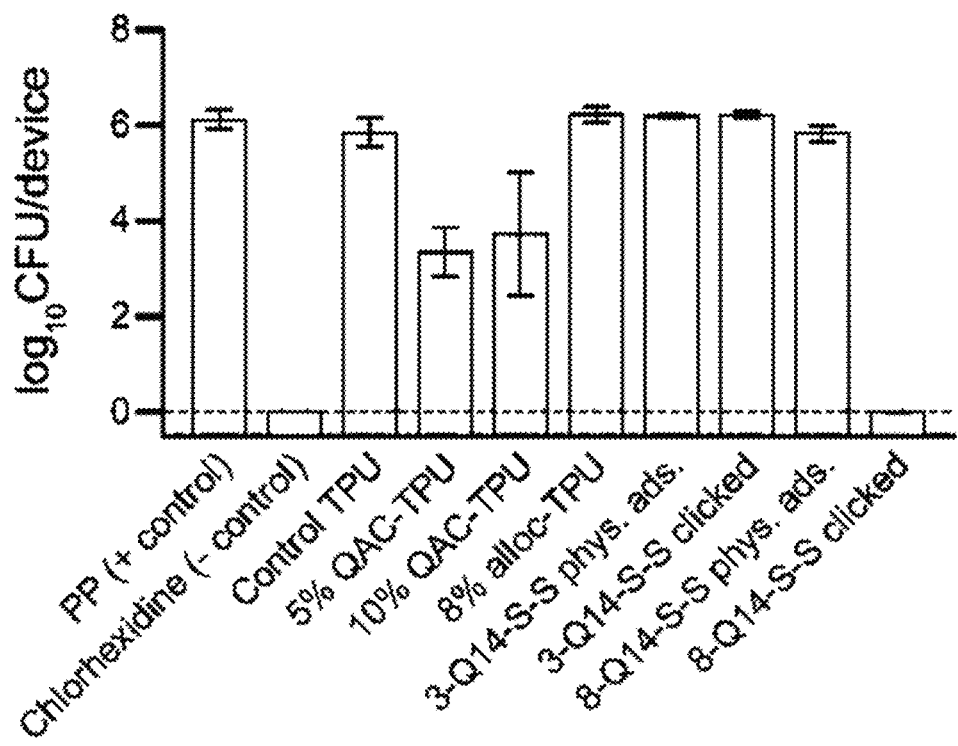
Figure 8:
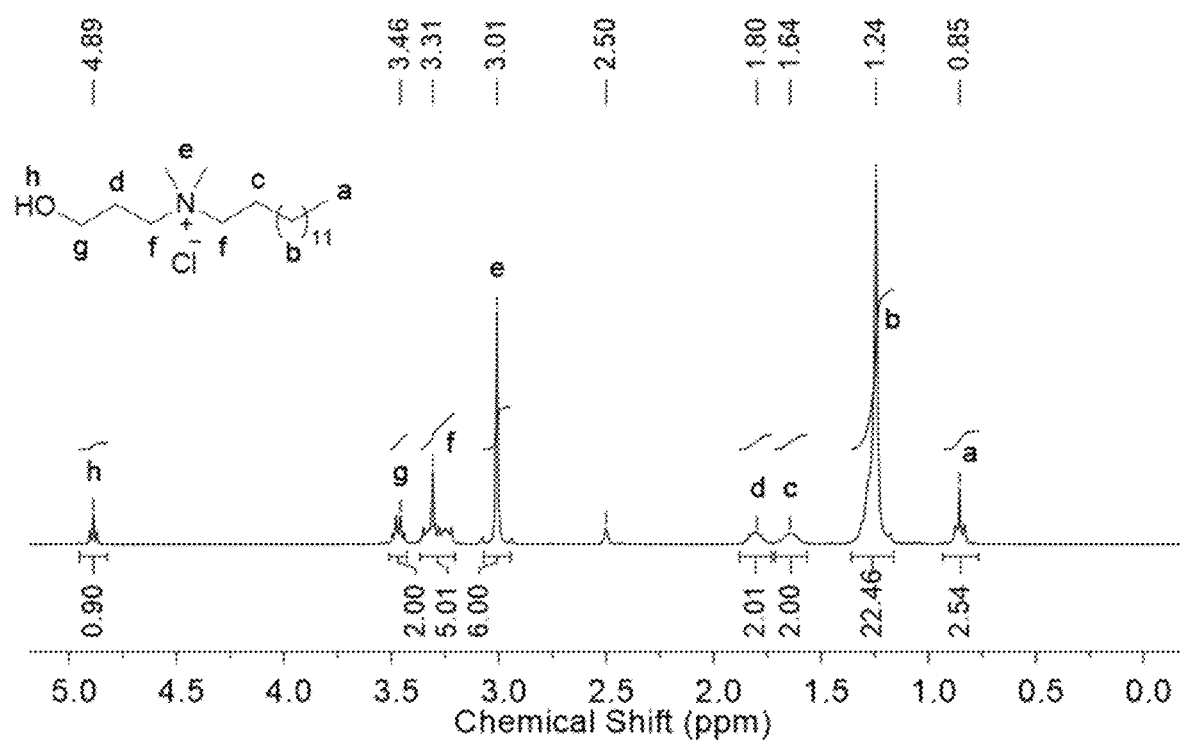
FIG. 8 is a $^1$H-NMR spectra of 3-Q14-OH demonstrating a 1:1 molar ratio of peaks c and d, which indicates the formation of the desired quaternary ammonium compound. Peak f overlaps with HDO (δ=3.30 ppm).
Figure 9:
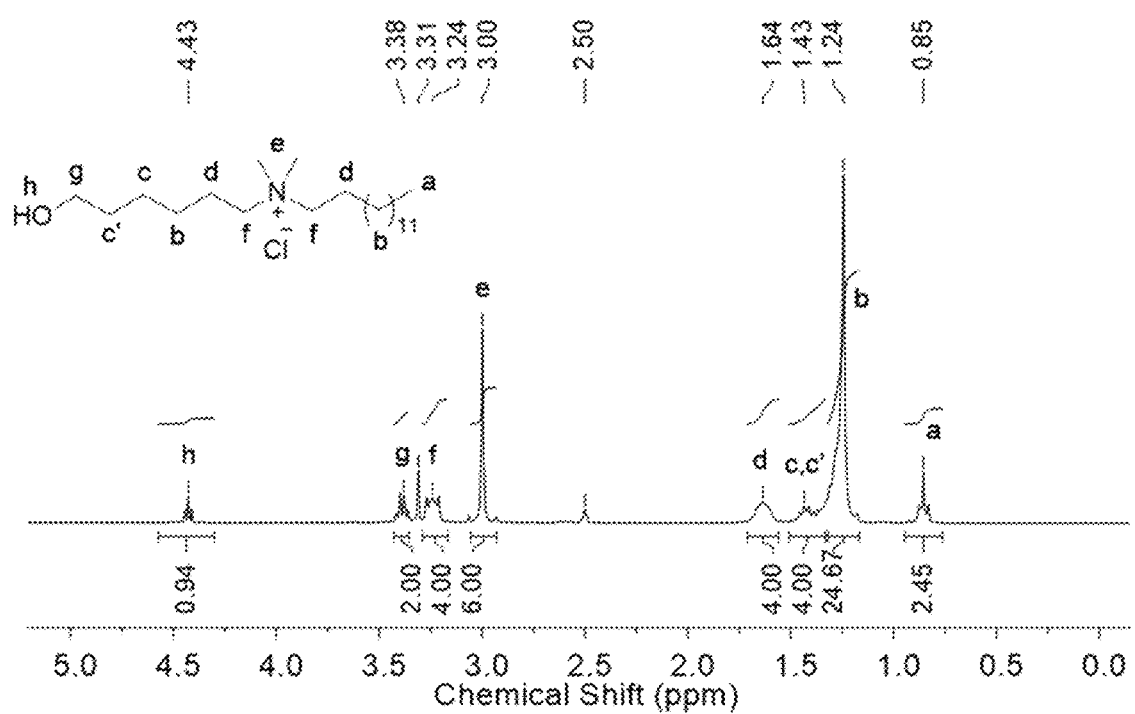
FIG. 9 is an $^1$H-NMR spectra of 6-Q14-OH demonstrating a 1:1 molar ratio of peaks e and g, as well as e and h, which indicates the formation of the desired quaternary ammonium compound.
Figure 10:
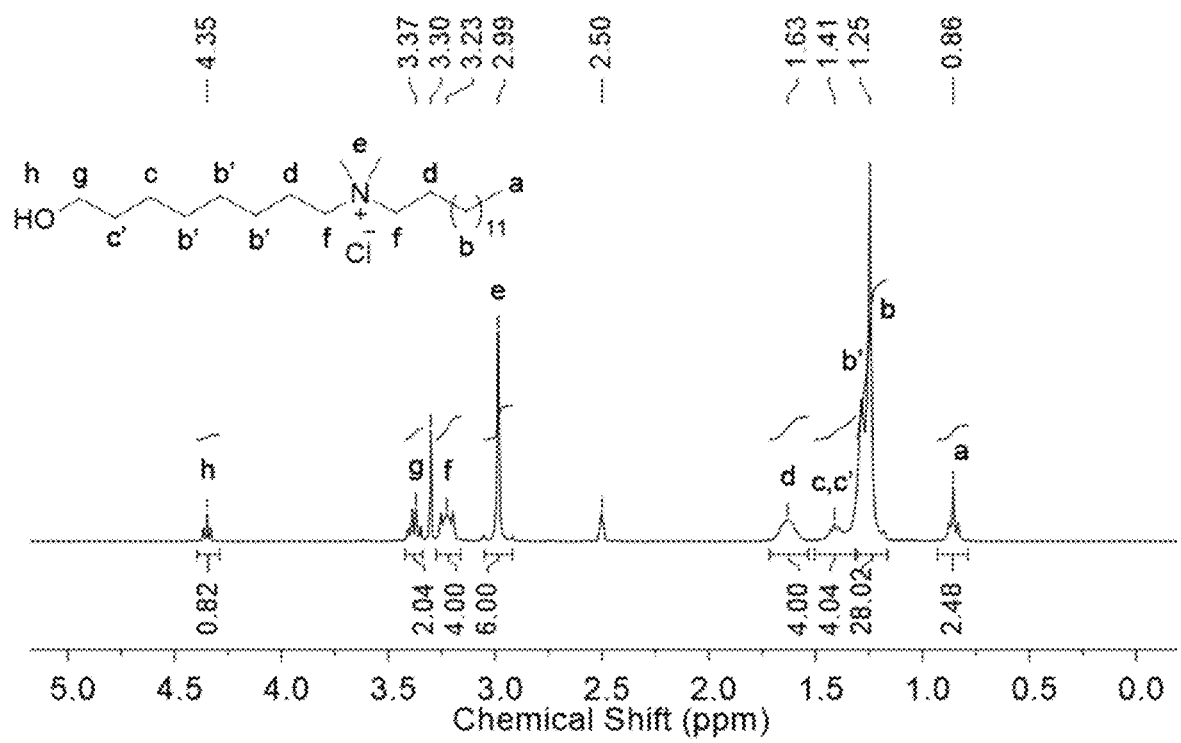
FIG. 10 is a $^1$H-NMR spectra of 8-Q14-OH demonstrating a 1:1 molar ratio of peaks e and g, which indicates the formation of the desired quaternary ammonium compound. The introduction of hydrocarbons from 8-chloro-1-octanol produces additional upfield peaks, b'-c'.
Figure 11:
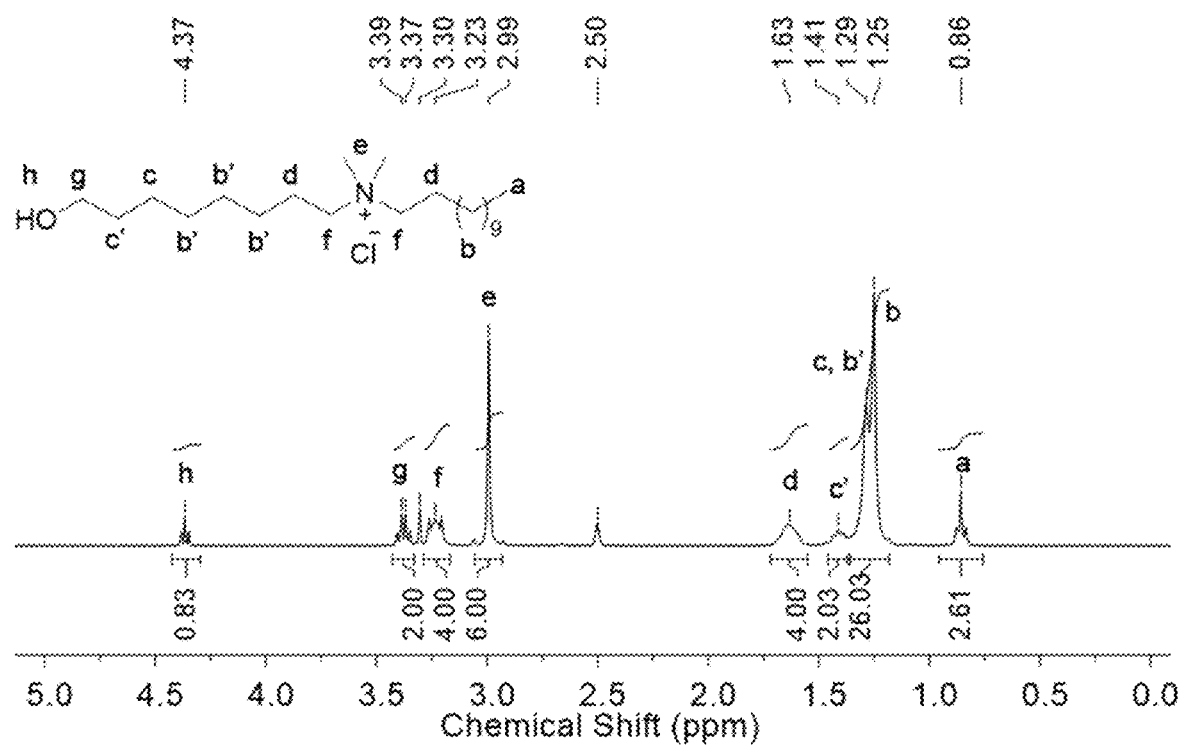
FIG. 11 is a $^1$H-NMR spectra of 8-Q12-OH demonstrating a 1:1 molar ratio of peaks e and g, which indicates the formation of the desired quaternary ammonium compound.

| | Molecular Weight Data | | | Physical Properties | | | |
|---|---|---|---|---|---|---|---|
| TPU | $\overline{M}_n$ (kDa) | $\overline{M}_w$ (kDa) | $Đ_m$ | $T_g$ (° C.) | $T_m$ (° C.) | $T_d$ (° C.) | Durometer |
| Control | 68 | 175 | 2.6 | −60.5 | 72, 119 | 255 | 90 |
| 8% alloc | 92 | 269 | 2.9 | −67.5 | 72, 115 | 245 | 90 |
| 5% QAC | 21 | 38 | 1.8 | −64.0 | 15-110, 124 | 180 | 70 |
| 10% QAC | 18 | 30 | 1.7 | −63.5 | 55-110, 119 | 180 | 50 | control TPU. The DSC data, in combination with durometer measurements, suggests that the 8% alloc-TPU is more similar from a thermo-mechanical standpoint to the control TPU than the QAC-TPUs. Lastly, the TGA data in FIGS. 6A-B shows that the 5% and 10% QAC-TPUs possess an earlier onset degradation temperature ($T_d$=180° C.) than the 8% alloc-TPU and control TPU ($T_d$=ca. 250° C.), which can likely be attributed to degradation of the active monomer. It should be noted, however, that the processing temperatures used (ca. 120° C.) are well below the $T_d$.

Surface-Reactive Allyl Quantification.

In order to determine the quantity of reactive allyl groups available on the surface of 8% alloc-TPU, a fluorescence assay was performed using a thiol-terminated PEG fluorophore tagged with FITC (FITC-PEG-SH). The κ% alloc-TPU was spin coated onto glass slides at various concentrations and RPMs (FIG. 22) in order to produce a thickness range of 50-600 nm. It was noticed that spin coated films produced at a spin rate of 5000 RPM were more consistent, and concentrations of 1, 3, and 5 wt. % were utilized to maximize the accessible thickness range. In addition to spin coated thin films, a hand-casted film of 50 μm thickness was also tested to provide insight to the effect of thickness and processing on the surface-reactive allyl content. Thus, samples of 8% alloc-TPU were generated at 50, 200, and 600 nm, as well as 50 μm thickness. Each sample was treated with a solution containing FITC-PEG-SH and photoinitiator, and the UV treated samples were irradiated with λ=365 nm light while physical adsorption controls were kept away from light. A standard curve of fluorescence intensity with varying concentration of FITC-PEG-SH was constructed (FIG. 23) and utilized to determine the quantity of covalently attached vs. physically absorbed dye on the 8% alloc-TPU samples. FIGS. 24A-D show the average fluorescence intensity for the UV treated samples and the physical adsorption controls at each film thickness, as well as covalent attachment (covalently bonded dye), which taken to be the difference between the UV treated and physically adsorbed samples; this represent the minimum amount of dye that is covalently attached to the substrate following UV treatment (i.e. the proportion of physically absorbed dye which becomes attached could not be determined). From the standard curve, the fluorescence intensity was converted to concentration, and after accounting for dilutions and sample size, the molar quantity per unit area of covalently attached and physically adsorbed dye was calculated, and the results are displayed in FIG. 25 and Table 3 (below).

The data suggests that increasing sample thickness increases both the specifically attached and physically absorbed dye, which is likely a result of the solution penetrating into the sample. It was hypothesized that a thickness threshold would eventually be reached where the sample would become saturated near the surface, and additional uptake of dye/photoinitiator solution would not be permitted. Hence, the 50 μm film was tested and it was found that the quantity of covalent attachment is comparable to the 600 nm thin film, while the physical adsorption was reduced. The reduction in physical adsorption may have been caused by varying the processing method and resulting morphology of the surface; although, an apparent maximum of ca. 0.45 nmol/cm² for covalent attachment was observed (Table 3, above). Thus, for a given sample of 8% alloc-TPU with ≥50 μm thickness, it was approximated that 0.4-0.5 nmol/cm² of allyl groups were available near the surface for post-processing functionalization reactions.

XPS Surface Characterization.

TPU films were surface functionalized with 8-Q14-S-S using a disulfide-ene reaction, illustrated in Scheme 7, and XPS was utilized for the identification of QAC compounds on the surface of 8% alloc-TPU samples.

Scheme 7

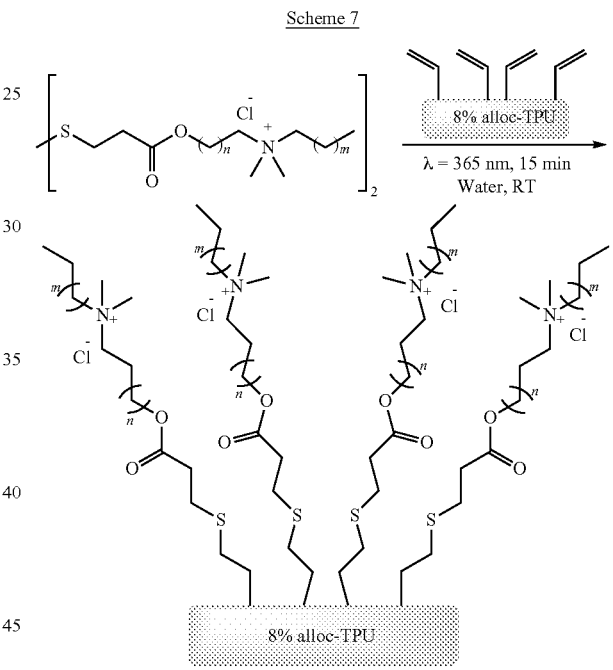

TABLE 3

Quantification of physically adsorbed and specifically attached fluorophore and QAC as determined by fluorescence and XPS experiments for each of the TPU film thicknesses.

| | Fluorescence Data/$10^{-10}$ mol/cm² | | | XPS Data (% $NR_4^+$ relative to N) | | |
|---|---|---|---|---|---|---|
| Sample Thickness | Physical Adsorption | UV Treated Sample | Covalent Attachment [d] | Physical Adsorption | UV Treated Sample | Covalent Attachment |
| 50 nm | 0.6 ± 0.1 | 1.1 ± 0.1 | 0.4 ± 0.1 | 2.8 ± 1.9 | 6.5 ± 1.3 | 3.7 ± 2.3 |
| 200 nm | 1.7 ± 0.3 | 3.6 ± 0.3 | 1.9 ± 0.4 | 0.8 ± 0.7 | 4.0 ± 0.8 | 3.2 ± 1.1 |
| 600 nm | 5.3 ± 0.4 | 10.4 ± 0.4 | 5.1 ± 0.6 | 0.8 ± 0.8 | 4.6 ± 2.2 | 3.8 ± 2.4 |
| 50 μm [a,b] | 1.3 ± 0.2 | 5.4 ± 0.5 | 4.1 ± 0.5 | — | — | — |
| 0.5 mm [c] | — | — | — | 2.5 | 5.5 | 3.0 |

[a] The sample was prepared by blade coating TPU/THF solution.
[b] The sample was irradiated under UV light for 8 min.
[c] The sample was prepared by compression molding at 120° C.
[d] Errors are reported as propagated standard deviations accounting for standard curve fit error. All other errors are standard deviations (n ≥ 3).

The QAC-S-S reagents shown in Scheme 7 were attached to the surface of 8% alloc-TPU using a disulfide-ene reaction wherein the TPU was submerged in a solution containing Irgacure-2959 and the desired QAC disulfide reagents and then irradiated for 15 min at room temperature under λ=365 nm light.

FIGS. 26A-D show representative hi-res N1s spectra with curve fits for a 50 nm untreated control, and UV-treated samples of 50, 200, and 600 nm thickness. The quaternary ammonium peak (401-402 eV) appears as a shoulder to the main nitrogen peak (398.5 eV) which is contained in the urethane bonds of the TPU. The curve fitting routine used for these spectra provided fits for the main nitrogen peak, the quaternary ammonium peak, and a summation of two. FIGS. 27A-D show representative hi-res N1s spectra for corresponding physical adsorption controls at each film thickness, and the relative ratio of quaternary ammonium to nitrogen was subtracted from that of the UV-treated samples to provide a QAC: nitrogen value for covalent attachment, which is recorded in Table 3, above. It can be seen from these figures that the QAC content was higher near the surface for 50 nm films, however, accounting for physical adsorption yielded a covalent attachment of QACs as ≥4% relative to urethane nitrogen (FIGS. 28A-B). A summary of the XPS results indicating QAC: nitrogen for covalent attachment and physical adsorption controls is provided in FIG. 28C and Table 3, above.

In a second set of experiments, thermoplastic polyurethanes according to various embodiments of the present invention containing allyl ether side-chain functionality (allyl-TPU) that allows for rapid and convenient surface modification with antimicrobial reagents post-processing were examined. In these experiments, a series of quaternary ammonium thiol compounds (Qx-SH) possessing various hydrocarbon tail lengths (8-14 carbons) were synthesized and attached to an allyl-TPU surface using thiol-ene "click" chemistry. A quantitative assessment of the amount of Qx-SH that is covalently attached and physically adsorbed on the surface following the "click" reactions was performed using fluorescence spectroscopy and X-ray photoelectron spectroscopy (XPS). In addition, contact-killing assays on QAC functionalized TPUs were used to screen a series of Qx-SH compositions for optimal antimicrobial activity against several microbes linked to catheter infections, and live/dead fluorescence staining was used to demonstrate their contact-killing efficiency. Scale-up, extrusion, and post-fabrication functionalization of these allyl-TPUs were performed with the most promising Qx-SH candidate. Finally, catheter prototypes according to various embodiments of the present invention were tested for biofilm formation resistance to *P. aeruginosa*, a film-forming bacterium commonly associated with biofilm-mediated infections on medical devices.

Characterization of Thiol-Ene Reagents.

The thiol based QAC reagents used for surface functionalization "Qx-SH" were produced by first generating the corresponding Qx-OH compounds (where x=8, 12, or 14 carbons) via neat quaternization reactions of DOA, DDA, and DTDA (m=6, 10, 12) with 8-chloro-1-octanol performed in bulk as shown in Scheme 8.

Scheme 8

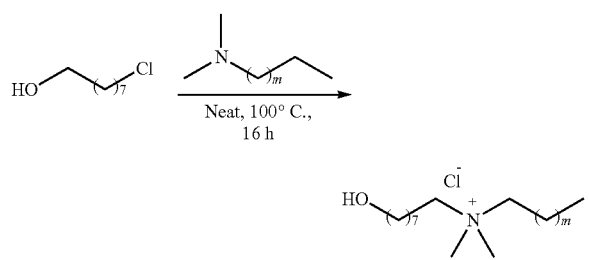

A series of quaternary ammonium alcohols with tail lengths (x) were produced by this method, and the purity of the compounds was confirmed by ¹H-NMR spectroscopy (FIGS. 29-31). The ¹H-NMR spectra revealed a sharp singlet (δ=3.00) corresponding to the methyl groups of the quaternary amine, which was integrated and compared to aliphatic resonances of the 8-carbon spacer and various carbon tail lengths for each Qx-OH compound. To achieve the corresponding disulfides, 3,3'-dithiopropionic acid was converted to a diacid chloride (see, Scheme 2, above) and subsequently reacted with the Qx-OH compounds to yield the Qx-S-S series as shown in Scheme 9, below.

Scheme 9.
Synthesis of QAC disulfide reagents (Qx—S—S) by esterification of the corresponding Qx—OH compounds with 3, 3'-dithiopropanoyl chloride.

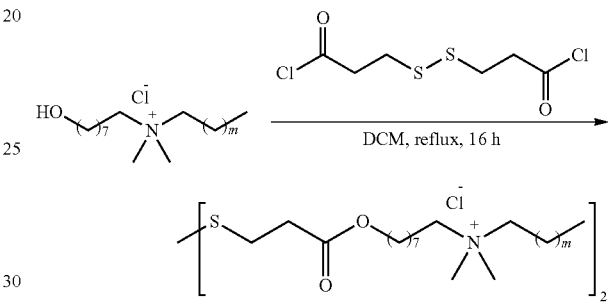

The conversion of 3,3'-dithiopropionic acid to 3,3'-dithiopropanoyl chloride was quantitative, as confirmed by ¹H-NMR and ¹³C-NMR spectra (FIG. 32 and FIG. 33, respectively), and esterification afforded the Qx-S-S reagents, which were also characterized by ¹H-NMR spectroscopy (FIGS. 34-36). Notably, the ¹H-NMR spectra for all Qx-S-S compounds demonstrated the appearance of two triplets (δ=2.70 and 2.90 ppm) corresponding to the methylene protons α and β to the disulfide, which were integrated and compared to the methylene protons (δ=4.03 ppm) adjacent to the newly formed ester, as well as the aliphatic protons of the hydrocarbon spacer and tail. The Qx-S-S compounds were reduced using TCEP (Scheme 10) to generate the desired Qx-SH reagents, which were also analyzed by ¹H-NMR spectroscopy (FIGS. 37-39).

Scheme 10
Reduction of Qx—S—S reagents with TCEP to generate the corresponding Qx—SH compounds.

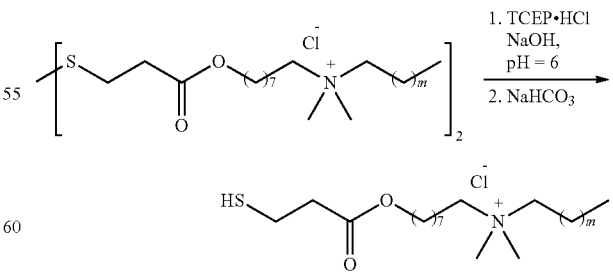

Figure 45:
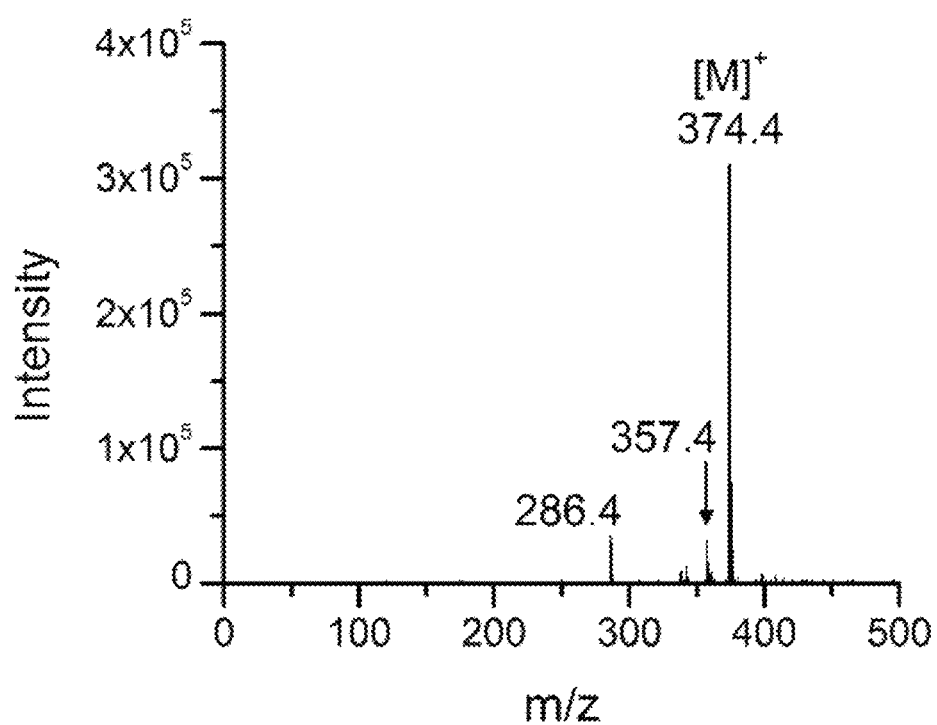

The ¹H-NMR spectra demonstrated the coalescence of the Qx-S-S triplets (δ=2.70 and 2.90 ppm) into a multiplet (δ=2.62 ppm) for the Qx-SH series. More convincingly, the ¹³C-NMR spectra overlay of Qx-S-S and Qx-SH demonstrated significant shifting of the carbon α to the carbonyl downfield (from 33.85 to 38.39 ppm) and the β carbon upheld (from 33.18 to 19.74 ppm) (FIGS. 40-42). ESI-MS also confirmed the mass for each Qx-SH compound; [M]⁺=458.5 Da (Q14-SH), 430.4 Da (Q12-SH), and 374.4 Da (Q8-SH) (FIGS. 43-45).

As set forth above, in order to quantitatively assess the amount of Qx-SH that was covalently attached and physically adsorbed on the surface following the "click" reactions fluorescence spectroscopy was performed using a thiol functionalized rhodamine dye (rhodamine-SH), synthesized and attached to an allyl-functionalized TPU as described below. The rhodamine-SH was achieved through esterification of rhodamine B 4-(3-hydroxylpropyl) piperazine amide with 3,3'-dithiopropanoyl chloride, followed by TCEP reduction (See, Scheme 14 and Examples 11 and 12, below). ¹H-NMR spectroscopy and ESI-MS were used to confirm each synthetic step towards producing rhodamine B 4-(3-hydroxylpropyl) piperazine amide (FIGS. 46-50). Following esterification with 3,3'-dithiopropanoyl chloride, the ¹H-NMR spectra revealed the appearance of the expected triplets (2.68 ppm and 2.89 ppm) and ESI-MS exhibited a doubly charged ion [M]²⁺=656.34 Da, which corresponds to the mass of rhodamine-S-S (1312.68 Da) (FIG. 50 and FIG. 52, respectively). TCEP reduction of rhodamine-S-S afforded the desired rhodamine-SH, and ¹H-NMR demonstrated the merging of the triplets (δ=2.68 and 2.89 ppm) into a multiplet (δ=2.61 ppm) (FIG. 53). ESI-MS confirmed the mass of the rhodamine-SH (molecular ion [M]⁺=657.4 Da) (FIG. 54). In addition, ¹³C-NMR spectroscopy reveals the shifting of the carbon α to the carbonyl downfield (from 33.79 to 38.36 ppm) and the β carbon upfield (from 33.07 to 19.72 ppm) (FIG. 55). UV-visible and fluorescence spectroscopy of rhodamine-SH in DMSO provided the $\lambda_{abs}$=568 nm and the $\lambda_{em}$=592 nm (FIG. 56), and a standard curve of the fluorescence intensity at $\lambda_{em}$ vs. concentration for rhodamine-SH in DMSO was constructed, yielding a slope of (168.7±0.1)×10⁹ M⁻¹ with an R²=0.99 (FIG. 57).

The LAP photoinitiator was synthesized using a Michaelis-Arbuzov reaction between the acid chloride and alkyl phosphonite to generate the acyl phosphinate, followed by treatment with LiBr. (See, Scheme 11 and Example 13).

Scheme 11
Synthesis of LAP using a Michaelis-Arbuzov reaction.

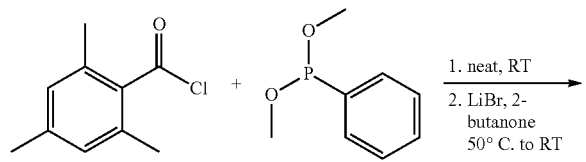

-continued

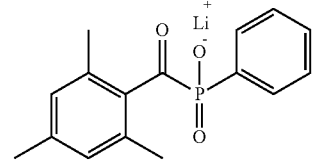

The presence of the LAP photoinitiator was confirmed with ¹H-NMR spectroscopy (See, FIG. 58). The integrations of peaks a-c were approximately equimolar to the integrations for peaks d-f, indicating a 1:1 substitution occurred. LAP photoinitiator was used for subsequent thiol-ene reactions due to its water solubility and substantially higher ε at λ=365 nm compared to other commercially available water-soluble photoinitiators, such as IRGACURE™ 2959 (δ= 4 M⁻¹cm⁻¹)³³ The UV-vis absorption spectra for LAP at several concentrations were recorded and a linear plot of the absorbance at λ=365 nm vs. concentration was constructed to determine the molar absorptivity of LAP (ε=179±3 M⁻¹cm⁻¹) (FIGS. 59A-B).

Characterization of Control-TPU and Allyl-TPU.

A control TPU consisting of an aliphatic diisocyanate (HMDI) and a mixture of diols including BDO and Arcol-E351 was synthesized to mimic a medical grade Tecoflex™ TPU with shore A hardness=90 (see, Scheme 12, below). These TPUs were synthesized under bulk conditions at 100° C. with mechanical stirring. To incorporate a functional moiety, the feed ratio of BDO was reduced, while maintaining the molar ratio of HMDI:Arcol E-351 used for the control TPU snythesis. To produce an allyl-TPU, diol A containing the allyloxy functionality (OCH₂—CH=CH₂) was incorporated into the backbone of the urethane polymer. To produce a 30 wt. % HMDI TPU containing 8 mol % of 3-allyloxy-1,2-propanediol, the molar ratios are reported in terms of the repeat unit, denoted as $n_R$; where $n_A$=0.16, $n_B$=0.64, $n_C$=0.20, and n is an integer representing the total number of repeat units in the polymer.

Scheme 12

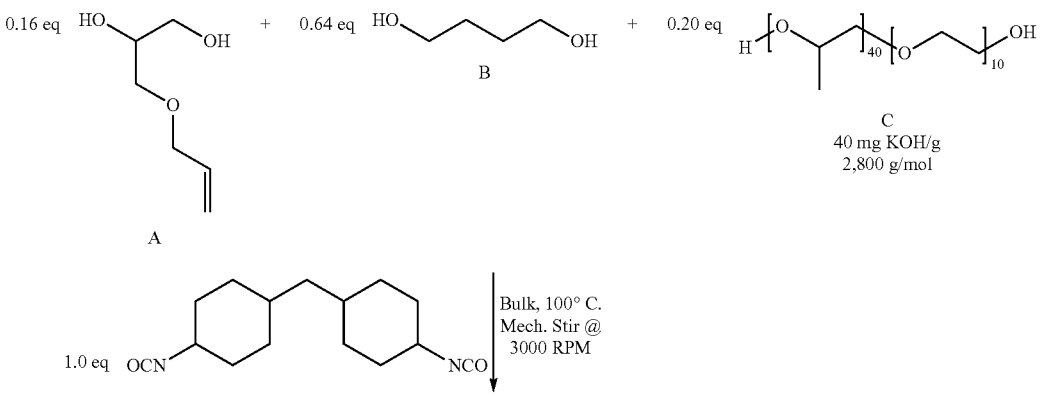

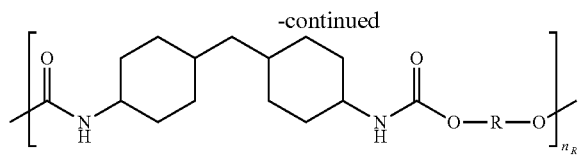

R = A, B, C $n_R = (n_A, n_B, n_C)*n$

¹H-NMR was used to determine the resulting composition by integration of peaks f, g, and h, providing the molar composition of HMDI:Acrol-E351:BDO=0.5:0.1:0.4. (See, FIG. 20).

The allyl-TPU was synthesized in the same manner as the control, except the feed ratio of BDO was reduced to include 3-allyloxy-1,2-propanediol to the mixture of diols (See, Scheme 13, below).

An additional 2.27 kg of allyl-TPU was synthesized in 0.454 kg batches for extrusion of the catheter tubes, and batches were designated numbers 1 through 5 (8% allyl-1-8% allyl-5). ¹H-NMR spectra were integrated for each batch to confirm the allyl content and SEC was performed to monitor molecular mass ($\overline{M}_n, \overline{M}_w$) and molecular mass distribution ($Đ_m$) consistency between batches; the data are recorded in Table 5, below. In addition, the durometer Scheme 13
Synthetic route for producing the allyl-TPU

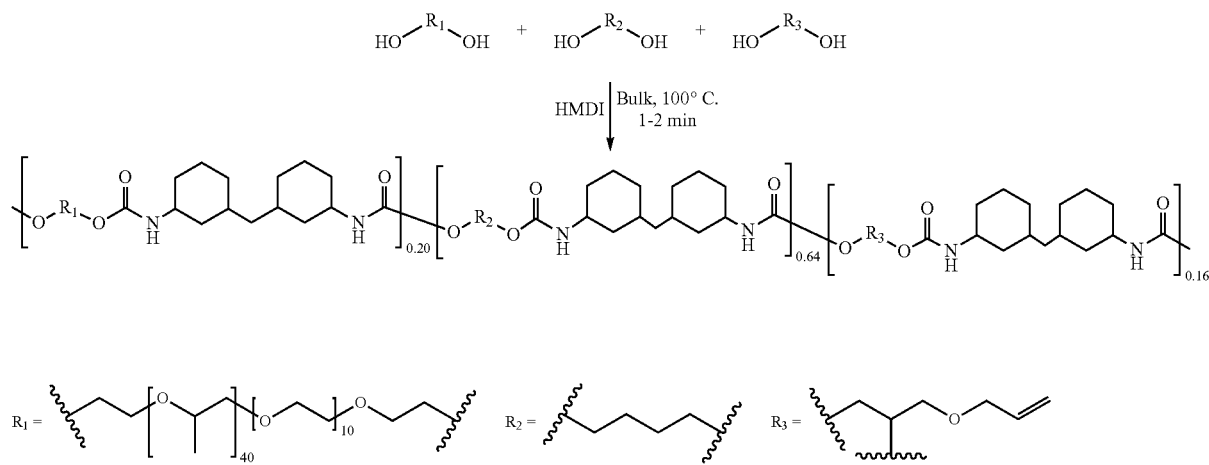

¹H-NMR of the allyl-TPU shows the appearance of a doublet of doublets (δ=5.22 ppm, $^3J_{H-H}$=24.2, 13.8 Hz) and a multiplet (δ=5.85 ppm) corresponding to the allylic protons (FIG. 21). The resulting composition (8% allyl) was determined by integration of peaks f, g, h, and n, which provided the molar composition of HMDI:Acrol-E351:BDO:allyl=0.5:0.1:0.32:0.08. (Table 4).

hardness of the allyl-TPU was the same as the control (shore A durometer=90), and the thermal properties were examined to gauge the extrusion conditions; TGA demonstrated the onset degradation temperature ($T_d$) for allyl-TPU was 245° C. while the control TPU was 255° C., and DSC thermograms revealed that the melting temperature ($T_m$) and glass transition temperature ($T_g$) were practically unaffected by

TABLE 4

Reagent table for compounds used in various TPU polymerizations.

| TPU | HMDI mL (mmol) | Arcol-E351 g (mmol) | BDO mL (mmol) | 3-allyloxy-1,2-propanediol mL (mmol) | Stannous octoate mL (mmol) |
| --- | --- | --- | --- | --- | --- |
| Control | 28.1 (114.3) | 61.7 (22.0) | 8.2 (92.3) | — | 0.15 (0.46) |
| 8% allyl | 139.6 (567.4) | 306.1 (109.3) | 32.6 (367.3) | 11.23 (90.8) | 0.40 (1.24) | the introduction of 3-allyloxy-1,2-propanediol into the TPU (see, Table 5). The resulting allyl-TPU blade-coated samples and extruded tubes were also optically clear.

TABLE 5

The molecular weight and physical properties for TPUs synthesized in this study.

| TPU | Molecular Weight Data | | | | Physical Properties | | | |
|---|---|---|---|---|---|---|---|---|
| | $\overline{M}_n$ (kDa) | $\overline{M}_w$ (kDa) | $Đ_m$ | % allyl [a] | $T_g$ (° C.) | $T_m$ (° C.) | $T_d$ (° C.) | Durometer [b] |
| Control | 68 | 175 | 2.6 | 0.0 | −60.5 | 72, 119 | 255 | 90 |
| 8% allyl | 92 | 269 | 2.9 | 8.0 | −62.5 | 72, 115 | 245 | 90 |
| 8% allyl-1 | 37 | 87 | 2.4 | 8.1 | — | — | — | — |
| 8% allyl-2 | 43 | 108 | 2.5 | 8.0 | — | — | — | — |
| 8% allyl-3 | 42 | 113 | 2.7 | 7.8 | — | — | — | — |
| 8% allyl-4 | 35 | 82 | 2.3 | 7..9 | — | — | — | — |
| 8% allyl-5 | 41 | 103 | 2.5 | 7.8 | — | — | — | — |

[a] Determined by $^1$H-NMR integration.
[b] Shore A durometer measurements were taken on compression molded samples in accordance with ASTM D2240.

Post-Fabrication Surface Functionalization and Quantification.

Surface modification of allyl-TPU blade-coated samples and catheter tubing was achieved using thiol-ene "click" chemistry (See FIG. 60). The thiol-ene reaction provides an efficient and convenient method to modify surfaces containing alkene functionalities, and can be performed in water with the assistance of a photoinitiator and UV light (365 nm). For a quantitative assessment of the amount of Qx-SH that attaches to the surface via thiol-ene reactions, a rhodamine-SH dye containing the same synthetic core as the Qx-SH compounds was reacted with allyl-TPU blade-coated samples and analyzed by fluorescence spectroscopy (FIG. 61). The samples were either treated with UV light (i.e. "UV-treated") or kept in the absence of UV light for 30 min to control for physical adsorption of the dye (denoted as "phys. ads." samples). Notably, the rhodamine-SH dye shares an identical chemical structure with the Qx-SH reagents up to 7 atoms from the thiol functionality, and should provide a reasonable comparison from a reactivity standpoint. As shown in FIG. 61, the untreated control does not exhibit fluorescence over the scanned emission range, while the UV-treated and phys. ads. samples achieved fluorescence intensities corresponding to 5.5±0.1 and 3.6±0.1 nmol·cm$^2$ of rhodamine-SH per sample surface area, respectively (See, Table 6).

The observed increase in dye quantity for UV-treated samples compared to phys. ads. controls may be attributed to an additional quantity of covalently attached rhodamine-SH; however, since the disappearance of the allyl functional groups located near the surface could not be resolved from the bulk signal due to instrumental resolution, the proportion of physically adsorbed dye that becomes covalently linked to the surface could not be elucidated. Hence, as a quantitative result, the subtraction of the phys. ads. dye quantity from the UV-treated dye quantity provides a minimum of attached rhodamine-SH, while the UV-treated sample alone provides the potential maximum quantity of attached rhodamine-SH. Therefore, a range regarding the expected quantity of covalently attached thiol compounds was reasoned to be between 1.9±0.1 to 5.5±0.1 nmol·cm$^2$ for allyl-TPU samples.

Additional characterization of surface-functionalized samples was performed using XPS. High-resolution N1s spectra were obtained for Qx-SH modified allyl-TPU samples and catheter tubing to confirm the presence of QACs on the surface, and to evaluate the proportion of Qx-SH present on UV-treated samples relative to phys. ads. controls (FIGS. 62A-B). High-resolution N1s XPS reveals a major peak at 398.4 eV corresponding to nitrogen (N) contained in the urethane bonds throughout the TPU backbone, as well as a minor peak between 401-402 eV corresponding to quaternary nitrogen (NR$_4^+$) introduced by the Qx-SH compounds. As shown, the UV-treated samples demonstrated a more pronounced NR$_4^+$ peak compared to the phys. ads. and untreated controls (FIG. 62A). For the Qx-SH series, XPS was performed in triplicate on independent batches of post-fabrication functionalized allyl-TPU blade-coated samples, and the average % NR$_4^+$ relative to urethane N was determined (See, FIG. 62B, Table 3). The results indicated that the UV-treated samples contained

TABLE 6

Quantification of rhodamine-SH and QAC present on UV treated and phys. ads. allyl-TPU samples as determined by fluorescence spectroscopy and XPS experiments, respectively.

| Thiol | Fluorescence Data/10$^{-9}$ mol · cm$^{-2}$ | | | XPS Data (% NR$_4^+$ relative to N) | | |
|---|---|---|---|---|---|---|
| | Physical Adsorption | UV Treated | Covalent Range [a] | Physical Adsorption | UV Treated | Portion of Physically Adsorbed QAC [b] |
| Rhodamine-SH | 3.6 ± 0.1 | 5.5 ± 0.1 | 1.9 ± 0.1-5.5 ± 0.1 | — | — | — |
| Q14-SH | — | — | — | 4.1 ± 0.6 | 12.4 ± 1.5 | 33.2 ± 6.1% |
| Q12-SH | — | — | — | 4.1 ± 0.2 | 14.1 ± 0.4 | 29.1 ± 1.6% |
| Q8-SH | — | — | — | 2.6 ± 2.2 | 9.4 ± 0.8 | 27.1 ± 23.8% |

[a] Errors are reported as propagated standard deviations after accounting for standard error in the calibration curve.
[b] Values are the quotient of physical adsorption divided by UV treated, errors are propagated standard deviations.
All experiments were performed in triplicate and averages and standard deviations are reported (n = 3).

significantly higher QAC content than their respective phys. ads. controls for each Qx-SH group. Furthermore, the average proportion ($\bar{x}$) of physically adsorbed Qx-SH across all groups was found to be $\bar{x}<\frac{1}{3}$ of the total Qx-SH present in UV-treated allyl-TPU blade-coated samples (See, Table 3, above). Additional high-resolution N1s spectra of the inner lumen of phys. ads. and UV-treated allyl-TPU catheter tubing (longitudinal sections) modified with Q8-SH were obtained. The phys. ads. sample did not exhibit an $NR_4^+$ peak, while the UV-treated tubing contained 14.4% $NR_4^+$ relative to urethane N (FIGS. 63A-B). However, it is possible that the phys.ads. catheter sample still possessed QAC on the surface and that the $NR_4^+$ peak was obscured due to the change in processing method from solvent casting to melt extrusion, which would increase the prevalence of polar segments near the surface (i.e. inflating the urethane nitrogen signal relative to $NR_4^+$).

Comparison of the XPS and fluorescence data suggests the relative proportion of physically adsorbed Qx-SH compounds is less than that shown for rhodamine-SH (FIGS. 61 and 62A-B). This may be contributed to differences in non-covalent interactions between the respective thiols and the allyl-TPU; while the Qx-SH may hydrogen bond via ester and thiol functional groups, the rhodamine-SH possesses tertiary amine, amide, ester and thiol functionalities, as well as potential π-π interactions between the rhodamine core and the allyl groups of the TPU. Overall, combining the quantitative results of the fluorescence assay with the XPS data suggests that the quantity of Qx-SH available on the surface of allyl-TPU samples post-functionalization is likely between 1.9±0.1 to 5.5±0.1 nmol·cm², of which <⅓ is physically adsorbed (See, Table 3, above).

Antimicrobial Testing.

As set forth above, contact-killing assays on QAC functionalized TPUs were used to screen a series of Qx-SH compositions for optimal antimicrobial activity against several microbes linked to catheter infections, and live/dead fluorescence staining was used to demonstrate their contact-killing efficiency. Initial screening for antimicrobial activity was performed on phys. ads. and UV-treated allyl-TPU blade-coated samples modified with the Qx-SH series using a 24 h contact-killing assay adapted from ISO 22196. The results of the assay demonstrated a 6-log reduction (99.9999%) in *E. coli* compared to the negative control for Q8-SH (UV-treated and phys. ads.) and Q12-SH (UV-treated) samples (Table 7). Less notable reductions were observed for the Q12-SH (phys. ads.) and Q14-SH (UV-treated and phys. ads.) samples, which demonstrated ca. 1-3-log reductions (90-99.9%) compared to the negative control. In addition, complete reductions (5-log) in *S. epidermidis* compared to the negative control were observed for all Qx-SH compositions (UV-treated and phys. ads). Further contact-killing assays with MRSA, *E. faecalis*, and *P. aeruginosa* were performed, demonstrating similar results (i.e. complete reduction of MRSA and *E. faecalis* for nearly all samples, and complete reduction of *P. aeruginosa* for Q8-SH phy. ads., Q8-SH UV-treated, and Q12-SH UV-treated samples). The contact-killing assay highlighted the antimicrobial efficacy of both phys. ads. and UV-treated samples modified with Q8-SH, suggesting this composition was the most potent of the Qx-SH series, and prompting further investigation into its antimicrobial properties. Interestingly, the antimicrobial activity of the Qx-SH series trended with the surface wettability determined by contact angle measurements (FIG. 64). As the alkyl tail length was decreased from 14 to 8 carbons, the hydrophilicity and the antimicrobial activity were simultaneously increased. (See, Table 7, below). Previous studies that have examined QACs and other synthetic mimics of antimicrobial peptides (SMAPs) have noted that the cationic charge and hydrophobic balance are important for the antimicrobial activity of these cationic moieties. Although, this effect appears to be highly dependent on the polymer system and generalized conclusions regarding the most effective charge density and degree of hydrophobicity may not translate. What is certain, however, is that this balance is indeed important for optimizing the antimicrobial activity of surface-immobilized QACs.

TABLE 7

Contact-killing assay (adapted from ISO 22196) results
Mean CFU/Sample Recovered

| Sample | | *E. coli* [a] | *S.epidermidis* [a] | MRSA [b] | *E. faecalis* [b] | *P. aeruginosa* [b] |
|---|---|---|---|---|---|---|
| Polypropylene [c] | | 2.04 (±0.06) × $10^6$ | 0.93 (±0.03) × $10^5$ | 1.51 × $10^5$ | 1.70 × $10^5$ | 7.94 × $10^6$ |
| Chlorhexidine [d] | | 0.00 ± 0.00 | 0.00 ± 0.00 | 0.00 | 0.00 | 0.00 |
| phys. ads. | Q8-SH | 0.00 ± 0.00 | 0.00 ± 0.00 | 0.00 | 0.00 | 0.00 |
| | Q12-SH | 1.17 (±0.41) × $10^3$ | 0.00 ± 0.00 | 0.00 | 0.00 | 7.24 × $10^5$ |
| | Q14-SH | 6.03 (±0.03) × $10^5$ | 0.00 ± 0.00 | 0.00 | 0.00 | 4.79 × $10^6$ |
| UV-treated | Q8-SH | 0.00 ± 0.00 | 0.00 ± 0.00 | 0.00 | 0.00 | 0.00 |
| | Q12-SH | 0.00 ± 0.00 | 0.00 ± 0.00 | 0.00 | 0.00 | 0.00 |
| | Q14-SH | 6.61 (±0.01) × $10^5$ | 0.00 ± 0.00 | 1.00 × $10^2$ | 0.00 | 5.25 × $10^6$ |

[a] Mean CFU/sample data were determined by serial dilution, performed in duplicate (n = 2).
[b] Mean CFU/sample data were determined by serial dilution (n = 1).
[c] Negative control for assay.
[d] Positive control for assay (chlorhexidine treated polypropylene).

To distinguish the antimicrobial activity of phys. ads. and UV-treated blade-coated samples modified with Q8-SH, and to gain an understanding of the contact-killing efficiency, a live/dead fluorescence assay was performed. The results demonstrate that the majority of the *S. aureus* and *E. coli* were killed with 5-10 min of exposure. Although the Q8-SH phys. ads. samples killed a comparable portion of the *S. aureus* (ca. 50%) to the UV-treated samples (ca. 75%) within 5 min, they were unable to match the killing efficiency of the UV-treated samples for *E. coli* at 10 min; UV-treated samples killed 90% of *E. coli* compared to 5% for the phys. ads. samples.

A biofilm formation assay was also performed to evaluate the antimicrobial effectiveness of Q8-SH functionalized catheter tubing, and its potential to prevent biofilm formation. *P. aeruginosa*, a particularly problematic biofilm forming species, was used to inoculate an assembly of catheter segments in the following order: CC1, untreated control, CC2, phys. ads., CC3, UV-treated, and CC4. (See, FIG. 65). The untreated, phys. ads, and UV-treated allyl-TPU catheters were post-fabrication modified on the inner lumen with Q8-SH, and the intermixing of CC segments served as a control to monitor downstream effects of the experimental group. Brightfield microscopy images of catheter cross-sections taken after 48 h of growth demonstrated a significant biofilm had formed on the interior of CC1 and untreated allyl-TPU catheters, while the phys. ads. and UV-treated catheters contained notably less material (FIG. 66A-D). The % biofilm occlusion was quantified from brightfield imaging (n=3) (FIG. 66E). It was evident that CC1 contained the highest % biofilm blockage (ca. 90% internal volume occlusion), while the UV-treated catheter contained the least (ca. 15%). Interestingly, the untreated control allyl-TPU suffered approximately 50% less biofilm blockage than CC1, and the performance of the phys. ads. and UV-treated samples was comparable (77% and 85% reductions from CC1; 53% and 69% reductions from the untreated control, respectively). CC2-CC4 were not notably different from CC1, indicating that the experimental group did not affect the downstream assay (data not shown). In addition, a photograph of the experimental catheters provided a visual observation of the biofilm (FIG. 66F); a thick off-white biofilm formed on the untreated control, while the phys. ads. and UV-treated allyl-TPU modified with Q8-SH remained relatively clear, with the phys. ads. catheter slightly more turbid than the UV-treated catheter.

SEM imaging was also performed to confirm that the blockage was created through biofilm growth. The presence of bacterial extracellular polymeric substance (EPS) is quite notable on CC1 and the untreated control catheter segments, but much less for the phys. ads. and UV-treated catheters modified with Q8-SH (FIGS. 67A-D). At higher magnification (300×), SEM reveals the 3-dimensional architecture of the EPS material, which is more mature on CC1 and the untreated control than the phys. ads. and UV-treated catheters (FIGS. 67E-H). Qualitatively, the biofilm appears to be sparser on the UV-treated catheter than the phys. ads. control.

Furthermore, cell viability testing was conducted to screen for potential toxicity of the Q8-SH functionalized surfaces. Control, phys. ads. and UV-treated samples modified with Q8-SH were compared to a glass slide, and did not exhibit notable cytotoxity towards mammalian cells (i.e. cell viability >90% relative to glass) over 24 h (FIG. 68). This data is in agreement with an abundance of literature that has examined the potential cytoxocicity of immobilized QAC compounds towards mammalian cells.

Overall, blade-coated samples of allyl-TPU modified with the Qx-SH series demonstrated variable antimicrobial activity that improved when increasing the surface hydrophilicity (decreasing the alkyl tail length), with Q8-SH proving to be the most effective. A live/dead fluorescence assay performed on allyl-TPU samples modified with Q8-SH revealed rapid contact-killing properties; nearly all the S. aureus inoculum was killed within 5 min and the E. coli within 10 min for UV-treated samples. In addition, a biofilm formation assay with P. aeruginosa showed that the catheter tubing functionalized with Q8-SH was more resistant to biofilm formation than a nylon-based Cook angiographic catheter (COOK™ BEACON™ TIP TORCON NB™ Advantage), as well as untreated and phys. ads. control catheters. A cell viability assay also demonstrated that the Q8-SH treated surfaces were non-cytotoxic towards mammalian cells.

In sum it has been found that incorporation of the commercially available 3-allyloxy-1,2-propanediol monomer into TPU provided a functional handle (alkene) that allowed for rapid and convenient surface modification (post-processing) using thiol-ene "click" chemistry, while maintaining relatively benign conditions (water, room temperature, UV light). Blade-coated samples of allyl-TPU were surface-functionalized with a series of Qx-SH compounds containing an 8-carbon spacer between the ester and ammonium head group, and various hydrocarbon tail lengths (8-14 carbons). A quantitative assessment of the amount of Qx-SH covalently bonded and physically adsorbed on the surface was performed using a fluorescence assay with a structurally comparable rhodamine-SH dye surrogate, and a series of XPS measurements on Qx-SH functionalized samples. The results suggested that quantity of Qx-SH on the surface of allyl-TPU samples post-modification was likely between $1.9\pm0.1$ to $5.5\pm0.1$ nmol·cm$^2$, of which $<\frac{1}{3}$ is physically adsorbed.

Further, it was determined via contact killing assays that surfaces modified with Q8-SH possessed the highest antimicrobial activity against both Gram-negative and Gram-positive bacteria, and that the antimicrobial activity trended with increasing hydrophilicity (decreasing alkyl tail length) for this system. A live/dead assay demonstrated that the UV-treated allyl-TPU samples modified with Q8-SH killed the majority of S. aureus and E. coli inocula (OD$_{600}$=0.15) within 10 min. In addition, it was evident that the UV-treated surfaces exhibited more rapid contact-killing than their respective phys. ads. controls. Biofilm formation testing also demonstrated that the accumulation of P. aeruginosa biofilm on UV-treated allyl-TPU catheters modified with Q8-SH was less compared to phys. ads., untreated, and CC controls as evidenced by brightfield microscopy and SEM imaging. It should be noted that Cook catheter samples served as a non-antibiotic control for comparison to a GMP, medical-grade catheter material; COOK™ BEACON™ TIP TORCON NB™ Advantage catheters do not claim antimicrobial activity.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Materials

All commercial reagent and solvents in these experiments were used as received without further purification. The chloroform-d (CDCl$_3$) and dimethyl sulfoxide-d$_6$ (DMSO-d$_6$) were purchased from Cambridge Isotopes Laboratories, Inc. (Tewksbury, Mass.) Calcium chloride (CaCl$_2$), tryptic soy broth, and Mueller-Hinton broth were purchased from VWR (Radnor, Pa.). The dimethyl sulfoxide (DMSO) was purchased from J. T. Baker (Phillipsburg, N.J.), and diethyl ether (Et$_2$O) and isopropyl alcohol ($^i$PrOH) were purchased from EMD Millipore (Burlington, Mass.). Anhydrous toluene, anhydrous methylene chloride (CH$_2$Cl$_2$), anhydrous tetrahydrofuran (THF), anhydrous pyridine, N,N-dimethyloctylamine (DOA), N,N-dimethyldodecylamine (DDA), N,N-dimethyltetradecylamine (DTDA), 3,3'-dithiopropionic acid, thionyl chloride (SOCl$_2$), 3-allyloxy-1,2-propanediol (alloc), 2-hydroxy-4'-(2-hydroxyethoxy)-2-methylpropiophenone (Irgacure-2959), 3-bromo-1,2-propanediol, tin(II) 2-ethylhexanoate (stannous octoate), 4,4'-methylenebis(cyclohexyl isocyanate) mixture of isomers (HMDI), and 1,4-butanediol (BDO), ethyl acetate (EtOAc), dimethylformamide (DMF), 2-butanone, methanol (MeOH), N,N-diisopropylethylamine (DIPEA), tris(2-carboxyethyl) phosphine hydrochloride (TCEP), 2,4,6-trimethylbenzoyl chloride, dimethyl phenylphosphonite, rhodamine B, trimethylaluminum solution (2.0 M in toluene), piperazine, 3-bromo-1-propanol, sodium chloride (NaCl), sodium hydroxide (NaOH), sodium sulfate (Na$_2$SO$_4$), sodium bicarbonate (NaHCO$_3$), lithium bromide (LiBr), ammonium sulfate ((NH$_4$)$_2$SO$_4$), magnesium chloride (MgCl$_2$), ethylenediaminetetraacetic acid iron(III) sodium salt (Fe-EDTA), were all purchased from Sigma-Aldrich (St. Louis, Mo.). The 3-chloro-1-propanol, 6-chloro-1-hexanol, and 8-chloro-1-octanol were purchased from Alfa Aesar. The fluorescein poly(ethylene glycol) thiol (FITC-PEG-SH) was purchased from Nanocs Inc., and the Arcol-E351 polyol (2,800 $\overline{M}_w$, 38.5-41.5 mg KOH/g) was donated by Covestro. The dimethyl sulfoxide (DMSO), sodium phosphate dibasic (Na$_2$HPO$_4$), potassium phosphate monobasic (KH$_2$PO$_4$), sodium citrate, and casamino acids were purchased from Fisher Scientific (Hampton, N.H.). Arcol-E351 polyol (2,800 $\overline{M}_w$, 38.5-41.5 mg KOH·g$^{-1}$) was kindly donated by Covestro.

Characterization

Unless otherwise indicated, the following equipment and methods were used herein. $^1$H-NMR spectra were obtained using a Varian Mercury 300 MHz NMR spectrometer operated at 303 K. All chemical shifts are reported in ppm ($\delta$) and referenced to the chemical shifts of residual solvent resonances (CDCl$_3$: $\delta$=7.26 ppm, DMSO-d$_6$: $\delta$=2.50 ppm). Mass spectrometry was performed using a HCT Ultra II quadrupole ion trap mass spectrometer (Bruker Daltonics, Billerica, Mass.) equipped with electrospray ionization (ESI) source. Samples were dissolved in MeOH and diluted to 0.01 µg·mL$^{-1}$ prior to injection. The sample solutions were injected into the ESI source by direct infusion, using a syringe pump, at a flow rate of 3 µL·min$^{-1}$. The tip of the ESI needle was grounded, and the entrance of the capillary, through which ions enter in the vacuum system of the mass spectrometer, was held at 3.5 kV. The pressure of the nebulizing gas (N$_2$) was set at 10 psi, and the flow rate and temperature of the drying gas (N$_2$) was 8 L·min$^{-1}$ and 300° C., respectively. Data collection was performed on positive mode and the ESI-MS data was analyzed by Bruker Daltonik's DataAnalysis v4.0 software.

Differential scanning calorimetry (DSC) was performed using a TA Instruments Q2000 DSC (TA Instruments—Waters L.L.C., New Castle, Del.) on sample sizes between 5-10 mg using temperature ramps for heating and cooling of 20° C.·min$^{-1}$ and a cooling rate of 20° C.·min$^{-1}$. Thermogravimetric analysis was performed using a TA Instruments TGA 2950 (TA Instruments—Waters L.L.C, New Castle, Del.) on sample sizes of ca. 10 mg using a heating ramp of 10° C.·min$^{-1}$, after holding temperature for 5 min at 110° C. to remove water.

Durometer measurements were performed on compression molded, cylindrical samples (stacked thickness >6.5 mm). A FOLWER™ Shore A Portable Durometer (Folwer High Precision, Auburndale, Mass.) was used for durometer hardness testing, following the procedure described in ASTM D2240 (2015), the disclosure of which is incorporated herein by reference in its entirety. The instrument was calibrated using a standardized Shore A 50 material prior to each measurement. Size exclusion chromatography (SEC) was performed using an EcoSEC HLC-8320GPC (Tosoh Bioscience LLC, King of Prussia, Pa.) equipped with a TSKgel GMH$_{HR}$-M mixed bed columns and refractive index (RI) detector. Molecular weights were calculated using a calibration curve determined from poly(styrene) standards (PStQuick MP-M standards, Tosoh Bioscience LLC) with THF as eluent flowing at 1.0 mL·min$^{-1}$, and a sample concentration of 4 mg·mL$^{-1}$. Contact angle measurements were conducted using a Ramé-Hart Model 500 Advanced Goniometer at room temperature with 5 µL droplets of deionized water. For each sample, 3 specimens were tested at 2 separate locations (n=6). Contact angles were determined using the DropSnake (drop analysis) plugin for ImageJ software.

Example 1

Quaternary Ammonium Diol "Q14-(OH)$_2$" Synthesis

In a 100 mL round bottom flask, 14.0 g (90.3 mmol, 1.0 eq) of 3-bromo-1,2-propanediol and 50.0 mL (164.6 mmol, 1.8 eq) of DTDA were added. The reaction flask was gradually heated to 60° C. while stirring under N$_2$ purge. A white precipitate began to form after 30 min, and the reaction was allowed to stir overnight. The crude product was precipitated in Et$_2$O (3×), then vacuum dried for 24 h to afford 32.2 g (90.0% yield) of white, solid product. $^1$H-NMR (300 MHz, 303 K, DMSO-d$_6$): $\delta$=0.85 (t, $^3J_{H-H}$=6.7 Hz, 3H), 1.24 (m, 22H), 1.69 (m, 2H), 3.08 (s, 6H), 3.18-3.48 (m, 6H), 4.00 (m, 1H), 4.96 (t, $^3J_{H-H}$=5.5 Hz, 1H), 5.33 (d, $^3J_{H-H}$=5.3 Hz, 1H) ppm.

Example 2

Quaternary Ammonium Alcohol "x-Qz-OH" Synthesis

To obtain a series of x-Qz-OH compounds with various hydrocarbon spacer lengths (x=3, 6, 8) and alkyl chain lengths (z=8, 12, 14), several chlorinated alcohols and tri-substituted amines were utilized. The general procedure is exemplified by the following: for 3-Q14-OH, 11.4 mL (37.4 mmol, 1.25 eq) of DTDA was added to a 100 mL round bottom flask and cooled to 0° C. under N$_2$ purge. Then, 2.5 mL (29.9 mmol, 1.0 eq) of 3-chloro-1-propanol was injected, and the temperature was gradually increased to 100° C. The reaction was allowed to stir overnight, which afforded a slightly yellow colored solid. After precipitation (3×) in Et$_2$O, a pure white solid was obtained (7.9 g, 78.6% yield). For a table of reagent quantities used in the syntheses of the various x-Qz-OH compounds, see Table 8.

3-Q-14-OH. $^1$H-NMR (300 MHz, 303K, DMSO-d$_6$): $\delta$=0.86 (t, $^3J_{H-H}$=6.7 Hz, 3H), 1.24 (m, 22H), 1.64 (m, 2H), 1.80 (m, 2H), 3.01 (s, 6H), 3.19-3.37 (m, 4H), 3.46 (q, $^3J_{H-H}$=5.5 Hz, 2H), 4.89 (t, $^3J_{H-H}$=5.1 Hz, 1H) ppm.

6-Q-14-OH. $^1$H-NMR (300 MHz, 303K, DMSO-d$_6$): $\delta$=0.85 (t, $^3H_{H-H}$=6.7 Hz, 3H), 1.24 (m, 24H), 1.43 (m, 4H), 1.64 (m, 4H), 3.00 (s, 6H), 3.17-3.29 (m, 4H), 3.39 (q, $^3J_{H-H}$=6.2 Hz, 2H), 4.43 (t, $^3J_{H-H}$=5.1 Hz, 1H) ppm.

8-Q-14-OH. $^1$H-NMR (300 MHz, 303K, DMSO-d$_6$): $\delta$=0.86 (t, $^3H_{H-H}$=6.7 Hz, 3H), 1.25 (m, 28H), 1.41 (m, 4H), 1.63 (m, 4H), 2.99 (s, 6H), 3.16-3.28 (m, 4H), 3.38 (q, $^3J_{H-H}$=6.3 Hz, 2H), 4.35 (t, $^3J_{H-H}$=5.1 Hz, 1H) ppm.

8-Q-12-OH. $^1$H-NMR (300 MHz, 303K, DMSO-d$_6$): δ=0.86 (t, $^3H_{H-H}$=6.7 Hz, 3H), 1.27 (m, 26H), 1.40 (m, 2H), 1.63 (m, 4H), 2.99 (s, 6H), 3.28-3.19 (m, 4H), 3.38 (q, $^3J_{H-H}$=6.4 Hz, 2H), 4.37 (t, $^3J_{H-H}$=5.1 Hz, 1H).

8-Q-8-OH. $^1$H-NMR (300 MHz, 303K, DMSO-d$_6$): δ=0.86 (t, $^3J_{H-H}$=6.6 Hz, 3H), 1.28 (m, 18H), 1.46-1.37 (m, 2H), 1.63 (m, 4H), 3.01 (s, 6H), 3.32-3.20 (m, 4H), 3.37 (q, $^3J_{H-H}$=6.4 Hz, 2H), 4.44 (t, $^3J_{H-H}$=5.1 Hz, 1H).

TABLE 8

Reagent quantities and yields for various x-Qz-OH precursors.

| x-Qz-OH | 3-chloro-1-propanol mL (mmol) | 6-chloro-1-hexanol mL (mmol) | 8-chloro-1-octanol mL (mmol) | DTDA mL (mmol) | DDA mL (mmol) | DOA mL (mmol) | Yield g (%) |
|---|---|---|---|---|---|---|---|
| 3-Q14-OH | 2.5 (29.9) | — | — | 11.4 (37.4) | — | — | 7.9 (78.6) |
| 6-Q14-OH | — | 5.0 (37.5) | — | 14.2 (46.8) | — | — | 10.2 (72.0) |
| 8-Q14-OH | — | — | 8.5 (50.4) | 16.1 (52.9) | — | — | 12.6 (61.6) |
| 8-Q12-OH | — | — | 8.5 (50.4) | — | 14.3 (52.9) | — | 12.7 (66.7) |
| 8-Q8-OH | — | — | 8.5 (50.4) | — | — | 10.9 (52.9) | 10.6 (65.4) |

Example 3

Quaternary Ammonium Alcohol "Qx-OH" Synthesis

To obtain a series of Qx-OH compounds with various alkyl chain lengths (x=8, 12, 14), 8-chloro-1-octanol and several tri-substituted amines were reacted neat. The general procedure is exemplified by the following: for Q14-OH, 28.4 mL (93.4 mmol, 1.05 eq) of DTDA was added to a 100 mL round bottom flask and stirred under N$_2$ purge. Then, 15.0 mL (88.9 mmol, 1.00 eq) of 8-chloro-1-propanol was injected dropwise via syringe and the temperature was gradually increased to 100° C. The reaction was allowed to stir overnight, which afforded a viscous yellow solution. After precipitation (3×) in Et$_2$O, a pure white solid was obtained (23.3 g, 64.6% yield). Reagent quantities for the syntheses of the various Qx-OH compounds are recorded in Table 9, below.

Q14-OH. $^1$H-NMR (300 MHz, 303K, DMSO-d$_6$): δ=0.86 (t, $^3J_{H-H}$=6.7 Hz, 3H), 1.25 (m, 30H), 1.41 (m, 2H), 1.63 (m, 4H), 2.99 (s, 6H), 3.16-3.28 (m, 4H), 3.38 (q, $^3J_{H-H}$=6.3 Hz, 2H), 4.35 (t, $^3J_{H-H}$=5.1 Hz, 1H) ppm.

Q12-OH. $^1$H-NMR (300 MHz, 303K, DMSO-d$_6$): δ=0.86 (t, $^3J_{H-H}$=6.7 Hz, 3H), 1.27 (m, 26H), 1.40 (m, 2H), 1.63 (m, 4H), 2.99 (s, 6H), 3.28-3.19 (m, 4H), 3.38 (q, $^3J_{H-H}$=6.4 Hz, 2H), 4.37 (t, $^3J_{H-H}$=5.1 Hz, 1H) ppm.

Q8-OH. $^1$H-NMR (300 MHz, 303K, DMSO-d$_6$): δ=0.86 (t, $^3J_{H-H}$=6.6 Hz, 3H), 1.28 (m, 18H), 1.46-1.37 (m, 2H), 1.63 (m, 4H), 3.01 (s, 6H), 3.32-3.20 (m, 4H), 3.37 (q, $^3H_{H-H}$=6.4 Hz, 2H), 4.44 (t, $^3J_{H-H}$=5.1 Hz, 1H) ppm.

TABLE 9

Reagent quantities and yields for Qx-OH precursors.

| Qx-OH | DTDA mL (mmol) | DDA mL (mmol) | DOA mL (mmol) | 8-chloro-1-octanol mL (mmol) | Yield g (%) |
|---|---|---|---|---|---|
| Q14-OH | 28.4 (93.4) | — | — | 15.0 (88.9) | 23.3 (64.6) |
| Q12-OH | — | 20.3 (74.7) | — | 12.0 (71.1) | 17.9 (66.7) |
| Q8-OH | — | — | 15.4 (74.7) | 12.0 (71.1) | 15.0 (65.4) |

Example 4

3,3'-Dithiodipropanoyl Chloride Synthesis

In an oven dried, two-neck 250 mL round bottom flask fixed with a condenser and rubber septa, 5.0 g (23.8 mmol, 1.0 eq) of 3,3'-dithiodipropionic acid was suspended in ca. 100 mL of anhydrous toluene. While stirring under N$_2$ purge at 25° C., 7.0 mL (96.0 mmol, 4.0 eq) of SOCl$_2$ was added dropwise over a period of 5 min. The temperature was gradually brought to 90° C., and the reaction was allowed to reflux for 16 h or until the solution turned clear yellow. Subsequently, the solvent and gaseous by-products were removed via vacuum transfer, while maintaining anhydrous conditions.

Example 5

3,3'-Dithiodipropanoyl Chloride Synthesis (Solvent-Free Method)

The procedure of Example 4 above was later modified in order to perform the reaction solvent-free; 10.0 g (47.6 mmol, 1.0 eq) of 3,3'-dithiopropionic acid was dissolved in 20.8 mL (285.3 mmol, 6.0 eq) of thionyl chloride and heated at reflux for at least 12 h. The gaseous by-products and excess thionyl chloride were removed by vacuum transfer and a yellow oil was obtained. The resulting yellow oil product, quantitative conversion by $^1$H-NMR, was used directly for further synthetic steps. $^1$H-NMR (300 MHz, 303 K, CDCl$_3$): δ=2.95 (t, $^3J_{H-H}$=7.0 Hz, 4H), 3.32 (t, $^3J_{H-H}$=7.0 Hz, 4H) ppm.

Example 5

3,3'-Dithiodipropanoyl Chloride Synthesis (Larger Batch Size)

In an oven dried, two-neck 250 mL round bottom flask fixed with a condenser, alkaline scrubber between the condenser and nitrogen line, and an addition funnel, 34.6 g (164.6 mmol, 1.00 eq) of 3,3'-dithiodipropionic acid was added. With stirring under $N_2$ at 23° C., 60.0 mL (827.1 mmol, 5.00 eq) of $SOCl_2$ was added dropwise via addition funnel over a period of 30 min. The suspension was gradually brought to reflux, and allowed to stir for 16 h or until the solution turned clear yellow. Subsequently, the excess thionyl chloride and gaseous by-products were removed by vacuum transfer, while maintaining anhydrous conditions. The resulting yellow oil product, quantitative conversion by $^1$H-NMR and $^{13}$C-NMR, was used directly for further synthetic steps. 3,3'-dithiopropanoyl chloride: $^1$H-NMR (300 MHz, 303 K, $CDCl_3$): δ=2.95 (t, $^3J_{H\text{-}H}$=7.0 Hz, 4H), 3.32 (t, $^3J_{H\text{-}H}$=7.0 Hz, 4H) ppm. $^{13}$C-NMR (300 MHz, 303 K, $CDCl_3$): δ=32.00, 46.05, 172.09 ppm.

Example 7

Disulfide-QAC "x-Qz-S-S" Synthesis

The disulfide-QAC (x-Qz-S-S) reagents having varying spacer lengths (x) and tail lengths (z) were produced using freshly prepared 3,3'-dithiodipropanoyl chloride and the desired quaternary ammonium alcohol. Anhydrous techniques were utilized to preserve the acid chloride functionality. The procedure for 3-Q14-S-S is provided as an example: 7.9 g (23.5 mmol, 2.0 eq) of 3-Q14-OH was dissolved in ca. 30 mL of anhydrous $CH_2Cl_2$ in a 100 mL schlenk flask, and 1.9 mL (23.5 mmol, 2.0 eq) of pyridine was added. The mixture was cooled in an ice bath to 0° C., and 2.0 mL (11.6 mmol, 1.0 eq) of 3,3'-dithiodipropanoyl chloride was added dropwise to the reaction flask over a period of 5 min. The reaction was allowed to gradually come to room temperature, while stirring under $N_2$ purge overnight. The solvent was removed and the crude product was dialyzed in water using 100-500 Da dialysis tubing for 48 h, then lyophilized to obtain 3-Q14-S-S (7.5 g, 75.8% yield). For shorter alkyl chain lengths (i.e. 8-Q12-S-S and 8-Q8-S-S) dialysis proved to be ineffective at removing residual pyridine and the procedure was modified to eliminate the use of pyridine as follows: using anhydrous technique, 6.6 g (17.4 mmol, 2.0 eq) of 8-Q12-OH was dissolved in ca. 25 mL of anhydrous $CH_2Cl_2$ in a 100 mL schlenk flask fixed with a reflux condenser. Then, 1.5 mL (8.7 mmol, 1.0 eq) of 3,3'-dithiodipropanoyl chloride was injected dropwise through the side arm of the flask, at room temperature. The $N_2$ flow was then fixed through the sidearm in order to push to the HCl gas through the top of the condenser and into a 1 M KOH solution for neutralization, and the reaction was heated at reflux for at least 16 h. The reaction was quantitative by $^1$H-NMR, and the resulting product was neutralized by evaporating the solvent, and re-dissolving in DI water with excess sodium bicarbonate. The water was then removed via rotary evaporation, and the contents were re-dissolved in DCM, stirred over magnesium sulfate, filtered, and dried under vacuum (5.9 g, 72.8% isolated yield). Reagent tables for the compounds used in the synthesis of the x-Q14-S-S series and the 8-Qz-S-S series are provided in Table 10 and Table 11, respectively. These compounds were characterized by $^1$H-NMR as follows:

3-Q14-S-S. $^1$H-NMR (300 MHz, 303 K, DMSO-$d_6$): δ=0.85 (t, $^3J_{H\text{-}H}$=6.7 Hz, 6H), 1.24 (m, 44H), 1.64 (m, 4H), 2.02 (m, 4H), 2.75 (t, $^3J_{H\text{-}H}$=6.8 Hz, 4H), 2.95 (t, $^3J_{H\text{-}H}$=6.9 Hz, 4H), 3.06 (s, 12H), 3.22-3.50 (m, 8H), 4.11 (t, $^3J_{H\text{-}H}$=6.0 Hz, 4H) ppm. (See, FIG. 15).

6-Q14-S-S. $^1$H-NMR (300 MHz, 303 K, DMSO-$d_6$): δ=0.84 (t, $^3J_{H\text{-}H}$=6.6 Hz, 6H), 1.23 (m, 56H), 1.62 (m, 12H), 2.70 (t, $^3J_{H\text{-}H}$=6.9 Hz, 4H), 2.91 (t, $^3J_{H\text{-}H}$=6.8 Hz, 4H), 3.03 (s, 12H), 3.20-3.33 (m, 8H), 4.04 (t, $^3J_{H\text{-}H}$=6.5 Hz, 4H) ppm. (See FIG. 16).

8-Q14-S-S. $^1$H-NMR (300 MHz, 303 K, DMSO-$d_6$): δ=0.84 (t, $^3J_{H\text{-}H}$=6.6 Hz, 6H), 1.13-1.44 (m, 64H), 1.51-1.72 (m, 12H), 2.69 (t, $^3J_{H\text{-}H}$=6.8 Hz, 4H), 2.90 (t, $^3J_{H\text{-}H}$=6.8 Hz, 4H), 3.03 (s, 12H), 3.22-3.32 (m, 8H), 4.03 (t, $^3J_{H\text{-}H}$=6.6 Hz, 4H) ppm. (See, FIG. 17).

8-Q12-S-S. $^1$H-NMR (300 MHz, 303 K, DMSO-$d_6$): δ=0.85 (t, $^3J_{H\text{-}H}$=6.7 Hz, 6H), 1.13-1.45 (m, 56H), 1.49-1.73 (m, 12H), 2.70 (t, $^3J_{H\text{-}H}$=6.8 Hz, 4H), 2.91 (t, $^3J_{H\text{-}H}$=6.8 Hz, 4H), 3.01 (s, 12H), 3.21-3.30 (m, 8H), 4.03 (t, $^3J_{H\text{-}H}$=6.6 Hz, 4H). (See, FIG. 18).

8-Q-8-S-S. $^1$H-NMR (300 MHz, 303K, DMSO-$d_6$): δ=0.86 (t, $^3J_{H\text{-}H}$=6.7 Hz, 6H), 1.13-1.43 (m, 40H), 1.52-1.70 (m, 12H), 2.69 (t, $^3J_{H\text{-}H}$=6.8 Hz, 4H), 2.91 (t, $^3J_{H\text{-}H}$=6.8 Hz, 4H), 3.02 (s, 12H), 3.22-3.31 (m, 8H), 4.03 (t, $^3J_{H\text{-}H}$=6.6 Hz, 4H). (See, FIG. 19).

TABLE 10

Reagent quantities and yields for x-Q14-S-S spacer length series.

| x-Qz-S-S | 3-Q14-OH g (mmol) | 6-Q14-OH g (mmol) | 8-Q14-OH g (mmol) | 3,3'-dithiodipropanoyl chloride mL (mmol) | pyridine mL (mmol) | Yield g (%) |
|---|---|---|---|---|---|---|
| 3-Q14-S-S | 7.9 (23.5) | — | — | 2.0 (11.7) | 1.9 (23.5) | 7.5 (75.8) |
| 6-Q14-S-S | — | 8.0 (21.2) | — | 1.8 (10.6) | 1.7 (21.2) | 7.2 (73.0) |
| 8-Q14-S-S | — | — | 8.6 (21.2) | 1.8 (10.6) | 1.7 (21.2) | 7.0 (66.9) |

TABLE 11

Reagent quantities and yields for 8-Qz-S-S alkyl tail length series.

| x-Qz-S-S | 8-Q14-OH g (mmol) | 8-Q12-OH g (mmol) | 8-Q8-OH g (mmol) | 3,3'-dithiodipropanoyl chloride mL (mmol) | pyridine mL (mmol) | Yield g (%) |
|---|---|---|---|---|---|---|
| 8-Q14-S-S [a] | 11.4 (27.9) | — | — | 2.4 (13.9) | 2.3 (27.9) | 8.2 (59.8) |
| 8-Q12-S-S | — | 6.6 (17.4) | — | 1.5 (8.7) | — | 5.8 (71.1) |
| 8-Q8-S-S | — | — | 5.6 (17.4) | 1.5 (8.7) | — | 5.5 (77.8) |

[a] Compound was purified by dialysis.

Example 8

Disulfide-QAC "Qx-S-S" Synthesis

The Qx-S-S reagents having different tail lengths (x) were produced using freshly prepared 3,3'-dithiodipropanoyl chloride and the desired Qx-OH. Anhydrous techniques were utilized to preserve the acid chloride functionality. The procedure for Q14-S-S is provided as an example: 9.44 g (23.2 mmol, 2.01 eq) of Q14-OH was dissolved in ca. 50-75 mL of anhydrous $CH_2Cl_2$ in a 250 mL 2-neck flask fixed with a reflux condenser, and an alkaline scrubber between the condenser and nitrogen line. Then, 2.00 mL (11.6 mmol, 1.00 eq) of 3,3'-dithiopropanoyl chloride was injected dropwise at room temperature, and the reaction was heated at reflux for at least 16 h. The conversion was quantitative by $^1$H-NMR, and the reaction solution was neutralized by evaporating the solvent, and re-dissolving in sat. $NaHCO_3$. The water was removed via rotary evaporation, and the product was extracted from the salts by re-dissolving in $CH_2Cl_2$ and filtering. The filtrate was then stirred over $Na_2SO_4$, filtered, and dried under vacuum (8.51 g, 74.3% isolated yield). Reagent quantities and yields for the synthesis of the Qx-S-S series are recorded in the Table 12, below. These compounds were characterized by $^1$H-NMR and $^{13}$C-NMR as follows:

Q14-S-S. $^1$H-NMR (300 MHz, 303 K, DMSO-$d_6$): δ=0.84 (t, $^3J_{H-H}$=6.6 Hz, 6H), 1.13-1.44 (m, 60H), 1.51-1.72 (m, 12H), 2.69 (t, $^3J_{H-H}$=6.8 Hz, 4H), 2.90 (t, $^3J_{H-H}$=6.8 Hz, 4H), 3.03 (s, 12H), 3.22-3.32 (m, 8H), 4.03 (t, $^3J_{H-H}$=6.6 Hz, 4H) ppm. (See, FIG. 34). $^{13}$C-NMR (300 MHz, 303 K, DMSO-$d_6$): δ=14.36, 22.15, 22.57, 25.70, 26.20, 26.28, 28.51, 28.86, 28.99, 29.21, 29.33, 29.45, 29.52, 29.56, 31.78, 33.18, 33.86, 50.27, 63.04, 64.52, 171.53 ppm. (See, FIG. 40).

Q12-S-S. $^1$H-NMR (300 MHz, 303 K, DMSO-$d_6$): δ=0.85 (t, $^3J_{H-H}$=6.7 Hz, 6H), 1.13-1.45 (m, 52H), 1.49-1.73 (m, 12H), 2.70 (t, $^3J_{H-H}$=6.8 Hz, 4H), 2.91 (t, $^3J_{H-H}$=6.8 Hz, 4H), 3.01 (s, 12H), 3.21-3.30 (m, 8H), 4.03 (t, $^3J_{H-H}$=6.6 Hz, 4H) ppm. (See, FIG. 35). $^{13}$C-NMR (300 MHz, 303 K, DMSO-$d_6$): δ=14.39, 22.13, 22.56, 25.69, 26.18, 26.25, 28.50, 28.85, 28.95, 29.18, 29.28, 29.41, 29.48, 31.76, 33.18, 33.85, 50.29, 63.11, 64.53, 171.57 ppm. (See, FIG. 41).

Q8-S-S. $^1$H-NMR (300 MHz, 303K, DMSO-$d_6$): δ=0.86 (t, $^3J_{H-H}$=6.7 Hz, 6H), 1.13-1.43 (m, 36H), 1.52-1.70 (m, 12H), 2.69 (t, $^3J_{H-H}$=6.8 Hz, 4H), 2.91 (t, $^3J_{H-H}$=6.8 Hz, 4H), 3.02 (s, 12H), 3.22-3.31 (m, 8H), 4.03 (t, $^3J_{H-H}$=6.6 Hz, 4H) ppm. (See, FIG. 36). $^{13}$C-NMR (300 MHz, 303 K, DMSO-$d_6$): δ=14.39, 22.15, 22.51, 25.68, 26.18, 26.26, 28.50, 28.85, 28.92, 28.94, 31.62, 33.19, 33.85, 50.28, 55.45, 63.13, 64.54, 171.58 ppm. (See, FIG. 42).

Example 9

General Procedure for TPU Polymerizations

TPU polymerizations of a 5% QAC-TPU, a 10% QAC-TPU, an 8% alloc-TPU and a control TPU were performed in bulk with mechanical stirring at 100° C. The following is provided as an example procedure: for a 100 g batch of 50 mol % (30 wt. %) HMDI control TPU, 61.7 g (22.0 mmol, 1.0 eq) of Arcol E-351 and 8.2 g (92.3 mmol, 4.2 eq) of BDO were preheated to 100° C. in a porcelain enamel-lined tin can with overhead mechanical stirring. Then, 28.1 mL (114.3 mmol, 5.2 eq) of HMDI was added, immediately followed by 2-3 drops of stannous octoate catalyst. The mixture was allowed to stir for 2-5 min, or until the mixture was too viscous to stir. The resulting TPU was oven cured at 90° C. for 24 h. For QAC-TPU or alloc-TPU, the molar ratio of BDO to Q14-$(OH)_2$ or BDO to alloc was modified, while maintaining the molar ratio of HMDI to Arcol-E351. Additionally, the Q14-$(OH)_2$ or alloc was added directly with the mixture of diols and preheated to 100° C. before adding HMDI. For reagent quantities used in the various TPU polymerizations, as well as the resulting polymer properties, see Table 1 and Table 2, respectively. These compounds were characterized by $^1$H-NMR as follows:

Control TPU. $^1$H-NMR (300 MHz, 303 K, DMSO-$d_6$): δ=0.97 (m, 10H), 1.02-1.20 (m, 120H), 1.26 (m, 10H), 1.37-1.81 (m, 100H), 1.99 (m, 10H), 3.16-3.89 (m, 135H), 4.07 (m, 16H), 4.20 (m, 5H), 4.51 (m, 6H), 4.65 (m, 4H), 4.79 (m, 6H), 4.91 (m, 4H) ppm. (See, FIG. 20).

5% QAC-TPU. $^1$H-NMR (300 MHz, 303 K, DMSO-$d_6$): δ=0.92 (m, 50H), 1.08-1.20 (m, 276H), 1.21-1.26 (m, 24H), 1.26-1.79 (m, 150H), 1.88 (m, 28H), 1.99 (m, 20H), 3.21-3.84 (m, 368H), 4.05 (m, 28H), 4.18 (m, 7.5H), 4.55 (m, 5H), 4.69 (m, 3H), 4.82 (m, 5H), 4.95 (m, 3H) ppm. (See, FIG. 2).

10% QAC-TPU. $^1$H-NMR (300 MHz, 303 K, DMSO-$d_6$): δ=0.92 (m, 20H), 1.06-1.19 (m, 120H), 1.20-1.29 (m, 22H), 1.29-1.79 (m, 84H), 1.81 (m, 12H), 1.95 (m, 10H), 3.14-3.87 (m, 160H), 4.05 (m, 12H), 4.19 (m, 5H), 4.58 (m, 3H), 4.68 (m, 1H), 4.84 (m, 3H), 4.94 (m, 1H) ppm. (See, FIG. 3)

8% Alloc-TPU. $^1$H-NMR (300 MHz, 303 K, DMSO-$d_6$): δ=0.96 (m, 25H), 1.07-1.16 (m, 145H), 1.21 (m, 12.5H), 1.24-1.78 (m, 86H), 1.85 (m, 16H), 1.99 (m, 12.5H), 3.23-3.83 (m, 194H), 4.05 (m, 16H), 4.20 (m, 5H), 4.54 (m, 2.5H), 4.67 (m, 2H), 4.82 (m, 3.5H), 4.93 (m, 2H), 5.22 (dd, $^3J_{H-H}$=24.2, 13.8 Hz, 2H), 5.85 (m, 1H) ppm. (See, FIG. 21).

Example 10

Synthesis Thiol-QAC "Qx-SH" Compounds

The Qx-SH reagents were obtained via reduction of Qx-S-S using TCEP. The general procedure is exemplified

TABLE 12

Reagent quantities and yields for Qx-S-S series.

| Qx-S-S | Q14-OH g (mmol) | Q12-OH g (mmol) | Q8-OH g (mmol) | 3,3'-dithiodipropanoyl chloride mL (mmol) | Yield g (%) |
|---|---|---|---|---|---|
| Q14-S-S | 9.44 (23.2) | — | — | 2.00 (11.6) | 8.51 (74.3) |
| Q12-S-S | — | 8.78 (23.2) | — | 2.00 (11.6) | 7.90 (73.2) |
| Q8-S-S | — | — | 7.48 (23.2) | 2.00 (11.6) | 6.72 (70.6) | by the following: 1.50 g of Q14-S-S (1.52 mmol, 1.00 eq) was added to a 150 mL round bottom flask and kept under a flow of Ar. Separately, 0.88 g of TCEP (3.07 mmol, 2.00 eq) was dissolved in 50 mL of Ar purged DI water and the pH was adjusted to ca. 6 using 1 M NaOH. The TCEP solution was added directly to the flask containing Q14-S-S, and allowed to stir for 4 h at 23° C. The reaction was then saturated with NaHCO$_3$ and stirred for an additional 30 min, then lyophilized for 24 h to remove water. The product was extracted out from the salts by dissolving in CH$_2$Cl$_2$ and filtering. The filtrate was stirred over Na$_2$SO$_4$, filtered, vacuum dried, and 1.22 g (81.3% yield) was recovered as a yellow semi-solid. Reagent quantities and yields for the synthesis of the Qx-SH series are recorded in Table 13, below. These compounds were characterized by $^1$H-NMR, $^{13}$C-NMR, and ESI-MS as follows:

Q14-SH. $^1$H-NMR (300 MHz, 303 K, DMSO-d$_6$): δ=0.85 (t, $^3J_{H-H}$=6.5 Hz, 3H), 1.17-1.37 (m, 30H), 1.52-1.69 (m, 6H), 2.62 (m, 4H), 3.02 (s, 6H), 3.20-3.32 (m, 4H), 4.03 (t, $^3J_{H-H}$=6.5 Hz, 2H) ppm. (See, FIG. 37). $^{13}$C-NMR (300 MHz, 303 K, DMSO-d$_6$): δ=14.39, 19.74, 22.11, 22.55, 25.69, 26.16, 26.23, 28.51, 28.83, 28.94, 29.18, 29.27, 29.40, 29.48, 29.52, 31.75, 38.39, 50.33, 55.41, 63.17, 64.36, 171.72 ppm. (See, FIG. 40). ESI-MS, m/z theoretical: [M]$^+$=458.40 Da, observed: [M]$^+$=458.5 Da. (See, FIG. 43).

Q12-SH. $^1$H-NMR (300 MHz, 303 K, DMSO-d$_6$): δ=0.85 (t, $^3J_{H-H}$=6.5 Hz, 3H), 1.17-1.35 (m, 26H), 1.50-1.70 (m, 6H), 2.62 (m, 4H), 3.02 (s, 6H), 3.20-3.31 (m, 4H), 4.03 (t, $^3J_{H-H}$=6.5 Hz, 2H) ppm. (See FIG. 38) $^{13}$C-NMR (300 MHz, 303 K, DMSO-d$_6$): δ=14.40, 19.74, 22.12, 22.55, 25.69, 26.16, 26.23, 28.51, 28.83, 28.93, 29.17, 29.27, 29.39, 29.47, 31.75, 38.39, 50.32, 55.41, 63.18, 64.36, 171.73 ppm. (See, FIG. 41). ESI-MS, m/z theoretical: [M]$^+$=430.37 Da, observed: [M]$^+$=430.4 Da. (See, FIG. 44).

Q8-SH. $^1$H-NMR (300 MHz, 303K, DMSO-d$_6$): δ=0.86 (t, $^3J_{H-H}$=6.5 Hz, 3H), 1.14-1.42 (m, 18H), 1.50-1.70 (m, 6H), 2.62 (m, 4H), 3.02 (s, 6H), 3.22-3.33 (m, 4H), 4.03 (t, $^3J_{H-H}$=6.5 Hz, 2H) ppm. (See, FIG. 39). $^{13}$C-NMR (300 MHz, 303 K, DMSO-d$_6$): δ=14.39, 19.75, 22.14, 22.51, 25.69, 26.16, 26.25, 28.51, 28.82, 28.91, 28.93, 31.62, 38.40, 50.30, 55.43, 63.18, 64.36, 171.74 ppm. (See, FIG. 42). ESI-MS, m/z theoretical: [M]$^+$=374.31 Da, observed: [M]$^+$=374.4 Da. (See, FIG. 45).

of EtOAc. The combined organic layers were washed with 1 M NaOH (3×) and brine (3×), then stirred over Na$_2$SO$_4$ and dried under vacuum. The product was isolated as a pink foam (12.5 g, 90.2% yield). $^1$H-NMR (300 MHz, 303K, CDCl$_3$): δ=1.18 (t, $^3H_{H-H}$=7.0 Hz, 12H), 3.37 (q, $^3J_{H-H}$=7.0 Hz, 8H), 6.35 (dd, $^3J_{H-H}$=8.9, 2.5 Hz, 2H), 6.46 (d, $^3J_{H-H}$=2.4 Hz, 2H), 6.59 (d, $^3J_{H-H}$=8.9 Hz, 2H), 7.21 (d, $^3J_{H-H}$=7.5 Hz, 1H), 7.53-7.68 (m, 2H), 8.01 (d, $^3J_{H-H}$=6.9 Hz, 1H) ppm (FIG. 46).

Next, rhodamine B piperazine amide was synthesized as follows: 11.1 g (25.1 mmol, 1.00 eq) of rhodamine B base was dissolved in an oven dried schlenk flask with 20 mL of anhydrous CH$_2$Cl$_2$. In a separate oven dried 2-neck, 250 mL flask fixed with a condenser, 8.63 g of piperazine (100.2 mmol, 4.00 eq) was dissolved in 35 mL of anhydrous CH$_2$Cl$_2$ under N$_2$. Using air-free techniques, 25 mL of a 2.0 M solution of trimethylaluminum in toluene (50.0 mmol, 2.00 eq) was added dropwise to the piperazine solution. Gas evolution occurred, and after one hour of stirring a white precipitate formed in the flask. The rhodamine B base solution was added dropwise to the heterogenous mixture, and the reaction was gradually heated to reflux and stirred for 24 h. To terminate the reaction, 0.1 M HCl was added dropwise (slowly) until gas evolution was no longer observed. The solution was filtered and rinsed with CH$_2$Cl$_2$, and the solvent was removed. The crude product was dissolved in dilute NaHCO$_3$, and washed with multiple portions of EtOAc to remove excess starting material. The aqueous layer was saturated with NaCl, acidified with 1 M HCl, and extracted (3×) with 2:1 $^i$PrOH/CH$_2$Cl$_2$. The combined organic layers were stirred over Na$_2$SO$_4$, filtered and dried under vacuum. The resulting purple solid was dissolved in a minimal amount of MeOH and precipitated into Et$_2$O, centrifuged at 5000 RPM for 2 min and decanted, then re-dissolved in CH$_2$Cl$_2$ and vacuum dried. A dark purple pearlescent solid was obtained (7.8 g, 56.8% yield). $^1$H-NMR (300 MHz, 303K, DMSO-d$_6$): δ=1.22 (t, $^3J_{H-H}$=6.9 Hz, 12H), 2.94 (m, 4H), 3.39-3.81 (m, overlaps with HDO, 12H), 6.95 (d, $^3J_{H-H}$=2.0 Hz, 2H), 7.09 (dd, $^3J_{H-H}$=9.6, 2.0 Hz, 2H), 7.16 (d, $^3J_{H-H}$=9.5 Hz, 2H), 7.49-7.59 (m, 1H), 7.70-7.85 (m, 3H), 9.71 (s, 1H) ppm. (See, FIG. 47). ESI-MS, m/z theoretical: [M]$^+$=511.31 Da, observed: [M]$^+$=511.3 and [M]$^{2+}$=255.7 Da. (See, FIG. 48).

TABLE 13

Reagent quantities and yields for Qx-SH series.

| Qx-S-S | Q14-S-S g (mmol) | Q12-S-S g (mmol) | Q8-S-S g (mmol) | TCEP g (mmol) | Yield g (%) |
|---|---|---|---|---|---|
| Q14-SH | 1.50 (1.52) | — | — | 0.88 (3.07) | 1.22 (81.3) |
| Q12-SH | — | 1.41 (1.52) | — | 0.88 (3.07) | 1.17 (82.8) |
| Q8-SH | — | — | 1.25 (1.53) | 0.88 (3.07) | 1.05 (83.8) |

Example 11

Synthesis of Rhodamine B 4-(3-Hydroxylpropyl) Piperazine Amide

The rhodamine B 4-(3-hydroxylpropyl) piperazine amide was obtained using a multistep procedure adapted from Nguyen, T.; Francis, M. B., "Practical Synthetic Route to Functionalized Rhodamine Dyes." *Org. Lett.* 2003, 5 (18), 3245-3248, the disclosure of which is incorporated herein by reference in its entirety. First, rhodamine B base was synthesized as follows: 15 g of rhodamine B (31.3 mmol) was dissolved in 1 M NaOH and extracted with multiple portions Finally, the rhodamine B 4-(3-hydroxylpropyl) piperazine amide was synthesized as follows: 4.00 g of rhodamine B piperazine amide (7.31 mmol, 1.00 eq) was dissolved in 15 mL of DMF, and 2.00 mL of 3-bromo-1-propanol (22.1 mmol, 3.03 eq) and 4.46 mL of DIPEA (25.6 mmol, 3.50 eq) were added. The reaction was stirred under N$_2$ for 24 h at 23° C., whereupon an additional 2.00 mL of 3-bromo-1-propanol (22.1 mmol, 3.03 eq) and 4.46 mL of DIPEA (25.6 mmol, 3.50 eq) were added and stirred for 24 h. The reaction solution was diluted with sat. NaHCO$_3$ and washed with EtOAc (3×) to remove DIPEA and excess 3-bromo-1- propanol. The aqueous layer was then extracted with 1:3 $^i$PrOH/CH$_2$Cl$_2$ and the organic layers were combined, stirred over Na$_2$SO$_4$, filtered, and dried under vacuum. A dark purple solid was obtained (3.99 g, 90.2% yield). $^1$H-NMR (300 MHz, 303K, DMSO-d$_6$): δ=1.21 (t, $^3J_{H-H}$=6.9 Hz, 12H), 1.47 (m, 2H), 2.07 (br, 4H), 2.19 (t, $^3J_{H-H}$=7.1 Hz, 2H), 3.17-3.45 (m, overlaps with HDO, 6H), 3.66 (q, $^3J_{H-H}$=7.0 Hz, 8H), 4.39 (s, 1H), 6.96 (br, 2H), 7.13 (m, 4H), 7.53 (dd, $^3J_{H-H}$=5.9, 2.9 Hz, 1H), 7.64 (m, 1H), 7.74 (dd, $^3J_{H-H}$=5.3, 3.6 Hz 2H) ppm. (See, FIG. 49). ESI-MS, m/z theoretical: [M]$^+$=569.35 Da, observed: [M]$^+$=569.4 Da. (See, FIG. 50.

Example 12

Rhodamine B Thiol "Rhodamine-SH" Synthesis

Rhodamine-SH was synthesized by esterification of rhodamine B 4-(3-hydroxylpropyl) piperazine amide with 3,3'-dithiopropanoyl chloride, followed by TCEP reduction to provide the corresponding thiol. The Rhodamine-SH synthetic scheme beginning with the formation of the lactone, amidation with piperazine, nucleophilic substitution of 3-bromo-1-propanol, esterification with 3,3'-dithiopropanoyl chloride, and reduction to thiol using TCEP are shown in Scheme 14, below.

Scheme 14

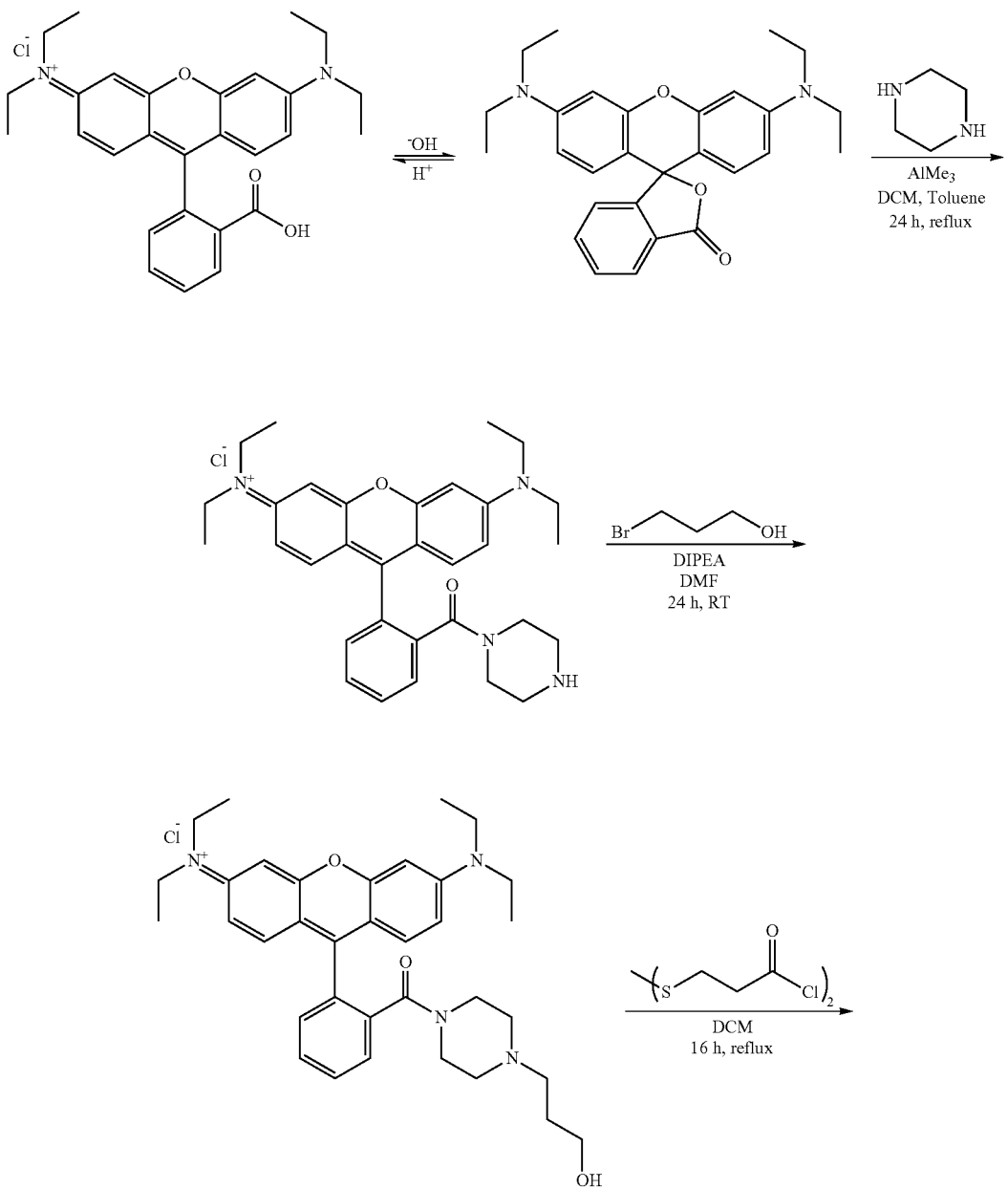

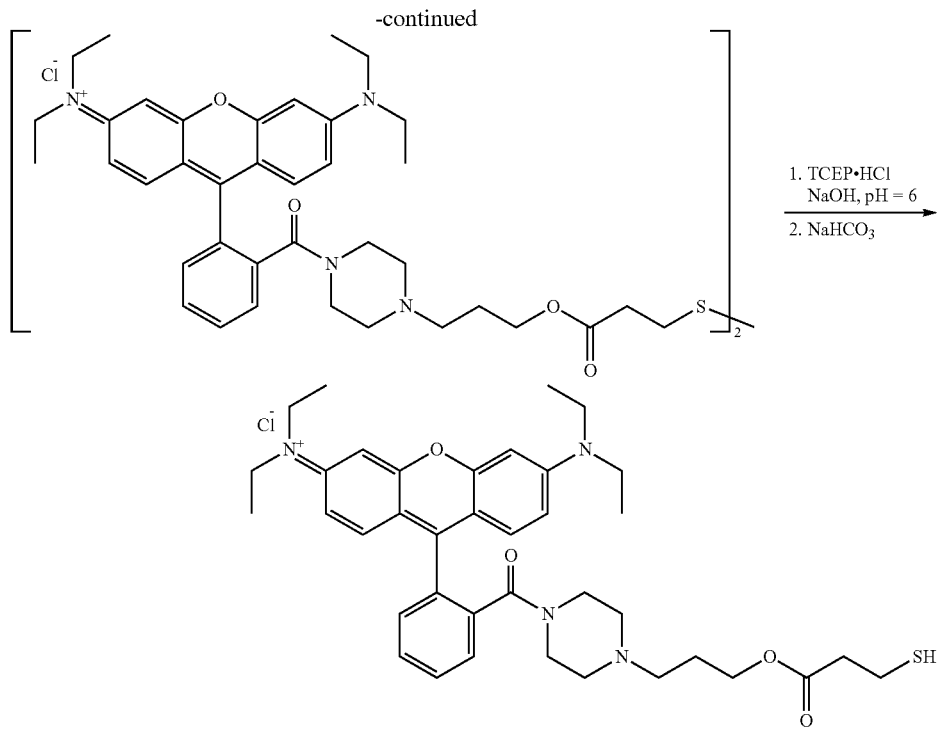

-continued

The rhodamine B disulfide was synthesized from the rhodamine B 4-(3-hydroxylpropyl) piperazine amide as shown in Scheme 14, above. Using anhydrous techniques, 3.50 g of rhodamine B 4-(3-hydroxylpropyl) piperazine amide (5.78 mmol, 2.00 eq) was added to a 150 mL, 2-neck flask fixed with a condenser and dissolved in ca. 40 mL of anhydrous $CH_2Cl_2$ with stirring under $N_2$. At room temperature, 0.50 mL of 3,3'-dithiopropanoyl chloride (2.90 mmol, 1.00 eq) was added dropwise and the reaction was gradually brought to reflux. After 16 h, the reaction was diluted with sat. $NaHCO_3$, stirred for 30 min, and extracted (3×) with $CH_2Cl_2$. The organic layers were collected, stirred over $Na_2SO_4$, filtered, and dried under vacuum. A dark purple solid was obtained (3.95 g, 99.3% yield) and characterized using $^1$H-NMR, $^{13}$C-NMR, and ESI-MS, confirming formation of the Rhodamine B disulfide. $^1$H-NMR (300 MHz, 303K, DMSO-$d_6$): δ=1.20 (t, $^3J_{H-H}$=6.6 Hz, 24H), 1.65 (m, 4H), 2.07 (br, 8H), 2.20 (t, $^3J_{H-H}$=7.1 Hz, 4H), 2.68 (t, $^3J_{H-H}$=6.6 Hz, 4H), 2.89 (t, $^3J_{H-H}$=6.5 Hz, 4H), 3.11-3.48 (m, overlaps with HDO, 8H), 3.65 (q, $^3J_{H-H}$=7.0 Hz, 16H), 4.01 (t, $^3J_{H-H}$=5.9 Hz, 4H), 6.95 (br, 4H), 7.13 (m, 8H), 7.53 (dd, $^3J_{H-H}$=5.2, 3.3 Hz, 2H), 7.64 (m, 2H), 7.73 (dd, $^3J_{H-H}$=5.2, 3.3 Hz 4H) ppm. (See, FIG. 51). $^{13}$C-NMR (300 MHz, 303 K, DMSO-$d_6$): δ=12.94, 25.67, 33.07, 33.79, 45.84, 54.49, 55.40, 62.98, 96.31, 113.44, 114.75, 127.85, 130.04, 130.25, 130.73, 130.97, 132.35, 135.94, 155.49, 156.03, 157.46, 166.57, 171.60 ppm. (See, FIG. 55). ESI-MS, m/z theoretical: $[M]^{2+}$=656.34 Da, observed: $[M]^{2+}$=656.4 and $[M+H]^{3+}$=438.0 Da. (See, FIG. 52).

The Rhodamine-SH was formed from the rhodamine B disulfide as follows (See Scheme 14): 346 mg of rhodamine B disulfide (0.25 mmol, 1.00 eq) was dissolved in 2 mL of DMF in a round bottom flask and kept under a flow of Ar. Separately, 150 mg of TCEP (0.52 mmol, 2.10 eq) was dissolved in 10 mL of Ar purged DI water and the pH was adjusted to ca. 6 using 1 M NaOH. The TCEP solution was added to the flask containing rhodamine B disulfide, and allowed to stir for 4 h at 23° C. The reaction was then saturated with $NaHCO_3$ and stirred for an additional 30 min. The resulting solution was extracted with $CH_2Cl_2$ (3×) and the organic layers were combined and washed with equal portions of sat. $NaHCO_3$ (2×) and sat. NaCl solution (3×), then stirred over $Na_2SO_4$, filtered, and dried under vacuum. A dark purple solid with notable odor was recovered (290 mg, 83.7% yield). and characterized using $^1$H-NMR, $^{13}$C-NMR, and ESI-MS, confirming formation of the Rhodamine-SH. $^1$H-NMR (300 MHz, 303K, DMSO-$d_6$): δ=1.20 (t, $^3J_{H-H}$=6.6 Hz, 12H), 1.67 (m, 2H), 2.11 (br, 4H), 2.23 (br, 2H), 2.61 (m, 4H), 3.15-3.47 (m, overlaps with HDO, 4H), 3.66 (q, $^3J_{H-H}$=7.0 Hz, 8H), 4.02 (t, $^3J_{H-H}$=6.1 Hz, 2H), 6.95 (br, 2H), 7.13 (m, 4H), 7.53 (dd, $^3J_{H-H}$=5.7, 2.9 Hz, 1H), 7.64 (m, 1H), 7.74 (dd, $^3J_{H-H}$=5.1, 3.5 Hz 2H) ppm. (See, FIG. 53). $^{13}$C-NMR (300 MHz, 303 K, DMSO-$d_6$): δ=12.93, 19.72, 25.65, 38.36, 45.85, 54.47, 54.49, 62.78, 96.33, 113.45, 114.75, 127.85, 130.05, 130.26, 130.71, 130.95, 132.33, 135.96, 155.52, 156.01, 157.47, 166.60, 171.72 ppm. (See, FIG. 55), ESI-MS, m/z theoretical: $[M]^+$=657.35 Da, observed: $[M]^+$=657.4 Da. UV-vis (DMSO), $\lambda_{abs}$=568 nm, $\lambda_{em}$=592 nm. (See, FIG. 54).

Example 13

Lithium Phenyl-2,4,6-Trimethylbenzoylphosphinate (LAP) Photoinitiator Synthesis

LAP was synthesized as previously reported. See, Majima, T.; Schnabel, W.; Weber, W., "Phenyl-2,4,6-trimethylbenzoylphosphinates as water-soluble photoinitiators. Generation and reactivity of O=Ṗ(C6H5)(O⁻) radical anions." *Die Makromolekulare Chemie* 1991, 192 (10), 2307-2315, the disclosure of which is incorporated herein by reference in its entirety. Briefly, 2.80 mL of dimethyl phenylphosphonite (17.6 mmol, 1.00 eq) was added to an oven dried flask under Ar at 23° C. While stirring, 2.94 mL of 2,4,6-trimethylbenzoyl chloride (17.6 mmol, 1.00 eq) was added dropwise and allowed to react for 18 h. Then, a four-fold excess of LiBr (6.1 g) in 100 mL of 2-butanone was added to the reaction mixture and heated to 50° C. for 10-15 min with stirring until a white precipitate formed. The solution was cooled to room temperature and set for 2 h, then suction filtered and rinsed generously with 2-butanone to remove excess LiBr. The solid white precipitate (4.45 g, 85.9% yield) was dried under vacuum and analyzed by $^1$H-NMR and UV-visible spectroscopy. ($^1$H-NMR (300 MHz, 303K, D$_2$O): δ=2.01 (s, 6H), 2.23 (s, 3H), 6.88 (s, 2H), 7.41-7.51 (m, 2H), 7.51-7.61 (m, 1H), 7.70 (m, 2H) ppm. UV-vis (H$_2$O), $\lambda_{abs}$=372 nm, ε=179±3 M$^{-1}$cm$^{-1}$ (lit. value=218 M$^{-1}$cm$^{-1}$)). The molar absorptivity (ε) was determined and compared to the literature (observed=179±3 M$^{-1}$cm$^{-1}$, lit. value=218 M$^{-1}$cm$^{-1}$). See, Fairbanks, B. D.; Schwartz, M. P.; Bowman, C. N.; Anseth, K. S., "Photoinitiated polymerization of PEG-diacrylate with lithium phenyl-2,4,6-trimethylbenzoylphosphinate: polymerization rate and cytocompatibility." *Biomaterials* 2009, 30 (35), 6702-6707, the disclosure of which is incorporated herein by reference in its entirety.

Example 14

Control and Allyl-TPU Polymerizations

TPU polymerizations were performed in bulk with mechanical stirring at 100° C. The following is provided as an example procedure: for a 100 g batch of 50 mol % (30 wt. %) HMDI control TPU, 61.7 g (22.0 mmol, 1.0 eq) of Arcol E-351 and 8.2 g (92.3 mmol, 4.2 eq) of BDO were preheated to 100° C. in a porcelain enamel-lined tin can with overhead mechanical stirring. Then, 28.1 mL (114.3 mmol, 5.2 eq) of HMDI was added, immediately followed by 2-3 drops of stannous octoate catalyst. The mixture was stirred for 2-5 min, or until the mixture became too viscous to stir. The resulting TPU was oven cured at 100° C. for 24 h. To produce a TPU containing 8 mol % (2.4 wt. %) 3-allyloxy-1,2-propanediol, denoted as "allyl-TPU", the molar ratio of BDO to 3-allyloxy-1,2-propanediol was modified, while maintaining the molar ratio of HMDI to Arcol-E351. Additionally, 3-allyloxy-1,2-propanediol was added directly with the mixture of diols and preheated to 100° C. before adding HMDI. Reagent quantities used for TPU polymerizations are recorded in Table 4, above.

Control TPU. $^1$H-NMR (300 MHz, 303 K, DMSO-d$_6$): δ=0.97 (m, 10H), 1.02-1.20 (m, 120H), 1.26 (m, 10H), 1.37-1.81 (m, 100H), 1.99 (m, 10H), 3.16-3.89 (m, 135H), 4.07 (m, 16H), 4.20 (m, 5H), 4.51 (m, 6H), 4.65 (m, 4H), 4.79 (m, 6H), 4.91 (m, 4H) ppm. SEC (THF): $\overline{M}_n$=68 kDa, $\overline{M}_w$=175 kDa, and Đ$_m$=2.6. DSC: T$_m$=72° C. and 119° C., T$_g$=−60.5° C. TGA: T$_d$=255° C.

Allyl-TPU. $^1$H-NMR (300 MHz, 303 K, DMSO-d$_6$): δ=0.96 (m, 25H), 1.07-1.16 (m, 145H), 1.21 (m, 12.5H), 1.24-1.78 (m, 86H), 1.85 (m, 16H), 1.99 (m, 12.5H), 3.23-3.83 (m, 194H), 4.05 (m, 16H), 4.20 (m, 5H), 4.54 (m, 2.5H), 4.67 (m, 2H), 4.82 (m, 3.5H), 4.93 (m, 2H), 5.22 (dd, $^3J_{H-H}$=24.2, 13.8 Hz, 2H), 5.85 (m, 1H) ppm. SEC (THF): $\overline{M}_n$=92 kDa, $\overline{M}_w$=269 kDa, Đ$_m$=2.9. DSC: T$_m$=72° C. and 115° C., T$_g$=−62.5° C. TGA: T$_d$=245° C.

Example 15

Polymer Processing

TPU films were produced by doctor blade coating a 30 wt. % solution of allyl-TPU in THF onto polyethylene terephthalate (PET) using a gap height of 1.0 mm, and line speed of 15 cm·min$^{-1}$. The blade-coated films were dried overnight at 23° C., and placed in a vacuum oven for 48 h at 25° C. The films were then punched to 2.0 cm in diameter using a manual punch set to produce cylindrical samples ca. 250 μm thick, which were measured using a digital caliper. Compression molded control and allyl-TPU samples were produced using a TMP 35-ton vacuum molding press by heating to 120° C. and pressing at 140 MPa for 15 min, followed by water cooling to room temperature. The molds were then punched to 2 cm in diameter using a manual punch set to produce cylindrical samples (1.0 mm thick, 2.0 cm diameter). Catheter tubes of allyl-TPU were extruded by Cook Polymer Technology (Bloomington, Ind.) using a custom designed, single screw extruder (general purpose 19.05 mm screw) with a 2.18 mm die and a 1.40 mm mandrel. The screw speed was 20 rpm and the line speed was 9.75 m·min$^{-1}$. Heating zones were ramped from 165° C. to 177° C., and the head pressure was 2.76 MPa (8.62 MPa behind the screens). The material was dried at 82° C. overnight.

Example 16

Alloc-TPU Surface Functionalization

For quantification of reactive allyl groups on the TPU surface, FITC-PEG-SH was reacted with the alloc-TPU using thiol-ene "click" conditions. A series of films ranging from 50 nm-50 μm thick (2.0 cm in diameter) were reacted under UV light for 15 min with physical adsorption controls in the absence of UV light tested in parallel. All films were treated with the same dye/initiator solution and experiments were conducted in triplicate. For example, a 2.5 mg thin film (50 μm thickness) of 8.0 mol % (2.4 wt. %) alloc-TPU (60 μg alloc, 0.5 μmol alloc) was placed in petri dish along with a 1.0 mL of solution containing 2.0 mg/mL (1.5 μmol) of FITC-PEG-SH and 0.2 mg/mL (0.9 μmol) of Irgacure-2959 dissolved in DI water. The solution was purged with argon for 30 min and then irradiated with 365 nm UV light for 15 min. The samples were then rinsed thoroughly (3×) with DI water, blown dry with compressed air, then dissolved in DMSO. Dilutions in DMSO were performed to achieve fluorescence intensities within the standard curve, and the covalent attachment (i.e. the difference between the UV treated sample and physical adsorption control) and physical adsorption values were calculated accordingly.

In order to functionalize the alloc-TPU thin films with QACs, disulfide-ene reactions were performed. A series of films ranging from 50 nm-600 nm thick (2.0 cm in diameter) were reacted under UV light for 15 min with physical adsorption controls in the absence of UV light tested in parallel. Each sample was treated with 1.0 mL of solution containing 5.0 mg/mL (5.2 μmol) of 8-Q14-S-S and 1.0 mg/mL (4.5 μmol) of Irgacure-2959 dissolved in DI water. The solution was purged with argon for 30 min and then irradiated with 365 nm UV light for 15 min. The samples were then rinsed thoroughly (3×) with DI water, blown dry with compressed air, and placed under vacuum for XPS analysis. The specific covalent attachment was taken to be the difference between the UV treated sample and the physical adsorption control. To functionalize compression molded coupons (2.0 cm diameter, 1.0 mm thickness) for antimicrobial testing, the coupons were submerged in 2.0 mL of a solution containing ca. 50 mg/mL (53.7 μmol) of x-Qz-S-S and 12.0 mg/mL (53.5 μmol) of Irgacure-2959, then irradiated for 15 min under 365 nm UV light. The coupons were then flipped over and fresh QAC/initiator solution was added, followed by an additional 15 min under UV light in order to functionalize both sides of the coupons. The coupons were then rinsed thoroughly with DI water, blown dry with compressed air, and placed under vacuum for 24 h before EtO sterilization.

Example 17

Polymer Processing

Spin coating was performed onto circular glass slides (2.0 cm diameter) using various solutions of alloc-TPU in dioxane, ranging from 1-5 wt. %, at 2500 and 5000 RPM for 45 s. The glass slides were rinsed prior to spin coating with toluene (3×) followed by methanol (3×) and blown dry with $N_2$, then placed in a UV Ozone cleaner for 15 minutes. After spin coating, the TPU coated slides were annealed in an oven at 60° C. for at least 2 h. A series of films with varying thickness, ranging from 50 nm to 600 nm, were achieved using these parameters. The film thicknesses were determined using an M-2000 Ellipsometer (J. A. Woollam Co., Nebraska) over the spectral range of 250 nm to 17000 nm, between angles of 50°-70° taken every 5°. The 50 μm film was produced via hand-casting a 5 wt. % solution of alloc-TPU in THF, and measured with a digital caliper. Compression molded TPU films (1.0 mm thick) were produced using a TMP 35 ton vacuum molding press by heating to 120° C. and pressing at 140 MPa for 15 min, followed by water cooling to room temperature. The films were then punched to 2 cm in diameter using a manual punch set to produce the compression molded coupons (1.0 mm thick, 2 cm diameter).

Example 18

Surface Quantification and Characterization

For surface quantification, fluorescence studies were carried out using the BioTek Synergy™ Mx Microplate Reader (BioTek, Vermont) with Gen 5™ Reader Control and Data Analysis Software. An excitation wavelength ($\lambda_{ex}$) of 490 nm was used while scanning the emission range of 520-700 nm at a step of 1 nm/s. A standard curve was generated by serially diluting a stock solution of FITC-PEG-SH in DMSO, pipetting 400 μL of each solution in triplicate into a quartz 96 well plate, measuring the emission intensity, and plotting the maximum emission intensity ($\lambda_{max}$=545 nm) vs. concentration for each solution. To quantify the dye attachment and physical adsorption on thin films, each film and their respective control groups were dissolved in DMSO after treatment, and diluted as necessary to achieve fluorescence intensities within the standard curve. Following dilution, 400 μL of each solution was pipetted in triplicate into a quartz 96 well plate, and the intensities at $\lambda_{max}$ were recorded using the plate reader. From the standard curve, the intensity at $\lambda_{max}$ for each sample provided the dye concentration, and after accounting for dilutions, the molar quantity of specifically attached and physically adsorbed dye was determined, and reported in Table 3, above.

X-ray photoelectron spectroscopy was used to characterize the surface chemistry of the alloc-TPU thin films treated with x-Qz-S-S reagents. The XPS spectra were obtained using a VersaProbe II Scanning XPS Microprobe from Physical Electronics (PHI), under ultrahigh vacuum conditions with a pressure of 2.0 μPa. Automated dual beam charge neutralization was used during the analysis of the samples to provide accurate data. The analyzer pass energy was 117.4 eV for the survey spectra and 46.95 eV for the high-resolution scans in the N1s regions. The survey scans in the range 0-700 eV were used to evaluate the percentage of different atoms present on the surface of the samples. Atomic concentrations were calculated with PHI MultiPak software. The XPS high resolution spectra of N1s were decomposed into two components by using the curve fitting routine in MultiPak. A goodness of fit ($\chi^2$) better than 1.6 was achieved for each fit. Each spectrum was collected using a monochromatic (Al Kα) x-ray beam (E=1486.6 eV) over a 100 μm×1400 μm probing area with a beam power of 100 W. The quaternary nitrogen peak (eV=401-402) was integrated and its quantity relative to urethane nitrogen (eV=398.5) was reported. (See, Table 3).

Example 19

Allyl-TPU Surface Functionalization with Rhodamine-SH Dye

For proof of concept and a quantitative estimate of the amount of Qx-SH that attaches to the surface via thiol-ene chemistry, a rhodamine-SH dye containing the same synthetic core as the Qx-SH compounds was reacted with allyl-TPU using thiol-ene "click" conditions. In a 12-well plate, blade-coated films of allyl-TPU (250 μm thick, 2.0 cm diameter, ca. 110 mg, 20 μmol allyl) were submerged in 2 mL of an Ar purged (30 min) aqueous solution containing rhodamine-SH (10.0 mM) and LAP (5.0 mM), and allowed to pre-soak for 30 min under Ar.

The samples were then treated with UV light ($\lambda$=365 nm, I=1.2 mW·cm$^{-2}$) or kept in the absence of UV light for 30 min to control for physical adsorption of the dye (denoted as "phys. ads." samples). Following treatment, the dye/photoinitiator solutions were drawn up and discarded, and the samples were rinsed with 5 mL of DI water (3×) then submerged in 5 mL of DI water. The samples were further rinsed with 10% EtOH (3×) and soaked in 10% EtOH for 15 min (3×), rinsing with 10% EtOH in between each soak. The samples were blown dry with $N_2$ and dissolved in DMSO for fluorescence studies.

To functionalize the allyl-TPU blade-coated samples with Qx-SH reagents, thiol-ene reactions were performed using the same procedure described for rhodamine-SH. Briefly, blade-coated films of allyl-TPU (250 μm thick, 2.0 cm diameter, ca. 110 mg, 20 μmol allyl) were submerged in 2 mL of an Ar purged (30 min) aqueous solution containing Qx-SH (10.0 mM) and LAP (5.0 mM), and allowed to pre-soak for 30 min under Ar. UV-treated samples were irradiated for 30 min ($\lambda$=365 nm, I=1.2 mW·cm$^{-2}$) while phys. ads. samples were kept in the absence of UV light for 30 min to control for any antimicrobial activity that is contributed by non-covalently attached QAC. Following treatment, the dye/photoinitiator solutions were drawn up and discarded, and the samples were rinsed with 5 mL of DI water (3×) then submerged in 5 mL of DI water. The samples were further rinsed with 10% EtOH (3×) and soaked in 10% EtOH for 15 min (3×), rinsing with 10% EtOH in between each soak.

For post-fabrication functionalization of the inner lumen of allyl-TPU catheter tubing with Qx-SH reagents, 0.5 mL of an Ar purged solution containing Qx-SH (10.0 mM) and LAP (5.0 mM) was flowed through 25.0 cm segments of catheter tubing every 7.5 min for the duration of a 30 min pre-soak and 30 min UV treatment (or absence of UV for phys. ads. control). Following treatment, the catheter tubes were rinsed continuously for 30 s with DI water (3×), then rinsed continuously for 30 s with 10% EtOH (3×). All samples were blown dry with $N_2$ and placed under vacuum for 24 h before X-ray photoelectron spectroscopy (XPS) analysis or ethylene oxide (EtO) sterilization.

Example 20

Surface Quantification and Analysis

For surface quantification, fluorescence studies were carried out using a BioTek Synergy™ Mx Microplate Reader (BioTek, Vermont) with Gen 5™ reader control and data analysis software. An excitation wavelength of $\lambda_{ex}$=568 nm was used while scanning the emission range of 586-700 nm at a step of 1 nm·s$^{-1}$. A standard curve was constructed by serially diluting a stock solution of rhodamine-SH in DMSO in triplicate, pipetting 300 μL of each solution into a quartz 96-well plate, measuring the emission intensity, and plotting the maximum emission ($\lambda_{em}$=592 nm) intensity vs. concentration. To quantify the dye present on UV-treated, phys. ads., and untreated allyl-TPU blade-coated samples, the films were dissolved in DMSO (5 mL) and diluted as necessary to achieve fluorescence intensities within the standard curve. Following dilution, 300 μL of each solution was pipetted into a quartz 96-well plate and the intensity at $\lambda_{em}$ for each sample was measured using the plate reader. The dye concentration was determined from the $\lambda_{em}$ intensity using the standard curve, and the molar quantity of dye present on each sample (n=3) was calculated (accounting for dilutions) and reported in terms of mol·cm$^{-2}$ based on the surface area of the samples (See, Table 3, above).

XPS was employed to characterize the surface composition of the allyl-TPU films and the inner lumen of catheter tubing (longitudinal sections) treated with Qx-SH reagents. The XPS spectra were obtained using a VersaProbe II Scanning XPS Microprobe from Physical Electronics (PHI), under ultrahigh vacuum conditions with a pressure of 2.0 μPa. Automated dual beam charge neutralization was used during the analysis of the samples to provide accurate data. The analyzer pass energy was 117.4 eV for the survey spectra and 23.5 eV for the high-resolution scans in the N1s regions. Survey scans in the range of 0-700 eV were used to evaluate the percentage of different atoms present on the surface of the samples. Atomic concentrations were calculated with PHI MultiPak software. The XPS high-resolution spectra of N1s were decomposed into two components by using the curve fitting routine in MultiPak. A goodness of fit ($\chi^2$) better than 1.5 was achieved for each fit. Each spectrum was collected using a monochromatic (Al K$_\alpha$) x-ray beam (E=1486.6 eV) over a 100 μm×1400 μm probing area with a beam power of 100 W. The quaternary nitrogen peak ($NR_4^+$, eV=401-402) was integrated and its quantity relative to urethane nitrogen (N, eV=398.5) was reported (See, Table 3, above).

Example 21

Sterilization and Antimicrobial Testing

Prior to antimicrobial testing, the coupons were sterilized using ethylene oxide (EtO) sterilization using an Anprolene benchtop sterilizer (Anderson Products, Inc., Haw River, N.C.) following the manufacturer's protocol to deliver approximately 0.5 cc/L of EtO gas over a 12 h sterilization cycle at 35% humidity and room temperature, followed by a 48 h purge under vacuum. UV treated, physically adsorbed and control coupons were evaluated using a method adapted from ISO 22196. Briefly, coupons were inoculated with same day broth cultures of select bacteria (including *E. coli* and *S. epidermidis*) in dilute nutrient media at approximately 150 CFU/mm$^2$ of coupon surface. Inoculums were dispersed across the surface of the coupons using cover films. Inoculated coupons were cultured in a humidified room air incubator for the desired 24 h. Following incubation, surviving cells were recovered from the coupons using vigorous agitation. Surviving cells were enumerated via plate counting and compared to internal controls of polypropylene and chlorhexidine.

Example 22

Antimicrobial Testing

For antimicrobial testing, blade-coated samples and catheter tubing of allyl-TPU were sterilized by EtO sterilization using an Anprolene benchtop sterilizer (Anderson Products, Inc., Haw River, N.C.) following the manufacturer's protocol to deliver approximately 0.5 cc·L$^{-1}$ of EtO gas over a 12 h sterilization cycle at 35% humidity and room temperature, followed by a 48 h purge under vacuum. The bacterial strains used in this study included *Staphylococcus epidermidis* (ATCC 12228), *Staphylococcus aureus* (25923), *Escherichia coli* (ATCC 25922), *Pseudomonas aeruginosa* (ATCC 27853), *Enterococcus faecalis* (ATCC 29212), and methicillin-resistant *Staphylococcus aureus* (MRSA) (ATCC BAA-41).

The contact-killing assay was performed on physically adsorbed (phys. ads.), and UV-treated blade-coated samples modified with a series of Qx-SH reagents using a method adapted from ISO 22196. See, International Organization for Standardization. *Measurement of antibacterial activity on plastics and other non porous surfaces* (ISO 22196:2011), the disclosure of which is incorporated herein by reference in its entirety. Briefly, the samples were inoculated with same day cultures of select bacteria (e.g. *E. coli, S. epidermidis*) in dilute nutrient media (0.2% tryptic soy broth (TSB) in 1× phosphate buffered saline (PBS)) at approximately 150 colony-forming units (CFU)·mm$^{-2}$. Generally, 35 uL of 8.5×10$^5$ CFU/mL cultures were dispersed across the surface of the sample using sterile polypropylene cover films (area=198 mm$^2$). Inoculated samples were incubated in a humidified room air incubator (36° C., ca. 80% rel. humidity) for 20 h. Following incubation, surviving cells were recovered from the samples using vigorous agitation (i.e. vortexing for 20 s in PBS). Surviving cells were enumerated via 10-fold series dilution and plating 100 μL onto tryptic soy agar (TSA), incubating overnight and then plate counting CFU. The mean CFU recovered per sample (CFU/sample) were calculated by accounting for dilutions. Internal controls samples of polypropylene and chlorhexidine treated with polypropylene were included in the assay.

A live/dead assay was performed using overnight cultures of *E. coli* grown in TSB and *S. aureus* grown in Mueller-Hinton broth (MH). The cells were washed with PBS (3×), resuspended in PBS, and diluted to obtain an OD$_{600}$=0.15 (measured using a Hach DR2800 Spectrophotometer, λ=600 nm). The bacterial suspensions (1.0 mL) were stained with 2.0 μL of a dye mixture containing equal portions of 3.34 mM SYTO 9 and 20 mM propidium iodide (L7012 LIVE/DEAD™ BACLIGHT™ Bacterial Viability Kit, ThermoFisher Scientific) and allowed to incubate at room temperature in the dark for 15 min. Then, 10 μL of stained bacterial suspension was placed on a glass slide and covered with either untreated, phys. ads., or UV-treated samples modified with Q8-SH for 5 min (*S. aureus*) or 10 min (*E. coli*) before imaging. Live/dead microscopy was performed using an IX81 inverted microscope (Olympus, Center Valley, Pa.) and images were processed and quantified using ImageJ software.

Biofilm formation was analyzed using overnight cultures of *P. aeruginosa* grown in TSB and adjusted to an $OD_{600}=0.10$. An assembly of catheter tubing was prepared using aseptic techniques, and included COOK™ BEACON™ TIP TORCON NB™ Advantage catheter segments (25.0 cm in length) denoted as "CC" and numbered 1-4 from upstream (1) to downstream (4). The catheter assembly was connected using 18 gauge blunt tip stainless steel needles (~25 mm in length) sterilized in 100% EtOH. CC segments were located before, after, and in between the untreated, phys. ads., and UV-treated allyl-TPU catheter segments modified with Q8-SH to account for any downstream influence of the experimental catheters. With a peristaltic pump flowing at 1.5 mL·min$^{-1}$, fresh bacterial inoculum was continuously streamed through the catheter assembly for 2 h, followed by FAB medium (0.10 mM $CaCl_2$, 0.01 mM Fe-EDTA, 0.15 mM $(NH_4)_2SO_4$, 0.33 mM $Na_2HPO_4$, 0.20 mM $KH_2PO_4$, 0.50 mM NaCl, 0.50% (wt/vol) casamino acids, 1.0 mM $MgCl_2$, and 10 mM sodium citrate) for 48 h. Samples were fixed with 50 mL of a 4% paraformaldehyde solution, rinsed with 200 mL of PBS, and submerged in PBS for further testing.

Photographs of the catheter tubing were taken using a camera with a 16-megapixel Sony Exmor RS IMX240 sensor and f/.19 lens. Catheter cross-sections were cut (ca. 2.5 mm in length) from each catheter segment, rinsed thoroughly with DI water, and lyophilized for 24 h for scanning electron microscopy (SEM) analysis. SEM was performed on gold sputter-coated samples using a JEOL-7401 Field Emission Scanning Electron Microscope (JEOL USA, Inc., Peabody, Mass.) at an accelerating voltage of 2.0 kV under 45× and 300× magnification. In addition, lyophilized cross-sections (3.0 mm in length) from randomly selected locations along each catheter segment were placed vertically on a glass slide and imaged under brightfield microscope at 4× magnification. Using Olympus VS-Desktop software, the % biofilm blockage was determined by measuring the inner luminal area of untreated catheters compared to the area of the biofilm on the interior of the contaminated catheters (Equation 1).

$$\% \text{ biofilm blockage} = \left[\frac{\text{biofilm area}}{\text{inner luminal area}}\right] \cdot 100 \quad \text{(Eq. 1)}$$

Results are reported as averages with standard deviations (n=3) for each catheter segment.

Example 23

Cell Viability

NIH/3T3 fibroblast cells (ATCC CRL-1658) were used to assess cell viability (passage 9) on the allyl-TPU films. The 8% allyl-TPU was spin-coated on blank glass coverslips (1 wt. % in chloroform) and samples were annealed at 60° C. for 1 h, then kept under vacuum for 24 h. The coated coverslips were then treated and rinsed as previously described to produce a control, phys. ads., and UV-treated sample modified with Q8-SH. Samples were sterilized by short-wave UV sterilization for 30 minutes. Cells were seeded at a cell density of 194,000 cells/cm$^2$ and cultured for 24 hours in a 37° C. incubator. Samples were then removed and stained with a LIVE/DEAD™ Viability/Cytotoxicity Kit (ThermoFisher Scientific L3224). Slides were analyzed with a Keyence BZ-X700 microscope at 20× magnification. Pictograms were analyzed with ImageJ software for cell viability counting (n=5). All groups were compared to the glass slide control.

In light of the foregoing, it should be appreciated that the present invention significantly advances the art by providing a quaternary ammonium functionalized thermoplastic polyurethane that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A quaternary ammonium functionalized thermoplastic polyurethane having antimicrobial properties for use in medical devices comprising:
   a polyurethane polymer backbone, said polyurethane polymer backbone comprising the residues of one or more diisocyanates, one or more soft segment diols, one or more functionalized diols, and one or more diol chain extenders;
   a plurality of side chains, said side chains extending from said polyurethane polymer backbone and comprising a quaternary ammonium functional group;
   wherein said plurality of side chains are covalently bonded to said one or more functionalized diol residues via a thioether bond.

2. The quaternary ammonium functionalized thermoplastic polyurethane of claim 1 wherein the residues of one or more functionalized diols comprises from 0.5 to 50 mole percent of said polyurethane polymer backbone.

3. The quaternary ammonium functionalized thermoplastic polyurethane of claim 1, wherein said one or more functionalized diols are allyl functionalized diols selected from the group consisting of 3-allyloxy-1,2-propanediol, 2-allyloxy-2-ethyl-1, 3-propanediol, 1-(allyloxy)-1,2-propanediol, pentaerythritol allyl ether, trimethylolpropane diallyl ether, trimethylolpropane allyl ether, 1,5-hexadiene-3,4-diol, 2-methylene-1,3-propanediol, 7-Octene-1,2-diol, 5-norbornene-2-endo, 3-endo-dimethanol, 5-norbornene-2-exo,3-exo-dimethanol, 5-Norbornene-2, 2-dimethanol, and combinations thereof.

4. The quaternary ammonium functionalized thermoplastic polyurethane of claim 1 wherein said one or more functionalized diol comprises 3-allyloxy-1,2-propanediol.

5. The quaternary ammonium functionalized thermoplastic polyurethane of claim 1 wherein said side chains further comprise a spacer comprising from about 2 to about 18 atoms selected from the group consisting of carbon, oxygen, nitrogen and sulfur atoms connecting said quaternary ammonium functional group to said polyurethane polymer backbone.

6. The quaternary ammonium functionalized thermoplastic polyurethane of claim 1 wherein said quaternary ammonium functional group comprises at least one alkyl chain having from about 1 to about 18 carbon atoms.

7. The quaternary ammonium functionalized thermoplastic polyurethane of claim 1 comprising the reaction product of:
   an allyl functionalized polyurethane polymer; and
   a disulfide or thiol compound containing at least one quaternary ammonium functional group.

8. The quaternary ammonium functionalized thermoplastic polyurethane of claim 7 wherein said allyl functionalized polyurethane polymer has a formula selected from:

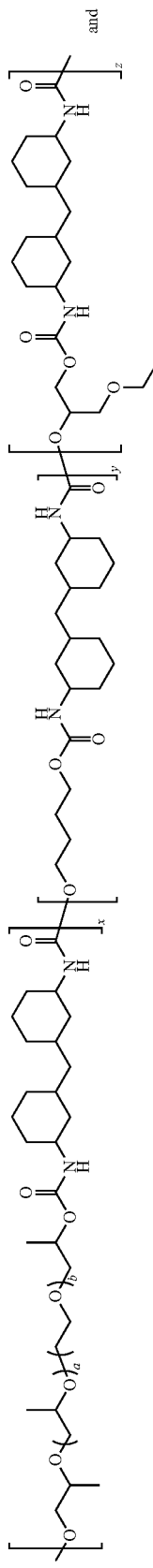 and 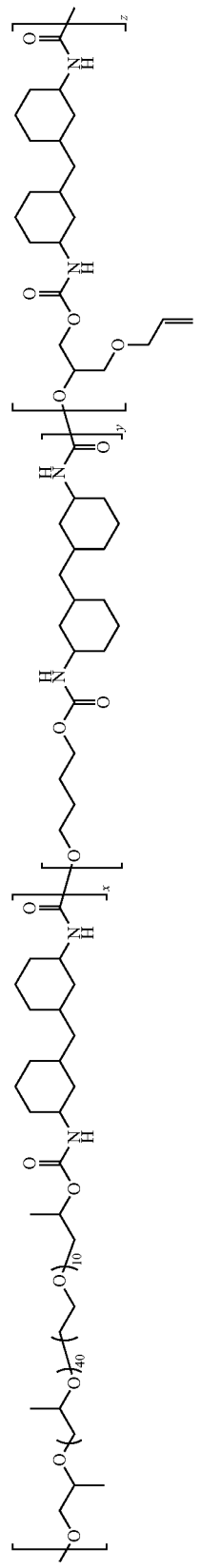

where a is an integer from 2 to 50; b is an integer from 2 to 50; x is a mole fraction from 0.01 to 0.8; y is a mole fraction from 0.01 to 0.8; and z is a mole fraction ranging from 0.01 to 0.8; and the sum of x, y, and z is equal to 1.

9. The quaternary ammonium functionalized thermoplastic polyurethane of claim 7 wherein said disulfide or thiol compound is a disulfide compound synthesized from a compound selected from the group consisting of 3,3'-dithiodipropionic acid, 4,4'-dithiodibutyric acid, dithiodiglycolic acid, 2-hydroxyethyl disulfide, cystamine dihydrochloride, and combinations thereof.

10. The quaternary ammonium functionalized thermoplastic polyurethane of claim 7 wherein said disulfide or thiol compound is a disulfide or thiol compound having a formula selected from:

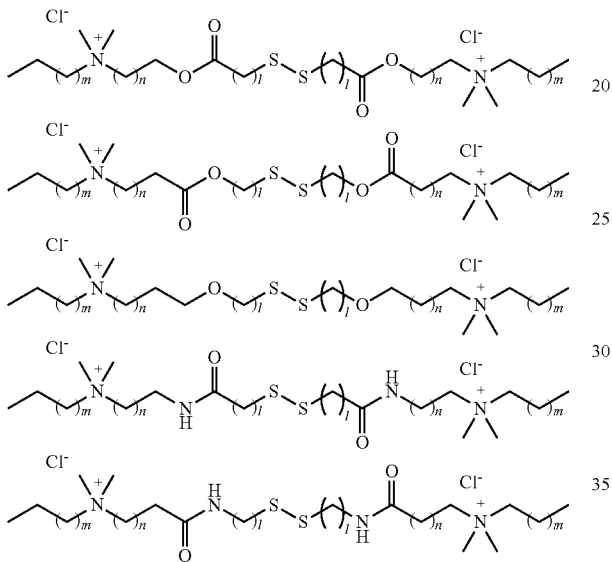

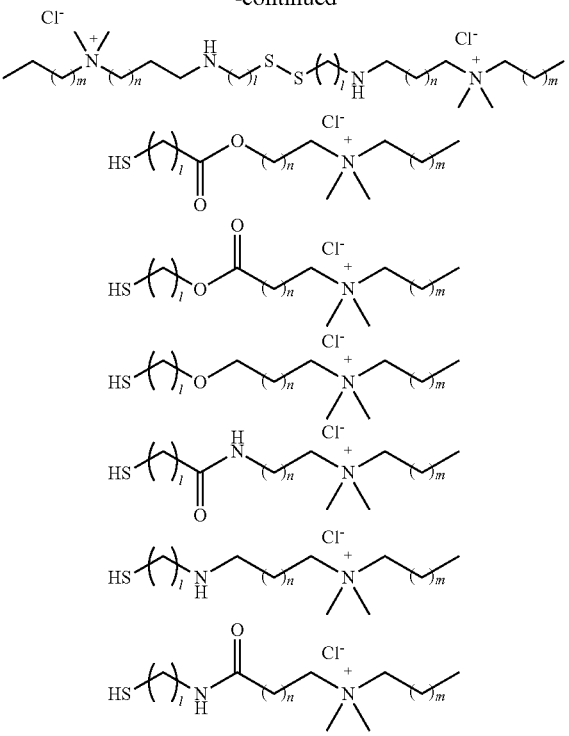

wherein l is an integer from 1 to 3, m is an integer from 1 to 18, and n is an integer from 1 to 19.

11. The quaternary ammonium functionalized thermoplastic polyurethane of claim 1 having a shore durometer hardness of from about 50 to about 100 as measured by a shore A durometer.

12. The quaternary ammonium functionalized thermoplastic polyurethane of claim 1 having a formula selected from:

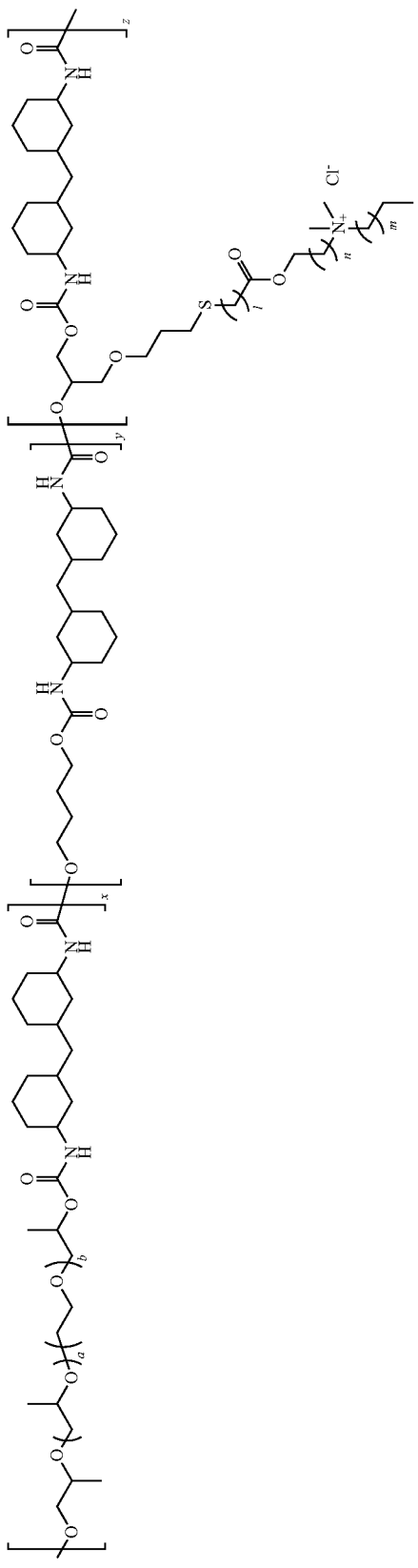 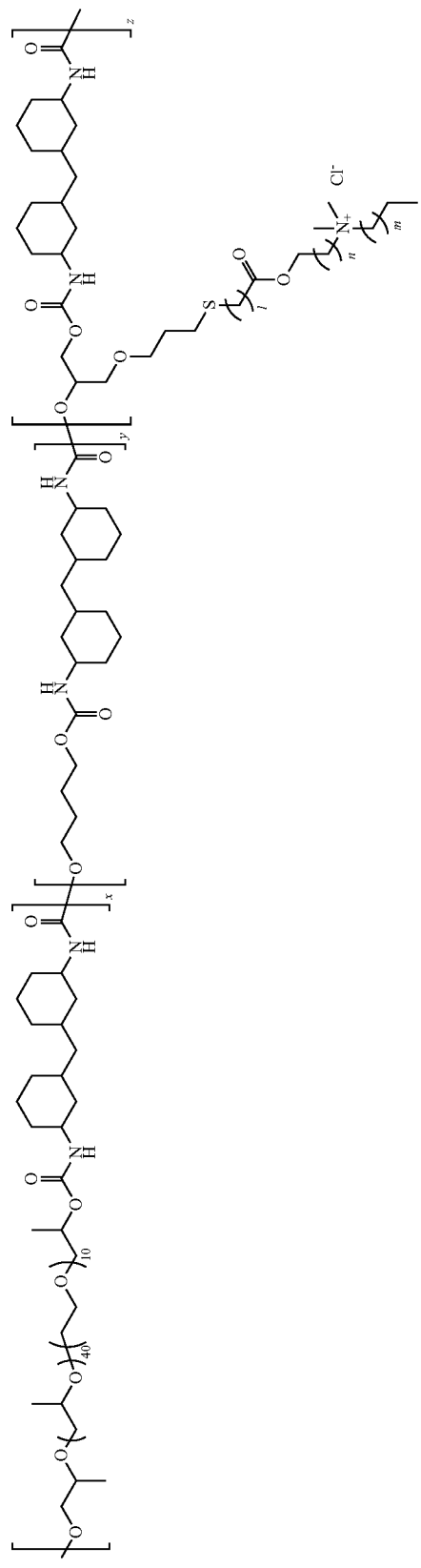

where a is an integer from 2 to 50; b is an integer from 2 to 50; x is a mole fraction from 0.01 to 0.8; y is a mole fraction from 0.01 to 0.8; and z is a mole fraction ranging from 0.01 to 0.8; the sum of x, y, and z is equal to 1; m is an integer from 1 to 18, n is an integer from 1 to 19, and l is an integer from 1 to 4.

13. A method for making the quaternary ammonium functionalized thermoplastic polyurethane of claim 1 comprising:
- A) preparing an allyl functionalized polyurethane polymer;
- B) preparing a bi-quaternary ammonium functionalized disulfide compound or a quaternary ammonium functionalized thiol compound;
- C) combining said allyl functionalized polyurethane polymer, said bi-quaternary ammonium functionalized disulfide compound or quaternary ammonium functionalized thiol compound, and an initiating catalyst under an inert atmosphere;
- D) activating said initiating catalyst to produce the quaternary ammonium functionalized thermoplastic polyurethane of claim 1.

14. The method of claim 13 wherein said allyl functionalized polyurethane has a formula selected from:

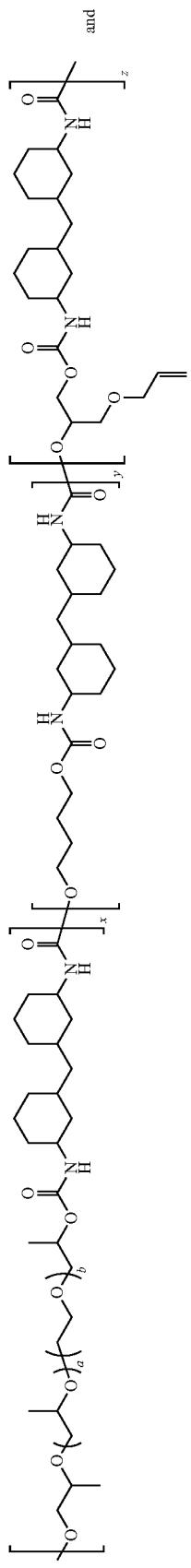 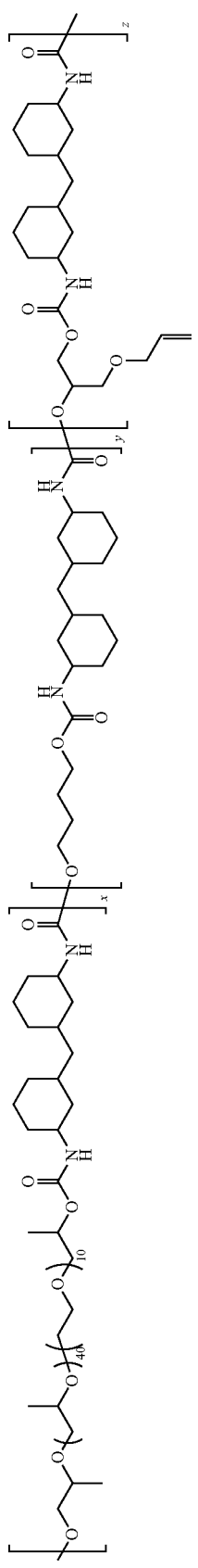

where a is an integer from 2 to 50; b is an integer from 2 to 50; x is a mole fraction from 0.01 to 0.8; y is a mole fraction from 0.01 to 0.8; and z is a mole fraction ranging from 0.01 to 0.8; and the sum of x, y, and z is equal to 1.

15. The method of claim 13 wherein said bi-quaternary ammonium functionalized disulfide compound comprises two quaternary ammonium functional groups each attached to a disulfide group by a spacer or said quaternary ammonium functionalized thiol compound comprises a quaternary ammonium functional group attached to a thiol group by a spacer, wherein said spacer comprises from about 2 to about 20 atoms selected from the group consisting of carbon, nitrogen and oxygen atoms.

16. The method of claim 13 wherein said bi-quaternary ammonium functionalized disulfide compound or said quaternary ammonium functionalized thiol compound is a disulfide or thiol compound having a formula selected from:

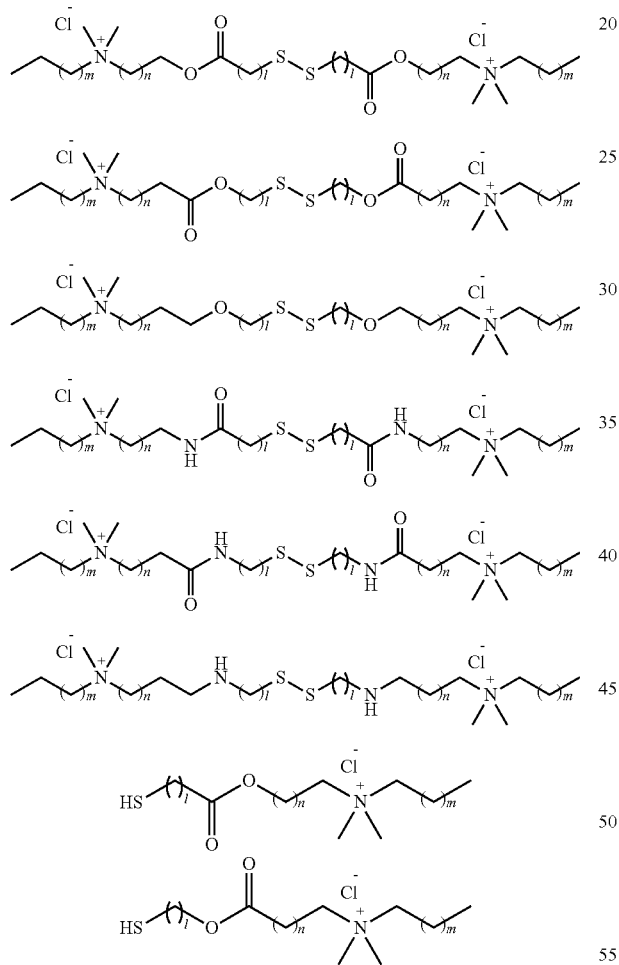

wherein l is an integer from 1 to 3, m is an integer from 1 to 18, and n is an integer from 1 to 19.

17. The method of claim 13 wherein the step of preparing an allyl functionalized polyurethane polymer (step A) further comprises forming said allyl functionalized polyurethane polymer into a three dimensional shape, film, or coating prior to said step of combining (step C).

18. The method of claim 17 wherein said three dimensional shape comprises a catheter, medical tubing, or a coating for medical devices.

19. The method of claim 13 wherein said quaternary ammonium functionalized thiol compound is prepared by the method comprising:
   a) reacting a chlorinated alcohol with a tri-substituted amine to form a chlorinated quaternary ammonium alcohol intermediate;
   b) combining 3,3'-dithiodipropionic acid, 4,4'-dithiodibutyric acid, or dithiodiglycolic acid with an excess of thionyl chloride or oxalyl chloride in a suitable container under an inert atmosphere and heating the combination to reflux for from about 4 to about 24 h to produce the corresponding acid chloride;
   c) dissolving said chlorinated quaternary ammonium alcohol intermediate in a solvent;
   d) cooling the solution of step (c) to a temperature of from about 25° C. to about 0° C. and adding said acid chloride disulfide under an inert atmosphere;
   e) heating the combination of step (d) to reflux for from about 12 to about 24 h to produce the bi-quaternary ammonium functionalized disulfide compound;
   f) and reacting said bi-quaternary ammonium disulfide compound with a solution of tris(2-carboxyethyl) phosphine hydrochloride at a pH from about 4 to about 7.

20. A medical device for use in the body of a patient comprising the quaternary ammonium functionalized thermoplastic polyurethane of claim 1.

* * * * *